US011511156B2

(12) United States Patent
Shavit

(10) Patent No.: US 11,511,156 B2
(45) Date of Patent: Nov. 29, 2022

(54) TRAINING SYSTEM AND METHODS FOR DESIGNING, MONITORING AND PROVIDING FEEDBACK OF TRAINING

(71) Applicant: Arie Shavit, Zikron Ya'acov (IL)

(72) Inventor: Arie Shavit, Zikron Ya'acov (IL)

(73) Assignee: Arie Shavit, Zikron Yaakov (IL)

( * ) Notice: Subject to any disclaimer, the term of this patent is extended or adjusted under 35 U.S.C. 154(b) by 0 days.

(21) Appl. No.: 15/594,562

(22) Filed: May 13, 2017

(65) Prior Publication Data

US 2017/0368413 A1    Dec. 28, 2017

Related U.S. Application Data

(60) Provisional application No. 62/307,477, filed on Mar. 12, 2016.

(51) Int. Cl.
*A63B 24/00* (2006.01)

(52) U.S. Cl.
CPC ...... *A63B 24/0075* (2013.01); *A63B 24/0062* (2013.01); *A63B 2024/0065* (2013.01); *A63B 2024/0068* (2013.01); *A63B 2024/0071* (2013.01); *A63B 2024/0081* (2013.01)

(58) Field of Classification Search
CPC ............ A63B 24/0062; A63B 24/0075; A63B 2024/0065; A63B 2024/0068; A63B 2024/0071; A63B 2024/0081; A63B 24/0006; A63B 2024/0015; A63B 71/0622; A63B 2071/0647; A63B 2220/10; A63B 2220/803; G06F 3/011; G06F 3/017; G06F 3/0304; G09B 19/0038; G16H 20/30

See application file for complete search history.

(56) References Cited

U.S. PATENT DOCUMENTS

| 3,770,267 A | 11/1973 | McCarthy |
| 3,815,904 A | 6/1974 | Weiss et al. |
| 3,871,646 A | 3/1975 | Slack |
| 4,564,191 A | 1/1986 | Atkin |

(Continued)

FOREIGN PATENT DOCUMENTS

| CN | 101912676 | 12/2010 |
| CN | 201815059 | 5/2011 |

(Continued)

OTHER PUBLICATIONS

Farbricio Ferreira, EGYM is Currently Live, Mar. 2014, available on http://igor.goldsmiths.ac.uk/~io301fds/category/physcomp/.

(Continued)

*Primary Examiner* — Joshua Lee

(57) ABSTRACT

Computing device enhanced training environment system comprising a computing device, I/O subsystem for permitting a user to enter at least one attribute of the training or of the trainee, a plurality of sensors for generating sensory information, a training environment in which a training activity takes place, a database containing training related information. The computing device enhanced training environment system configured for at least one of the following: design a training program for a plurality of users, monitor training program performance, monitor training performance, instruct a user about the training, determine and/or set difficulty level in training apparatus.

20 Claims, 64 Drawing Sheets

(56) References Cited

U.S. PATENT DOCUMENTS

| | | | |
|---|---|---|---|
| 4,600,196 A | 7/1986 | Jones | |
| 4,666,149 A | 5/1987 | Olschansky et al. | |
| 4,706,953 A | 11/1987 | Graham | |
| 4,725,057 A | 2/1988 | Shifferaw | |
| 4,811,946 A | 3/1989 | Pelczar | |
| 5,066,005 A | 11/1991 | Luecke | |
| 5,074,551 A | 12/1991 | Olschansky et al. | |
| 5,451,191 A | 9/1995 | Beenken | |
| 5,462,503 A | 10/1995 | Benjamin et al. | |
| 5,522,784 A | 4/1996 | Grant | |
| 5,586,962 A | 12/1996 | Hallmark | |
| 6,013,007 A | 1/2000 | Root et al. | |
| 6,042,523 A | 3/2000 | Graham | |
| 6,045,491 A | 4/2000 | McNergney et al. | |
| 6,774,885 B1 | 8/2004 | Even-Zohar | |
| 6,952,060 B2 | 10/2005 | Goldner et al. | |
| 7,125,368 B2 | 10/2006 | Endelman | |
| 7,192,391 B2 | 3/2007 | Kim | |
| 7,288,053 B2 | 10/2007 | Endelman et al. | |
| 7,597,653 B1 | 10/2009 | Lindemeier | |
| 7,608,025 B1 | 10/2009 | Best | |
| 7,722,503 B1* | 5/2010 | Smith | A63B 24/0062 482/8 |
| 7,815,552 B2 | 10/2010 | Dibble et al. | |
| 7,874,957 B2 | 1/2011 | Hurwitz et al. | |
| 7,931,570 B2 | 4/2011 | Hoffman | |
| 7,955,229 B2 | 6/2011 | Graham | |
| 8,052,585 B2 | 11/2011 | Donaldson | |
| 8,137,247 B2 | 3/2012 | Gerschefske et al. | |
| 8,192,338 B2 | 6/2012 | Solow et al. | |
| 8,337,365 B2 | 12/2012 | Kim et al. | |
| 8,784,115 B1* | 7/2014 | Chuang | A63B 24/0075 434/326 |
| 9,318,030 B2* | 4/2016 | Harris | G09B 19/0038 |
| 9,613,659 B2* | 4/2017 | Maser | G09B 19/0038 |
| 9,691,428 B2* | 6/2017 | Maser | G06F 16/639 |
| 9,861,855 B2* | 1/2018 | Foley | A63F 13/798 |
| 10,223,931 B1* | 3/2019 | Clark | G16H 40/67 |
| 10,839,954 B2* | 11/2020 | Flavell | G16H 20/30 |
| 2002/0002103 A1 | 1/2002 | Watterson et al. | |
| 2002/0183961 A1 | 12/2002 | French et al. | |
| 2002/0187846 A1 | 12/2002 | Funk | |
| 2003/0032529 A1 | 2/2003 | Alessandri et al. | |
| 2003/0073518 A1 | 4/2003 | Marty et al. | |
| 2003/0151554 A1 | 8/2003 | McCarthy | |
| 2003/0211916 A1 | 11/2003 | Capuano | |
| 2003/0219704 A1 | 11/2003 | Bleckley et al. | |
| 2003/0232627 A1 | 12/2003 | Tu et al. | |
| 2004/0029684 A1 | 2/2004 | Zarif | |
| 2004/0248071 A1 | 12/2004 | Bedziouk et al. | |
| 2005/0054457 A1 | 3/2005 | Eyestone et al. | |
| 2005/0209049 A1 | 9/2005 | Shields | |
| 2005/0288159 A1 | 12/2005 | Tackett | |
| 2006/0025701 A1* | 2/2006 | Kasahara | A61B 5/0537 600/547 |
| 2006/0073449 A1 | 4/2006 | Kumar et al. | |
| 2006/0166737 A1 | 7/2006 | Bentley | |
| 2006/0217233 A1 | 9/2006 | Lee | |
| 2006/0284979 A1 | 12/2006 | Clarkson | |
| 2006/0287612 A1 | 12/2006 | Duda et al. | |
| 2007/0033069 A1 | 2/2007 | Rao et al. | |
| 2007/0219059 A1 | 9/2007 | Schwartz et al. | |
| 2007/0225118 A1 | 9/2007 | Giorno | |
| 2007/0256494 A1 | 11/2007 | Nakamura et al. | |
| 2007/0270293 A1 | 11/2007 | Zhuang | |
| 2007/0275830 A1 | 11/2007 | Lee et al. | |
| 2008/0005276 A1 | 1/2008 | Frederick | |
| 2008/0015089 A1 | 1/2008 | Hurwitz et al. | |
| 2008/0119332 A1 | 5/2008 | Roman | |
| 2008/0182685 A1 | 7/2008 | Marty et al. | |
| 2008/0221487 A1 | 9/2008 | Zohar et al. | |
| 2009/0023561 A1 | 1/2009 | Ross et al. | |
| 2009/0048044 A1 | 2/2009 | Oleson et al. | |
| 2009/0085864 A1 | 4/2009 | Kutliroff et al. | |
| 2009/0144080 A1 | 6/2009 | Gray et al. | |
| 2009/0227424 A1 | 9/2009 | Hirata et al. | |
| 2009/0298650 A1* | 12/2009 | Kutliroff | A63B 71/0622 482/8 |
| 2009/0312152 A1 | 12/2009 | Kord | |
| 2010/0015585 A1 | 1/2010 | Baker | |
| 2010/0022351 A1 | 1/2010 | Lanfermann et al. | |
| 2010/0030532 A1 | 2/2010 | Arora et al. | |
| 2010/0041498 A1 | 2/2010 | Adams | |
| 2010/0120537 A1 | 5/2010 | Yamaoka et al. | |
| 2010/0145232 A1 | 6/2010 | Jang et al. | |
| 2010/0173276 A1 | 7/2010 | Vasin | |
| 2010/0194872 A1 | 8/2010 | Mathe et al. | |
| 2010/0195869 A1 | 8/2010 | Geiss | |
| 2010/0197399 A1 | 8/2010 | Geiss | |
| 2010/0199230 A1 | 8/2010 | Latta et al. | |
| 2010/0208945 A1 | 8/2010 | Te Vrugt et al. | |
| 2010/0222179 A1 | 9/2010 | Temple et al. | |
| 2010/0234699 A1 | 9/2010 | Lanfermann et al. | |
| 2010/0246898 A1 | 9/2010 | Izumi | |
| 2010/0277489 A1 | 11/2010 | Geisner et al. | |
| 2010/0280418 A1 | 11/2010 | Klose | |
| 2010/0281432 A1 | 11/2010 | Geisner et al. | |
| 2010/0302015 A1 | 12/2010 | Kipman et al. | |
| 2010/0303289 A1 | 12/2010 | Polzin et al. | |
| 2011/0006926 A1 | 1/2011 | Kim et al. | |
| 2011/0054870 A1 | 3/2011 | Dariush et al. | |
| 2011/0072457 A1 | 3/2011 | Lanfermann et al. | |
| 2011/0080336 A1 | 4/2011 | Leyvand et al. | |
| 2011/0082007 A1 | 4/2011 | Birrell et al. | |
| 2011/0087137 A1 | 4/2011 | Hanoun | |
| 2011/0093820 A1 | 4/2011 | Zhang et al. | |
| 2011/0105278 A1 | 5/2011 | Fabbri et al. | |
| 2011/0105279 A1 | 5/2011 | Herranen | |
| 2011/0105962 A1 | 5/2011 | Ochi et al. | |
| 2011/0124445 A1 | 5/2011 | Uehling, III | |
| 2011/0172060 A1* | 7/2011 | Morales | A63B 69/004 482/8 |
| 2011/0175809 A1 | 7/2011 | Markovic et al. | |
| 2011/0262002 A1 | 10/2011 | Lee | |
| 2011/0275042 A1* | 11/2011 | Warman | G06K 9/00342 434/247 |
| 2011/0279368 A1 | 11/2011 | Klein et al. | |
| 2011/0281249 A1* | 11/2011 | Gammell | G16H 20/30 434/247 |
| 2011/0289456 A1 | 11/2011 | Reville et al. | |
| 2011/0302293 A1 | 12/2011 | Buban | |
| 2011/0306468 A1 | 12/2011 | Wilson et al. | |
| 2012/0047468 A1 | 2/2012 | Santos et al. | |
| 2012/0051588 A1 | 3/2012 | McEldowney | |
| 2012/0094649 A1 | 4/2012 | Porrati et al. | |
| 2013/0072353 A1* | 3/2013 | Alessandri | A63B 21/062 482/8 |
| 2014/0235409 A1 | 8/2014 | Salmon et al. | |
| 2014/0280219 A1* | 9/2014 | Maser | G09B 19/0038 707/748 |
| 2015/0319424 A1 | 11/2015 | Haimovich-Yogev et al. | |
| 2016/0121165 A1* | 5/2016 | Foley | G06F 19/00 482/9 |
| 2017/0087415 A1* | 3/2017 | Nandimandalam | G16H 10/60 |
| 2017/0216671 A1* | 8/2017 | Wisbey | G16H 50/30 |
| 2017/0263147 A1* | 9/2017 | King | G11B 27/026 |
| 2018/0178066 A1* | 6/2018 | Krueger | G09B 19/003 |

FOREIGN PATENT DOCUMENTS

| | | |
|---|---|---|
| DE | 3717789 | 12/1988 |
| DE | 102009003734 | 1/2012 |
| EP | 1758040 A3 | 8/2007 |
| EP | 2040807 | 8/2012 |
| GB | 2483117 | 2/2012 |
| WO | 1988006776 A | 9/1988 |
| WO | 2000033924 A | 6/2000 |
| WO | 2001016855 A | 3/2001 |
| WO | 2003082411 A1 | 10/2003 |
| WO | 2005021107 A | 3/2005 |
| WO | 2006038815 | 4/2006 |

(56) References Cited

FOREIGN PATENT DOCUMENTS

| WO | 2009074942 A | 6/2009 |
|---|---|---|
| WO | 2010102037 | 9/2010 |
| WO | 2010145896 A | 12/2010 |

OTHER PUBLICATIONS

Ming-Zher Poh et al, "Non-contact, automated cardiac pulse measurements using video imaging and blind source separation", Optics Express 18 (2010) © 2011 Optical Society of America (14 pages).
Karl Hoffman, "An Introduction to Measurements using Strain Gages", Hottinger Baldwin Messtechnik GmbH, Darmstadt (1989) (273 pages).
Components Catalog and Data Sheet—"Strain Gages for Transducer" by ZEMIC © 2010, (26 pages).
Katherine McL. Byers James M. Henle, "Where the Camera Was", Mathematics Magazine vol. 7, No. 4, Oct. 2004 (9 pages).
Trevor Hastie, Robert Tibshirani and Jerome H. Friedman (2001). The Elements of Statistical Learning, Springer. ISBN 0-387-95284-5.
Ian H. Witten and Eibe Frank (2011). Data Mining: Practical machine learning tools and techniques Morgan Kaufmann, 664pp., ISBN 978-0-12-374856-0.
Ethem Alpaydin (2004). Introduction to Machine Learning, MIT Press, ISBN 978-0-262-01243-0.
David J. C. MacKay. Information Theory, Inference, and Learning Algorithms Cambridge: Cambridge University Press, 2003. ISBN 0-521-64298-1.
Richard O. Duda, Peter E. Hart, David G. Stork (2001) Pattern classification (2nd edition), Wiley, New York, ISBN 0-471-05669-3.
Christopher Bishop (1995). Neural Networks for Pattern Recognition, Oxford University Press. ISBN 0-19-853864-2.
Stuart Russell & Peter Norvig, (2002). Artificial Intelligence—A Modern Approach. Prentice Hall, ISBN 0-136-04259-7.
Alpaydin, Ethem (2010). Introduction to Machine Learning. London: The MIT Press. ISBN 978-0-262-01243-0. Retrieved Feb. 4, 2017.
A. M. Tillmann, "On the Computational Intractability of Exact and Approximate Dictionary Learning", IEEE Signal Processing Letters 22(1), 2015: 45-49.
Bassel, George W.; Glaab, Enrico; Marquez, Julietta; Holdsworth, Michael J.; Bacardit, Jaume (Sep. 1, 2011). "Functional Network Construction in *Arabidopsis* Using Rule-Based Machine Learning on Large-Scale Data Sets". The Plant Cell. 23 (9): 3101-3116. doi:10.1105/tpc.111.088153. ISSN 1532-298X.

\* cited by examiner

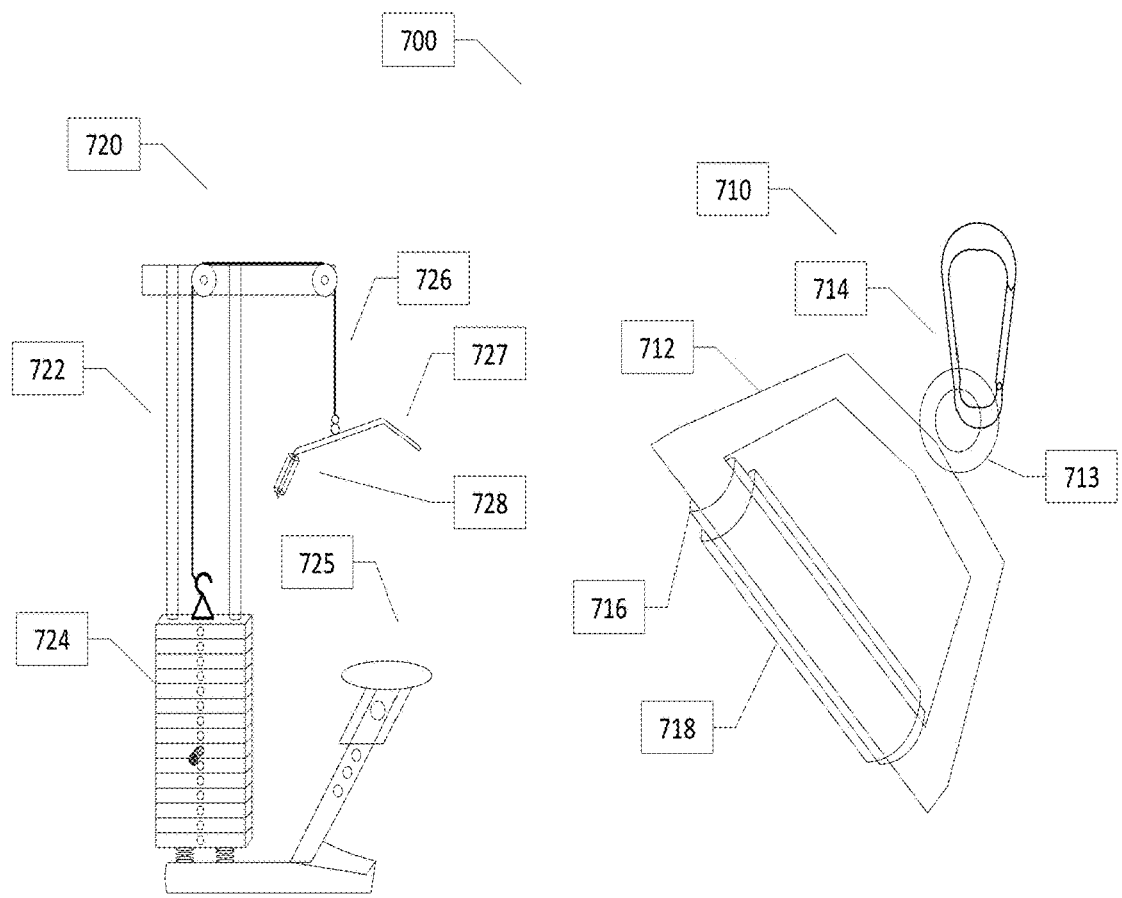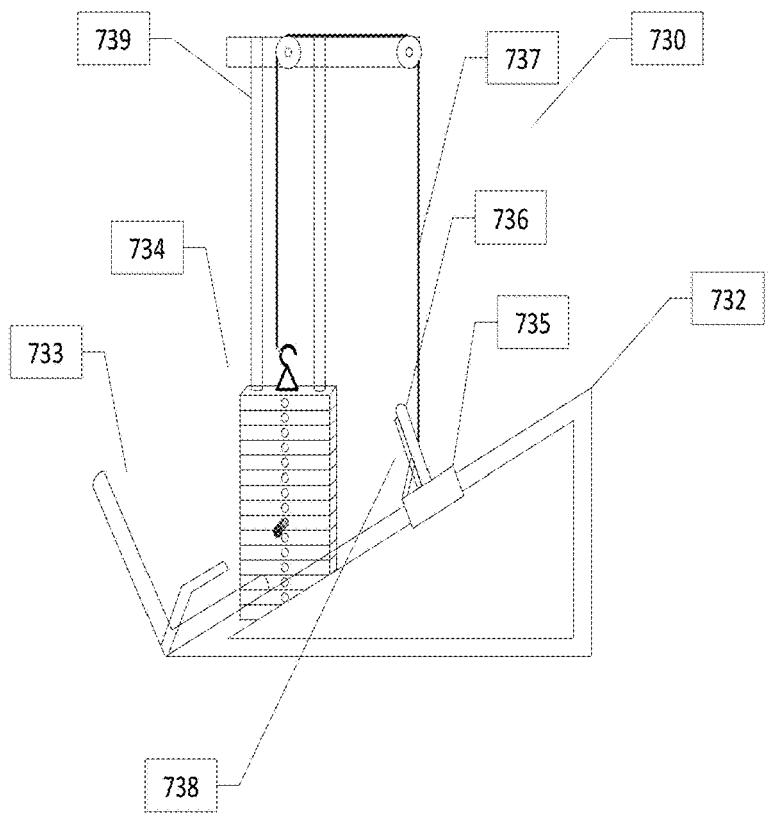
Figure 7

3200

| 3210 | |
|---|---|
| Exercise Name | The Exercise name — 3211 |
| Serial # | Serial number. Can describe the exercise location in the DB or additional entry can be added for that. — 3212 |
| Exercise Type | For example exercise type can be Cardio / Strength / Flexxibility / Stamina etc. — 3212 |
| Exercise Machine | If the exercise requires an exercise machine and if yes, which. — 3214 |
| Description | Description of the exercise. Description can also be in machine language so it can be used by the system to track the performance. — 3215 |
| Link to Frames DB | Link to a DB holding reference performance of the exercise as described in "METHOD AND SYSTEM FOR MONITORING AND FEED-BACKING ON EXECUTION OF PHYSICAL EXERCISE ROUTINES" — 3216 |
| Main Muscle Groups | Main Muscle Group or Groups the exercise effects. — 3217 |
| Main Muscle Groups Excersion Level Constant/Formula (per Kg and per rehersal) | A constant a formula or a link to a calulation method for calculating the intensity or level of progress this execise causes per unit of difficulty and per performance. — 3218 |
| Secondary Muscle Groups | Secondary Muscle Group or Groups the exercise effects. — 3219 |
| Secondary Group Excersion Level Constant/Formula (per Kg and per rehersal) | A constant a formula or a link to a calulation method for calculating the intensity or level of progress this execise causes per unit of difficulty and per performance. — 3220 |
| Third Muscle Group | Additional muscles or muscle groups can be added if necessary. — 3221 |
| : | |
| Recommended Experience Level | Recommended trainee experience level required for performing the exercise. — 3222 |
| Time Requirecd Per Rehersal | time required for performing one rehersal correctly. Can also be a formula which is effected for example from the user's level of experience, the number of rejersals per set, the number of sets etc. — 32232 |
| Recovery Time Between Sets | Time required for recovery and or after the exercise (can be in different entries to the table), an also be a formula which is effected for example from the user's level of experience, the number of rejersals per set, the number of sets etc. — 3224 |

FIG. 32A

| | | |
|---|---|---|
| ... | | |
| Exersion / Fatigue Level Formula/Constant | A measure of the level of Exersion or Fatiguness after performing the exercise. Can be a constant or a link to formula/ calculation method that can depend for example on the user's level of experience, the number of rejersals per set, the number of sets etc. There can be seperate entries for different types of fatigueness for example entry for physical fatiguness and mental fatiguness, Or for example fatiguness formulas for muscle groups. | 3225 |
| Muscle Group Exersion Conversion | (can be an entry for each muscle or muscle group the exercise works on). Coversion factor or formula from another exercise working on the same muscle group to the difficulty level and/or number of repeatitions | 3226 |
| Exercise Grade | Grade given to the exercise - can refer to the exercise preference level or quality level. Several grades can be saved in data-base. For example trainees grade, coach grade, safty grade etc. | 3227 |
| Recommended for other sports | When training for improvement in other sports (such as Ski, BasketBall, Golf etc.) which sports if any can benfit from this exercise | 3228 |
| Recommended in case of limitations: | In case of trainee limitations, conditions, what such conditions allow this exercise or recommend this exercise | 3229 |

| Exercise Name | Abs push ups |
|---|---|
| Serial # | 1 |
| Type | Strength / Mass |
| Exercise Machine | None |
| Description | Start Position - Lie down flat on the ground knees bent at a 90 degree angle, hands placed on either side of the trainees head keeping elbows in. Exercise progress - Traineee Rolls his shoulders off the floor using his abdoman muscles pushing his shoulders up toward your knees. Trainee exhales while pushing up. End Position - Elbows touching the traines knees or legs. From the End Position the trainee lowers his shoulders down to the start position slowly inhalig. One repeatition is Start Position -> End Position -> Start Position. |
| Main Muscle Groups | Abdominals |
| Secondary Muscle Groups | Quadriceps |
| Recommended Experience Level | Beginner |
| Time Requirecd Per Rehersal | 4 |
| Recovery Time Between Sets | 4 |
| Recommended for other sports | All |
| . | . |
| . | . |
| . | . |

3242

| Exercise Name | Abs Crunch Machine |
|---|---|
| Serial # | 2 |
| Type | Strength / Mass |
| Exercise Machine | Abs Crunch Machine |
| Description | Start Position - Trainee seated on the machine arms should be bent at a 90 degree angle and the triceps rested on the hand pads. feet under the feet pads grabbing the top handles. Exercise - Trainee Lifts legs up while crunching the upper torso, trainee exhales while moving toward End Position. End Position - Elbows touching knees or legs. From the End Position the trainee moves back slowly to start position while inhling. One repeatition is Start Position -> End Position -> Start Position. |
| Main Muscle Groups | Abdominals |
| Secondary Muscle Groups | Quadriceps |
| Recommended Experience Level | Intermediate |
| Time Requirecd Per Rehersal | 4 |
| Recovery Time Between Sets | 32 |
| Recommended for other sports | All |
| . | . |

| Exercise Name | Abs Air Bike |
|---|---|
| Serial # | 3 |
| Type | Strength / Mass |
| Exercise Machine | None |
| Description | ... |
| Main Muscle Groups | Abdominals Side, Abdominals |
| Secondary Muscle Groups | |
| Recommended Experience Level | Beginner |
| Time Requirecd Per Rehersal | 5 |
| Recovery Time Between Sets | 6 |
| Recommended for other sports | All |
| . | . |
| . | . |

3246

| Exercise Name | Hyperextensions (Back Extensions) |
|---|---|
| Serial # | 4 |
| Type | Strength / Mass |
| Exercise Machine | Hyperextension Machine |
| Description | ... |
| Main Muscle Groups | Lower Back |
| Secondary Muscle Groups | Glutes, Hamstrings |
| Recommended Experience Level | Beginer |
| Time Requirecd Per Rehersal | 4 |
| Recovery Time Between Sets | 4 |
| Recommended for other sports | All |
| . | . |
| . | . |
| . | . |

| Exercise Name | Alternate Hammer Curl |
|---|---|
| Serial # | 5 |
| Type | Strength / Mass |
| Exercise Machine | Free weights |
| Description | ... |
| Main Muscle Groups | Biceps |
| Secondary Muscle Groups | Forearm |
| Recommended Experience Level | Beginner |
| Time Requirecd Per Rehersal | 8 |
| Recovery Time Between Sets | 4 |
| Recommended for other sports | Basketball |
| . | . |
| . | . |
| . | . |

3250

| Exercise Name | Machine Preacher Curls |
|---|---|
| Serial # | 6 |
| Type | Strength / Mass |
| Exercise Machine | Machine Preacher Curl Machine |
| Description | ... |
| Main Muscle Groups | Biceps |
| Secondary Muscle Groups | Forearm |
| Recommended Experience Level | Beginner |
| Time Requirecd Per Rehersal | 5 |
| Recovery Time Between Sets | 4 |
| Recommended for other sports | Basketball |
| . | . |
| . | . |
| . | . |

| Exercise Name | Chin Up |
|---|---|
| Serial # | 7 |
| Type | Strength / Mass |
| Exercise Machine | Chin Up Pole |
| Description | ... |
| Main Muscle Groups | Back |
| Secondary Muscle Groups | Biceps, Forearm |
| Recommended Experience Level | Intermediate |
| Time Requirecd Per Rehersal | 5 |
| Recovery Time Between Sets | 7 |
| Recommended for other sports | Climbing |
| . | . |
| . | . |
| . | . |

3254

| Exercise Name | Wide Grip Lat Pulldown |
|---|---|
| Serial # | 8 |
| Type | Strength / Mass |
| Exercise Machine | Wide Grip Pulldown Machine |
| Description | ... |
| Main Muscle Groups | Back |
| Secondary Muscle Groups | Biceps, Shoulders |
| Recommended Experience Level | Beginner |
| Time Requirecd Per Rehersal | 5 |
| Recovery Time Between Sets | 6 |
| Recommended for other sports | Climbing |
| . | . |
| . | . |
| . | . |

| Exercise Name | Butterfly |
|---|---|
| Serial # | 12 |
| Type | Strength / Mass |
| Exercise Machine | Butterfly Machine |
| Description | ... |
| Main Muscle Groups | Chest |
| Secondary Muscle Groups | Shoulders |
| Recommended Experience Level | Beginner |
| Time Requirecd Per Rehersal | 5 |
| Recovery Time Between Sets | 6 |
| Recommended for other sports | |
| . | . |
| . | . |
| . | . |

3262

| Exercise Name | Decline Dumbell Bench Press |
|---|---|
| Serial # | 13 |
| Type | Strength / Mass |
| Exercise Machine | Bench, Barbells |
| Description | ... |
| Main Muscle Groups | Chest, Lower Chest |
| Secondary Muscle Groups | Triceps, Shoulders |
| Recommended Experience Level | Intermediate |
| Time Requirecd Per Rehersal | 6 |
| Recovery Time Between Sets | 6 |
| Recommended for other sports | |
| . | . |
| . | . |
| . | . |

| Exercise Name | Treadmill |
|---|---|
| Serial # | 14 |
| Type | Cardio |
| Exercise Machine | Treadmill |
| Description | ... |
| Main Muscle Groups | Cardio |
| Secondary Muscle Groups | Legs- Glutes, Quads, Culfs... |
| Recommended Experience Level | Beginner |
| Time Requirecd Per Rehersal | N.A |
| Recovery Time Between Sets | N.A |
| Recommended for other sports | Warm Up, All Cardio Sports |
| . | . |
| . | . |
| . | . |

3266

| Exercise Name | Eliptical / Ski |
|---|---|
| Serial # | 15 |
| Type | Cardio |
| Exercise Machine | Eliptical Machine |
| Description | ... |
| Main Muscle Groups | Cardio |
| Secondary Muscle Groups | Legs- Glutes, Quads, Tricepcs |
| Recommended Experience Level | Beginner |
| Time Requirecd Per Rehersal | N.A |
| Recovery Time Between Sets | N.A |
| Recommended for other sports | Warm Up, Ski |
| . | . |
| . | . |
| . | . |

| | |
|---|---|
| Exercise Name | Pilates Frog |
| Serial # | 16 |
| Type | Pilates, Strength Mass |
| Exercise Machine | Pilates Reformer Machine |
| Description | ... |
| Main Muscle Groups | Abdominals |
| Secondary Muscle Groups | Lower Back, Core |
| Recommended Experience Level | Intermediate |
| Time Requirecd Per Rehersal | 10 |
| Recovery Time Between Sets | 6 |
| Recommended for other sports | All, Rehabilitation |
| . | . |
| . | . |
| . | . |

3270

| | |
|---|---|
| Exercise Name | Dumbbell Shoulder Press |
| Serial # | 17 |
| Type | Strength Mass |
| Exercise Machine | Bench, Barbells |
| Description | ... |
| Main Muscle Groups | Shoulders |
| Secondary Muscle Groups | Triceps |
| Recommended Experience Level | Intermediate |
| Time Requirecd Per Rehersal | 6 |
| Recovery Time Between Sets | 6 |
| Recommended for other sports | |
| . | . |
| . | . |
| . | . |

| Exercise Name | Alternating Cable Shoulder Press |
|---|---|
| Serial # | 18 |
| Type | Strength Mass |
| Exercise Machine | Dual Pulley Machine |
| Description | ... |
| Main Muscle Groups | Shoulders |
| Secondary Muscle Groups | Triceps |
| Recommended Experience Level | Beginner |
| Time Required Per Rehersal | 10 |
| Recovery Time Between Sets | 6 |
| Recommended for other sports | |
| . | . |
| . | . |
| . | . |

3274

| Exercise Name | Rotating Shoulder Press (Arnold) |
|---|---|
| Serial # | 19 |
| Type | Strength Mass |
| Exercise Machine | Bench, Barbells |
| Description | ... |
| Main Muscle Groups | Shoulders |
| Secondary Muscle Groups | Triceps |
| Recommended Experience Level | Intermediate |
| Time Required Per Rehersal | 6 |
| Recovery Time Between Sets | 6 |
| Recommended for other sports | |
| . | . |
| . | . |
| . | . |

| Exercise Name | Lateral Raise - With Bands |
|---|---|
| Serial # | 20 |
| Type | Strength Mass |
| Exercise Machine | Bands |
| Description | ... |
| Main Muscle Groups | Shoulders |
| Secondary Muscle Groups | |
| Recommended Experience Level | Beginner |
| Time Requirecd Per Rehersal | 6 |
| Recovery Time Between Sets | 4 |
| Recommended for other sports | |
| . | . |
| . | . |
| . | . |

3258

| Exercise Name | Cable Rows |
|---|---|
| Serial # | 10 |
| Type | Strength / Mass |
| Exercise Machine | Cable Rows Machine |
| Description | ... |
| Main Muscle Groups | Back |
| Secondary Muscle Groups | Biceps |
| Recommended Experience Level | Beginner |
| Time Requirecd Per Rehersal | 5 |
| Recovery Time Between Sets | 6 |
| Recommended for other sports | Rowing, Climbing |
| . | . |
| . | . |
| . | . |

| Exercise Name | Chest Bench Press |
|---|---|
| Serial # | 11 |
| Type | Strength / Mass |
| Exercise Machine | Bench, Barbell |
| Description | ... |
| Main Muscle Groups | Chest |
| Secondary Muscle Groups | Triceps, Shoulders |
| Recommended Experience Level | Beginner |
| Time Requirecd Per Rehersal | 5 |
| Recovery Time Between Sets | 7 |
| Recommended for other sports | |
| . | . |
| . | . |
| . | . |

3282

| Exercise Name | Leg Press |
|---|---|
| Serial # | 23 |
| Type | Strength / Mass |
| Exercise Machine | Leg Press Machine |
| Description | ... |
| Main Muscle Groups | Quadriceps |
| Secondary Muscle Groups | Calves, Glutes, Hamstrings |
| Recommended Experience Level | Beginner |
| Time Requirecd Per Rehersal | 5 |
| Recovery Time Between Sets | 8 |
| Recommended for other sports | ... |
| . | . |
| . | . |
| . | . |

| Exercise Name | Standing Leg Curl |
|---|---|
| Serial # | 25 |
| Type | Strength / Mass |
| Exercise Machine | Standing Leg Curl Machine |
| Description | ... |
| Main Muscle Groups | Hamstrings |
| Secondary Muscle Groups | |
| Recommended Experience Level | Beginner |
| Time Requirecd Per Rehersal | 8 |
| Recovery Time Between Sets | 5 |
| Recommended for other sports | ... |
| . | . |
| . | . |
| . | . |

3278

| Exercise Name | Cable One Arm Tricep Extension |
|---|---|
| Serial # | 21 |
| Type | Strength Mass |
| Exercise Machine | Cable Pulley Machine |
| Description | ... |
| Main Muscle Groups | Triceps |
| Secondary Muscle Groups | |
| Recommended Experience Level | Beginner |
| Time Requirecd Per Rehersal | 10 |
| Recovery Time Between Sets | 4 |
| Recommended for other sports | Ski, Climbing... |
| . | . |
| . | . |
| . | . |

| Exercise Name | Triceps Pushdown |
|---|---|
| Serial # | 22 |
| Type | Strength Mass |
| Exercise Machine | Cable Pulley Machine |
| Description | ... |
| Main Muscle Groups | Triceps |
| Secondary Muscle Groups | |
| Recommended Experience Level | Beginer |
| Time Requirecd Per Rehersal | 5 |
| Recovery Time Between Sets | 4 |
| Recommended for other sports | Ski, Climbing |
| . | . |

3284

| Exercise Name | Leg Extension |
|---|---|
| Serial # | 24 |
| Type | Strength / Mass |
| Exercise Machine | Leg Extension Machine |
| Description | ... |
| Main Muscle Groups | Quadriceps |
| Secondary Muscle Groups | |
| Recommended Experience Level | Beginner |
| Time Requirecd Per Rehersal | 5 |
| Recovery Time Between Sets | 6 |
| Recommended for other sports | ... |
| . | . |

3288

| Exercise Name | Calf Press on Leg Press Machine |
|---|---|
| Serial # | 26 |
| Type | Strength / Mass |
| Exercise Machine | |
| Description | Leg Press Machine |
| Main Muscle Groups | Calf |
| Secondary Muscle Groups | |
| Recommended Experience Level | Beginner |
| Time Requirecd Per Rehersal | 5 |
| Recovery Time Between Sets | 4 |
| Recommended for other sports | ... |
| . | . |
| . | . |
| Order Aid | Comes right after Leg Press because - the same Machine |

FIG. 32N

| 3410 | 3400 |
| --- | --- |
| Exercise Name | Abs push ups |
| Serial # | 1 |
| Type | Strength / Mass |
| Exercise Machine | None |
| Description | Start Position - Lie down flat on the ground knees bent at a 90 degree angle, hands placed on either side of the trainees head keeping elbows in. Exercise progress - Traineee Rolls his shoulders off the floor using his abdoman muscles pushing his shoulders up toward your knees. Trainee exhales while pushing up. End Position - Elbows touching the traines knees or legs. From the End Position the trainee lowers his shoulders down to the start position slowly inhalig. One repeatition is Start Position -> End Position -> Start Position. |
| Main Muscle Groups | Abdominals |
| Secondary Muscle Groups | Quadriceps |
| Recommended Experience Level | Beginner |
| Time Requirecd Per Rehersal | 4 |
| Recovery Time Between Sets | 6 |
| Recommended for other sports | All |
| Exertion Level | 8 |
| Exercise Grade | 9 |
| ... | ... |

FIG. 34A

| 3412 | |
|---|---|
| Exercise Name | Abs Air Bike |
| Serial # | 3 |
| Type | Strength / Mass |
| Exercise Machine | None |
| Description | ... |
| Main Muscle Groups | Abdominals Side, Abdominals |
| Secondary Muscle Groups | |
| Recommended Experience Level | Beginner |
| Time Required Per Rehersal | 6 |
| Recovery Time Between Sets | 3 |
| Recommended for other sports | All |
| Exertion Level | 6 |
| Exercise Grade | 7.5 |
| ... | ... |

| 3414 | |
|---|---|
| Exercise Name | Hyperextensions (Back Extensions) |
| Serial # | 4 |
| Type | Strength / Mass |
| Exercise Machine | Hyperextension Machine |
| Description | ... |
| Main Muscle Groups | Lower Back |
| Secondary Muscle Groups | Glutes, Hamstrings |
| Recommended Experience Level | Beginner |
| Time Required Per Rehersal | 4 |
| Recovery Time Between Sets | 4 |
| Recommended for other sports | All |
| Exertion Level | 6 |
| Exercise Grade | 8 |
| ... | ... |

FIG. 34B

| 3416 | |
|---|---|
| Exercise Name | Chest Bench Press |
| Serial # | 11 |
| Type | Strength / Mass |
| Exercise Machine | Bench, Barbell |
| Description | ... |
| Main Muscle Groups | Chest |
| Secondary Muscle Groups | Triceps, Shoulders |
| Recommended Experience Level | Beginner |
| Time Required Per Rehearsal | 5 |
| Recovery Time Between Sets | 7 |
| Recommended for other sports | |
| Exertion Level | 9 |
| Exercise Grade | 9 |
| ... | ... |

| 3418 | |
|---|---|
| Exercise Name | Butterfly |
| Serial # | 12 |
| Type | Strength / Mass |
| Exercise Machine | Butterfly Machine |
| Description | ... |
| Main Muscle Groups | Chest |
| Secondary Muscle Groups | Shoulders |
| Recommended Experience Level | Beginner |
| Time Required Per Rehearsal | 5 |
| Recovery Time Between Sets | 6 |
| Recommended for other sports | |
| Exertion Level | 7 |
| Exercise Grade | 7.5 |
| ... | ... |

FIG. 34C

| 3420 | |
|---|---|
| Exercise Name | Wide Grip Lat Pulldown |
| Serial # | 8 |
| Type | Strength / Mass |
| Exercise Machine | Wide Grip Pulldown Machine |
| Description | ... |
| Main Muscle Groups | Back |
| Secondary Muscle Groups | Biceps, Shoulders |
| Recommended Experience Level | Beginner |
| Time Required Per Rehersal | 5 |
| Recovery Time Between Sets | 6 |
| Recommended for other sports | Climbing |
| Exertion Level | 9 |
| Exercise Grade | 8.5 |
| ... | ... |

| 3422 | |
|---|---|
| Exercise Name | Cable Rows |
| Serial # | 10 |
| Type | Strength / Mass |
| Exercise Machine | Cable Rows Machine |
| Description | ... |
| Main Muscle Groups | Back |
| Secondary Muscle Groups | Biceps |
| Recommended Experience Level | Beginner |
| Time Required Per Rehersal | 5 |
| Recovery Time Between Sets | 6 |
| Recommended for other sports | Rowing, Climbing |
| Exertion Level | 8.5 |
| Exercise Grade | 8 |
| ... | ... |

FIG. 34D

| 3424 | |
|---|---|
| Exercise Name | Leg Press |
| Serial # | 23 |
| Type | Strength / Mass |
| Exercise Machine | Leg Press Machine |
| Description | ... |
| Main Muscle Groups | Quadriceps |
| Secondary Muscle Groups | Calves, Glutes, Hamstrings |
| Recommended Experience Level | Beginner |
| Time Required Per Rehersal | 5 |
| Recovery Time Between Sets | 8 |
| Recommended for other sports | ... |
| Exertion Level | 9.5 |
| Exercise Grade | 9.5 |
| ... | ... |

| 3426 | |
|---|---|
| Exercise Name | Standing Leg Curl |
| Serial # | 25 |
| Type | Strength / Mass |
| Exercise Machine | Standing Leg Curl Machine |
| Description | ... |
| Main Muscle Groups | Hamstrings |
| Secondary Muscle Groups | |
| Recommended Experience Level | Beginner |
| Time Required Per Rehersal | 5 |
| Recovery Time Between Sets | 6 |
| Recommended for other sports | ... |
| Exertion Level | 7 |
| Exercise Grade | 8 |
| ... | ... |

FIG. 34E

| 3428 | |
|---|---|
| Exercise Name | Calf Press on Leg Press Machine |
| Serial # | 26 |
| Type | Strength / Mass |
| Exercise Machine | |
| Description | Leg Press Machine |
| Main Muscle Groups | Calf |
| Secondary Muscle Groups | |
| Recommended Experience Level | Beginner |
| Time Required Per Rehersal | 5 |
| Recovery Time Between Sets | 4 |
| Recommended for other sports | ... |
| Exertion Level | 7 |
| Exercise Grade | 8 |
| Order Aid | Comes right after Leg Press because - the same Machine |

| 3430 | |
|---|---|
| Exercise Name | Leg Extension |
| Serial # | 24 |
| Type | Strength / Mass |
| Exercise Machine | Leg Extension Machine |
| Description | ... |
| Main Muscle Groups | Quadriceps |
| Secondary Muscle Groups | |
| Recommended Experience Level | Beginner |
| Time Required Per Rehersal | 5 |
| Recovery Time Between Sets | 6 |
| Recommended for other sports | ... |
| Exertion Level | 7 |
| Exercise Grade | 8 |

FIG. 34F

| 3432 | |
|---|---|
| Exercise Name | Alternating Cable Shoulder Press |
| Serial # | 18 |
| Type | Strength Mass |
| Exercise Machine | Dual Pulley Machine |
| Description | ... |
| Main Muscle Groups | Shoulders |
| Secondary Muscle Groups | Triceps |
| Recommended Experience Level | Beginner |
| Time Required Per Rehersal | 10 |
| Recovery Time Between Sets | 6 |
| Recommended for other sports | |
| Exertion Level | 7 |
| Exercise Grade | 9 |
| ... | ... |

| 3434 | |
|---|---|
| Exercise Name | Lateral Raise - With Bands |
| Serial # | 20 |
| Type | Strength Mass |
| Exercise Machine | Bands |
| Description | ... |
| Main Muscle Groups | Shoulders |
| Secondary Muscle Groups | |
| Recommended Experience Level | Beginner |
| Time Required Per Rehersal | 6 |
| Recovery Time Between Sets | 4 |
| Recommended for other sports | |
| Exertion Level | 6 |
| Exercise Grade | 8 |
| ... | ... |

FIG. 34G

| 3436 | |
|---|---|
| Exercise Name | Machine Preacher Curls |
| Serial # | 6 |
| Type | Strength / Mass |
| Exercise Machine Description | Machine Preacher Curl Machine |
| Main Muscle Groups | Biceps |
| Secondary Muscle Groups | Forearm |
| Recommended Experience Level | Beginner |
| Time Required Per Rehearsal | 4 |
| Recovery Time Between Sets | 5 |
| Recommended for other sports | Basketball |
| Exertion Level | 6 |
| Exercise Grade | 8 |
| ... | ... |

| 3438 | |
|---|---|
| Exercise Name | Alternate Curl |
| Serial # | 5 |
| Type | Strength / Mass |
| Exercise Machine Description | Free weights |
| Main Muscle Groups | Biceps |
| Secondary Muscle Groups | Forearm |
| Recommended Experience Level | Beginner |
| Time Required Per Rehearsal | 9 |
| Recovery Time Between Sets | 4 |
| Recommended for other sports | Basketball |
| Exertion Level | 6 |
| Exercise Grade | 8 |
| ... | ... |

FIG. 34H

| 3440 | |
|---|---|
| Exercise Name | Cable One Arm Tricep Extension |
| Serial # | 21 |
| Type | Strength Mass |
| Exercise Machine | Cable Pulley Machine |
| Description | ... |
| Main Muscle Groups | Triceps |
| Secondary Muscle Groups | |
| Recommended Experience Level | Beginer |
| Time Required Per Rehersal | 8 |
| Recovery Time Between Sets | 4 |
| Recommended for other sports | Ski, Climbing... |
| Exertion Level | 6 |
| Exercise Grade | 8 |
| ... | ... |

| 3442 | |
|---|---|
| Exercise Name | Triceps Pushdown |
| Serial # | 22 |
| Type | Strength Mass |
| Exercise Machine | Cable Pulley Machine |
| Description | ... |
| Main Muscle Groups | Triceps |
| Secondary Muscle Groups | |
| Recommended Experience Level | Beginer |
| Time Required Per Rehersal | 5 |
| Recovery Time Between Sets | 4 |
| Recommended for other sports | Ski, Climbing |
| Exertion Level | 6 |
| Exercise Grade | 8 |
| ... | |

FIG. 34I

| 3444 | | |
|---|---|---|
| Exercise Name | | Treadmill |
| Serial # | | 14 |
| Type | | Cardio |
| Exercise Machine | | Treadmill |
| Description | | ... |
| Main Muscle Groups | | Cardio |
| Secondary Muscle Groups | | Legs- Glutes, Quads, Culfs... |
| Recommended Experience Level | | Beginer |
| Time Required Per Rehersal | | N.A |
| Recovery Time Between Sets | | N.A |
| Recommended for other sports | | Warm Up, All Cardio Sports |
| . | | . |
| . | | . |

| Exercise Name | Raindrops |
|---|---|
| Serial # | 1 |
| Type | Mind Game |
| Exercise Machine | Computer/ Mobile |
| Description | |
| Main Skill | Mathematical Skill |
| Secondary Skills | Speed |
| Difficulty Level Measurement | Raindrops spped of dropping is increased while the mathematical exercises in them become more difficult. The starting drop speed and difficulty of the exercises starts according to the user's level. The current user level is measured according to the amount of time the player "survives" in the game, not survivining in the game means 3 times that a raindrop have reached the ground without the exercise in it being solved. There is a limit time which is given in "Time Requirecd/Given Per Exercise" if the player reaches this time the game ends with victory and the difficulty level is updated upwards. |
| Recommended Experience | Beginner |
| Time Requirecd/Given Per Exercise | 4 min * Level Constant Level Constant is 1- For Beginner, 1.5 for Intermediate, 1.75 for Advanced |
| Exercise Grade | 7.5 |
| ... | ... |

3620

| Exercise Name | Sudoko |
|---|---|
| Serial # | 2 |
| Type | Mind Game |
| Exercise Machine | Computer/ Mobile |
| Description | The known Sudoko Puzzles |
| Main Skill | Mathematical Skill |
| Secondary Skills | N.A |
| Difficulty Level Measurement | Each Sudoko Puzzle difficulty level is according to the user level. Current Difficulty level is measured according to the number of puzzles solved in the given time |
| Recommended Experience | Beginner |
| Time Requirecd/Given Per | 5 Minutes |
| Exercise Grade | 8 |
| ... | ... |

| Exercise Name | Series Rule |
|---|---|
| Serial # | 3 |
| Type | Mind Game |
| Exercise Machine | Computer/ Mobile |
| Description | Series of Numbers is presented the trainee need to understand the rule that dominates the series and input the next member of the series |
| Main Skill | Mathematical Skill |
| Secondary Skills | N.A |
| Difficulty Level Measurement | The number of series the player solves in the given time. The series difficulty level is set according to the user current level. Above a certain number of series Solved in a given time the level is raised. |
| Recommended Experience | Intermediate |
| Time Requirecd Per Exercise | 5 Minutes |
| Exercise Grade | 8 |
| ... | ... |

3635

| Exercise Name | Simon |
|---|---|
| Serial # | 4 |
| Type | Mind Game |
| Exercise Machine | Computer/ Mobile |
| Description | The know Simon game where a series of lights with matching sounds is presented to the trainee. The trainee needs to repeat the series correctly. |
| Main Skill | Memory |
| Secondary Skills | Attention, Speed |
| Difficulty Level Measurement | The length of each sequence - which is its difficulty level the user level is measured by how many sequences he completes in the given |
| Recommended Experience | Beginner |
| Time Requirecd Per Exercise | 3 minutes |
| Exercise Grade | 8 |
| ... | ... |

| Exercise Name | Rectangle Recall |
|---|---|
| Serial # | 5 |
| Type | Mind Game |
| Exercise Machine | Computer/ Mobile |
| Description | A rectangle divided into smaller rectangles is presnted to the user. For a brief time a number of small rectangles which is proportional to the total number of small rectannles, selected randomly, is lit up. Afterwards the player needs to remember and mark the rectangles which were lit. success is marking all the rectangles that were lit up and no rectangle that was not lit up. The game allows the user 1-2 |
| Main Skill | Memory |
| Secondary Skills | Spatial Perception |
| Difficulty Level Measurement | The number of the small rectangles the large one is divided to, and how many of them are shown to the user determines the difficulty level. To measure the users level how many seccessful recalls in a given time is measured. The game starts with the rectangles dificulty level according to the users level |
| Recommended Experience | Beginner |
| Time Requirecd Per Exercise | 5 minutes |
| Exercise Grade | 8.5 |
| ... | ... |

3645

| Exercise Name | Sniper |
|---|---|
| Serial # | 6 |
| Type | Mind Game |
| Exercise Machine | Computer/ Mobile |
| Description | A villian figure appears for a short time in a random location on screen. The player need to bring the sight using the mouse or touch screen to the villian figure and press fire (Mouse button or nothing in case of touch screen). This needs to be done before the figure disappears or "run to shelter". |
| Main Skill | Speed |
| Secondary Skills | Coordination |
| Difficulty Level Measurement | The amount of time the figure is on screen, and the distance and time between two sequent figures sets the difficulty level. The user level can be measured qaccording to how many figures he hit in a given |
| Recommended Experience | Beginner |
| Time Requirecd Per Exercise | 3 minutes |
| Exercise Grade | 7 |
| ... | ... |

| Exercise Name | Keyboard Response |
|---|---|
| Serial # | 7 |
| Type | Mind Game |
| Exercise Machine | Computer/ Mobile |
| Description | A certain key from the keyboard flickers on screen. The user needs to hit this key as soon as possible. |
| Main Skill | Speed |
| Secondary Skills | Attention |
| Difficulty Level Measurement | The user level is measured according to the amount of time it takes him to hit the keys, and the number of correct keys he hits in the exercise given time. |
| Recommended Experience | Beginner |
| Time Requirecd Per Exercise | 3 minutes |
| Exercise Grade | 5 |
| ... | ... |

3655

| Exercise Name | Last Light |
|---|---|
| Serial # | 8 |
| Type | Mind Game |
| Exercise Machine | Computer/ Mobile |
| Description | A pattern appears on screen. The pattern is made of smaller shapes for example rectangles. A light flickers inside a smaller shape and moves rapidly from shape to shape. Then it turns off. The user needs to click or touch the last shape where the light flickered in. |
| Main Skill | Attention |
| Secondary Skills | N.A |
| Difficulty Level Measurement | Higher difficulty level is achieved using a pattern with more smaller shapes, faster movement of the light from shape to shape and longer sequences. The difficulty starts according to the user level. It is then measured how many sequnces he recognizes in a given time |
| Recommended Experience | Beginner |
| Time Requirecd Per Exercise | 4 min * Level Constant Level Constant is 1- For Beginner, 1.5 for Intermediate, 1.75 for Advanced |
| Exercise Grade | 7 |
| ... | ... |

| Exercise Name | Appearing Sequence |
|---|---|
| Serial # | 9 |
| Type | Mind Game |
| Exercise Machine | Computer/ Mobile |
| Description | Few numbers (can be surrounded by a shape - for example circle) appear in random places on screen for a short time. The location remain marked but without the numbers. The user then need to rcall and mark on the locations the sequence of the numbers. |
| Main Skill | Attention |
| Secondary Skills | Memory |
| Difficulty Level Measurement | The difficulty level increases as the number of the flikerring number increases and the time they flickers decreases. The game can continue until a certain number of unccessful attempt have been reached or measure the number of successful answers in a given time or a given number of exercises. |
| Recommended Experience | Beginner |
| Time Requirecd Per Exercise | 4 min * Level Constant Level Constant is 1- For Beginner, 1.5 for Intermediate, 1.75 for Advanced |
| Exercise Grade | 8 |
| ... | ... |

FIG. 36E

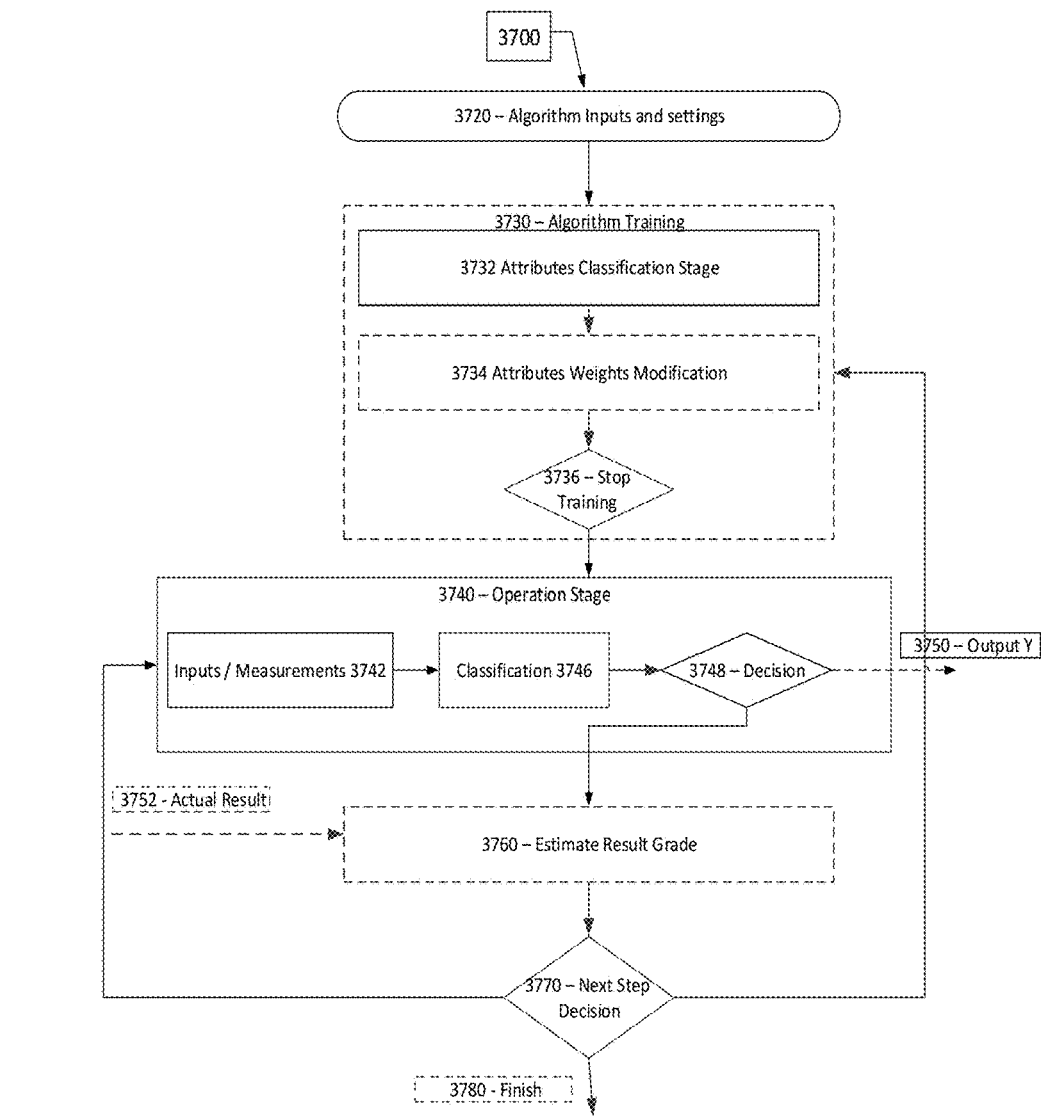
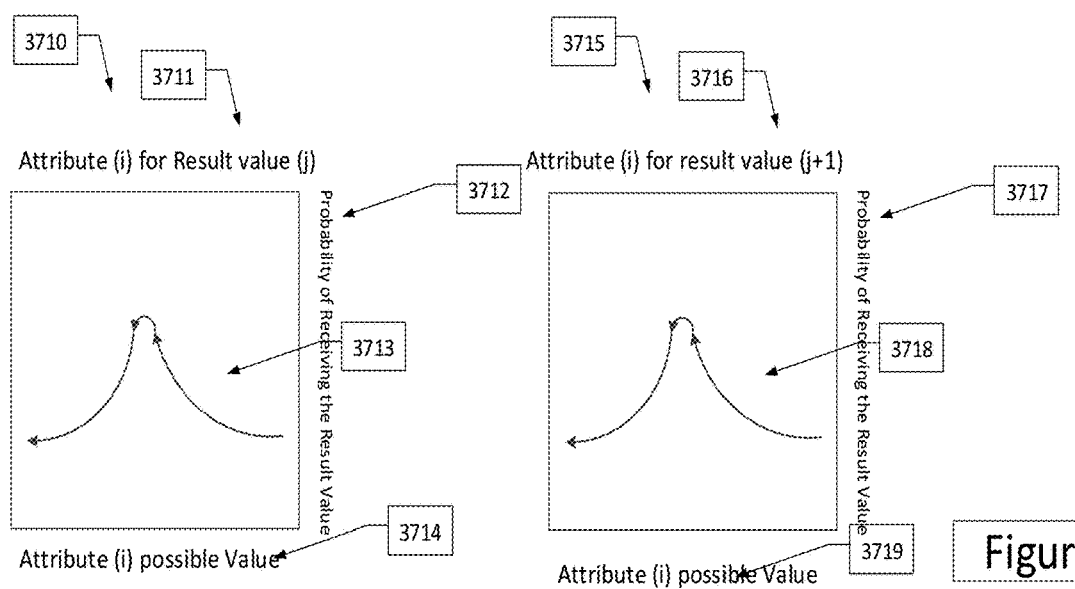
Figure 37

TRAINING SYSTEM AND METHODS FOR DESIGNING, MONITORING AND PROVIDING FEEDBACK OF TRAINING

CROSS REFERENCE TO RELATED APPLICATIONS

This application claims the benefit of U.S. provisional application No. 62/307,477 filed on Mar. 12, 2016, the contents of which are herein incorporated by reference.

TECHNICAL FIELD

The present disclosure relates generally to systems and techniques for planning, presenting, monitoring, feed-backing and improving training in various disciplines. One example of such discipline is physical exercise procedures.

BACKGROUND

Computerization of exercise machines and other activities in the field of sports and training in general, is becoming popular in recent times. Recently developed computerization applications include sensors for tracking a sports trainee or player during a game or exercise session. The sensors, track the player's motion in space and other measures. One example is "miCoach Elite®" provided by Adidas® Corporation. Another example is Gymwatch® a smart watch like gadget to monitor and computerize gym training. Further examples include numerous Smartphone applications for tracking fitness sports such as "RunKeeper®" and "Adomondo®".

In the field of resistance based exercise machinery applications related to computerization are beginning to immerge. An example is the "Isocontrol®" system by TechnoGym® Corporation. This system interfaces Resistance based exercise equipment—mainly gym machines, and allows: Displaying the applied workload, the sets and repetitions to be performed. Displays equipment setting, helps users keep the correct range of motion and more. The "Isocontrol®" system is limited to TechnoGym® products only and to the high-end series of products. It is apparent that this solution requires mechanical and electronical integration with the exercise machine.

Wearable computer devices (WCDs) are becoming a practical solution for machine-person interaction. The WCD may be, for example, a bracelet, glasses, pendant, headgear, etc. that is capable of collecting signals related to the user's activity and worn by the user in order to ease or supplement daily life. WCDs are already employed in the field of monitoring and feedbacking exercises, but they are mostly limited to fitness exercises.

Recently developed game consoles include sensors for tracking a game player playing an electronic game. The sensors, in part, identify the player's body position and motion in space. One example is "Kinect®" which is integrated in a XBOX One® gaming console provided by Microsoft® Corporation.

The motion and position sensors identify and track the position and movements of a player and are provided as inputs to the console system. The game console, based on such inputs, executes the game scenes (e.g., performs actions by the game's characters) or allows a player to change the game's setting by browsing through menus. Thus, such motion and position sensors enhance the overall gaming experience or provide a unique experience altogether. Some of these experiences include training programs.

Recent developments in Machine Learning (which may be abbreviated "ML" in this document and some of the references), and in Computer Technology, enable many new advantageous applications. Systems employing ML can identify objects, whether moving or stationary, respond autonomously to developments and changes in their environment and even invent and create new products. An example is IBM® Watson® Super Computer, which is capable of producing for example novel scientific research papers based on ML of other scientific papers and other materials. IBM® Watson® is further capable of giving medical prognosis based on autonomous Machine Learning of medical literature, medical information and receiving symptoms related with a medical condition. The Machine Learning in this case and other example can be based on analysis of natural language. The machine can "read" a book intended for humans or be involved in a conversation with a human and analyze the input in a manner that allows it to draw conclusions and learn the subject at hand. It is thus able to interact with humans using natural language.

Recent developments in Networking and Cloud Computing allow having the power and advantages of powerful computing machines such as IBM® Watson® at hand. A user of such technology as IBM® Watson® may suffice with a mobile device or a weak computing machine communicating via Cloud Computing or similar networking techniques with a remote powerful machine such as IBM® Watson®. The user may be able to benefit from all the remote machine most powerful features as if it is "in his hands" or his close vicinity.

It would therefore be advantageous to provide an efficient and elegant solution for planning, presenting, monitoring, feed-backing and improving training in various disciplines. It would be further advantageous if such a solution would utilize WCDs and sensors such as 3D cameras to identify and monitor training routines performed by a user. It could be further advantageous to if such solution utilizes computerized training devices and apparatuses or sensors attached to training devices to analyze the user's performance, and provide a feedback as to how the user should improve the performance. It could be even further advantageous if the solution utilizes Machine Learning to design training programs, Learn how to improve training programs, monitor the training and give feedback.

BRIEF DESCRIPTION OF THE DRAWINGS

The subject matter disclosed herein is particularly pointed out and distinctly claimed in the claims at the conclusion of the specification. The foregoing and other features and advantages of the disclosed embodiments will be apparent from the following detailed description taken in conjunction with the accompanying drawings.

FIG. 7. Is another example embodiment of a carried sensor.

FIG. 32. a, b, c, d, e, f, g, h, i, j, k, 1, m, n describe example embodiment of part of the Computing Device Enhanced Training Environment data base organization.

FIG. 34. a, b, c, d, e, f, g, h, i, j describes example part of the Computing Device Enhanced Training Environment data base organization after few algorithm steps.

FIG. 36. a, b, c, d, e describes example part of the Computing Device Enhanced Training Environment data base organization after some more algorithm steps FIG. 37. Describes Machine Learning Methods.

DETAILED DESCRIPTION

Figure 1:
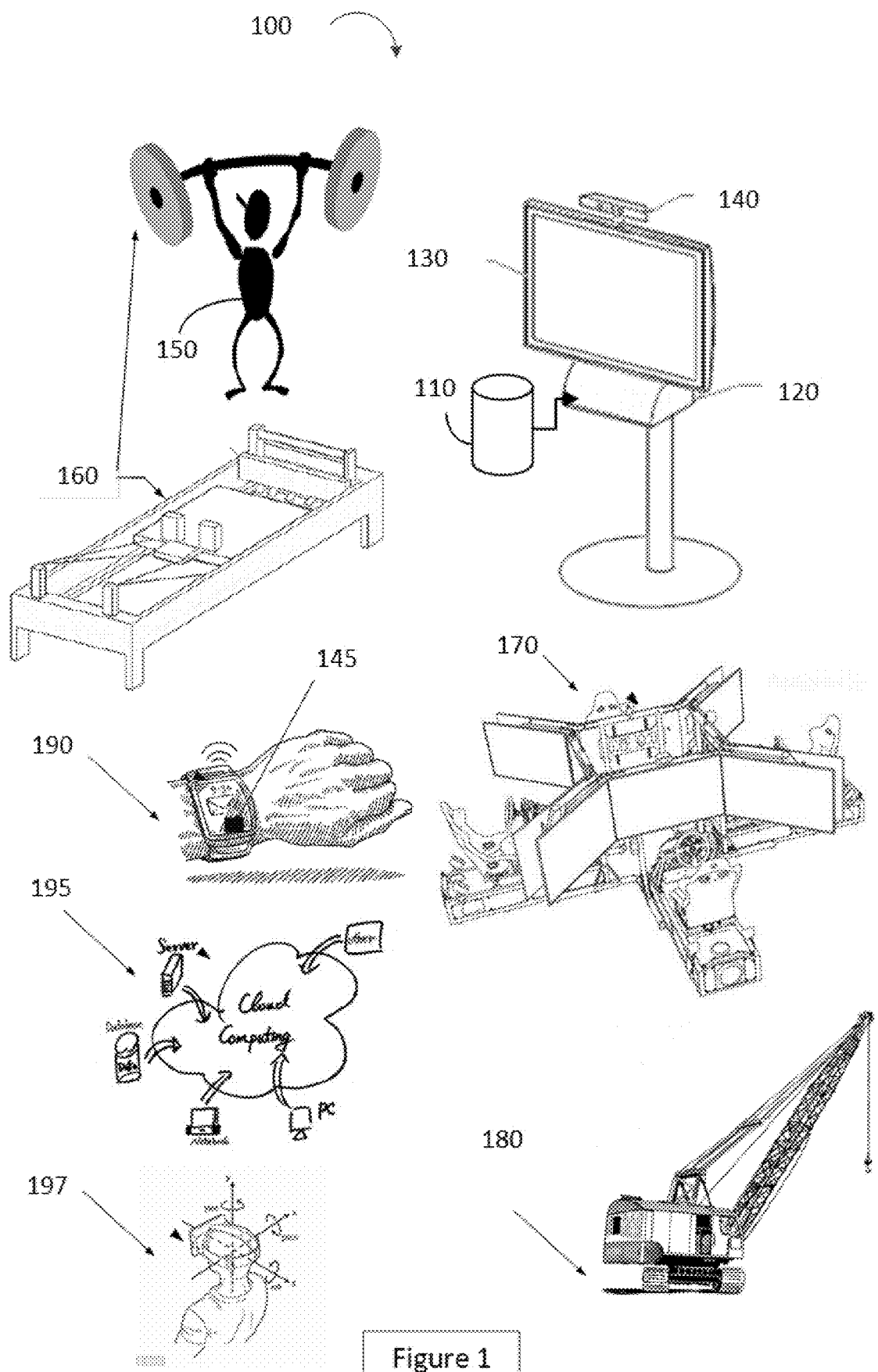
FIG. 1 is a visual representation of a system for Computing Device Enhanced Training Environment according to an embodiment.

It is important to note that the embodiments disclosed are only examples of the many advantageous uses of the innovative teachings herein. In general, statements made in the specification of the present disclosure do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

Certain exemplary embodiments include herein include a method for tracking and designing exercises and training sessions and providing feedback thereof, which serves as a knowledge base for a chosen field of sports or employee training or military training or field of rehabilitation or any other activity, enabling the user to create a personally tailored training program, while tracking and documenting their performance of the exercises and providing continuous live feedback, including performance information and entertainment content, in order to help the user get the most out of their preparation or training or program.

FIG. 1 shows an exemplary and non-limiting visual representation of a system 100 utilized to describe the various embodiments disclosed herein. A training module 110 comprises a database 120. The training module may take a variety of different forms including, but not limited to, general purpose computers, specific purposes computers, specific purpose boards, gaming consoles, military systems, character acquisition systems offering green-screen or motion-capture functionality, and the like. The database 120 is configured to store training and exercise information. Such information may be exercise routines, training techniques, and the like.

Further connected to the training module 110 is at least one output device 130. The output device 130 may be a screen, a projector, a hologram projector, a speaker, a means for voice communication, a combination thereof, and the like. Further connected to the training module 110 is at least one input device 140 such as a microphone, a keyboard, a gesture recognition apparatus, a plurality of motion and position sensors for generating sensory information that may include the position and movements of a user performing the exercise routine, and the like. The sensors may be a camera or an optical sensor that can produce 2D or 3D still or video images. The sensors may further include acoustical LIDAR or RADAR sensors that can produce 2D or 3D still or moving images or mapping in any method known in the art.

The term "Training Environment" used in this disclosure is not limited to a training facility or gym or health club or sports facility and alike. They can be used in every work or living environment, game environment, military training environment and in general in every environment where sensors can be placed and movement activity takes place.

The Computing Device Enhanced Training Environment system 100 may further includes training equipment 160 enabling a user 160 to perform an exercise routine. In an embodiment, the training equipment 190 may be a physical exercise device such as a Pilates Reformer, Weights, a treadmill, and the like. In a further embodiment, training equipment 160 may be a tool or device of with the user wishes to learn or practice an operation, such as military weaponry or a vehicle. For example a crane 180 or any other heavy machinery equipment which the user whishes to train or learn to operate. In yet a further embodiment, the training equipment 160 may be a simulation apparatus for such a tool or device. For example 170 is a simulator for a car or can be a simulator to any other vehicle or manually operated machine such as an airplane, a ship a military vehicle a submarine and alike. In yet another example the training equipment may be a professional tool or apparatus which the user whishes to train or learn to operate like a medical or operating tool for example a scalpel or a CPR machine (Not shown). It can be for example a professional tool such as electrical saw, a drill a welding machine and alike. In yet another example, the training equipment 160 may be an actual piece of gymnastic equipment or a cheaper imitation of said gymnastic equipment. The Computing Device Enhanced Training Environment system 100 further includes a wearable computing device 160 which is worn on the user's body, such as a smart watch, bracelet, glasses, pendant, headgear, and the like.

The training module 110 may control certain settings or attributes of the training equipment 160. For example, the training module 110 may be able to change the size or shape or location of the training equipment 160 or any of its parts.

The training equipment 160, 170, 180 may comprise motion and position sensors, input and output devices, computing system and any other of the system components.

The training module 110 or parts thereof may reside in the wearable computing device 190 or on a mobile computing system such as a Smartphone or tablet. Other parts of the system such as I/O devices 130 and 140, sensors, and the like may also reside on wearable computing device or mobile apparatuses.

In an embodiment, training module 110, or parts of it such as the database 120, may reside in the cloud 195. Many training modules 110 may be connected to each other wirelessly or wired via a network (not shown) or cloud 195.

The Computing Device Enhanced Training Environment system 100 may further include a virtual or augmented reality rendering device 197. The rendering device 197 may render all or part of the training scheme, all or part of the training equipment 160, a virtual coach, virtual training partners or opponents, and the like. The rendering device 197 may create augmented reality. For example, a virtual coach or trainer may be shown on the actual training equipment 160 which demonstrates the proper exercise or usage. Virtual training peers and/or opponents may be shown. For example, when practicing minor warfare tactics, a trainee or trainees can train for a battle situation in an environment with real weapons and augmented reality opponents, terrain, buildings, and the like.

Figure 2:
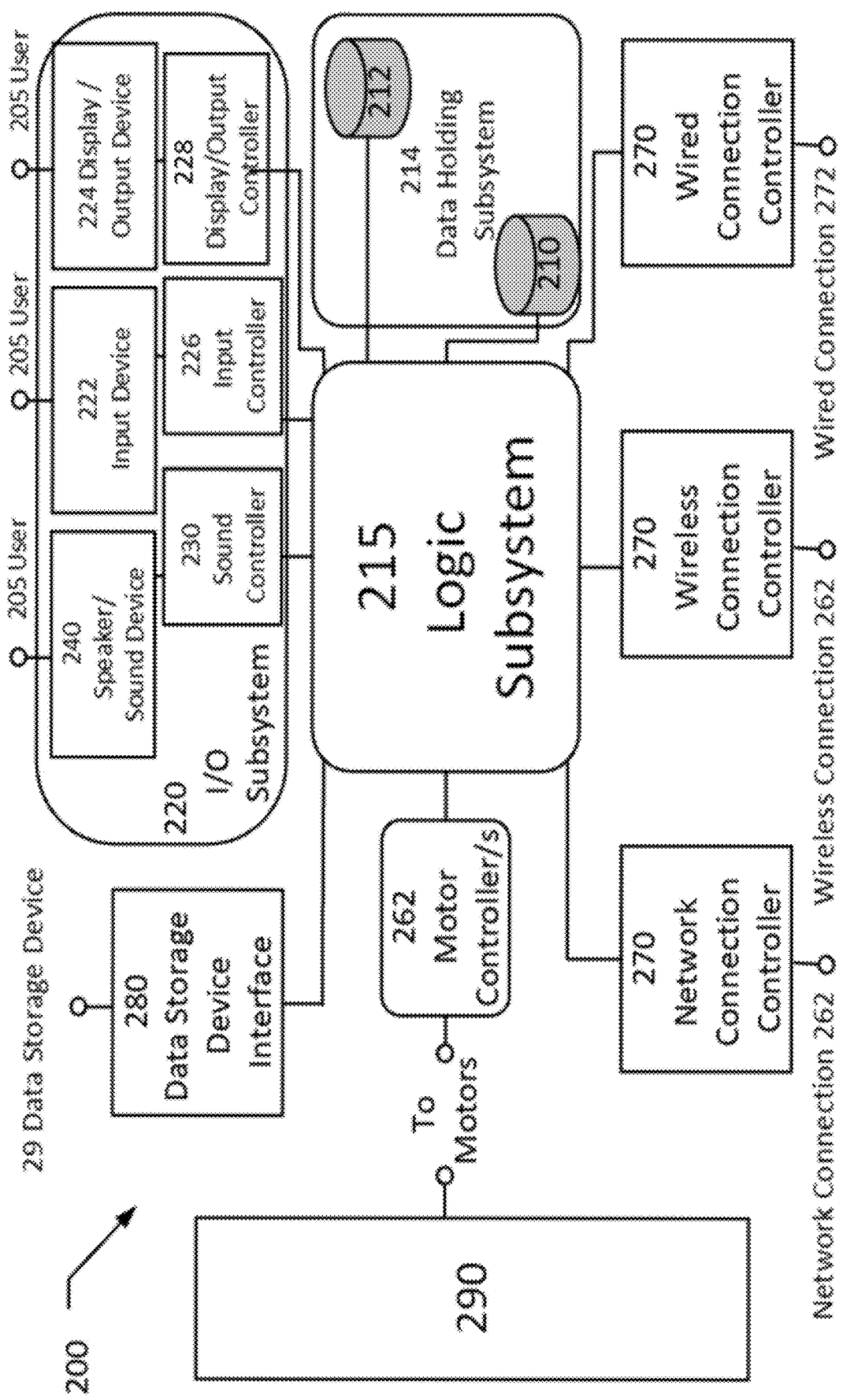
FIG. 2 is a schematic block diagram of a system for Computing Device Enhanced Training Environment according to an embodiment.

An example embodiment of the system can be explained with the help of U.S. Patent Application Publication 2007/0033069 A1 titled "FITNESS NETWORK SYSTEM" Incorporated here by reference. FIG. 1 and FIG. 2 and the rest of this patent application discloses a fitness network system. In an embodiment of the system disclosed herein designated for Gym or sports training, the system of Patent Application Publication 2007/0033069 A1 can be used as part of the example embodiment. Some of the additions to this system may include motion and position sensors disclosed herein and in the references, the computerized training devices disclosed herein and in the references, plurality of cameras or an optical sensors that can produce 2D or 3D still or video images disclosed herein and in the references, the use of WCDs and mobile devices as disclosed herein and in the references, the use of Machine Learning methods and other methods disclosed herein and in the references. Some of the methods disclosed herein can be implemented on the system disclosed in Patent Application Publication 2007/0033069 A1, and some may require the additions and/or modifications disclosed in this disclosure and in the references.

Additional addition over Patent Application Publication 2007/0033069A1 is that the training devices (numbered 116 in Patent Application Publication 2007/0033069) may be replaced by any device or apparatus the user wishes to train or learn. The proper modifications to the system of 2007/0033069, if required in an example embodiment are disclosed herein or in the references or are known in the art.

FIG. 2 illustrates an exemplary and non-limiting embodiment of a schematic block diagram of a training module 200, the processing unit 215, and additional peripheral components that are associated with the training module 200 and processing unit 215. The processing unit 215, which functions as a logic subsystem within the computing and control system architecture, may be connected to a data-holding subsystem 214, an input/output (I/O) subsystem 220, and/or other devices not shown in FIG. 2. In an embodiment, some of the components shown in FIG. 2 may be peripheral components that are not integrated into the overall computing system associated with the training module 200 and processing unit 215 but that are separately attachable.

The processing unit 215 may include one or more processors. The one or more processors may be implemented with any combination of general-purpose microprocessors, multi-core processors, microcontrollers, digital signal processors (DSPs), field programmable gate array (FPGAs), programmable logic devices (PLDs), controllers, state machines, gated logic, discrete hardware components, dedicated hardware finite state machines, or any other suitable entities that can perform calculations or other manipulations of information.

The processing unit 215 may be coupled to a memory included in a data-holding sub-system 214. In an embodiment, the memory contains instructions that when executed by the processing unit 215 results in the performance of the methods described herein below with regards to FIGS. 3-6. Specifically, the processing unit 215 may include machine-readable media for storing software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the one or more processors, cause the processing unit 215 to perform the various functions described herein. The processing unit 215 may also be connected to motors 290 or actuators and alike via a plurality of motor controllers 263. These can transform commands from the processing unit 215 to mechanical movements.

Data-holding subsystem 214 may include one or more physical devices, such as the memory, configured to hold data and/or instructions executable by the processing unit 215 to implement the herein described methods and processes. The data-holding subsystem 214 is configured to allow transformation of data (e.g., to hold different data). Data-holding subsystem 214 may further include removable media and/or built-in devices including optical memory devices, semiconductor memory devices (e.g. RAM, EEPROM, flash. etc.), and/or magnetic memory devices, and the like, including volatile memory 212 and non-volatile memory 210. Data-holding subsystem 214 may also include devices with one or more of the following characteristics: volatile, nonvolatile, dynamic, static, read/write, read-only, random access, sequential access, location addressable, file addressable, and content addressable. In some embodiments, the processing unit 215 and the data-holding subsystem 214 may be integrated into one or more common devices, such as an application specific integrated circuit, a single chip, and the like. FIG. 2 shows an embodiment where the data-holding subsystem 214 is in the form of computer-readable removable media 280, which may be used to store and/or transfer data and/or instructions executable to implement the herein described methods and processes. 29 is a Data storage Device, and 280 is Data Storage device Interface.

The I/O subsystem 220 may be used to present a visual representation of data held by data-holding subsystem 214. The I/O subsystem 220 can include, but is not limited to, input and output devices 222 and 224, such as a display or displays, a keyboard, touch screen, and the like, that are driven by input and display controllers 226 and 228. For example, with reference to FIG. 1, the I/O subsystem 220 may be represented by the output device 130.

The processing unit 215 may be connected to a sound controller 230 and further connected to a speaker and/or microphone 240 via the sound controller 230. The speaker and/or microphone 240 are configured to interface with users 205 by giving voice details about the system status, alarms, counting repetitions, and the like. In an embodiment, the microphone 240 is be used by the user 205 to give the training module 110 voice commands, record notes, and the like. The processing unit 215 may be further connected to a variety of controllers and other devices and systems including computers, mobile devices, mobile phones, smart devices, and the like. The controllers may include a network connected controller 250 via a network connection 252, a wireless controller 260 via a wireless connection 262, a wired controller 270 via a wired connection 272, and so on.

A variety of feedback measurements can be achieved by associating various components with certain elements of the training module 200 and of the exercise equipment 160. For example, a force measurement device (not shown) can be connected to the exercise equipment 160 to measure the amount of force a user 205 is applying to the exercise equipment 160 during use. Other types of feedback can be delivered to a user 205 based on various measurements taken from various sensors incorporated into the Computing Device Enhanced Training Environment system 100 and training module 200, as described herein below.

The interface or connection between any two or more system parts can be by means of a wired connection, a wireless connection, or combination thereof. Such connections can be realized through a USB, Bluetooth, NFC, RFID, HDMI, DisplayPort, Bluetooth, ZigBee, or a communication standard and/or a network connection such as a local area network (LAN), a wireless LAN, and the like.

The computing system or parts thereof may reside in a wearable computing device or on a mobile computing system such as a smartphone or tablet. Other parts of the system, such as I/O devices, sensors, and the like, may also reside on wearable or mobile devices.

All of the components of the Computing Device Enhanced Training Environment system 100 and the training module 200 may be utilized for various applications such as, for example, identifying the user and setting the difficulty level according to the specific user, sharing information about exercise programs, setting the difficulty level based upon indications from other systems, and the like. With reference to FIG. 1, a user can select an exercise regimen using the I/O devices 130 and 140, where at least one exercise regimen is stored within the data holding system 214, or wherein an exercise regimen is available through a network connection 252, such as through a website provided by the manufacturer of the exercise device, or wherein the exercise regimen might be stored on a user's mobile device that can communicate with the Computing Device Enhanced Training Environment system 100 and training module 200 via a wireless connection 262, such as a Bluetooth connection.

Figure 3:
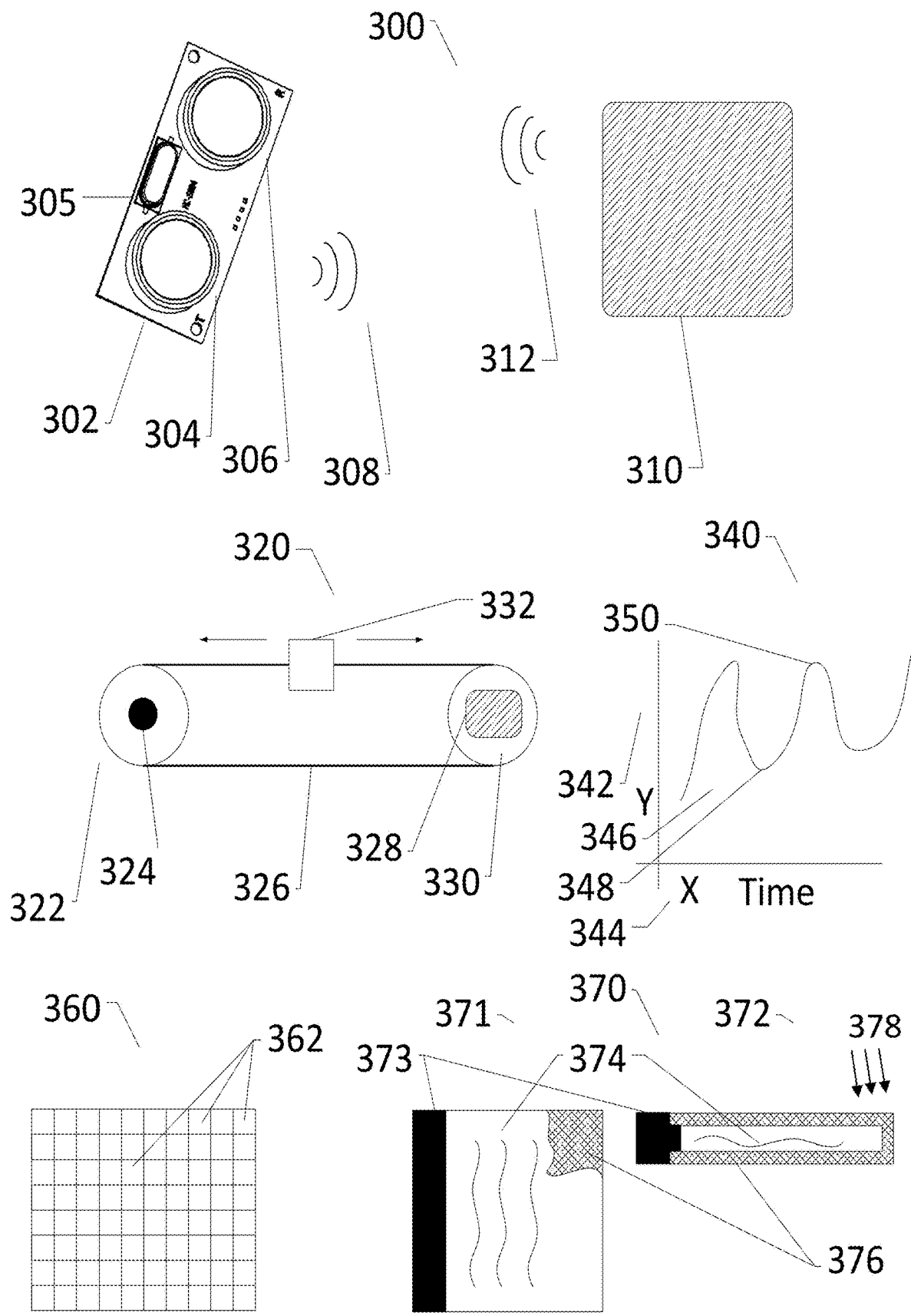
FIG. 3 described some of the methods that shall be further used in this disclosure.

An example embodiment of a training module 200 can be explained with the help of U.S. Patent Application Publication 2007/0033069 A1 FIG. 3.

Computerized Training Modules

FIG. 3 described some of the methods that shall be further used in this disclosure. In some cases these methods are related to the training module possible outputs or functions. Some of the training modules possible outputs and functions are:

Configuring the training equipment 160-180, 197 for the user 150. This configuration may include configuring the dimensions of the exercise equipment 160-180, 197 according to the dimensions or requirements of the user 150, for example adjusting the seat height to the height of the user, adjusting handles location, adjusting straps length, adjusting speakers volume screen resolution and/or brightness and alike.

The configuration of the training equipment may include or further include adjusting the level of resistance or difficulty level to the trainee or to the trainee's training program.

The training system may also document and track the difficulty level (that may be measured by resistance) the user is using, In case the resistance is set by the user the system may measure automatically the difficulty level that was set by the user, may present/output it to the user and may store it for tracking and monitoring purpose.

Count the repetitions and sets of a training procedure or exercise the trainee is doing.

The system may monitor and track the range of motion performed.

The system may monitor and track the speed and or paste of exercise or training procedure performance.

The system may monitor and track the recovery period between sets or between exercises.

The system may monitor and track the location of certain body parts of the user, the user's direction of motion, acceleration and other kinematic measurements. This data may be incorporated with other sensors data to achieve for example identification of the exact exercise the user is doing or creating an image or skeleton diagram or alike representing the user and its motion. This image or diagram can be 2D or 3D.

The system may use the following methods for finding the location of certain elements of the training device 160-180, 197 or the location of the user 150 body parts:

1. Use of any transmission from the parts of the training device 160-180,197, or wearable computing device 190 for triangulation. The transmission may be any wireless communication protocol, such as those described above, any type and frequency of aquatics or electromagnetic wave such as radio waves, light, x-ray etc.

2. Use of a GPS or IPS (Indoor Positioning System) device or method used on the training device 160-180,197 or the wearable computing device 190. Such methods may include RTLS, ISO/IEC 24730, magnetic positioning, dead reckoning, optical, acoustic, and the like. For example, the wearable computing device 190 or exercise equipment 160-180,197 may have a small sonar-like location detector which finds the wearable computing device's 190 or exercise equipment's 160-180,197 location based on acoustical reflections from stationary objects in the surrounding area. The wearable computing device 190 or exercise equipment 160-180,197 may then transmit this location to the training module 110.

3. Use of a marker for one of the sensors in the Computing Device Enhanced Training Environment system 100. For example, the Computing Device Enhanced Training Environment system 100 may have an infrared camera. The wearable computing device 160 or exercise equipment 160-180,197 may include an infrared marker or be colored with a paint which has infrared marker qualities. Therefore, the infrared camera is capable of locating the wearable computing device 190 or exercise equipment 160.

4. A dominant feature or pattern on the wearable computing device 190 or exercise device 160-180, 197 that can be identified by one of the Computing Device Enhanced Training Environment system's 100 sensors, such as an optical, an acoustical, magnetic, radio wave pattern, and the like.

5. An on-board camera on the training device 160-180, 197 or if the wearable computing device 190 comprises a camera, the camera may be used to find the location of the part in the exercise device 160 or the wearable computing device 190 by identifying fixed or non-fixed objects in the surrounding area.

6. Using mechanical means: For example a cord or a cable attached to a moving part of the exercise device 160-180, 197 can be used to measure this moving part's location and speed. If this part is connected mechanically to other parts of the exercise device 160-180, 197 then the location and speed of these parts can be calculated. The cord or cable may for example slide on a pulley or a wheel and rotate it. Measuring the rotations of the pulley or wheel by methods known in the art can give the moving part speed and location.

An example for location measuring apparatus is given in FIG. 3 300. 302 is the HC-SR04—a commercially available component which its datasheet is attached. It is an ultrasonic ranging module comprising an ultrasonic transmitter 304, an ultrasonic receiver 306 and additional electronics 305. The HC-SR04 302 can measure the distance to an object 310 by transmitting an ultrasonic pulse 308, receiving the reflection 312 and calculating the distance by the known time of flight method (TOF).

In training machines most moving parts follow a mechanically pre-defined and known paths. For example in plates loaded gym machines the stack of weight plates are pulled by a cable up and down against gravity. Measuring the distance of the moving stack of plates relative to a stationary point on the exercise machine or near it and comparing it to the measurement when the stack is at rest, can yield the exact location of the stack at the moment of the measurement. In a similar manner the location of the cart in Pilates Reformer can be found, as discussed in the reference.

As discussed above knowing the location of one moving part can be used to establish the location or parts which are mechanically related to it. In the gym machine example the stack of weights is mechanically related to the machine handle usually trough the cable which passes a series of pulleys and leavers. Since the mechanical ratio between the stack of weights movement and the handle movement is set by the series of pulleys and leavers, and thus known, the location of the handle can be found at anytime according to the weights location.

The Speed, acceleration, distance traveled and alike can be found by sampling the location in time using methods well known in the art.

Knowing the location of the machine handles for example can indicate the location of the trainee's body parts such as the hands holding the handles. Similar information be deduced from known locations of the machine parts which touch the trainee body like seats, leg stools and alike. This information can assist the system build an image or skeleton model of the trainee body as discussed above.

At FIG. 3 320 is an example for a mechanical method of measuring distance. Two stationary pulleys 322, 330 are configured so that a cable loop or a rubber loop and alike 326 is stretched moving on them and rotating them as it moves. The moving part for which the distance is measured is connected to the cable at 322. 324 is the pully hinge or axle. 328 is an electronic encoder mechanically connected to the pulley 330 pivot axis. When the moving part 322 moves to either direction the pulley 330 rotate and the encoder 328 can measure the rotations. Using methods well known in the art, the location of the moving part can be calculated from the rotations measurements. A similar method can be applied to any of the pulleys in an exercise machine—an encoder or any other method known in the art for tracking and measuring the pulley rotations can be employed. If a pulley does not exist in the exercise machine one can be added and configured to be rotated by a moving cable or part in the machine. For example the apparatus and method 320 can be used.

The following example methods can be employed to measure force or pressure: Load cells: a load cell is a transducer that is used to create an electrical signal whose magnitude is directly proportional to the force being measured. The various types of load cells include hydraulic load cells, pneumatic load cells and strain gauge load cells. Additional methods for measuring pressure are detailed below.

360 and 370 in FIG. 3 schematically describe methods for measuring force or pressure applied on a surface. 360 is a top view of an array of a plurality of load cells or pressure sensors 362, which create a surface. The sensors 362 are configured to measure pressure or force applied to them.

370 is an apparatus configured to measure surface pressure. 371 is a top view and 372 a side view. 370 can replace a single sensor 362 in 360, or be used as an entire surface on its own. 374 is a preferably a fluid advantageously a hydrostatic fluid. 376 is a jacket that encloses 362, and is sealing it. The sealed jacket 374 can be made out of an elastic material or a non-rigid material such as rubber or plastic. Such an elastic material may enable the surface 370 to be an elastic measurement apparatus. It thus may allow shaping of the measuring apparatus 370 or wrapping it around objects.

373 is a hydrostatic pressure measuring device. It is attached to the jacket 376 in a such a way that the apparatus 370 remains sealed under pressure, and the fluid 374 is kept inside it. The methods known in the art for measuring hydrostatic pressure can be used. An external pressure 378 can be applied at any point on the jacket 376 or on a plurality of points at the same time. The pressure is transferred to the fluid 374 trough the jacket 376 in part or in full. The level of rigidity and pressure transfer of the jacket 376 can be configured, using known methods, in accordance with the pressure range which is expected or required.

The pressure applied on the jacket is transferred to hydrostatic pressure in the fluid. This hydrostatic pressure is in the first order uniform throughout the fluid 374. Thus the sensor or measuring device 373 measures the integration of pressure applied on the jacket 376.

Using an array of sensors such as 360 may have the advantage of identifying the location or locations where pressure is applied or even map the shape of the plurality of bodies applying the pressure. The quality of this identification and/or mapping may be dependent on the resolution or the number of sensors 362 per unit of area.

An array like 360 may also be configured or built to be shapeable and elastic as the measuring apparatus 370 can.

Another example for measuring stress on a surface can be to measure electrical capacity. Two conductive material plates can be separated by insulating material with elastic qualities. When stress is applied on the plates they change the distance between them, as the elastic material between them reacts to the stress by mechanical strain. As a result the electrical capacity between the plates change. This change can be measured and thus the strain from it stress can be calculated.

Additional methods for measuring pressures or stress on a surface are known in the art. For example U.S. Pat. No. 5,917,180 and US publication 2002/0193707 A1 describe such apparatuses. Other methods given in the references or known in the art can also be used.

An accelerometer is a device that measures proper acceleration ("g-force"). Proper acceleration is not the same as coordinate acceleration (rate of change of velocity). For example, an accelerometer at rest on the surface of the Earth will measure an acceleration g=9.81 m/s2 straight upwards. By contrast, accelerometers in free fall orbiting and accelerating due to the gravity of Earth will measure zero. Single- and multi-axis models of accelerometer are available to detect magnitude and direction of the proper acceleration (or g-force), as a vector quantity, and can be used to sense orientation (because direction of weight changes), coordinate acceleration (so long as it produces g-force or a change in g-force), vibration, shock, and falling in a resistive medium (a case where the proper acceleration changes, since it starts at zero, then increases). Micromachined accelerometers are increasingly present in portable electronic devices and video game controllers, to detect the position of the device or provide for game input.

Accelerometers and/or gyros found in the wearable computing device 160 or attached to the exercise equipment 160 can measure the body part or wearable computing device 190 angle, tilt, speed, acceleration, direction of movement, and the like.

Counting repetitions: Using the methods above and others known in the art it is possible to count repetitions of an exercise done on an exercise device. Measuring a moving part location can yield the repetitions: 340 of FIG. 3 is a graph where X axis 344 represents time, while the Y axis 342 represents in the first case the moving part's location. Repetitions can be identified on this graph by identifying points where the moving part changes the direction of movement such as 348 and 350. At 348 the moving part changes location from going down to going up and in 350 vice versa. An example method for counting repetitions can count for example one type of points with direction change (for example from down to up). A More robust method may detect one type of direction change and when it is followed by the second type of direction change count a repetition. Various methods known in the art and given in the references can be employed.

The Y axis 342 can also represent force or pressure measured. If 346 represents the force or pressure in time, similar methods can be applied to count repetitions, using points like 348 and 350 where the direction of the force or pressure changes.

The Y axis can also represent acceleration, speed, and alike. All may be used for counting repetitions in similar methods as above or other methods known in the art.

More elaborate training measures such as calorie burn, distance travelled can be calculated from the above measurements in methods given in the references or known in the art. For example if the resistance is known the energy exerted can be calculated as the integral of the applied force (or resistance) and the location.

The system 100 may use the trainee or user's motion to generate some or all of the energy it requires for operation. A generator, alternator, or the like can be mechanically connected to any of the Computing Device Enhanced Training Environment system's moving parts such as pulleys, rods, springs, strings, belts, and the like by methods known in the art. Mechanical means of transfer such as belts, wheels, leavers, cog-wheels and the like can be used as known in the art. For a non limiting example the method 320 from FIG. 3 can be used to generate rotation of a pulley or wheel 330 by a movement of a moving part 332. A generator can be mechanically connected to the pulley or wheel 330 and generate electrical power from its rotations.

All methods known in the art can be used to mechanically attach or couple sensors or other system components of the system (100, 200) to the training device 160-180, 197 or to the user 150 or to other system components. UK Patent Application GB-2483117-A Incorporated here by reference, elaborates many examples for methods for mechanically attaching or coupling sensors to training apparatuses. For example in pages 8-9. These methods and others known in the art or given in this disclosure or the references shall be used for mechanically attach or couple sensors or other system components.

Another group of methods and apparatuses known in the art, which is referenced in this disclosure, is methods and apparatuses for converting movement to energy. The movement can be from a moving body which can for example be a human, an animal, a machine, a training devices and alike, Some examples for such methods and apparatuses:

The device known in the art as Linear Generator. Its design operation and examples of usage are described for example in U.S. Pat. No. 6,952,060 B2 and in US Patent Application Publication 2003/0232627 A1. Both documents are incorporated here by reference. Linear Generator is capable of converting energy from linear motion into electric energy. An example of use in commercially available products is what is commonly known as "Shake Flashlights". Similar methods to those used in Shake Flashlight can be incorporated in the apparatuses disclosed herein to convert movement to electric energy.

Another example is "Micro Generators" commonly used to power watches known as "Automatic Quartz". These generators also convert movement energy to electric energy. Examples for commercial modules are the ones produced by KINETRON some of them can be viewed at http://www.kinetron.eu/micro-generator-technology/. A Data Sheet of such Micro Generator which has the model number MGS26.4 is also attached.

Yet another example of commercially available means of harvesting energy from mechanical movement are the Piezoelectric Energy Harvesters. For example Piezo Harvesting Kit by Piezo Systems available on http://www.peizo.com/. A Data Sheet is attached. Such energy harvesters can be connected to moving parts. Then can be utilized to harvest energy in interesting ways: Fluids (including air) pressure changes can be used to harvest energies for example by coupling a membrane like piezoelectric energy harvester or coupling a membrane like structure with a piezoelectric energy harvester by methods known in the art. Another example is a spring elongation and contraction coupled with a plurality of piezoelectric energy harvester. Similar mechanical dimensions changes can be used to harvesting energy using piezoelectric energy harvester.

The amount of energy harvested and/or voltage and or current at a certain point in time can be made proportional to the mechanical dimension change in the body. This way the piezoelectric energy harvesters can be also used forces and other mechanical sizes in a manner similar to strain gauges as known in the art.

Commercially available or other means of transferring movement energy to electric energy may have low energy and/or voltage and/or current output. A number of them can be connected in series or in parallel by the skilled in the art to produce the desired output. Additional components can be used to achieve the desired voltage, power, and/or current. For example charge pump circuits and/or voltage level shifters and/or capacitors and/or intermediate batteries. The required circuitry is well known in the art.

Figure 4:
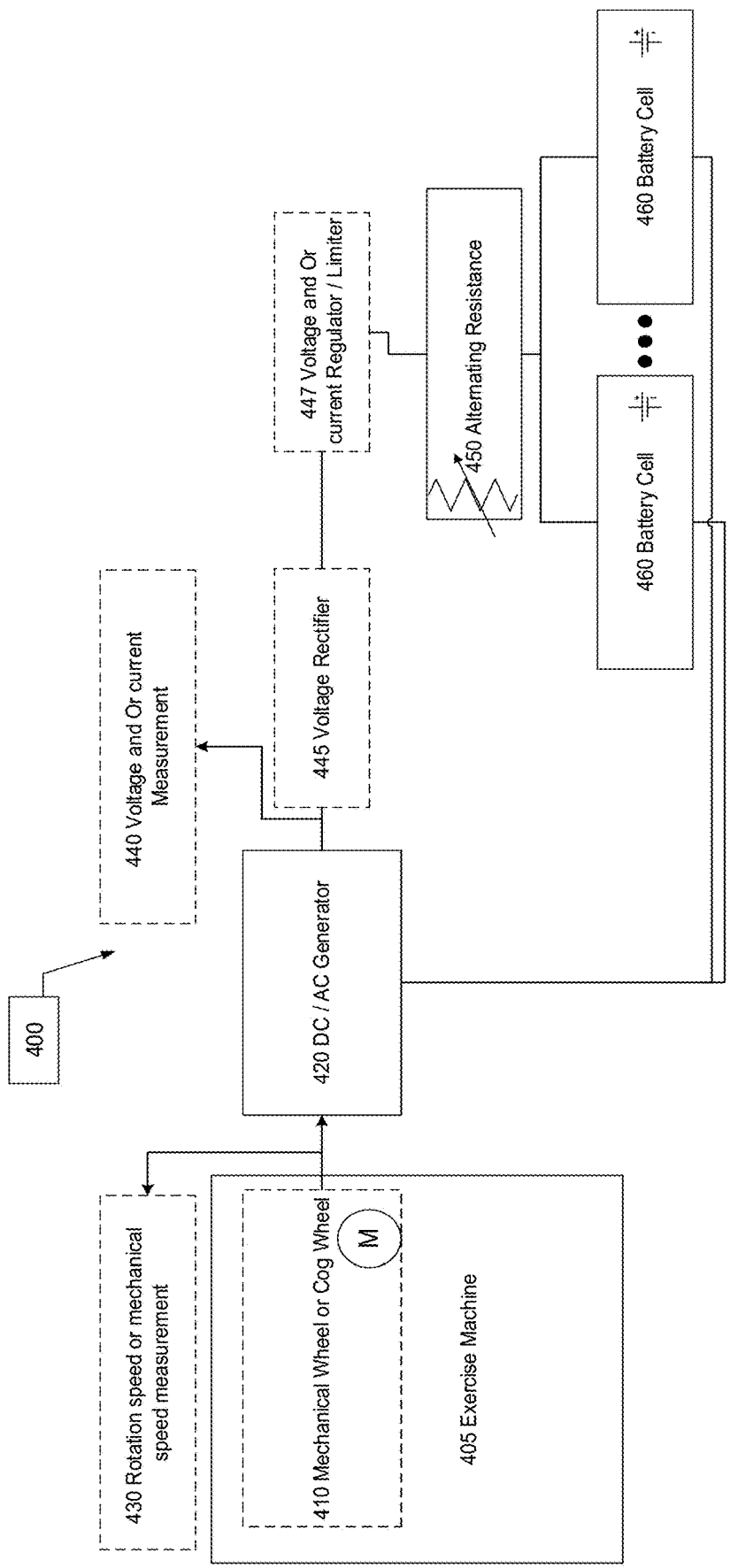
FIG. 4 describes an example embodiment method for generating power from movement and controlling the resistance.

FIG. 4 is an exemplary and non-limiting block diagram of a generator 400 used for generating resistance for the exercise machine by itself. An exercise machine 405 is configured to transfer mechanical power to a wheel, a cog wheel 410 or the like, or to be connected to a generator 420 through any of its moving parts by any method known in the art as described in this disclosure, or references. An apparatus 430 is configured to measure the wheel 410 or the moving part rotation speed or movement speed. The apparatus 430 may be of any apparatus known in the art or given in this disclosure or references, such as an encoder, tachometer, distance meter, and the like. Electrical output voltage and/or current measuring devices 440 may be connected at the generator 420. In an embodiment, a voltage rectifier 445 may be connected if the generator 420 is an AC generator. A voltage and/or current regulator or limiter 447 may also be connected. The order of connection in the diagram is not limiting. An alternating resistance 450 is configured to allow the Computing Device Enhanced Training Environment system 100 to control all the electric components including the variable resistance. A plurality of battery cells 460 is connected in series and/or parallel to where the Computing Device Enhanced Training Environment system 100 may decide which ones to connect to the circuit and which ones to disconnect.

It is mentioned that the generator may be used for the sole purpose of harvesting energy from movement without means of controlling the resistance.

In general the equation for the energy conversion between the mechanical side and the electrical side in a generator is:

$$\omega T = E \cdot I \cdot V$$

where ω is the angular speed which is proportional to linear speed 'v'; 'T' is the torque which equals the exerted force (F) multiplied by the mechanical "arm" length; 'E' is the generator energy efficiency coefficient which may be a constant in the first order, 'I' is the electrical current; and 'V' is the electrical voltage; 'I' multiplied by V is also the electrical power which can also be derived from I2R or V2/R where R is the electrical resistance or load.

Given that the mechanical arm, the efficiency constant and the proportion between angular and linear speeds are known we can write:

$$Fv = \text{Const} \cdot 1 \cdot V \text{ or}$$

$$Fv = \text{Const} \cdot \frac{V^2}{R} \text{ or}$$

$$Fv = \text{Const} \cdot I^2 R$$

Thus, the resistance level F can be controlled by controlling two of the three variables I, V, R, where the value of the constant 'v' is well known.

In generator 400, the load or resistance R can be controlled by the Computing Device Enhanced Training Environment system 100 by controlling the alternating resistance 450 and/or by connecting and disconnecting different battery cells. Voltage and/or current can be controlled by the voltage and/or current regulators 447 if present and measured by the voltage and/or current measurement devices 440. The angular or linear speed can be measured by the apparatus 430.

In some embodiments, the mechanical speed can be controlled as well. Some possible schemes for controlling the resistance F may include: measure the speed v and the voltage V control R so that $$F = \text{Const} \cdot \frac{V^2}{Rv},$$

measure the speed v regulate the voltage V to a certain voltage and control R to receive the desired force, or similarly regulate or measure, measure v and control R to receive the desired force F. Control of v may also be added to this method where this control is possible.

This method can replace weight plates in gym machines, springs in Pilates machines or any other means of creating resistance in any kind of resistance based machines. It can also be combined with other methods of creating resistance such as weight plates or springs and create some of the resistance.

Figure 5:
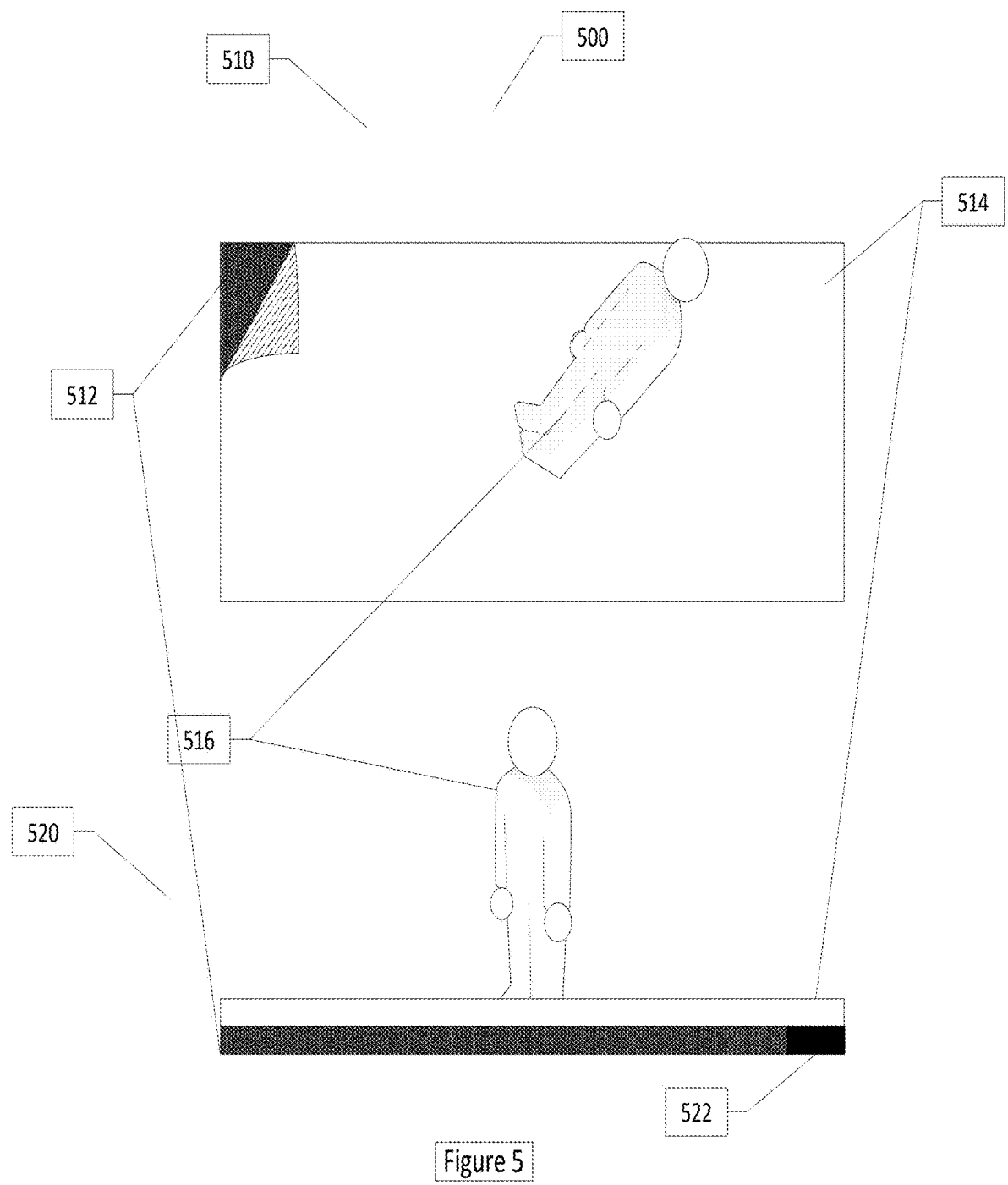
FIG. 5 describes an example embodiment of computerization of a mattress or floor.

FIG. 5 depicts an example embodiment of a computerized mattress or health club floor; 510 is a top view and 520 is a side view. 512 is the sensor lair that comprises a plurality of force/pressure sensors as in 360 or 370. The lair may include additional sensors to the pressure or force sensors in 360 or 370. These additional sensors may include: touch sensors, temperature sensors, humidity sensors, volume sensors, movement sensors and alike.

514 in FIG. 5 is a lair that may reside above the sensor layer 512. This layer 514 may provide required visual looks, functionality or softness and comfort. For a non limiting example being comprised of a mattress like material required in activities such as martial arts, Pilates, Yoga, gym activities and alike. Another non limiting example may 514 be a parquet floor layer to give visual looks and comfort when walking on if the apparatus 500 is for example a part of the gym floor. The layer 514 may be absent altogether or be found bellow the sensor layer 512. For example if 512 is comprising a plurality of pressure measuring devices such as 370 and the jacket 376 of 370 is of the elastic type, the layer 512 may have the qualities of a mattress required for example in a Pilates studio so additional layer may not be required.

The layer 514 if present may itself contain additional sensors to the ones found in the sensor layer 512. These sensors may be of any kind mentioned above or known in the art.

516 is an example person walking, standing or doing activity on the example embodiment 500.

522 is schematically describing the electronic block in the example embodiment 500. This block may comprise a processing unit 215, a data repository system 214, I/O subsystem 220, a plurality of wireless or wired communication devices ad any other part of the system described in conjunction with FIGS. 1 and 2. Some of the advantageous components may be Bluetooth and NFC wireless communications components for interaction with Smart—phones or WCDs, a processor component and a RF communication component for higher range wireless communications.

The example embodiment may also comprise a battery or a power source (not shown) such as a fuel-cell or any other known in the art. It may also comprise a generator to produce power from the user's movements and the pressures acted on 500. Such a generator can comprise a piezoelectric energy harvesting device as described above. The piezoelectric energy harvesting can be done from the fluid pressure change for example. Also the following apparatuses disclosed can use such generators.

The example embodiment 500 may have wide range of applications:

It can identify people, weigh them, and measure attributes and information about them. Weighing is done by summing the pressure or force on a plurality of sensors, when a person 516 is found above them exerting his weight on them. The example embodiment 500 may also include electric sensors to measure a person's body conductivity or resistivity. Such sensor may include a part that emits a small electric current and a part that measures the returning current. The conductivity measurement together with the weight measurement can give a measurement of the person's body fat percentage, using methods known in the art. Furthermore the value of conductivity or resistivity that can be measured can be unique to each person and assist in identifying him.

By mapping the pressure points of the person's feet or shoe soles the example embodiment 500 can create a mapping or an image of the feet or shoe sole. This may be enough or be an aid in identifying the person (by for example comparing to a data-base of patterns or previously known information). Additional data collected by the example embodiment 500 can complete the data necessary for identification. Such data may include the weight and body fat percentage mentioned earlier, data from interaction with the persons membership card, smart-phone or WCD, data from optical or voice sensors and more. A group or a single form of such sensor data may be enough for identification. An example can be the person's weight together with the sound of his voice etc.

The example embodiment 500 incorporated in parts of the health club or training facility floor may further assist monitoring the users. It can track the location of the users by tracking their footsteps, or by other methods known in the art. This way, for example, what is known in fields of marketing and ergonomics as spaghetti charts of the health club or training facility can be made. Such charts can map the most popular areas, facilities or machines, the order in which they are used, the amount of time spent on each etc. This may aid arrange the health club or training facility in a better way, detect problems or difficulties, receive marketing voluble information and more.

Such tracking or users by the example embodiment 500 may also assist in user's retention. Known patterns of users thinking about leaving can be put in the Data-Base and compared on the fly to the patterns of the users being recorded. The system may be pre programmed to warn when it detects certain states or series of states. For example identifying a user that spends too much time (relative to a threshold) on each exercise, a user who takes long recesses etc. Machine-Learning algorithms can be used on receded and on the fly patterns of users to learn when a user is probably satisfied and when a user is probably unsatisfied and thinking about leaving. The health club or training facility may then take steps to improve the satisfaction level of the identified users or take steps to improve their retention.

The example embodiment 500 can be used to count repetitions of exercises. For example when a trainee is performing pushups on the example embodiment 500, the force or pressure he applies changes during the exercise and has a periodic pattern. Therefore methods such as 340 can be used to count repetitions. Furthermore, in some exercises different body parts are touching the surface and not touching it during different parts of the exercise. For example in the exercise known as Sit-up, parts of the upper back are touching the surface at the beginning and end of each repetition and are not touching during most of the repetition. This gives a prominent pressure pattern on the example embodiment 500. This pattern allows identifying repetitions.

Reparations can also be identified in exercises where weights or training apparatuses are used. When using weights pressure/force patterns applied on the example embodiment 500 are also formed. Movement of weights in space causes required changes in the human body balance. These changes cause change to the pressure pattern that the body parts touching the surface are causing. For example a person doing an exercise of stretching his hands with weights while standing on his feet, will experience change in pressure between the inner side of the feet and the outer side. These changes are timed with the timing of the weight changing location in space. This pattern can be recorded or followed by the example embodiment 500. Using methods like 340 the repetitions can be identified.

If the user is using free weights, or any other apparatus where resistance is proportional to the apparatus weight, the example embodiment 500 can identify the resistance used. This can be done easily by subtracting the user's previously measured (Or known) weight from the total weight measured, or in similar or other methods known in the art.

The example embodiment 500 can measure the paste and rhythm in which an exercise is made by timing patterns like 340. It can then notify the user about to slow or too fast paste.

These and the following methods are applicable to many types of sports such as gymnastics, gym, Pilates, Yoga and alike.

In case of activities such as martial arts, dancing, tactical training and alike, but also gymnastics, gym, Pilates, Yoga and alike, or training in general. The example embodiment 500 can be used to identify the exercise or routine and correct it. The example embodiment 500 can produce mapping of the parts touching it (and thus also identify them) and timed sequences of the parts touching it. Therefore similar methods to the ones disclosed in U.S. Pat. No. 9,011,293 B2 incorporated here by reference can be used.

Additional sizes such as performance speed, motion range, energy burn in calorie and alike can be thus calculated in methods described above or known in the art.

Figure 6:
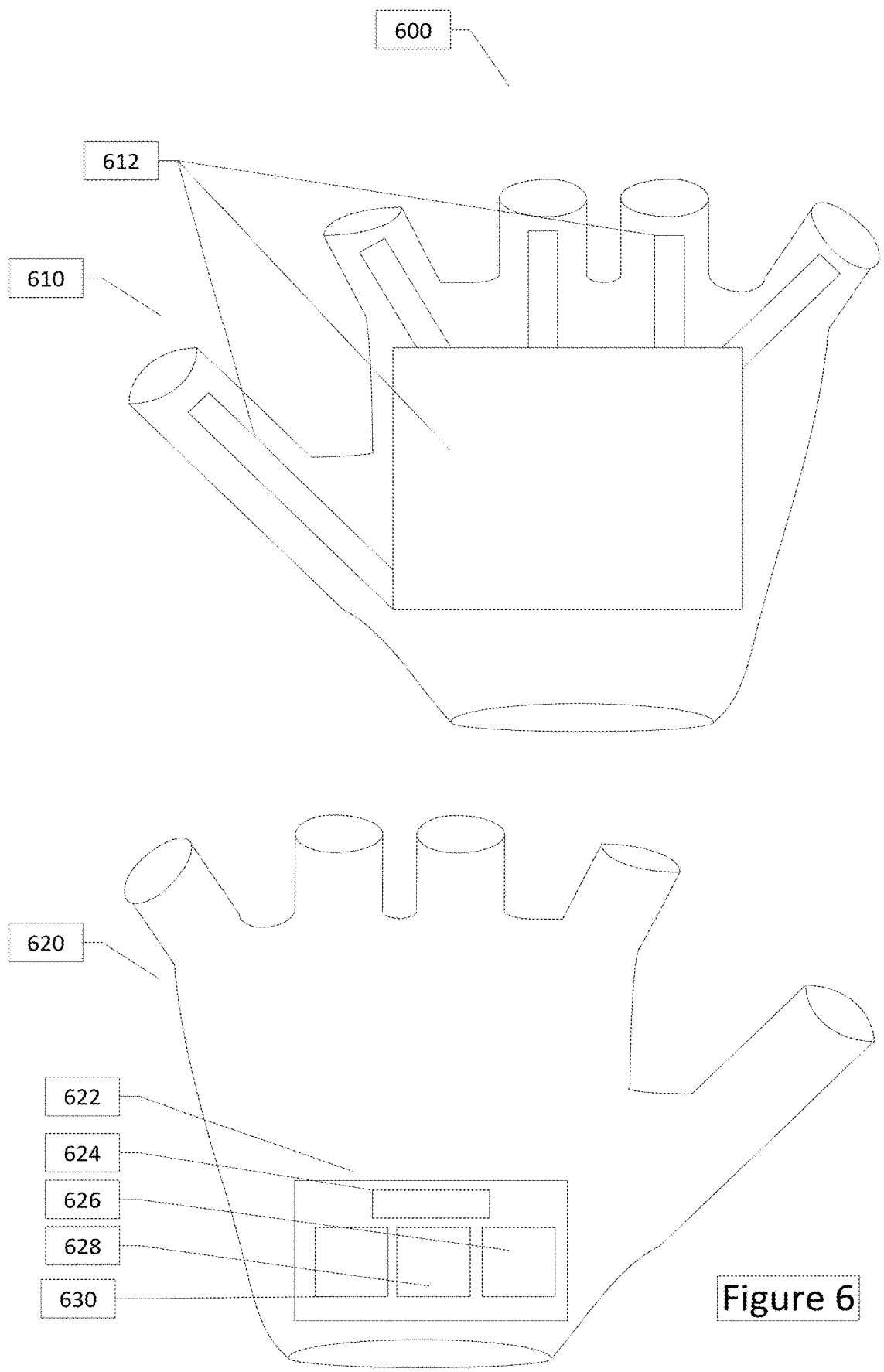
FIG. 6 describes an example embodiment of computerization of a training glove.

FIG. 6 describes another example embodiment 600. This is a glove worn on the user's hand. In FIG. 6 the left hand glove is depicted. 610 is a front hand view of this left hand glove. 620 is a back hand view.

612 is a sensor layer comprising a plurality of force/pressure sensors as 360 or 370. The lair may include additional sensors to the pressure or force sensors in 360 or 370. These additional sensors may include: touch sensors, temperature sensors, humidity sensors, volume sensors, movement sensors and alike.

The sensor layer 612 can be attached inside the glove (between the layers making the glove), underneath the gloves layers, above it or in any other advantageous location. Advantageously it is inside the glove or above its layers, so to be touching without "barriers" what the glove is holding.

622 is schematically describing the electronics block in the example embodiment 600. This block may comprise a processing unit 215, a data repository system 214, IO subsystem 220, a plurality of wireless or wired communication devices ad any other part of the system described in conjunction with FIGS. 1 and 2.

The location chosen in this example embodiment for the electronics block is advantageous. This is since it is at the lower back of the glove thus not interfering with the glove operation in holding things. Also it's weight is less noticeable since it is in the lower part of the glove where the physical moments are weaker. Other locations are possible including the front of the glove 600 or its side. Also the components don't have to be adjacent to each other and may be scattered thought the glove 600. Some of them may be external and connected by wired or wireless connection to the rest. For example a processor may reside only in one of the gloves 600 and the transceiver for RF for example may only reside in the other. This is in order to save weight and space. The gloves may use a smart-phone or WCD processing power and thus not contain a processing unit or contain only a small and low power one.

The example embodiment 600 may also comprise a battery or a power source (not shown) such as a fuel-cell or any other known in the art. It may also comprise a generator to produce power from the user's movements.

Some of the advantageous components are depicted in FIG. 6: 626 is a Bluetooth and NFC wireless communications component for interaction with Smart—phones or WCDs, 628 is a processor component, 624 is a RF communication component for higher range wireless communications. 630 is an array of accelerometers and or motion sensors and or gyros.

The example embodiment 600 may have wide range of applications:

The sensor array 611 can be used to determine the resistance used in an exercise. For a non limiting example if the user is holding the handle of a gym machine and performs an exercise, for example chest press, the gloves in both hands can measure the pressure or force applied. Thus 600 can calculate the weight lifted. This can be done in every exercise where the gloves are pushing/pulling/resisting/holding and alike the resistance or a mean which is mechanically linked to it (such as machine handle).

Paragraph 125 below details some more about methods for finding the resistance in a similar example embodiment.

As in the previous example embodiment the force or pressure change pattern can be used to find the repetitions done and the paste of the exercise. If an accelerometer 630 is present as part of the example embodiment 600 it can count repetitions and measure the exercise paste calculate the motion speed (by integrating the acceleration with time) or the hands location (another integration with time); and thus the handles (in case of exercise with handles) location and speed.

The acceleration measured by the accelerometer 330 or the force measured by the sensor array 612 may be further used to count repetitions in methods similar to what described for FIG. 3-340.

Additional sizes such as performance speed, motion range, energy burn in calorie and alike can be thus calculated in methods described above or known in the art.

The sensor array 612 and the accelerometers 330 can record or compare the force/pressure and acceleration and or speed and or movement patterns they measure to patterns recorded in a data base. Similar methods to those described in U.S. Pat. No. 9,011,293 B2. To identify the exercise performed and/or correct it.

In the example embodiment the gloves (or just one of them) can include a marker or reflector for optical or other sensor types (such as acoustical, RF and alike—as described in the section dealing with methods above). A glove may be colored or contain a distinct pattern for optical or other identification. This way an external sensor can detect or track the glove or gloves location or movements in space.

In case other body parts are used to drive the resistance, the concept can be generalized. For example the example embodiment 1800 of FIG. 18, where a glove like apparatus is worn on the feet.

FIG. 7 shows another example embodiment. In this example embodiment an elastic or non elastic apparatus can be attached or wrapped around exercise machines handles or free weights. Elastic or non elastic can be attached to other points of contact between the trainee and the exercise apparatus. Preferably the points of contact are those which are driving the resistance.

710 is an example embodiment on a gym machine handle. In this case it is a common one hand handle. 712 is the body of the handle, usually made out of metal. 713 is a ring which is a part of the handle or attached to it. 714 is a Karabiner for harnessing the handle to an exercise machine. 716 is a cover usually made out of plastic material to make the hand grip more convenient. 718 is a surface similar to the example embodiment 500 in FIG. 5 but in a smaller scale. It comprises similar elements to the ones described when referring to FIG. 5 (Not shown—because configuration is similar to FIG. 5): a plurality of pressure measuring devices such as 370 (512), additional layer may be present like 514, an electronic block such as in the example embodiment 500. This block may comprise a processing unit 215, a data repository system 214, IO subsystem 220, a plurality of wireless or wired communication devices ad any other part of the system described in conjunction with FIGS. 1 and 2. Some of the advantageous components may be Bluetooth and NFC wireless communications components for interaction with Smart—phones or WCDs, a processor component and a RF communication component for higher range wireless communications.

Components that may be unique to the example embodiment 700 and may be added over the example embodiment 500 is accelerometers or motion (not shown).

In 710 the apparatus 718 is wrapped around the softer layer of the handle 716. This is only an example implementation. Its advantage is that the apparatus 718 can be wrapped around an existing handle without any need of modifications in the existing handle and without any permanent changes to the machine. In other implantation examples the apparatus 718 can replace 716 or reside under it and so the ergonomic qualities of 716 can be exploited.

The resistance set in the exercise machine can be calculated from measuring the pressure or force on the pressure measuring devices 512 in 718. This pressure may be the sum of the force the user exerts against the resistance, and the grip force the user exerts on the handle. The force the user exerts against the resistance may itself be the sum of the resistance weight and the force used to accelerate the resistance.

It may be possible to isolate the actual resistance set in the machine. Usually the resistance set has singular values in steps. For example in weight stack machines the values of resistance step is the weight values of single weight plate. In many cases the effect of the user grip force and the acceleration induced force may be smaller then the gap between two adjacent values of set resistance. Therefore rounding down to the closest value of possible resistance will give the set resistance.

The accelerometer can be used to measure the acceleration and thus subtract its effect. The rounding method or other method can then be used.

A bit more elaborate calculation can be used: few samples of the force or pressure can be taken during the exercise together with measurement of the acceleration at the same time. At this stage there are two unknown variables: the gripping force and the set resistance. The measurements of the total force and acceleration can be used to create a set of simple equations. In these equations the total force is the sum of the three forces mentioned. The total force and acceleration are known from measurements, while the resistance and average gripping force are the unknown variables. Solution of these equations in methods known in the art will yield the set resistance. This method can be generalized or other methods known in the art can be used.

The above methods from paragraph 125 can be used in the glove example embodiment 600 and in other similar embodiments such as the sliding disc 1800.

718 can be used like 500 and 600 to find the repetitions, paste, calories, identify the exercise, and correct it. All this can be done in similar methods to 500 and 600 using the force/pressure sensors, the accelerometer, the processor and the other sensors and apparatuses mentioned in 500 and 600 and can also be present in 700.

720 describe a similar non limiting example of this embodiment. 722 is a non limiting example of a gym machine. 724 are the weight plates, 726 the series of pulleys and cable used to transfer the mechanical resistance to the handle 727. 725 is the chair used by the user. In this case the added apparatus is 728 wrapped around the handle in a similar manner to 718.

728 is similar to 718 and can perform the same tasks in a similar manner.

730 is another non limiting example of this embodiment. In this case a gym machine known as leg press machine 732. The trainee is sitting in a chair 733 while his plate press on a surface 735 found on a cart. The cart is moving on a rail or rods 735. The cart is mechanically connected to the stack of plates 734 trough a cable and a series of pulleys 737.

In this case the apparatus 738 is spread on the leg press surface 735 and measures, among other measurements, the pressing force exerted by the feet on the surface it covers 736.

The methods and functions are very similar to 728, 718 and especially 500. 738 can be viewed as the example embodiment 500 covering the leg pressing surface instead of the gym floor.

738 can find the repetitions, paste, calories, identify the exercise and correct it. All this can be done in similar methods to 500 and 600 using the force/pressure sensors, the accelerometer, the processor and the other sensors and apparatuses mentioned in 500 and 600 and can also be present in 700.

The example embodiment 700 can be used for any resistance machine or apparatus in similar ways, such as Pilates machines, free weights or any other resistance machines, where it can be spread or wrapped and alike on handles, surfaces rods, and alike.

Figure 8:
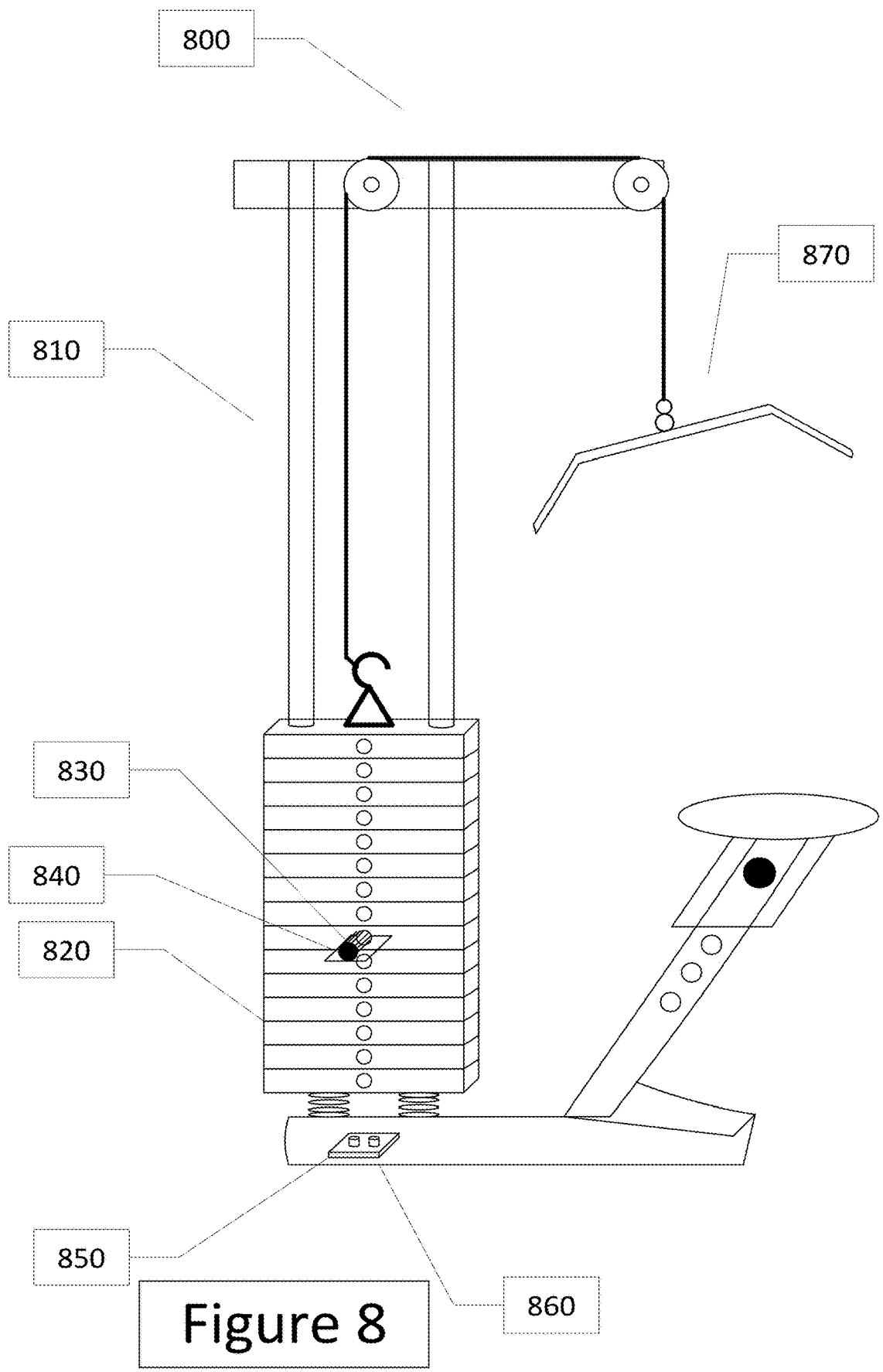
FIG. 8. Is an example embodiment of ranging device utilization.

FIG. 8 example embodiment 800, depicts a simple example embodiment of the system. 810 is a non limiting example of a gym resistance based machine with weight plates 820. 830 is the selection pin. 850 is a distance measuring device such as the HC-SR04 or any other device or method for measuring distance or location from the methods explained above. 840 can be an ultrasonic or other reflector attached to the pin 830. 860 is the electronics block containing more electronic components of the system such as parts of the computing system and wireless receiver transmitter described above.

The reflector 840 may not be necessary in some implementation and the cross section of the pin 830 may be large enough to be identified and give a good measurement in the required distance range.

By measuring the distance of the pin from the stationary sensor 850, the selected resistance can be calculated. Say for example that each weight plate has the height of 2.5 [cm] and the distance from the weight stack base to the sensor is 10 [cm] and each weight plate weighs 5 [Kg] the resistance W can be calculated by the computing system 860 according to the measured distance d:

$$W=\text{Max\_Weight}-[(d-10)/2.5]*5$$

Where Max_Weight is the sum of all the weights together and [ ] is round down to the nearest integer.

When the user exercises the sensor can continue to measure the distance to the pin. Thus the location of the weight plate stack can be known at all times. As explained above it is proportional to the movement of the handle 870. Thus the movement range, the speed of performance can be known. Repetitions can be counted from the distance measurement during performance as explained above. Further attributes and sizes can be calculated like calorie burn and alike.

The wireless receiver transmitter can use any protocol mentioned in this disclosure or known in the art. It can be used to communicate with WCDs or smart phones which may contain some of the systems computing system. For example the I/O devices on a smart-phone like the screen and speaker can be used to display the resistance and or repetitions and/or any other output or function to the user. The smart phone speaker may be used for example to issue a voice message to the user if he is doing the exercise to fast or too slow. Repetitions can be counted by voice. Another example is—the resources of the smart-phone or WCD can be used to communicate with a cloud data-base.

Figure 9:
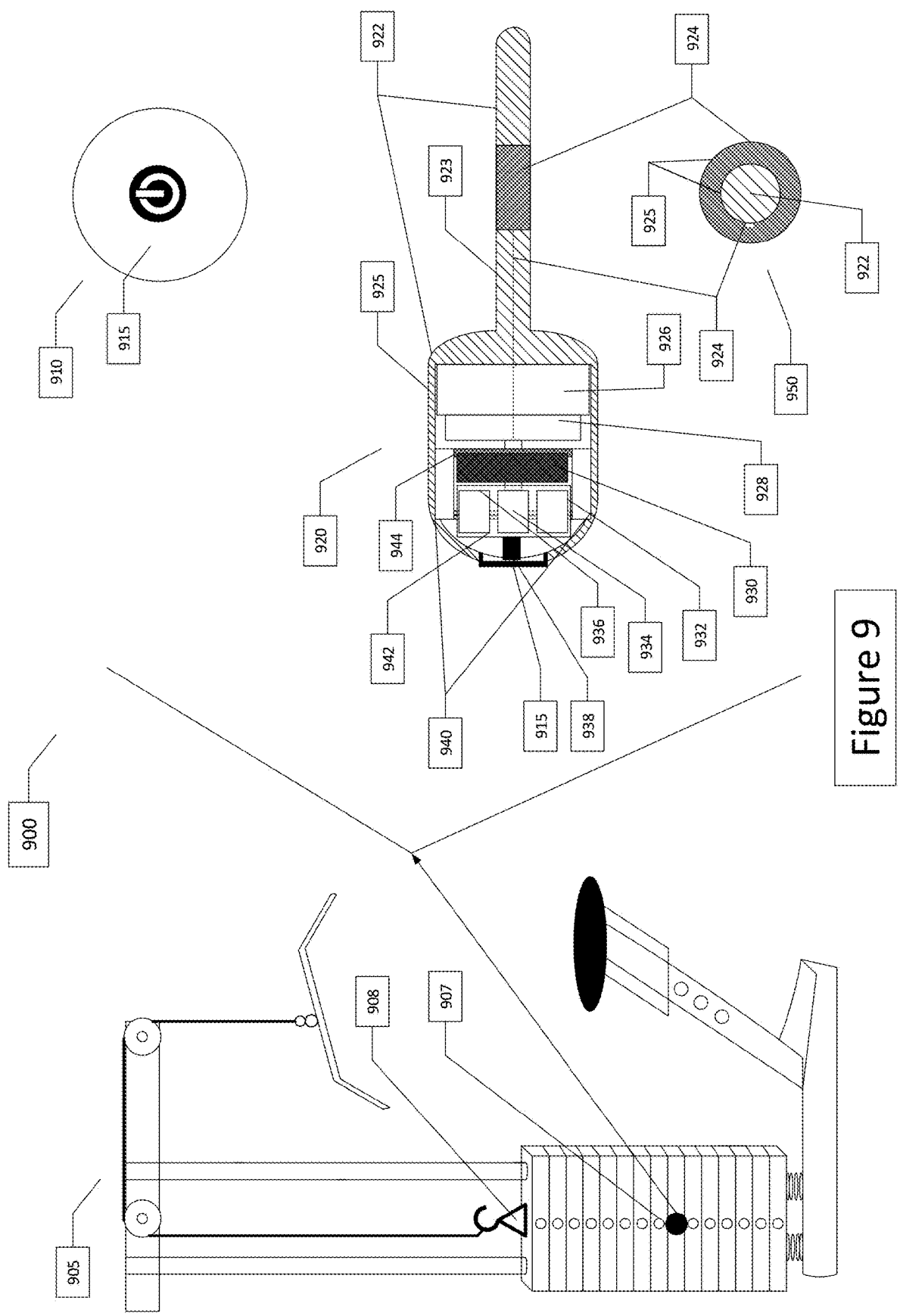
FIG. 9. Is an example embodiment of a computerized selector pin.

FIG. 9 depicts a different example embodiment for gym machines. 905 is the gym exercise machine. 907 is the selection pin 830. In this example embodiment a large portion of the system is implemented inside the pin 907.

910 is a rearview of the selection pin depicting a possible on/off button 915 in this example it is in the center of the pin rear casing. The pin may also be colored or contain a marker or reflector for optical or other sensor types.

920 is a cross section of the pin and system viewed from the side. 922 is the chassis of the pin. The chassis is preferably made out of rigid material a preferable example can be steel. 923 is the pin section of the chassis while 925 is the handle part. The chassis can be made of one part or a plurality of detachable parts. 924 is a load cell or a load cell army configured to measure radial force or pressure on the pin. 950 is a rear view cross section of the load cell area. The load cell can be mounted on the chassis 922 or connected to it in methods known in the art. A small channel for wiring 924 can be made in the chassis to connect the load cell to the electronic board 936.

In an example embodiment the load cell array 924 can be replaced by what is known in the art as load pin—a device for measuring shear and other forces on a pin. Datasheets of a commercially available load pins are attached. One is the "FN1010" from "Measurements Specialists" and one from "Sensy" model number 5000-5300-5600. Commercially available Load pins comes in many shapes and sizes and can be custom made to fit required size, diameter and load sensing requirements. The pin section 923 can be made out of 3 parts where 924 is a load cell covering the area which is expected to be inside the central rod 835. Passive sections from both sides can be attached to it to extend the total pin length on both sides. In another embodiment example the entire pin section 923 can be a long load pin.

The force measuring ring 924 can be implemented in many ways. For example the methods described above in reference to FIG. 3 can be used. Specifically the methods described for creating a pressure measuring surface can be used where the surface can be shaped as a ring. Other methods known in the art can be used. For example the ring 924 can be made out of piezoelectric material which changes its resistance or electrical characteristics in response to applied pressure and/or strain. In another example the ring can be comprising two conductive material cylinders 925 one on the outer surface of the ring and one on the inner surface. The space between them can be made of insulating and/or dielectric elastic material. When stress is applied on the ring strain occurs which changes the distance between the conductive material cylinders 925. As a result the electric capacity of the ring changes. This capacity change can be measured and thus the strain can be calculated. Knowing the strain and the elastic material properties such as its young modulus can give the stress applied.

926 is a linear generator or other form of generator or mechanical to electric energy conversion device. Its purpose is to convert the mechanical energy from the pin movement when the trainee exercises to electrical energy and charge the battery 930. 928 is an accelerometer. 926 and 928 may be connected to the main chassis 922. 940 are shock and vibration absorbers fabricated in methods known in the art. For example to relatively thick straps of shock absorbing material such as rubber or sponge e like martial or a combination of both. The shock absolvers, absorb vibrations and shocks between the chassis 922 and the secondary chassis 944 connected to it. The electronics board 936 and a battery 930 are mounted on the secondary chassis. 915 is the possible on/off button connected to the board 936 trough a relay 938. 932, 942, and 934 are microchips and electronics found on the board implementing some or whole of the computing system.

An example electronics configuration found on the board 936 is using 2 commercially available microchips: One is the Texas Instruments CC2541 (Data Sheet attached): The CC2541 combines the excellent performance of a leading Bluetooth RF transceiver with an industry-standard enhanced 8051 MCU, in-system programmable flash memory, 8-KB RAM, and many other powerful supporting features and peripherals. The second commercially available chip can be the RFM69 (Data Sheet attached) which is small RF transceiver chip that allows multiple nodes RF communication for ranges of up to 900 [m] and more. The electronic configuration may further include capacitors, resistors and other electronic components required to operate and integrate the microchips. It can also include antenna arrays for the Bluetooth and/or RF and/or other protocols used. This configuration can also be used in the other example embodiments described above and below in this disclosure.

When the pin 907 is inserted to select resistance the load cell array (or force measuring ring) 924 is configured to be inside the hole 835 in the central rod 830. Once the weights are lifted the rod is pulled by the cable 815. At this time the weight of the connected weight plates or a portion of it is applied to the selection pin 907 by the central rod. The load cell array (or load pin) 924 senses this force and can transfer the measurement to the part of the computing system found on the board 936. This way the computing system can calculate the resistance selected. The force measured may include a component of acceleration from the user's motion and not from the earth gravity (weight). If this component is small it can be filtered by rounding down the force found to the closest possible weight (Since the possible weights are known and are separated from one another by jumps, for example 5[Kg]).

In case where the additional component may be large a measurement of the user caused acceleration over known gravity can be measured by the accelerometer 928 and used in known methods to reduce the user caused acceleration component from the weight measured. Thus the resistance selected can be measured quite accurately.

Another method for finding the resistance can use the principal of distance measurement similar to 900. However a distance measuring device such as 950 or other can be put inside the pin 907. This device can measure the distance to the floor or any moving or non moving part on the machine, or a marker or a reflector mounted on it. If this measurement is done when the machine is at rest the distance can tell which weight plate the pin is selecting in similar principals to 900. The measurement can be also to a moving part or to a marker or reflector mounted on it when the machine is not at rest. For example an RFID chip mounted on a moving part such as 908—the connection of the cable to the weight stack. The distance to this RFID Chip can be measured also during movement using RF methods, and the distance of the pin from it can give the resistance in similar principles to 900. Any method for distance measuring and any type of marker, repeater, reflector can be used.

The accelerometer 928 may be further used to calculate the motion speed (by integrating the acceleration with time) or the weight stack location integration with time) and thus the handles location and speed.

The acceleration measured by the accelerometer 928 or the force measured by the load cell array (or load pin) 924 may be further used to count repetitions in methods similar to what described for FIG. 3-340.

Additional sizes such as performance speed, motion range, energy burn in calorie and alike can be thus calculated in methods described in this disclosure, the references or known in the art.

In this case too parts of the system may reside outside the pin and the communication may be wireless. The above example of using an eternal device such as WCD or smartphone display or speaker or communicating with an external DB or computing system apply as well.

Figure 10:
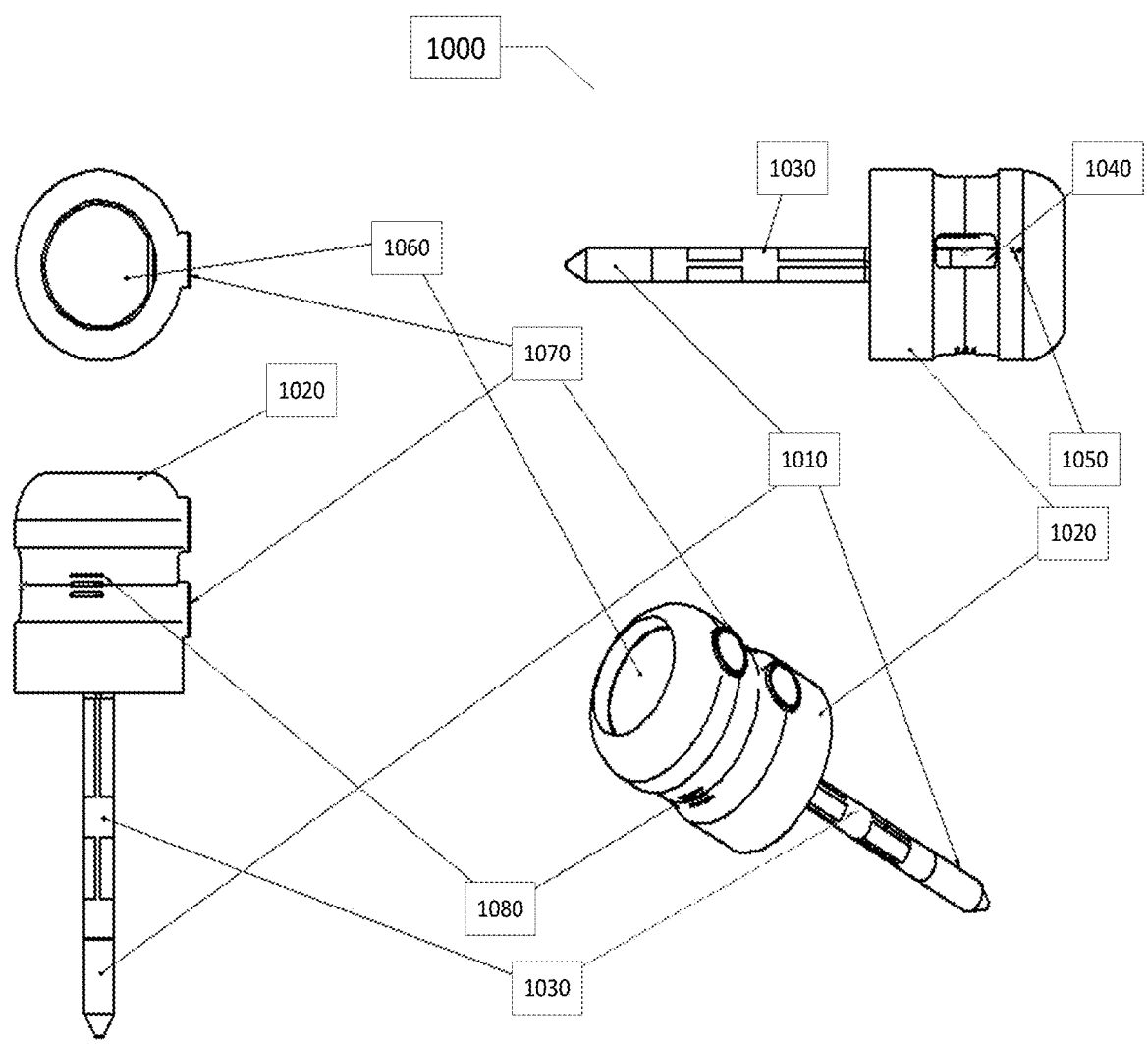
FIG. 10. Is another example embodiment of a computerized selector pin.

The next figures describe a similar example of computerized selector pin for use in resistance based exercise machines. FIG. 10 embodiment 1000 describes the outer surface of this embodiment. 1010 is the shaft portion of the selector pin similar to the shaft portion described in the previous figure. It is preferably made out of rigid material and is inserted to the weight stack of the resistance based training machine to select the desired weight. 1020 is the handle cover. 1030 is an optional cover for pattern of optional groves and channels (not seen in this figure) made in the shaft portion of the pin to allow advantageous but optional configuration of mechanical sensors such as strain gauges and piezoelectric sensors and their wiring configured on the shaft portion.

1040 is an optional opening or a "window" in the handle cover to allow for optional optical or electromagnetic sensor or alike. A cover (not shown) for this opening is also optional where the cover is made out of material which allows as free as possible transition of the entity that the sensor below it is sensing. For example, if the sensor below is a camera for visible light the optional cover can be made out of material transparent to visible light to allow the sensors operation. Such optional cover may have advantages in protecting the devices from humidity, dust and also aesthetic advantage.

1050 are optional holes for an optional microphone inside the handle cover. 1060 is an optional screen or touch screen. In an example embodiment it can be 1.5 Inch round color touch screen like model PV1501B3CZ0 by Elsun. 1070 is an optional ranging device which can be ultrasonic or by another method. In an example embodiment the HC-SR04 is used. In an example embodiment the handle cover is configured so that the receiver and transmitter cylinders of the ultrasonic ranging device are not obstructed, for example in the figure the cover 1020 has holes from which the cylinders of 1070 peak. 1080 are grids or cuts in the cover 1020 for optional speakers found inside the handle cover 1020.

Figure 11:
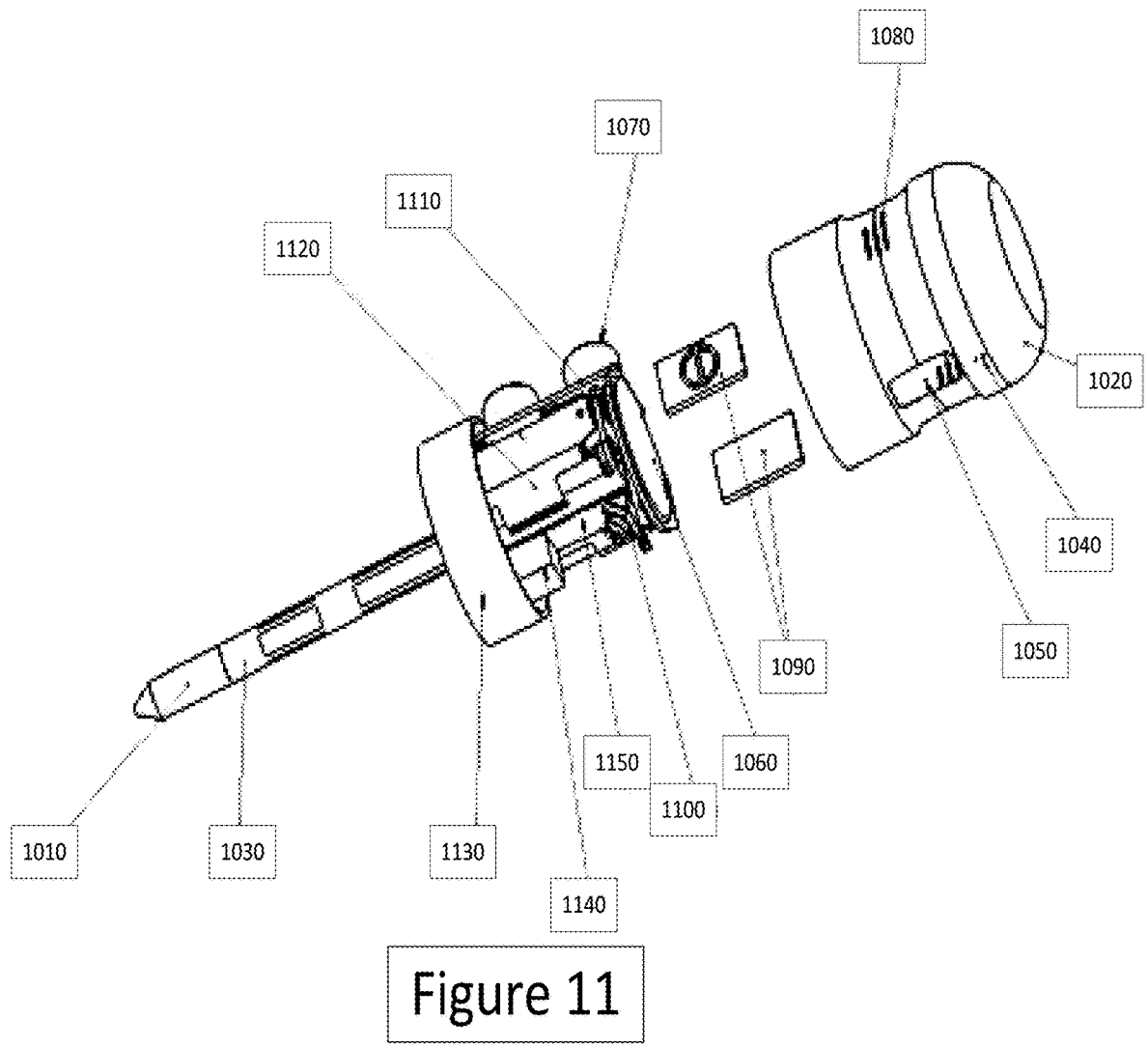
FIG. 11. Is another example embodiment of a computerized selector pin.

FIG. 11 depicts the computerized selector pin embodiment with the handle cover 1020 removed to reveal the example embodiment underneath it. 1090 are optional speakers for example BeStar mini speakers Par t No: BLS1525-11-08H05 LF (Data-sheet attached). In this example embodiment the speakers are fastened to the handle cover 1020 right under the speaker groves 1080 in the cover 1020, on the other side of the cover 1020 from the groves. For better clarity and generality fastening means such as screws nuts and bolts are not shown in the drawings. Any of the fastening means and methods given in this disclosure, in the references or known in the art can be used. For example the speakers can be glued to the inner surface of the handle cover 1020 under the groves 1080. The shaft portion 1010 is fastened to the chassis 1130. The cover 1020 can be fastened to the chassis 1130 by screwing it where the round part of the chassis 1130 can be configured with thread matching a thread on the inner side of the cover 1020. The chassis contain a platform 1150 for harnessing the inner parts and electronics to it. 1100 is an optical or electromagnetic sensor in this example a camera such as "See3CAM_12CUNIR" or "See3CAM_CU130" by e-con Systems India Pvt Ltd. In the example embodiment the camera or sensor has a view of the exercise machine weight stack or other dominant features trough the opening 1050. Using this view the system can calculate the pin location in the weight stack and calculate the resistance. 1140 is a linear generator or other type of system for converting the selector pin movement energy to electrical energy and charging the power source. In this example embodiment the power source are batteries 1120. 1110 is a battery case. The batteries in this example embodiment are AAA rechargeable batteries.

Figure 12:
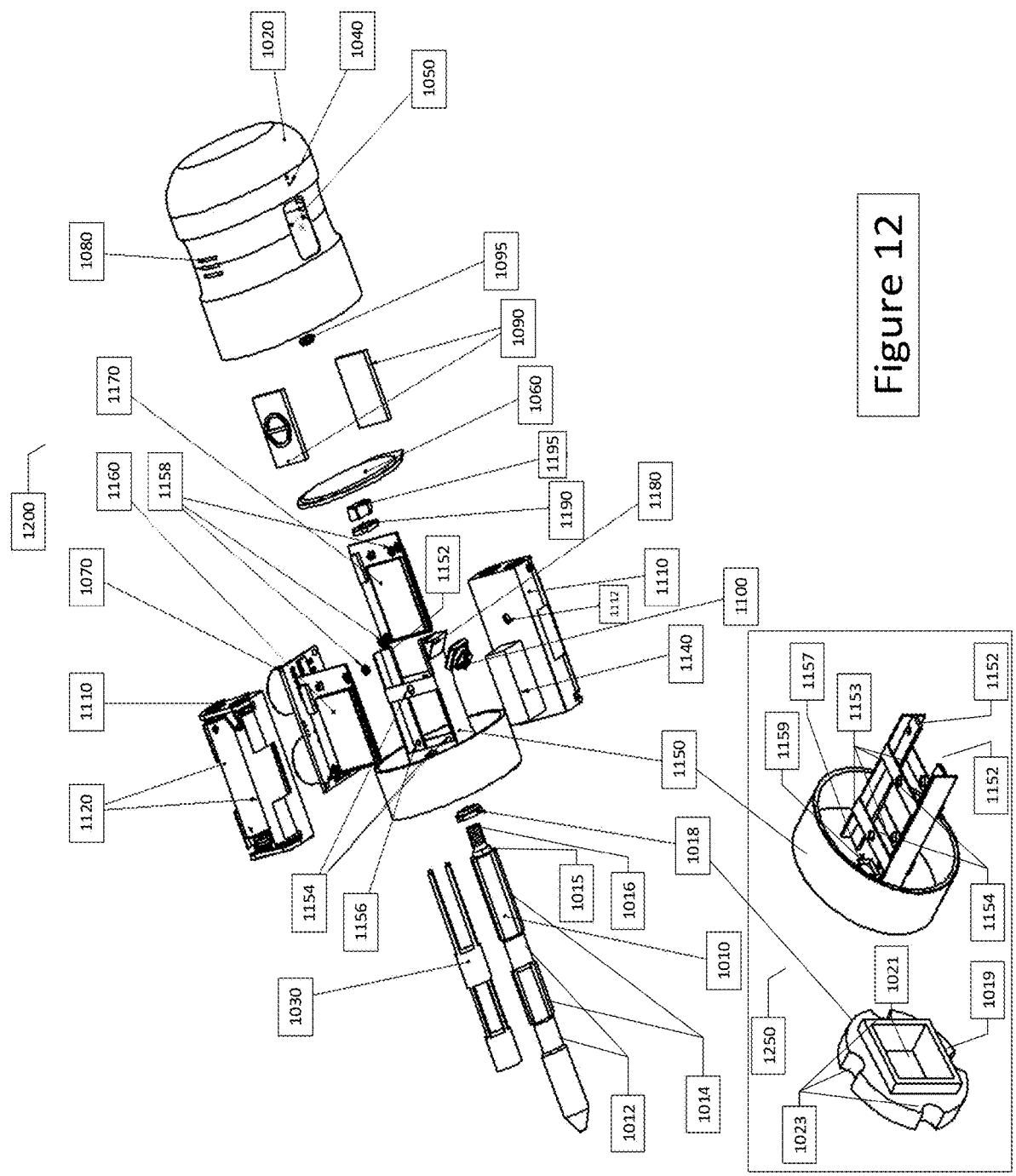
FIG. 12. Is another example embodiment of a computerized selector pin.

FIG. 12, 1200 is an exploded view of the computerized selector pin example used to further describe the example embodiment. 1095 is a small microphone such as Sonion 9240/1 microphone (Datasheet attached) that can be used for voice activation and commands. In a similar manner to the fastening means, the electric connections or wiring of the electronic components is not shown in order to facilitates better clarity of the drawings and avoid limitations. As described above in reference to FIG. 2 above, all components can be electronically and electrically connected to the system or other components using any method known in the art including wired and wireless connections. Examples are given throughout this disclosure and in the references. For example the microphone 1095 and speakers 1090 can be connected by wires to the mezzanine board 1170 or to the main board 1160 using the I2S Audio transfer protocol. The Screen 1160 connected to one of the boards 1160 or 1170 for examples using MIPI DSI protocol wires and connectors. The camera 1100 can be connected to the boards 1160 or 1170 for examples using the MIPI CSI protocol wires and connectors or for example USB protocol wires and connectors.

The exploded view of FIG. 12, 1200 exposes optional revolved cuts 1012 and optional wiring tunnels 1014 in the pin shaft portion 1010. The revolved cuts 1012 can be used in an example embodiment to accommodate strain gauges or other sensors as shall be further elaborated below. The wiring tunnels 1014 can then be used to lead the sensor wiring towards the system electronic boards 1160 and 1170. 1030 is a cover made for example from silicon or plastic or rubber and can be used to cover the cuts and tunnels in order to protect the sensors and wires. The optional cover 1030 can also have aesthetical advantage.

In the example, the shaft portion 1010 has a rectangular shape 1015 curved near the right end of it which fits the pattern in the shock absorber 1018 so the shaft portion 1010 will not move too much in the shock absorber 1018 shown enlarged in the in 1250—bottom left of the drawing. 1250 is enlarged and not in scale view of the shock absorber 1018 and the chassis 1150. The rectangular pattern 1019 is seen in the enlarged drawing 1250 of the shock absorber 1018. The shock absorber has a cavity 1021 trough which the edge 1016 of the shaft portion 1010 goes trough and it fits around the rectangular pattern 1015 curved in the example shaft portion 1010. 1023 are optional cuts in 1018 made to allow sensor wiring passing easily between the shaft portion and the internal components of the computerized pin. The shock absorbant 1018 is preferably made out of shock absorbing material or layers of such materials. Such materials can be found for example in shock absorbing cases for smart phones. Its objectives in the example are to assist the fasten the shaft portion 1010 to the chassis and to absolve shocks and vibrations coming from the shaft portion 1010 before reaching the chassis on which the electronics is mounted.

The chassis 1150 has a rectangular hole 1157 that fits the outer part of the shock absorber 1018. Trough which the shock absorber 1018 and shaft portion 1010 connect to the chassis. An example for a possible fastening of the shaft portion to the chassis is shown in 1200: 1190 is another ring shaped shock absorber which goes over the edge of the shaft portion 1016 after it has passed through the shock absorber 1018 fitted inside the rectangular hole 1021 in the chassis 1150. This ring outer diameter is larger than the whole 1021 dimensions. A nut 1195 fits the tread 1016 on the shaft portion 1010 and fastens the system of shock absorbers 1016, 1190 and shaft portion 1010. 1190 can be also made out of shock absorbing materials and use shock absorbing techniques known in the art in its formation. The chassis 1150 and shock absorber 1190 may also contain holes like 1159 for wiring.

The chassis in the example 1150 is built with rails 1152 for the mainboard 1160 and mezzanine board 1170 and can include holes 1156 for harnessing these boards. Above and below the rails in a height that allows for the boards there are bars 1153 for fastening the two battery cases 1110. There can be holes 1154 in these bars fitting the battery cases holes 1112 for fastening the battery cases 1110. At the edges of the rails 1152 there can be provisions for fastening the screen 1060 (not shown) or the screen can be fastened to the case 1020. Another scheme for the screen can be that the chassis physically pushes it and holds it in place by its dimensions further assisted by the shape of the case 1020 without additional fastening means. The chassis 1050 can also include similar mean or methods to fasten the SR04 1070 and Linear generator 1140 or they can be glued to it for example. In the example 1158 are small rings that are preferably made out of shock absorbing materials. They are put above the holes 1156 in the rails 1152 so that they provide support for the boards 1160, 1170. The fastening means for the boards can pass through the ring shape. The rings 1158 can provide additional shock absorbing for the electronics found on the boards 1160, 1170. By configuring their height they can also insure that the boards 1160, 1170 will not touch each other or other parts in the system. They also create some spacing for better airflow and cooling of the boards 1160, 1170.

1180 is the optional camera/sensor stand or platform. Beside its role of assisting the camera fastening to the chassis, it hold the camera in a desired angle so that it will have a view trough the opening 1050 to the weight stack or other desired feature in the training machine.

The boards 1160 and 1170 include the required electronics: 1160 is the main board. In the example it includes a logic subsystem 215, data holding subsystem 214, Data storage Device 29, and Data Storage device Interface 280. For example the mainboard 1160 can be Intel Edison Platform (Product brief attached). In this case the mainboard will also include WiFi modem and Antenna (Wireless Connection controller 260) Sound Controller (230) and more like for example the Edison GPIOs can be used to control the HC-SR04. In this configuration the mezzanine board 1170 may include circuits to supply the desired voltage to the boards from the batteries like Voltage Converters, circuits for power management such as switches and suppliers regulators; charge pump circuits, circuits to control the linear generator 1140 and the battery charging from it (all circuits can be managed from the main computing unit). The mezzanine board can further include USB HUB or switch connected to the Edison USB port. It may include MIPI DSI and CSI Integrated circuits that connect to the main board via the USB HUB or different connections such as I2C and/or SPI and/or any other available connection in the Edison. These Integrated circuits will serve as the Display and Camera controllers (220). In an example a video processor such as the BCM2835 by Broadcom Corporation (Interface DS attached) can be used in the mezzanine board 1170 to interface the display and camera. The mezzanine board 1170 may further include accelerometers and/or Gyro and/or other sensors.

In another example configuration the main board 1160 can be one of the Raspberry Pi series systems. Preferably in this example the Raspberry Pi Zero because of its small size and low cost. In this case the Raspberry Pie includes a video processor but does not include WiFi and Bluetooth connections. The mezzanine board 1170 configuration in this case can include circuits to supply the desired voltage to the boards from the batteries like Voltage Converters, circuits for power management such as switches and suppliers regulators; charge pump circuits, circuits to control the linear generator 1140 and the battery charging from it (all circuits can be managed from the main computing unit). The mezzanine board can further include USB HUB or switch connected to the Raspberry Pi. It may further include HDMI to MIPI DSI Integrated circuit such as the ADV7480 (Data Sheet attached) for interfacing the display 1060. It may further include WiFi and/or Bluetooth modems and antennas. The mezzanine board 1170 may further include accelerometers and/or Gyro and/or other sensors. The camera in this case can be connected to the logic unit trough USB or trough USB to MIPI converter component.

The example embodiment computerized selector pin can use the ranging sensor 1070 to detect the range to the floor, ceiling, dominant feature in the exercise machine a reflector and alike. Ranging sensors like 1070 can be mounted on both sides instead of the optical sensor 1100. In this case the ranging sensors can detect the range to more than one feature and thus increase accuracy or increase robustness of operation if one or more feature ranging fails. In a similar manner the camera 1100 can be mounted on both sides instead of the ranging sensor 1070 to increase accuracy and robustness of its method of operation. In the example depicted in the last 3 figures both the camera 1100 and ranging sensor can operate at the same time thus also increase accuracy or robustness if one of the methods fail.

Above in this disclosure and in the references the operation of a system including a ranging sensor external to the selector pin is described. The method of operation of the ranging sensor mounted on the pin is similar with the proper adaptations given in this disclosure or known to the skilled in the art. Having the ranging sensor mounted on the pin may have several advantages one of them being that the computerized selector pin can become an independent unit which can be ungrouped from a specific training machine. The pin may be used with regular machines which did not have any adaptations or computerization.

As explained the system may also have Accelerometers and Gyros. These can be used to assist in counting repetitions and other features as described in this disclosure and the references. They can be also utilized to specific functions advantageous to this example embodiment: Accelerometers and/or Gyros can measure the angle of orientation of the pin Say for example the pin is inserted to the weight stack in a way that either the ranging sensor and/or camera is not perpendicular to the floor/ceiling or not in the expected angle relative to another feature for which measurement is required. By measuring the orientation using the Gyro/Accelerometer the system can correct a measurement taken by the ranging sensor or camera. For example the system can multiply the ranging measurement by Cosine the of the difference between the desired and actual angle. In the case of the camera it can for example apply transformation or rotation operators to the image or patterns compared to the image using the measured angle.

Accelerometers and or Gyros can be used to better utilize the system energy: The system may be kept mostly in power down or in low power states where some of its components are turned off. A plurality of Accelerometers and/or Gyros may be left on in these cases to sense for movement. In case the movement or acceleration is above a certain threshold the system maybe powered up or made to leave the low power states and turn on the required components.

Other methods known in the art to achieve such "awakening" process can be utilized. For example the range sensor can be made active once every period of time to check if there were a change in range over a certain threshold. Another example the camera can be made active from time to time to detect movement. Yet another example can be addition of magnetic or proximity sensor for example to the chassis 1150. Such a sensor can detect disconnection and attachment to the weight stack or in general to a training machine and wake the system up. The above methods can be combined for maximum power save. For example on every detection of disconnection and attachment wake the system up for a short time to calculate the new resistance and outputting it to the user. Then go to low power mode till a movement is detected in one of the previous methods. When movement stops go to low power state again. In the time of the movements after the resistance has been calculated only parts of the system can be on for example some of the accelerometers and/or Gyros can be active to count repetitions and monitor movement range and maybe some of the I/O systems in order to give this information to the user (For example the screen 1060 is moving at this stage so is not seen well by the user and therefore off, repetitions are counted by voice outputted from the speakers 1090). The camera and/or range sensor can be off at this time if they are not used to count repetitions, monitor movement range or other required functions. After the movement ceases for some time the system can infer that the exercise is done and turn on some I/O devices such as the screen to present exercise summery and also for example turn on the WIFI modem and antenna to transmit the exercise data and summary to the cloud or user WCD or mobile for example. Other power schemes using similar and other method are also possible.

Figure 13:
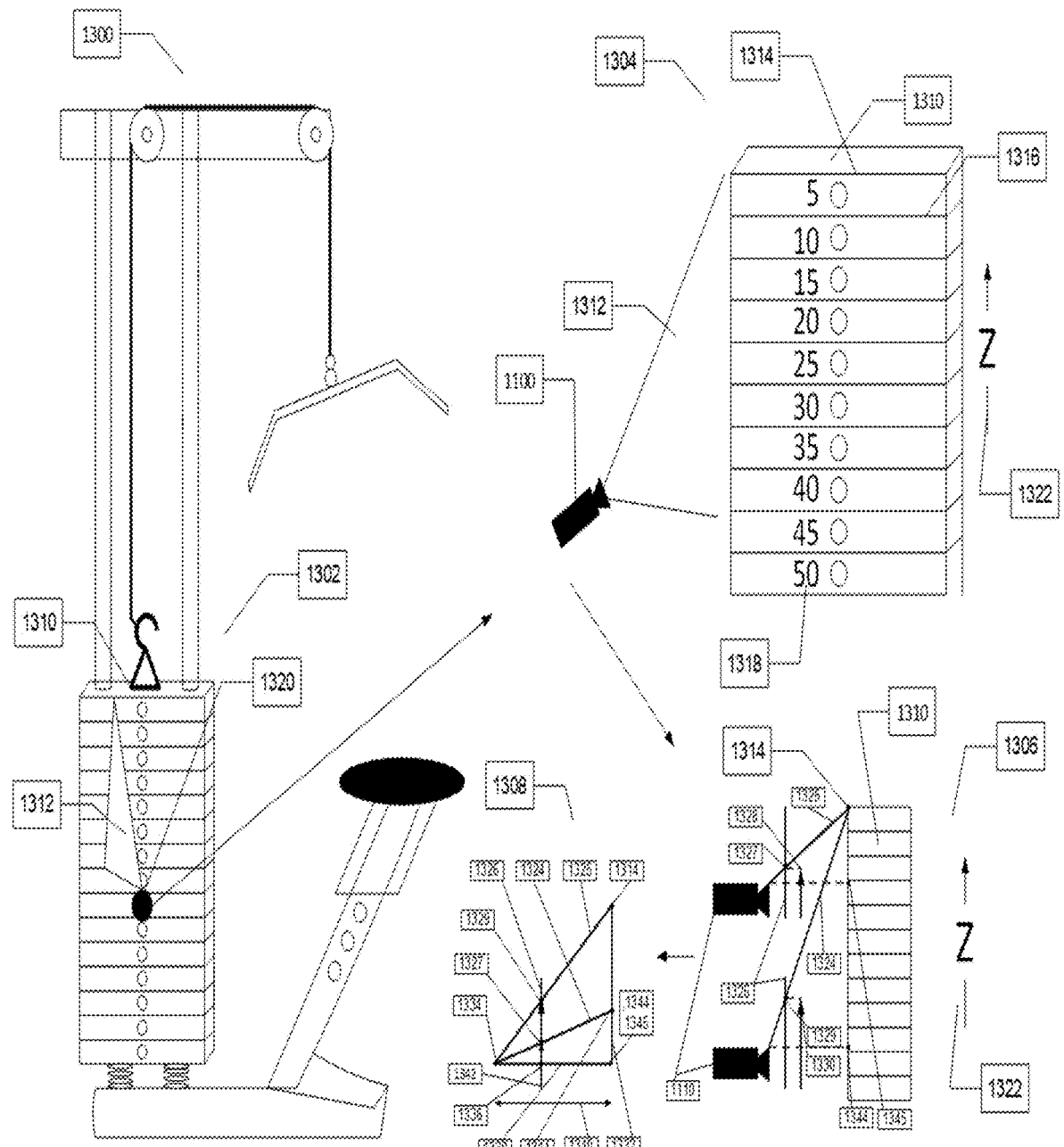
FIG. 13. Is another example embodiment of a computerized selector pin.

FIG. 13 described a possible method for calculating the resistance using the camera or sensor 1100. 1300 is a view of the entire resistance based machine. 1304 is an enlarged view of the weight stack and sensor 1100. 1308 is a side view of the weight stack and sensor 1100. 1308 is a focused view of the image geometry of the of the weight stack and sensor 1100. 1302 is an example resistance based exercise machine. 1320 is the selector pin with the sensor 1100. 1310 is the weight stack. 1312 represents the sensor viewing angle in the Z (vertical) axis. 1318 represents each one of the individual weights. 1314 is the hole in each one of the weights or another visible pattern on the weight common to all weights. 1318 is the numbering on each weight or a pattern unique to each weight.

The identification of the resistance in some of the methods below and above is based on identifying the pin 1320 location relative to the weight stack 1310. Such methods are not limited to weight stack machines, but can be applied on any exercise machine in which the resistance can be calculated or inferred from a proportional location of a part of the exercise machine relative to another part. For example spring loaded machines such as Pilates machines, Machines based on slope or angle where the location of part of the machine can be used to calculate the slope or angle and alike. In these cases the methods utilized using the selector pin can be utilized on these parts of the machine with the obvious modifications.

In U.S. Pat. No. 9,011,293 B2, below in this disclosure and in other references methods for comparing patterns and images to other images, and methods for pattern identification are disclosed. For example such methods are disclosed in U.S. Pat. No. 9,011,293 B2 for identifying an exercise performed by a user. These methods can be applied in this example. For example identification of pattern in an image can use the same methods with minor obvious modifications of replacing "exercise" in "pattern". Many additional methods are known in the art for pattern recognition.

In the example methods disclosed for example in U.S. Pat. No. 9,011,293 B2 the input from the optical sensor first goes trough corrections and filtering stages such as aberration corrections, noise reductions and alike. It is then compared to a pattern saved in the data base for identification. These and all other methods disclosed there can be used in this example embodiment.

A simple method to identify the relative location of the selector pin is to first identify a pre-defined pattern on the machine or on its surroundings. This pattern can be for example the edge of the weight stack 1310, denoted in FIG. 13 as 1314. Other examples for patterns can be the first hole in the weight stack, one of the machine pulleys or any other feature visible to the pin sensor 1100. It is recommended that the selected pattern will be stationary at the time of measurement. From the relative location of the pattern in the image the system can deduce the selector pin relative location. For example if the pattern has a certain distance in the Z (vertical) axis relative to the lower edge of the captured image the system can use known trigonometric relations calibrated with constants to find the selector pin relative location. The location in the captured image can be used to pick the pin relative location from a look up table.

The article "Where the Camera Was" from volume 77 of "Mathematics Magazine" issued at 2004 and incorporated here by reference and this article references give methods to calculate the camera position based on patterns in the image such as lines, rectangles and alike. These methods can be used here to calculate the pin relative position.

Other methods are well known in the art of computer vision. Anywhere in this disclosure when an optical sensor of camera is referred, the meaning is broader as disclosed. The sensor can be a stereoscopic camera or a sensor designed to obtain the exact coordinates of the reference pattern in space, like one based on Time Of Flight method. Thus from the exact coordinates in two different images the relative location can be calculated.

A simple method is disclosed in FIG. 13. In 1306 the sensor 1110 is displayed in two possible locations 1344, 1345 relative to the weight stack 1310 on the Z axis (1322). 1326 is the image plane of the sensor viewed from the side for each location of the sensor 1110. 1314 in a reference pattern location—for example the upper edge of the weight stack. The view is from the side 1322 shows the location and orientation of the vertical axis—the Z axis. 1324 and 1325 are optical lines from the reference pattern to where this pattern is located on the sensor intersecting the image plane. The intersection points 1329, 1327 are the location of the pattern 1314 on the image planes 1326, accordingly. 1328 and 1330 represent the relative distance on the Z axis from the bottom of the image plane to the points 1327, 1329 accordingly. The distances 1328, 1330 are different when the sensor 1110 location is different.

In view 1308 both cases from 1306 are drawn on the same image plane 1326. A line 1338 from the point on the sensor of the reference pattern 1314, perpendicular to the image plane 1326 can be drawn. 1336 is the point where this line crosses the image plane. The distance from 1336 to the bottom of the image plane can be measured by the sensor 1110. So can the distances from 1336 to 1327 and from 1327 to 1329. Based on known geometry it can be proven that the triangles formed by 1329, 1334, 1336 and 1334, 1314 and 1344 are geometrically similar. So are the rectangles 1327, 1334, 1336 and 1314, 1334, 1345. Therefore from basic geometry it can be deduced that (since the line 1334, 1344 is common to both) that the ratio between the distance 1327-1336 and the distance 1329-1336 equals the ratio between 1314-1345 and the distance 1314-1344. The distances 1327-1336 and 1329-1336 and their ration can be measured by the sensor on the image plane. Therefore if one of the distances 1314-1345 and 1314-1344 is known from calibration measurements, the other distance can be calculated. Therefore using this method and a calibration measurement for the distance on the Z axis to the pattern from the sensor, the relative distance to the sensor can be calculated using measurements from the sensor 1110 every time the relative pattern 1314 is identified in the image.

Another example method is to identify and count repeated patterns. For example 1360 is a pattern existing on every weight. The system can identify them and count how many times they repeat for example from the edge. The system can for example count the lines separating between weights to know the relative location of the pin. If for example the 2 or 3 lines closest to the pin are invisible the system can be set to know this in advance and add them to the count. In case the relative location of the pin is such that it is connected in the upper weights of the weight stack and the lines above it are out of the field of view, another method can be used or it can decided that the pin does not calculate the resistance in these cases. A possible solution to this issue is having a camera on each side of the selector pin (top and bottom for example), and thus when one side does not see the repeated pattern 1360, the other side can see it or be set to look for a different pattern.

Yet another example method can be to identify the unique pattern 1380. This pattern can be for example the value of the weight represented by this specific location in the weight stack. For example the system can use the identified pattern to pull the relative location from a table matching between pattern seen in a certain predefined location in the image and the relative location or resistance. In another example the system can use text recognition algorithms such as OCR algorithms to identify the actual resistance written on the weights which may be the pattern 1380. The system may add certain predefined offset to the identified resistance value, to account for a gap between it and the actual resistance not in field of view 1340.

Another method not based on the Optical sensor or Range sensor can be to read a pattern or indication on the weight stack trough means of magnetic signaling RFID, NFC or alike. For example each weight on the weight stack 1310 contains a marking or pattern that can be identified or read at proximity. For example each weight has a magnetic coding inside the hole in it through which the selector pin 1320 passes when it selects it. When the pin passes through it, it reads this magnetic code and decodes it to the resistance value. In this case the pin can have a magnetic code reader an RFID reader and alike added to it.

An advantage of the sensor 1110 in the system is in identifying additional resistance when there is no information about it from the relative location in the weight stack. In some resistance machine configurations additional weights can be added for example above the weight stack. Usually these additions are weight with lower weights that allow setting resistance with fractional granularity relative to what is possible using only the weight stack. The sensor 1110 can use pattern recognition and other methods disclosed to identify the presence of such additional weights and add them to the resistance calculation.

Figure 14:
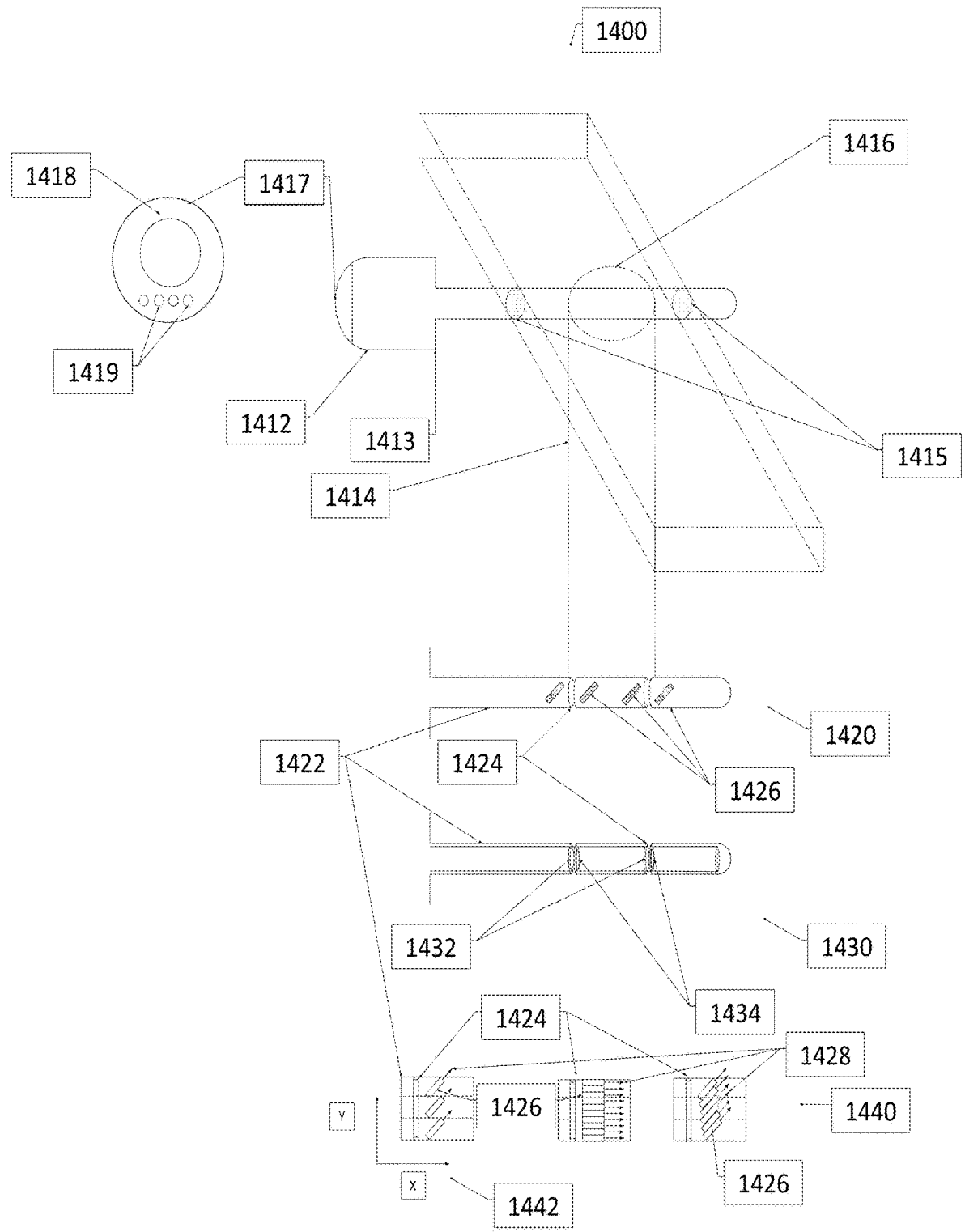
FIG. 14. Is another example embodiment of a computerized selector pin.
Figure 15:
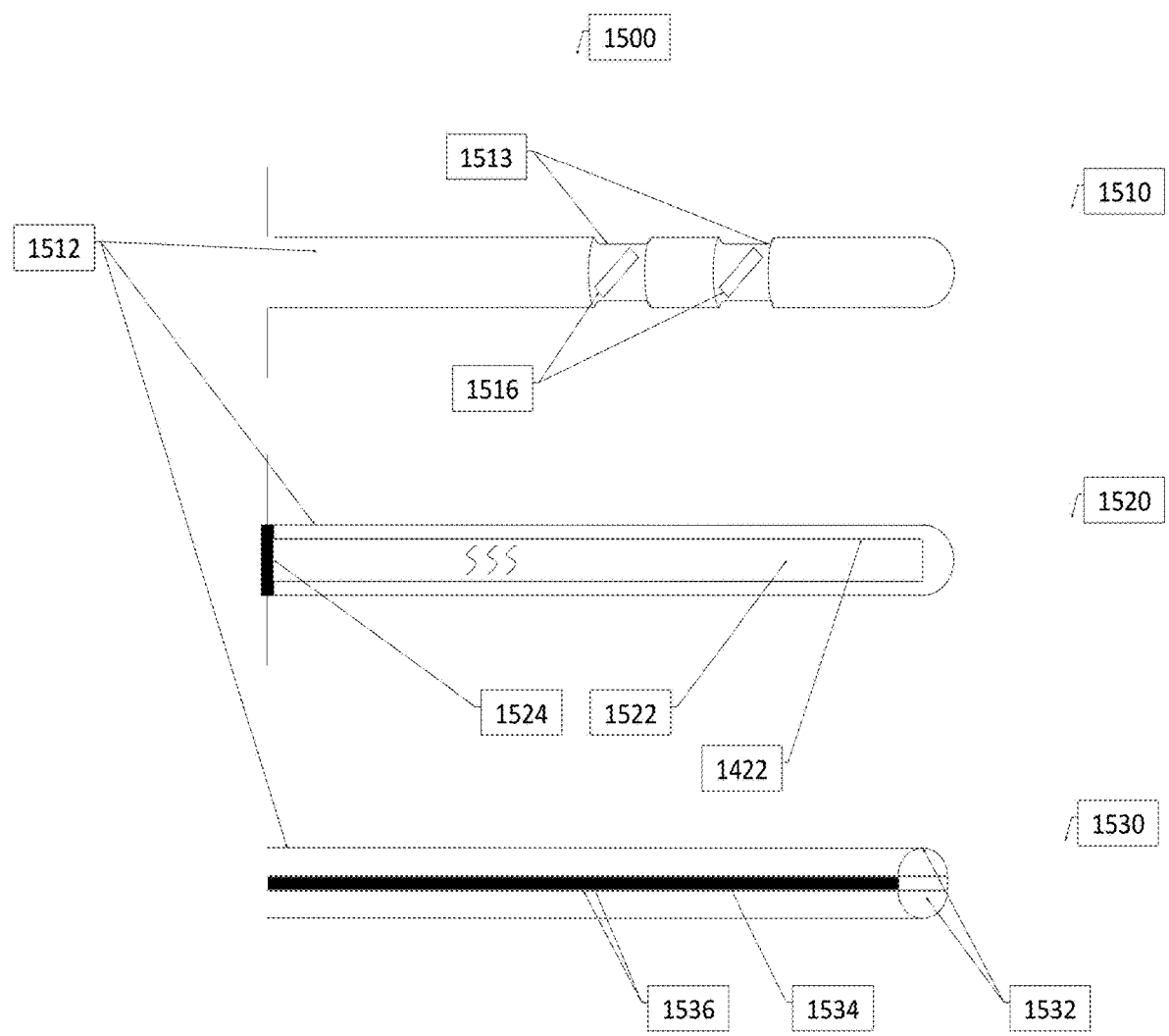
FIG. 15. Is another example embodiment of a computerized selector pin.

FIGS. 14 and 15 show additional example embodiments for the pin idea depicted in the above figures and in. U.S. Pat. Nos. 7,909,741 and 8,337,365 by Kim et al. Incorporated here by reference. The methods disclosed in U.S. Pat. Nos. 7,909,741 and 8,337,365 for measuring the weight have a few disadvantages:

1. They require that the pin will be placed in a specific orientation relative to the weight plates in order to enable the measurement. Placing the pin in a different angle then required may not allow measurement and may therefore harm the pin functionality. The requirement for placement in a specific orientation may also require additional attention from the user and thus may affect the training flow experience of the user.

2. The pin is required to withstand heavy loads from one hand, and be relatively small from the other hand. It is hard to fit the mechanisms described in U.S. Pat. Nos. 7,909,741 and 8,337,365 in an acceptable size pin and still make it strong enough to withstand the required loads.

FIGS. 14 and 15 show several example embodiments of the pin that allow the load measurement and/or documentation given the requirements of a relatively small pin that is required to withstand heavy loads.

In FIG. 14, example embodiment 1400, 1412 is the pin 1414 is the weight plate, 1415 are the edges of the hole in the weight 1414 for the pin entrance, and 1416 is the central hole. 1417 is the back of the pin handle portrayed from back view on the upper-left corner of FIG. 14. 1448 is a screen found on the back of the pin 1412. 1419 are a plurality of operation buttons. The screen and buttons are input and output measures for the pin 1412. The screen 1418 can be a touch screen eliminating the need for buttons 1419. Using the screen and buttons it is possible to enter the weight selected or the weight which will be selected in the future. This may eliminate the need for measuring the weight, thus allowing a much simpler build of the pin shaft portion. The input/output devices/measures may be further used to enter additional data such as the number of repetitions required, the user data such as weight/height etc., select training plan and more. The output measures such as the screen can be used to view data such as the number of repetitions done, the next exercise in the plan, have a feedback on the speed of exercise performance and alike.

The weight data can be inputted to a WCD or a mobile device and transferred wirelessly or in a wired manner to the pin. The weight and other data can be entered vocally via WCD or mobile microphone or vocally directly to the pin. For enabling vocal entering of the weight and other data the pin may include a microphone and voice recognition software found on its computing unit, or interface to a software found on a remote computing system as disclosed in reference to FIG. 2.

The selected weight may be fed to the pin from the training plan. The training session plan may be documented in the system's computing system or in other computing system, and may be transferred to the pin. The session plan may include the weight to be selected in each exercise. By tracking the exercise performance order or based on the using selecting or entering the current or next exercise the user is going to do the system may know or receive the required weight. This way the pin may know the required weight, thus eliminating the need for measurement. The required weight may be presented on the screen 1418 and/or outputted as voice using speakers on the pin or somewhere else in the training environment for the user. This way it would be easier for the user to connect the correct weight.

Another feature assumed to be novice is using a magnetic switch (not shown) for electronically activating the pin or identifying exit and entrance to power save mode. The weight plates 1414 are usually made of cast iron or other material which reacts to magnets. It is also costumed to put a magnet in the handle part of the pin 1413 closest the weight 1414. This way there is a magnetic attachment between the pin 1412 and the weight 1414. The attachment prevents the pin from moving when the weights 1414 moves. The handle portion 1413 of the pin 1412 may further include a sensor to sense this magnetic attachment or the magnetic pull (for example using a load cell to sense the pull). Sensing a magnetic attachment or the magnetic field generated between the magnet and the weight 1414, or a magnetic pull, above a certain threshold may be used to turn on the electronics in the pin or take it out of power save mode. When the pin is not in use or taken out of the weight 1414 the sensor may indicate this and put the system back to power save mode or turn it off. Other methods for achieving power save may involve the accelerometers if exist which may switch out of power save mode when sensing acceleration above a certain threshold. Of course the weight measuring can also be used for that purpose in a similar manner.

At 1420 another possible example embodiment is depicted. 1422 is the shaft portion of the pin. 1424 are optional revolved cuts (1012) also referred to as slits in the shaft portion preferably (but not limited to) located inside the diameter of the central hole 1416 but outside the location where the central rod touches the pin shaft portion 1422. The slits 1012/1424 are aimed to focus the stresses and strains in the pin in order to improve the measurement, however measurement may also be accurate enough without them. The slits if exist are preferably as shallow as possible for focusing the strains and stresses without weakening the pin too much.

1426 are strain gauges coupled to the surface of the pin 1422 near the slits 1424. 1428 are arrows marking the direction in which the strain gauge is most sensitive to strain. The book by Karl Hoffman, "An Introduction to Measurements using Strain Gages" incorporated here by reference, and the Components Catalog and Data Sheet—"Strain Gages for Transducer" by ZEMIC give methods for using strain gauges which are used in this disclosure. If the slits 1424 do not exist the strain gauges preferred locations are inside the diameter of the central hole 1416 but outside the location where the central rod touches the pin shaft portion 1422. 1440 shows example schemes for locating strain gauges on the circumference of the pin shaft portion 1422. 1440 shows the circumference of the pin 1422 spread for convenience. 1424 is the slit and 1426 are the strain gauges. 1442 is a coordinate system used in this explanation. X is parallel to the axis of the shaft portion 1422. Y is parallel to the shaft portion circumference. Two non limiting example placing of strain gauges are shown aimed at allowing measurement at every orientation of the pin inside the hole 1415. At the left side preferably linear strain gauges are put in a known angle (preferably 45 degrees) relative to the shaft portion 1422 axis (X). The entire Y axis is covered by projections of the strain gauges 1426 in order to cover all possible orientations.

At the right side the entire circumference is covered with linear strain gauges in order to cover all possible orientations. Other configurations of strain gauges known in the art can be used.

When stress is applied to the shaft portion 1422 by the central rod and weight 1414, the slits 1424 focus it and a strain in their area is formed. The strain gauges 1426 measure this strain and as a result of measuring the strain the stress can be calculated in methods known in the art.

At 1430 the most of the pin shaft portion 1422 is hollow. Strain gauges 1434 are attached to internal walls 1432 made inside the shaft portion 1422 adjacent to the slits 1424 or under them. If the slits do not exist the walls are preferably located in the preferred location of the slits as explained above. The strain gauges 1434 are preferably aimed at measuring radial strain and can be for example of the rosette type or KA type measuring radial strain. When stress is applied it is focused by the slits to the wall areas which experience strain. The strain gauges 1434 measure this radial strain and as a result of measuring the strain the stress can be calculated in methods known in the art.

FIG. 15, embodiment 1500 is additional possible embodiments. 1512 is the pin shaft portion. 1513 are wide slits, preferably wider than the slits 1424 preferably located inside the diameter of the central hole 1416. 1516 are strain gauges attached to the circumference of the slits in a similar manner the gauges in FIG. 14 are attached to the pin. This scheme have several advantages over 1420. For example: In 1510 the strain gauges are located inside the slits and can be covered by material for example elastic material like for example rubber or plastics to protect them from the environment and give the pin a better visual look. The operation is similar to 1420.

In 1520 the shaft portion 1512 is hollow. A fluid 1522 preferably hydrostatic is found inside the shaft portion 1422. A hydrostatic pressure measuring device 1524 preferably close to the pin handle portion measures the fluid hydrostatic pressure. When stress is applied on the shaft portion 1422 it causes strain which in turn transfer a portion of the stress to the fluid. Since hydrostatic pressure is equal anywhere in the fluid 1522, it can be measured by the measuring device 1524. Methods known in the art can then be used to calculate the stress and the weight applied as a result.

In 1530 the shaft portion 1422 in made out of 2 parts preferably halves 1532. 1534 is an elastic insulating material found between them. 1536 are optional plates of conductive material found on both sides of the elastic material. Alternatively the two halves 1532 can be used as the plates of conductive material. When stress is applied on the shaft portion 1422 the halves induce strain on the elastic material 1534. As a result the distance between the conductive plates 1536 changes. This causes change in capacitance which can be measured. This way the strain of the elastic material can be measured. If the properties of the elastic material are known such as its Young modulus, the stress can be calculated in known methods. To make this example embodiment less sensitive to the pin orientation the pin shaft portion 1512 may be divided into more then portions separated by an elastic insulating material between them.

The past few examples were detailed examples of computerization of exercise devices. Using the same methods and principles other exercise devices can be computerized. Below are some more examples. Some of them are given in less detail. From the details that are given using the principles and methods disclosed in the past examples and in the references it should be possible for the skilled in the art to fully understand and build all the proposed inventions. For example in the following examples the entire harnessing configuration is disclosed. The skilled in the art can use the methods and configuration given and apply them to the harnessing configuration in the proposed inventions with modifications obvious to the skilled in the art.

Figure 16:
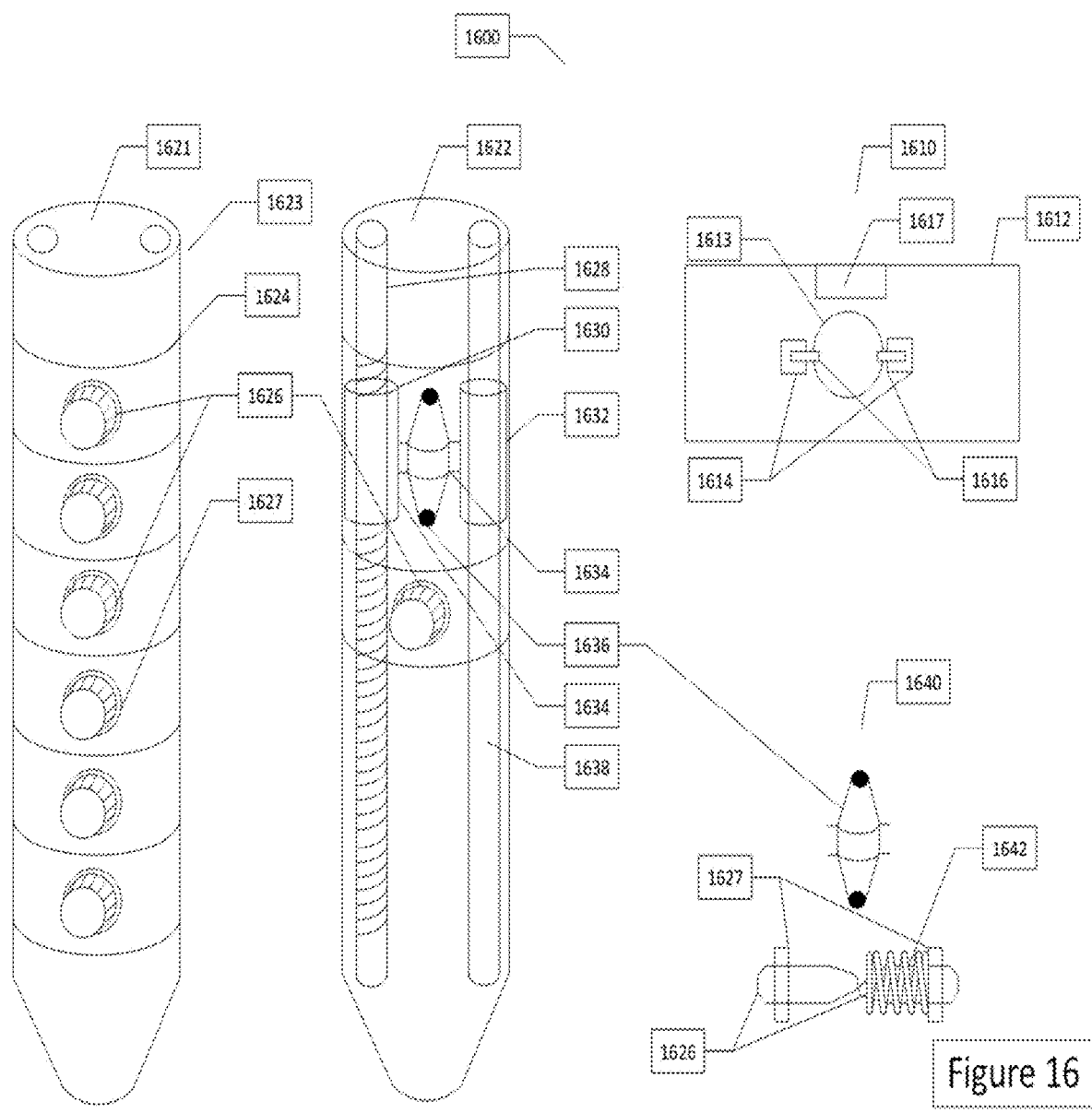
FIG. 16. Is an example embodiment of a computerized Gym resistance machine.

FIG. 16 depicts example embodiments 1600 that allows automatically setting the resistance in a gym machine. In 1610, 1612 is a weight plate (820) from top view, 1613 is the central hole 840 trough which the central rod 830 is passing. 1614 are solenoids inside the weight plate 1612. The solenoids are controlling pins 1616 which can be pushed by the solenoids 1614 and/or springs (not shown) into the holes in the central rod. The pins can also be extracted by the solenoids 1614 and/or springs (not shown). By having the pins 1616 enter the holes in the central rod the weight plates are coupled to the central rod and the weight is selected.

1617 is the electronic block. It contain the electronics required to control the solenoids 1616 (not shown), may contain a battery (not shown) for supplying the electronics and solenoids power. It may also contain a generator (not shown). It may contain wired or wireless communication components, a processing unit, sensors like accelerometers and additional components mentioned in conjunction with FIG. 1, FIG. 2 or mentioned in this disclosure.

To select resistance a computing unit in one of the plates electronics block 1617, or mounted somewhere else on the machine, or external (can be in a smart-phone or WCD) may calculate which is the lowest plate to select. It can then issue a command trough wireless or wired communication to the correct plate 1612, which in turn activate it's solenoids and attach itself to the central rod.

Communication to the individual plates 1612 can be wired: for example the plates 1612 are in many cases made out of cast iron, which is conductive for both electricity and magnetism. At rest the plates are usually touching each other and so a conductive path between all plates 1612 is formed. Each plate 1612 may be given for example a number or a code. After the processing unit decides which weight to select it can transmit the number or code in magnetic or electric pulses trough the plates 1612. The plate that identifies its code or number being transmitted can then turn on the solenoids and connect.

In this example embodiment and the others dealing with automatic setting of resistance in gym machines or exercise machines in general, it may be advantageous to preserve the ability to select the resistance manually. A non limiting example how this can be achieved for the example embodiments of FIG. 16 and others is hereby given The central rod 830 may be configured to include both holes for a plurality of selection pins (1614, 1626 etc.) and both notches and gaps between plates (The plates can still touch each other in areas not abstracting the flat pin). This way the automatic resistance setting mechanism can use the holes while the manual mechanism can use the notches and flat selection pin, or vice versa.

The second example embodiment in FIG. 16 is explained: 1621 and 1622 are two views of the central rod. Movable pins 1626 are extruding the rod 1621. These pins are preferably found on both sides of the rod so to enter the holes from within, from both sides of the central hole. The pins 1626 are configured so that their location will be in front of the holes in the plates, when the machine is at rest. The movable pins 1626 are sliding in and out from the rod 1621 trough bearings 1627.

Each pin can be controlled by a corresponding solenoid and spring (not shown), like in the example embodiment 1610. Similar electronic components (not shown) and control methods to 1610 can be used. The rod 1621, or at least the outer section of it may be made out of sections 1623 where 1624 describes the borderline between the sections. The sections size may correspond to the weight plate 1612 size, and the border between the sections 1624 may correspond and/or aligned to the border between the weight plates 1612 in rest position or weight change position.

1622 is an example embodiment showing how to selectively extract the required pins without the use of a solenoid for every pin. 1622 is describing similar setup in which there are pins 1626 in the central rod for every hole, similar to 1621. Only one of the pins 1626 is shown in the FIG. 1600 for the sake of clarity, but the principle is easily generalized to multiple pins configured as in 1621.

1628 is a screw rod and 1630 is a moving cart mounted on it. A motor or a stepper motor can be in the cart 1630 or somewhere else along the screw rod rotating it. The cart has a slide bearing 1632 supporting it moving on a sliding rod 1638. The screw rod 1628, cart 1630, slide bearing 1632 and slide rod 1638 form a linear positioning system to position 1634. Other forms of linear positioning systems known in the art can be used, for example it is maybe sufficient to use a screw rod and a stepping motor for the linear positioning of 1634.

1634 is a rigid body for which the top and bottoms 1636 are preferably cone shaped. The rigid body 1634 is positioned vertically in the level of the pins 1626 that are desired to be extracted. This can be seen in 1640. 1640 shows the rigid body 1634, two pins 1626, a spring attached to one of the pins 1642 and the slide bearing 1627 connecting the pins to the central rod 1622. Springs 1642 are attached to all pins, and retract them or keep them inside the central rod 1622 when the rigid body 1634 is not mechanically pushing them out.

The rigid body 1634 has a central diameter big enough to push the pins to the desired extent.

When a certain weight plate is required to be selected, the linear positioning system (1628, cart 1630, slide bearing 1632 and slide rod 1638), position the rigid body 1634 vertically so that it will be in the height of the pins 1626 wished to be extracted to engage the weight plate. The pins 1626 are preferably also configured in a cone shape on their side that points to the center of the central rod 1622. The preferably cone shaping of the pins 1626 and the rigid body 1634 help the rigid body 1634 push the pins 1626 against the springs 1642 and extract them to engage the weight plate 820 by extracting the pins 1626 trough the holes. When a different weight plate 820 is required to be engaged, the rigid body is moved to another location by the linear positioning system. The springs 1642 then retract the pins 1626.

Electronics block (not shown) can reside for example in the top of the central rod 1622, 1621, above the level of the moving parts. It can also reside for example in the bottom of it—below the level of moving parts, or in any other location chosen by one skilled in the art. This block may comprise a processing unit 215, a data repository system 214, I/O subsystem 220, a plurality of wireless or wired communication devices ad any other part of the system described in conjunction with FIGS. 1 and 2. It may also comprise a battery or a power source such as a fuel-cell or any other known in the art. It may also comprise a generator to produce power from the user's movements.

The electronics block may also include accelerometers gyros or motion detectors.

Using the electronics block or other methods such as the distance sensor of FIG. 3, the example embodiments 1621, 1622 can know the resistance used (by connecting it or by measuring it), they can count repetitions, measure the exercise paste, measure the motion range, identify the exercise, correct it and alike in methods already discussed more than once in this disclosure.

Figure 17:
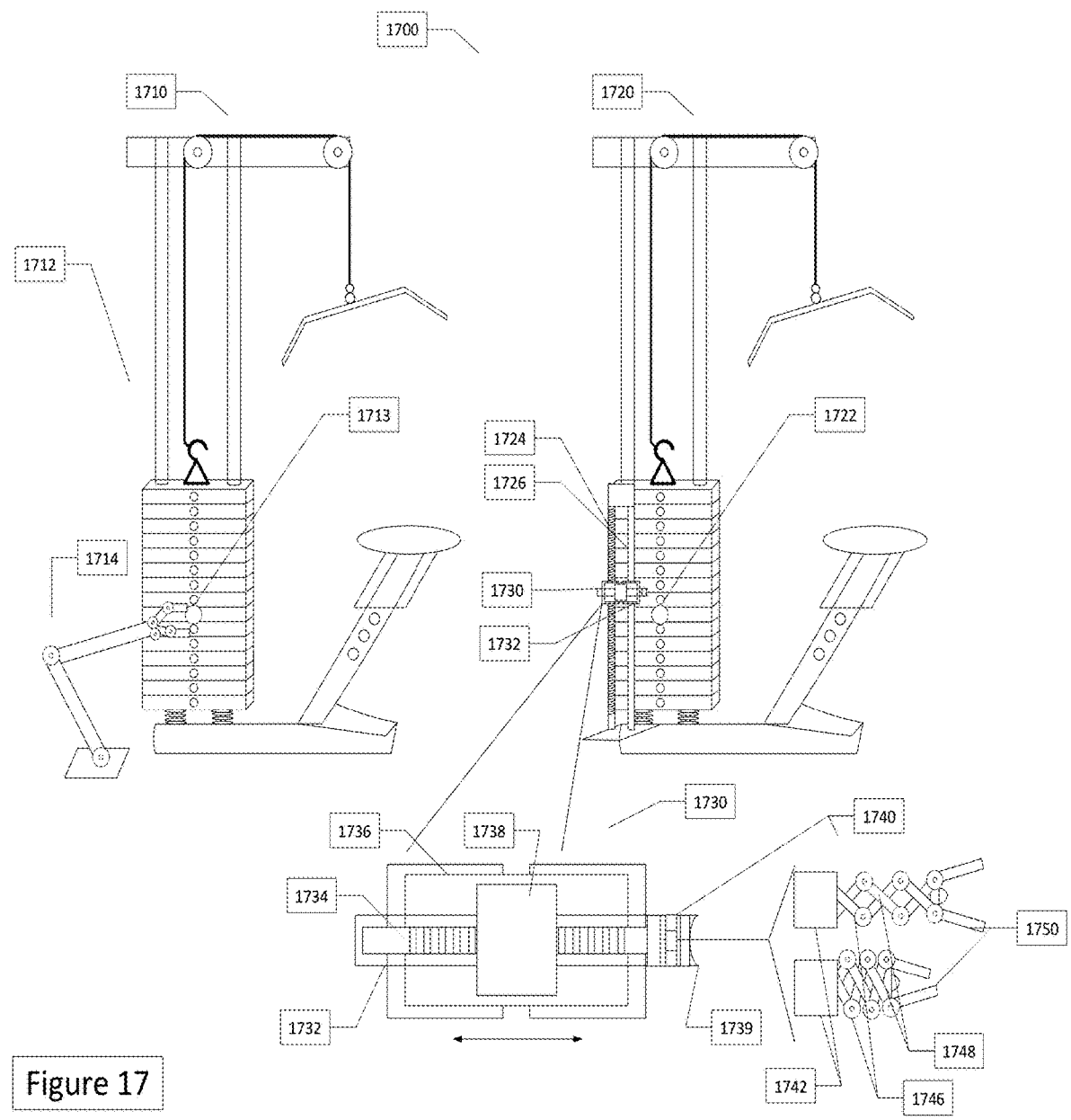
FIG. 17. Is another example embodiment of a computerized Gym machine

FIG. 17, example embodiment 1700, describes more example embodiments for selecting resistance automatically in a gym machine or similar resistance machines. In this case the example embodiments are external to the machine and require minimum or no changes to the machine. They also do not require substitution of parts such as for example the selecting pin or central rod.

In 1710 a robotic arm 1714 adjacent to the gym machine 1712 or attached to it is used. It is used to move the selection pin 1713 from its previous location to its desired location and select the resistance. The robotic arm 1714 can be designed and integrated in methods well known in the art of mass production machines.

In 1720 a linear positioning system comprising, a screw rod 1724 cart 1730, slide bearing 1732, slide rod 1726 and step motor (inside the cart—not shown), or similar linear positioning system known in the art, moves a cart 1730 to the pin 1722. Control of the position of the cart can be done in methods known in the art such as optical identification, open loop, micro switches, mechanical or optical identification of the border between plates etc.

1730 is a magnified top view of the cart. 1734 is a screw rod or linear cog rail. 1738 is the electronics block and step motor. Together 1734, 1738 are another linear positioning system positioning 1740, which is an arm for grabbing the pin 1722, near the pin 1722. 1739 is the arm 1740 connection to the linear positioning system 1730. 1742 is the arm 1740 base.

1740 is an example embodiment of the arm grabbing the pin when required. In 1730 it is viewed from the top and 1740 is a side view. The arm comprises rods 1748 and bearings 1746 connecting them. It is actually a scissor linkage acting in a similar manner to a scissor lift. At the end of it attached two "fingers" 1750 or rods to grab the pin. Unlike the drawing the preferred configuration is the "fingers" being tangent to the scissor assembly axis, as to grab the pin from the side. The fingers can be implemented and operated in methods well known in the art.

When a new resistance setting is required the first linear positioning system (1724, 1730, 1732, 1726) positions the cart near the pin. The second linear positioning system (1734, 1738) extracts and position the arm 1740 side by side with the pin. The fingers 1750 grab and tighten around the pin 1722. The scissor assembly 1746, 1748 then extracts and push the pin 1722 out of the hole in the weight plate. Then the first linear positioning system (1724, 1730, 1732, 1726) positions the cart above the required setting weight plate. The scissor assembly 1746, 1748 then retracts and push the pin 1722 into the hole in the selected plate. The second linear positioning system (1734, 1736) then retracts and moves away from the pin in order not to obstruct the exercise machine movement. This concludes the setting.

To measure repetitions, movement range paste etc. additional methods can be used such as the distance meter of FIG. 3, accelerometers and other methods discussed in this disclosure.

In an example implementation mechanical means integrated in the exercise machine can also be used to measure repetitions etc: a load pin can be used as the rotating axis of a pulley, or as a suspension base to other mechanical element such as a leaver or a cable. It can measure the load or force exerted on this pulley or leaver. Measuring this force or load can give the resistance using the mechanical transfer function between the resistance and the element. Using the methods described more than once throughout this disclosure such as 340 and the methods described at the beginning of the disclosure, the resistance, repetitions, paste and more can be found.

Measuring the rotations of a pulley a leaver or any rotating part or axis in the machine can also give repetitions, movement range, paste etc. in methods described in this disclosure. The actual measuring can be done in methods detailed in this disclosure such as using an encoder or other known in the art.

Figure 18:
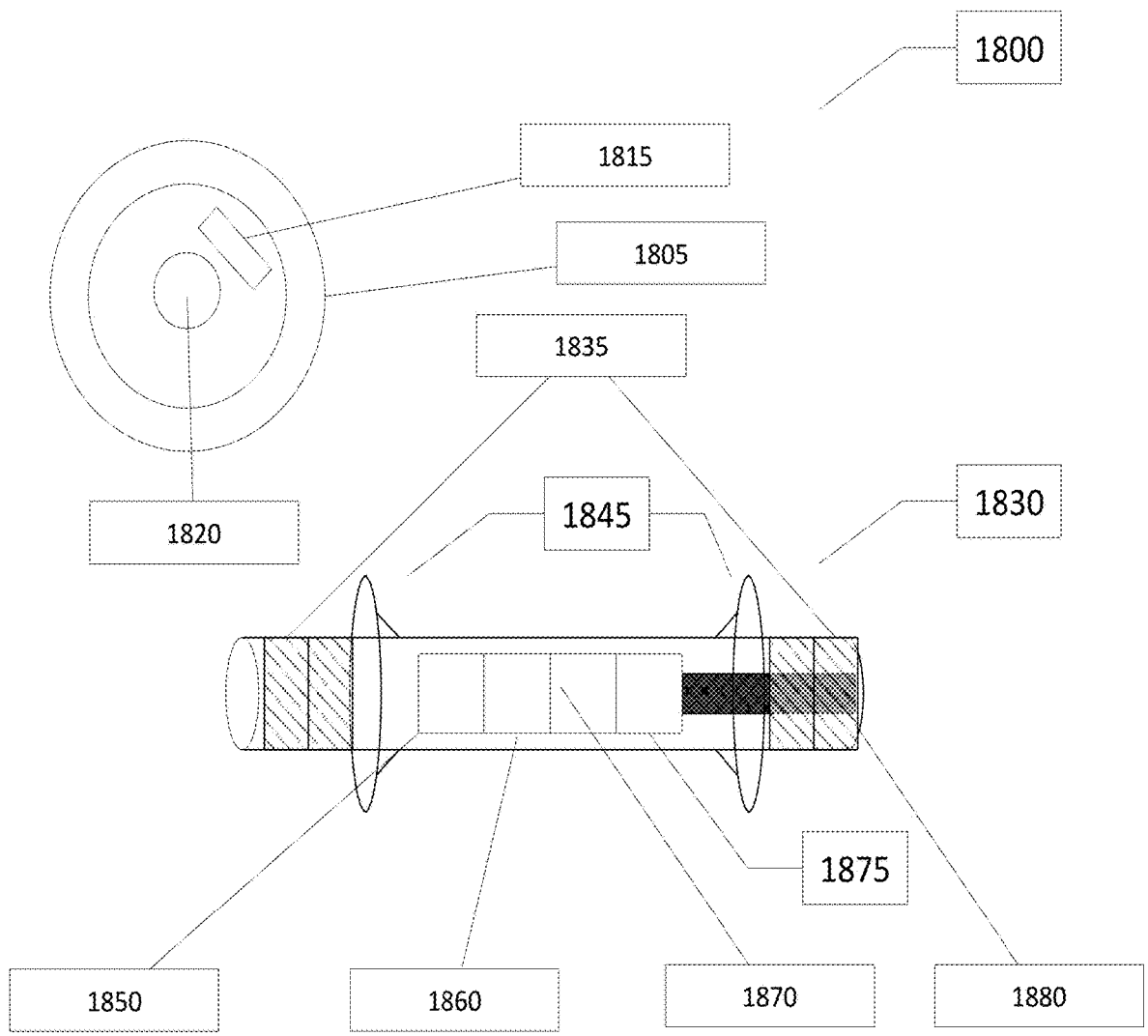
FIG. 18. Is an example embodiment of a computerized free weights.

FIG. 18 depicts another example embodiment. In this case for free weights. 2330 is the pole on which the weight plates are mounted in order to produce a weight with the proper resistance. 1805 is an example weight plate. 1845 are mechanical stoppers holding the weight plates in place from one side. On the other side a fastener usually spring based (Not shown) hold the weights in place. The pole 1830 goes through the hole 1820 in the weight plate 1805. Several weight plates 1805 may be mounted on each side of the pole 1830. 1815 is a possible RFID chip attached to the weight plate by adhesive material or in any other method known in the art. 1835 is a plurality of load cells array that may be separated from one another and maybe configured to measure radial force or pressure on the pin. 1850 is the electronic board that may reside inside the pole the electronic configuration on it may resemble the configuration in the example above. 1860 is a possible RFID reader. 1870 is an accelerometer. 1875 is a possible linear generator or other form of generator or mechanical to electric energy conversion device. Its purpose is to convert the mechanical energy from the pole movement when the trainee exercises to electrical energy and charge the battery 1880.

As in the other embodiments and using the methods described above and known in the art the accelerometer 1870 can be used to find the acceleration, speed, orientation and maybe even location of the pole. It can also be used to count repetitions in an exercise performance.

The resistance determined by the weight plates loaded on the pole can be identified by reading the RFID tags 1815 on the weight plates 1805. Each RFID tag 1815 may contain the data on the weight of the plates it is attached to. Thus the pole can sum up the weights of the plates mounted on it. To prevent taking into account plates which are not mounted the RFID range may be very short, or a filter that filters RFID signals coming from larger distances (according to signal strength for example) may be utilized. The RFID protocol in this case may be replaced by any other suitable protocol.

Another approach to recognizing the resistance mounted can be similar to the pin example embodiment. Load cell arrays 1835 may be used to measure the force the plates are applying on the pole. Here too the accelerometer may be used to vector subtract the acceleration caused by the user. Some of the pressure on the load cells can be applied by the fastener. This additional load can be filtered or subtracted from the force measurement if its quantity is known in advance. Another method can be separating the load cell array to several arrays each one the width of a weight plate. In this case the fastener will pressure the outmost array load cell which measures pressure. If the two outmost load cells that feel pressure will be filtered or not taken into the calculation the problem will be solved.

Additional sizes such as performance speed, motion range, energy burn in calorie and alike can be thus calculated in methods described above or known in the art.

The example of FIG. 18 is also applicable to Kettlebells which can be viewed as free weights.

In this case too parts of the system may reside outside the pin and the communication may be wireless. The above example of using an eternal device such as WCD or smartphone display or speaker or communicating with an external DB or computing system apply as well.

Figure 19:
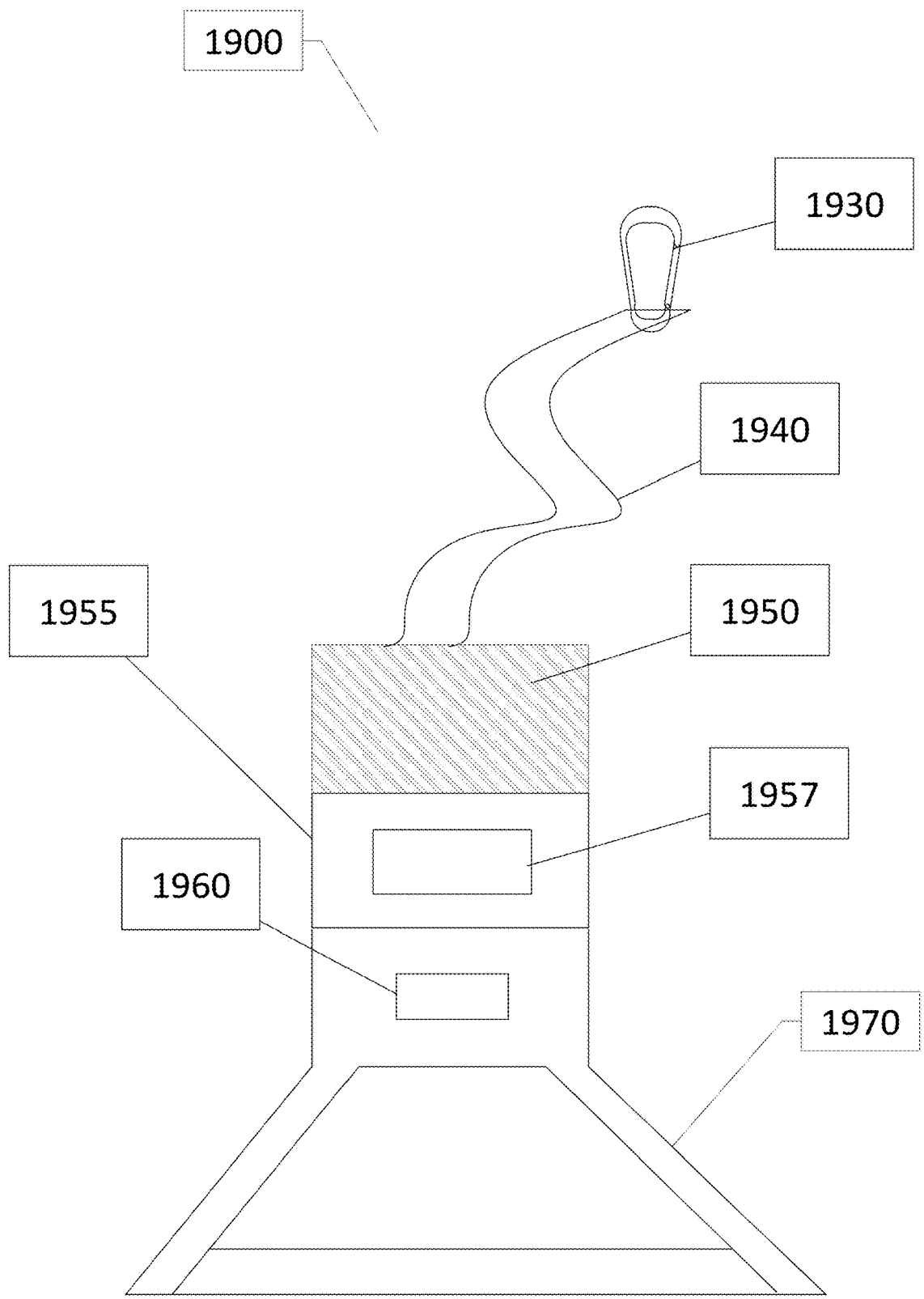
FIG. 19. Is an example embodiment of a computerized TRX suspension trainer.

FIG. 19 is an example embodiment aimed for TRX suspension trainer or other forms of strap or suspension trainers (such as for example Olympic Rings). 1900 is the example embodiment. 1940 is a strap for harnessing the system 1900 to external harnessing point such as the horizontal bar. 1930 is a Karabiner used to fasten the harnessing. 1950 is a load cell array configured to measure the force between the harnessing strap 1940 and the system chassis 1955. 1957 is the electronics board which may be configured as in the examples above. 1960 is an accelerometer and 1970 is a frame for harnessing the TRX suspension trainer.

In this example embodiment the load cell array can measure the force the user exerts on the TRX suspension trainer transferred to the system chassis 1955 trough the harnessing frame 1970. The accelerometer may measure the system and straps inclination or direction.

Using the load cells and or the accelerometer it is possible to count repetitions in the methods described above. It is also possible in some cases to measure the resistance as being the force the user exerts on the straps and passes to the load cell array.

In this case too parts of the system may reside outside the pin and the communication may be wireless. The above example of using an eternal device such as WCD or smartphone display or speaker or communicating with an external DB or computing system apply as well.

Figure 20:
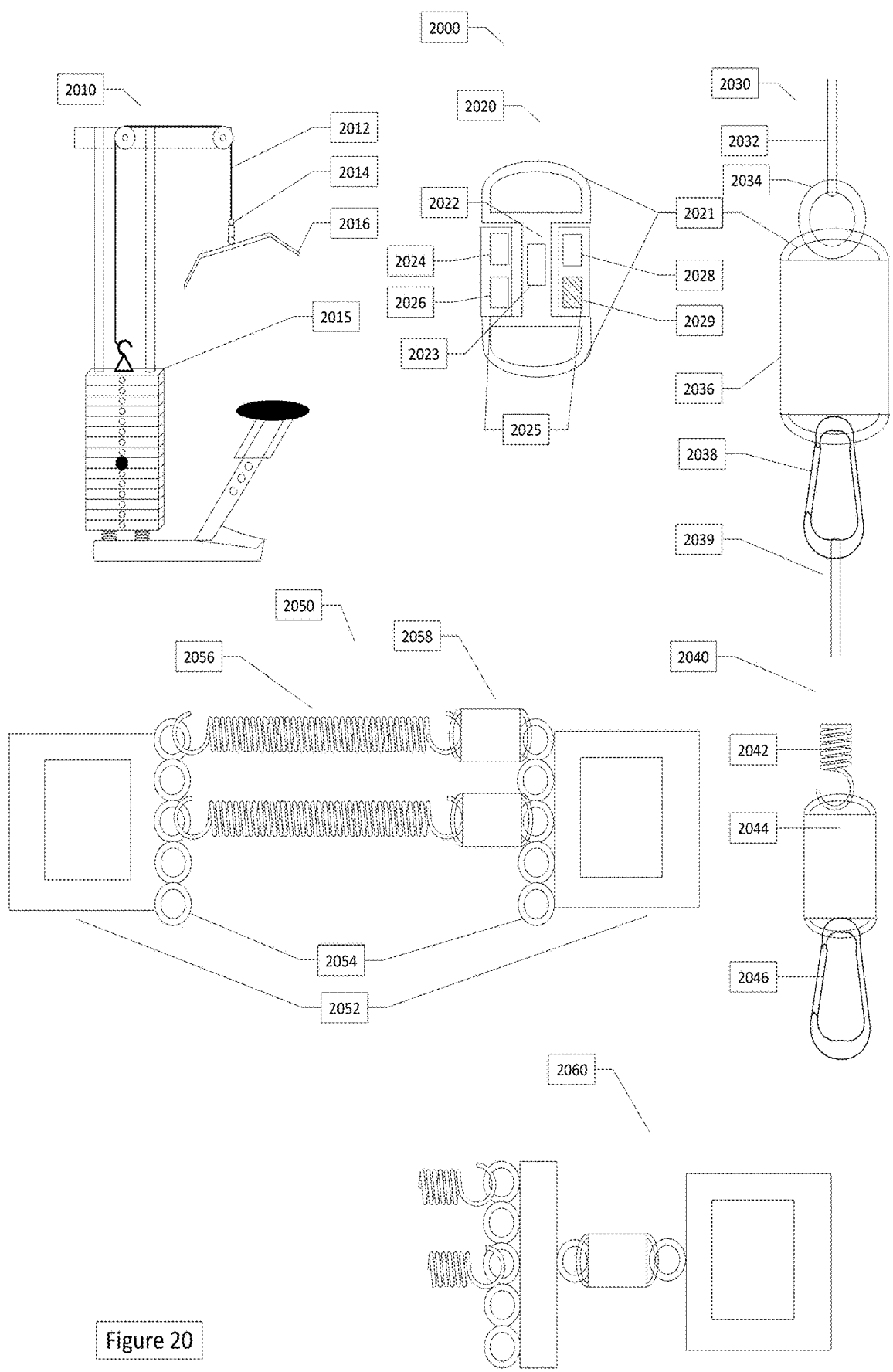
FIG. 20. Is an example embodiment of a computerized spring loaded machines.

FIG. 20 describes another example embodiment 2000. 2010 is a non limiting example of a gym machine. 2012 is the cable that connects between the resistance 2015 and handle 2016. 2014 is the example embodiment connected between the cable and handle.

2020 is a close up on this example embodiment. 2021 are ring type assemblies, used to connect the apparatus to external apparatuses. 2022 is a bar of material connecting the two rings. The rings 2021 and the bar 2022 can be one piece. 2023 is a Strain Gauge that measures the bar 2022 strain. Alternatively it can be replaced by a load cell. The bar itself connecting the rings can be replaced by a load cell or a strain measuring device (for example a spring type). The idea is that the Strain Gauge 2023 measures the strain that develops between the rings 2021. This idea can be implemented in the apparatus 2020 in any way known in the art.

2025 are electronic housings or boards. They are mounted so they will not interfere or be affected by the strain measuring. In the example they are mounted and connected to one of the rings (the bottom one) but not to the bar or other ring in order not be exposed to the measured strain. On the electronic boards or housing depicted accelerometers array 2024, a computing system or processor 2026, wireless communication unit 2028 and a battery 2029. Other components not shown can include a generator, I/O subsystem 220, a plurality of wireless or wired communication devices and any other part of the system described in conjunction with FIGS. 1 and 2.

By measuring the strain or between the cable and handle the apparatus 2020 can measure: the resistance, the acceleration the repetitions, movement range and more using the methods described several times throughout this disclosure, for example when describing the selection pin example embodiment of FIG. 10. The use of the accelerometers 2024 can further assist that as described before. Additional attributes like calorie burn and more can also be calculated as described before.

The apparatus 2020 may also comprise a marker or reflector or repeater for optical or acoustical or any other wavelength or spectrum type. This can be used for tracking the apparatus location in space as described for the other example embodiments such as the selector pin of FIG. 10.

2030 describes another application of the example embodiment 2020. In this case cables 2032, 2039 are attached to both sides of the apparatus 2036 (2020). One cable using a ring 2034 and one using a carabineer (2038). The example embodiment 2020 can thus be connected to any cable in an exercise machine, and can even split one cable to two cables.

In 2040 the example embodiment 2044 (2020) is connected to a spring 2042. From the other side of 2044 there can be a carabiner 2046 or any such fastening apparatus known in the art. If the spring is used as the resistance element, the example embodiment can thus measure the resistance at any moment from measuring the strain between its rings 2021. All other measurements and calculations such as paste, repetitions, calories etc. are thus also possible for spring based resistance.

2050 shows an application of the example embodiment 2058 (2020) to a spring loaded exercise device. This is the device known as "Chest Expander" comprising two handles 2052, Rings for mounting springs 2054, and springs 2056. The devices 2058 can measure the resistance and all other measurements mentioned above at any moment. They can communicate with each other to synchronize the total resistance and the other measurements. Only one element 2058 can be used as in the connection depicted in 2060.

Figure 21:
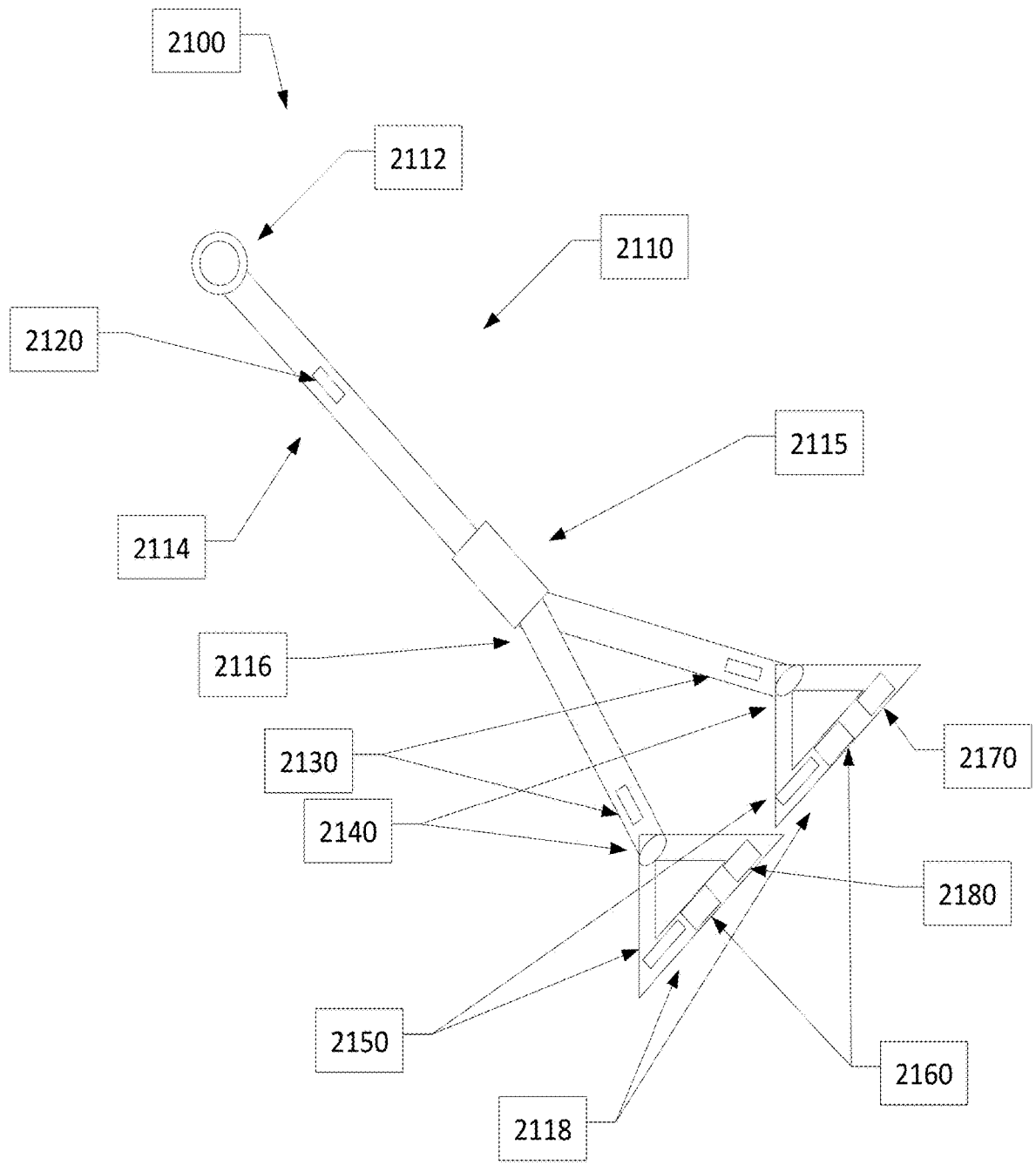
FIG. 21. Is another example embodiment of a computerized TRX suspension trainer.

FIG. 21 is a schematic drawing of the known TRX suspension trainer exercise equipment 2100. The equipment 2110 typically includes a Carabiner 2112, the intermediate anchor loops 2114, the main loop 2115, the straps 2116, and the handles 2118 while the foot cradles are not shown.

A mechanical force measurement device 2120 such as a load cell or a strain gauge can be attached to the intermediate anchor loops 2114. It may replace part of the loop or strap.

There can be also force measuring device 2130 on each strap or on a single strap. Accelerometers 2140 and transceivers 2150 can be found in the handles and are employed using any known method for use in location fixing as described in this disclosure and known in the art. Pressure sensors 2160 may also be used in the handles. They can be comprising components such 360, 370 in FIG. 3 or others known in the art. They can be configured to detect when the handle is in use and may be also configured to measure the force applied on the handle.

A modem 2180 for wireless connection with an external computing system of any kind, or various components supporting wireless communication, for example the computing system 2170, may be outside the TRX and reside in a user's mobile device. In an embodiment, the computing system 2170 can manage the system as described in FIG. 2 (and can also be external). All the components 2120-2180 may be connected by wires or by any form of wireless connection known as described above. The proposed invention may include all or some of them and also additional components not shown as described above.

The components described can be used for any of the usages described in this disclosure or references. For example, the force measuring devices 2120 or the pressure sensors 2160 may help produce the resistance applied. They may also be used to count repetitions by finding the cycle in the force measured pattern, counting the cycles, or by any other method mentioned in this disclosure or known in the art. The accelerometers 2140 may also be used to count repetitions. They can also be used to tell the angle of the straps at each stage and the direction of their movement. The angle of the straps and their direction may help the system identify the stage in the exercise, the exercise itself, and whether an exercise is done correctly. The transceivers 2150 can help external sensors of the system identify the exact location of the handles at each moment and enhance the abilities of identifying the exercise and correct performance as described above.

These transceivers 2150 may be simply optical IR or any other wavelength spectrum markers. They can be used as part of the body mapping method as described above, as can the accelerometers and the other sensors. Using the descriptions above, one skilled in the art can easily understand how other training measures such as calorie burn, distance traveled, and the like can be obtained using this embodiment of the system.

Figure 22:
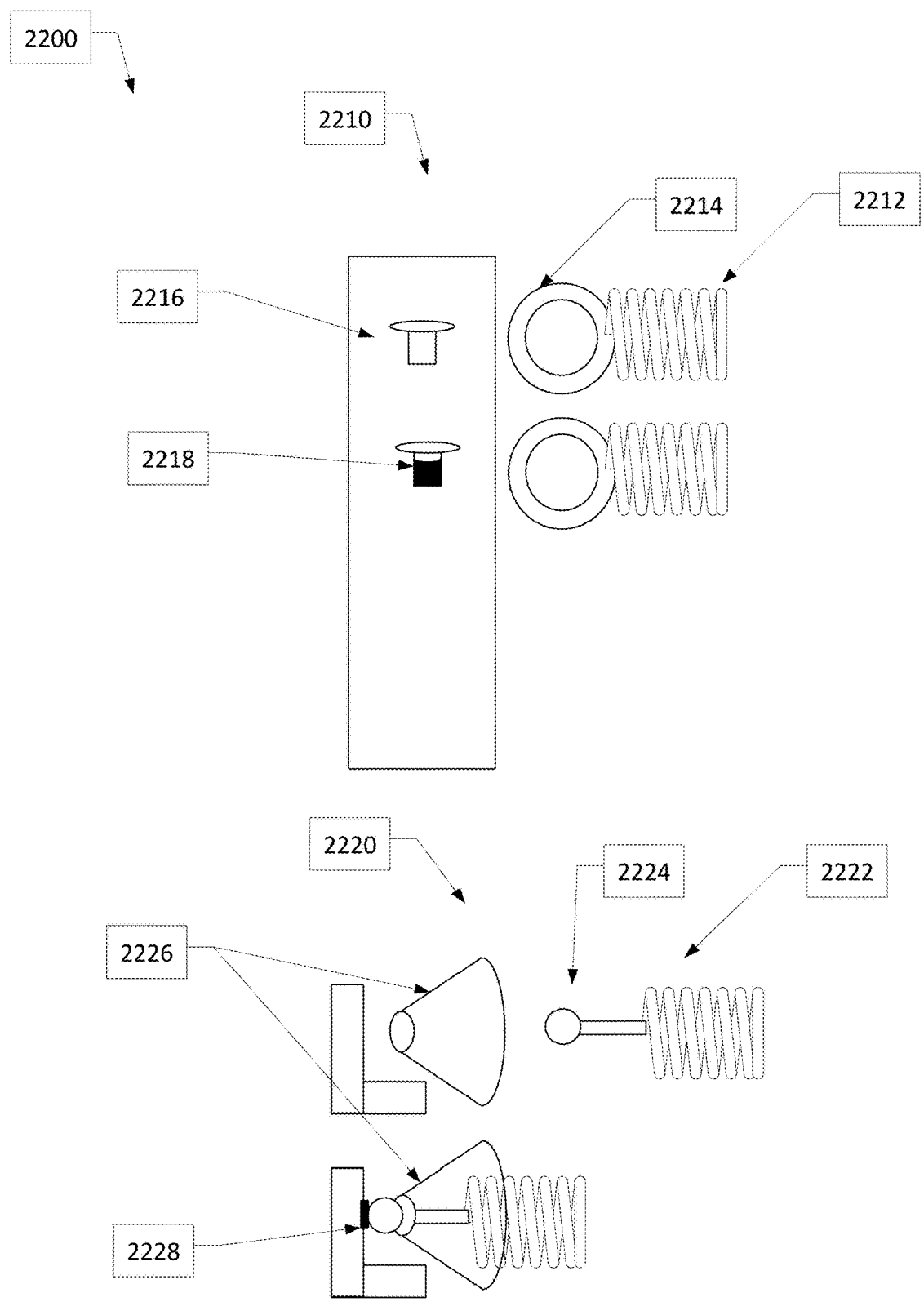
FIG. 22. Is an example embodiment of a computerized Pilates Machine.

FIG. 22 is an example embodiment 2200 that relates to spring loaded machines, for example Pilates Reformer machines. This example embodiment is aimed to find which of the existing springs are connected and which are not, and thus the resistance can be known. 2210 is the example embodiment for one method of connecting the springs. To connect a spring ring 2214 at the end of each spring 2212 is put on a shaped pin 2216. In order to detect if a spring is connected a simple device 2218 can be put on the pin 2216 or next to it. 2218 can be a small force measuring device, load cell, strain gauge, micro switch and alike. By detecting force or pressure on the pin 2216 it can detect that a spring is connected. If the sensor 2218 is more sensitive it can measure the strain or force at each moment and thus calculate the exact resistance the spring is applying at every moment. The sensor can wire or wirelessly connected to the rest of the system.

2220 depicts a similar embodiment for different spring connection method. The spring 2222 has a ball shape 2224 at the end of it. It enters a cone shape 2226 and it is can be harnessed in several known methods (not shown) when it exits the cone from the other side. The force measuring device can be connected to the harnessing element in a similar manner described for 2210. The ball can also press a sensor or micro switch 2228 once it is at his harnessing location.

Figure 23:
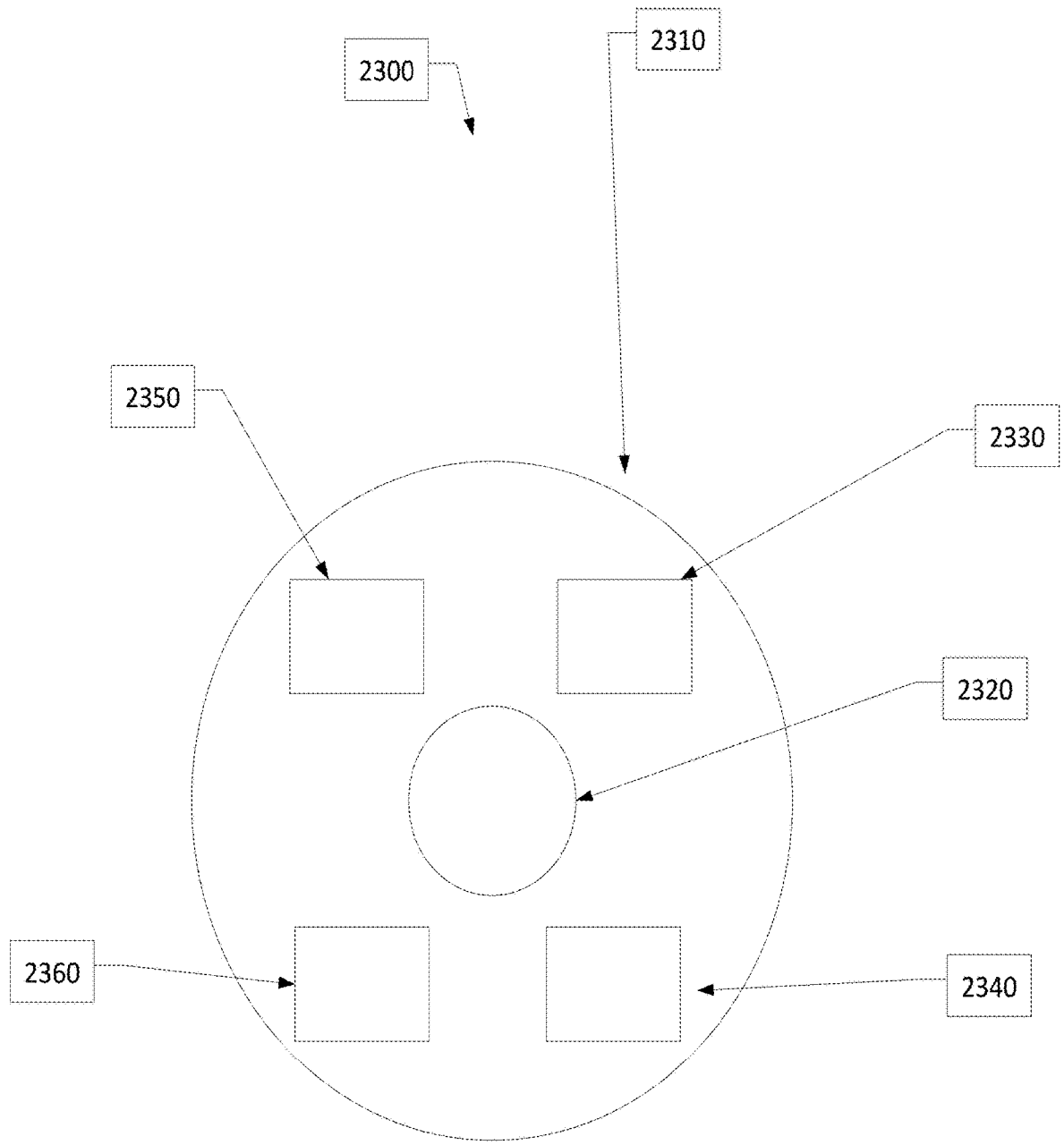
FIG. 23. Is an example embodiment of a computerized Slide Plate.

FIG. 23 shows yet another example implementation 2300 for utilizing the disclosed embodiments for monitoring exercise. In this example, glider discs 2310 are equipped with some of the sensors and components described above. A pressure sensor 2320 is configured to detect when the glider disc is in use and how much pressure or weight is applied on it. It is also equipped with an accelerometer 2330, a computing system 2340 (which can also be external), transceivers 2350, and a modem 2360.

Using the descriptions above, one skilled in the art can easily understand how training measures such as counting steps, calculating the resistance or effort, calorie burn, distance traveled, and the like can be obtained using this embodiment of the system. As described above the use of the accelerometers 2330, the transceivers 2350 and other sensors can be used in exercise identification, exercise performance correction, body and skeleton mapping, and the like.

Figure 24:
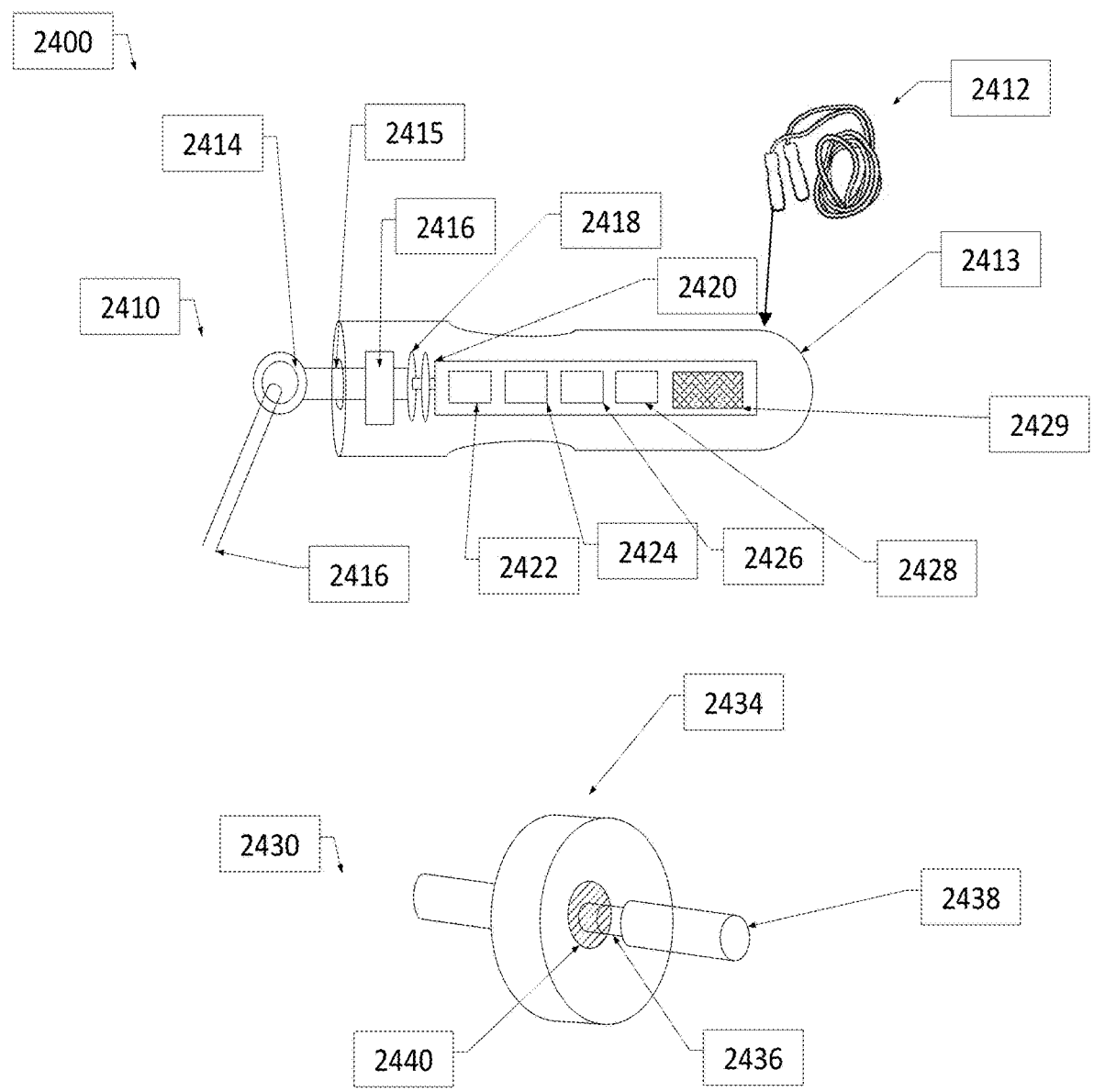
FIG. 24. Is an example embodiment of a computerized jumping rope.

FIG. 24, example embodiments 2400, describes two more example embodiments using rotation measurements.

2410 describes a Skipping rope 2412. 2413 is a handle of the skipping rope. 2416 is the rope which is connected to a ring 2414 which is then connected to a pivot 2415. The pivot 2415 passes through a bearing 2416 that attaches it to the handle 2413. 2418 is a rotation measuring device implemented in methods previously described in this disclosure such as an encoder, or known in the art. 2420 is a generator that can be used to produce power from the rope rotations. It can also be used to add resistance to the rotations, thus increasing the power required to rotate the rope. 2422 is a processor or processing unit. 2424 an accelerometer array. 2426 Wireless Transceiver unit, 2428 Bluetooth transceiver unit. 2429 is a battery. Each one of the units can be in only one of the handles. The units in the two handles can be connected between them and between the handles in wired or wireless connection.

Wired connection can utilize the rope to pass a conductive thread through it. The ring 2414, and pivot 2415 can also be conducting to allow this form or wired connection.

The example embodiment can comprise additional components mentioned in this disclosure especially in conjunction with FIG. 1 and FIG. 2 such as I/O components and alike.

The apparatus may also comprise a marker or reflector or repeater for optical or acoustical or any other wavelength or spectrum type. This can be used for tracking the apparatus location in space as described for the other example embodiments such as the selector pin of FIG. 9.

Measuring the rope rotations in time can give repetitions, paste and alike. Knowing the trainee body weight an estimate of the energy and power. Other attributes can be calculated from these in methods known in the art.

The location of each of the handles can be found using the transceivers, marker, repeater or reflector found on the handles in methods described in this disclosure. This can assist identifying the exercise and/or correcting it.

The accelerometers 2424 can also aid this end and others as described in this disclosure.

2430 describes an example embodiment of computerization of an "Ab wheel". This apparatus comprises a wheel 2434, a pivot 2436 trough the center of the wheel connected to the wheel using a bearing (not shown). Handles 2438 are connected to the pivot from both sides.

In the example embodiment 2440 is a rotation measuring device implemented in methods previously described in this disclosure such as an encoder or others known in the art. The example embodiment may further comprise a generator (not shown) that can be used to produce power from the wheel rotations, but also to add resistance to the rotations, in methods described in this disclosure. Thus the generator can increase the power required to rotate the wheel. It may also comprise a processor or processing unit (not shown), Wireless Transceiver unit (not shown), Bluetooth transceiver unit (not shown), a battery (not shown), or additional components mentioned in this disclosure especially in conjunction with FIG. 1 and FIG. 2 such as I/O components and alike.

The apparatus may also comprise a marker or reflector or repeater for optical or acoustical or any other wavelength or spectrum type. This can be used for tracking the apparatus location in space as described for the other example embodiments such as the selector pin of FIG. 9.

Furthermore the example embodiment may also comprise a force measuring device connected to its handles or wheel.

For example the wheel and its bearing can be mounted on a load pin that can measure the load or force applied on the handles.

Measuring the wheel rotations in time can give repetitions, paste, speed, distance traveled and alike. Measuring the trainee body weight (using the load pin for example) and the wheel resistance, can be used to calculate the energy and power. Other attributes can be calculated from these, using methods known in the art. Identification of the exercise and correcting it can also be done knowing the wheel motion parameters and location, and the amount of body weight applied to it. All can be done in methods described in this disclosure and the references.

Figure 25:
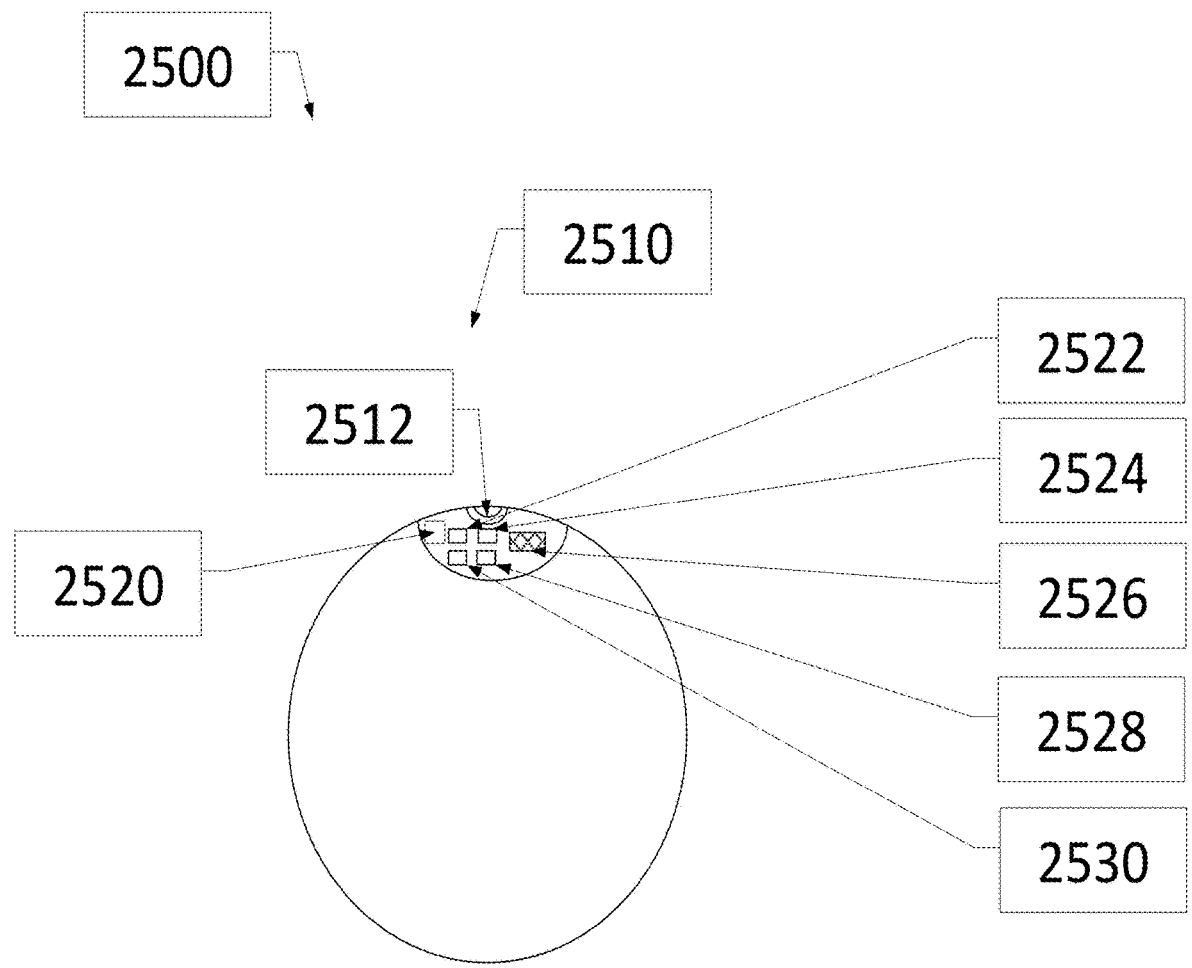
FIG. 25. Is an example embodiment of a computerized "Fit Ball".

FIG. 25 presents yet another example embodiment 2500, in this case computerization of the ball known as "Fit-Ball" or "Pilates Ball". 2510 is the Fit-Ball. 2512 is the inflation hole. The computerization components may be concentrated around the inflation hole, although this is not a must. This is because the inflation hole is usually a rigid structure in the ball which allows harnessing the electronic components and other components to it by for example using a chassis similar to the one in FIGS. 9, 11 and 12. 2520 is an air pressure gauge found inside the ball. By sensing the air pressure inside the ball it is possible to calculate the load on the ball, count repetitions and more. A load present on the ball surface will increase the air pressure inside the ball. By comparing the pressure when no load is applied to when a load is applied it is possible to calculate the external pressure applied in methods known in the art. Using methods described above in reference to FIG. 3-340 applied to the air pressure measured it is possible to count repetitions.

2530 is a processor or processing unit. 2522 an accelerometer array. 2524 Wireless Transceiver unit, 2528 Bluetooth transceiver unit. 2526 is a battery. Each one of the units can be located anywhere in the ball. For example an extender rod (not shown) can be based on the inflation hole 2512 and extend inward to the inside of the ball. The components or some of them can be mounted around its end or on the extension. This way a user touching the ball or sitting on the inflated ball will not feel them against the ball walls. The units in the ball can be connected between them in wired or wireless connection.

A generator activated by changes in air pressure and/or movements (not shown) can be used to produce power from the exercise performance and/or ball movements. Such a generator may by configured to produce power from the movements of a membrane effected by the air pressure for example or a propeller effected by air pressure and alike, or use other methods known in the art.

Using the knowledge of the load applied on the ball, repetitions, and using the accelerometer army, additional sizes such as performance speed, motion range, energy burn in calorie and alike can be thus calculated in methods described above or known in the art.

The Use of Motion Sensors, Image Sensors, WCDs and Mobile Devices in the System Referring to back to FIG. 1, the user may wear a plurality of wearable computing devices 190 that can be used for identifying the user by the system and carrying out any of the methods described herein. The wearable computing device 190 may be connected to the system via a wireless or wired connection. Various protocols known in the art can be used for the user identification such as RFID, NFC, WiFi, LTE, Bluetooth, and the like. In an embodiment, a third device, for example a smartphone, may be used as a bridge or a router between the rest of the training module and the plurality of wearable computing devices 190.

The wearable computing devices 190 may be configured to transfer or receive additional data such as the user's attributes like age, gender, height, weight, training history, experience level, and the like. The wearable computing device 190 may be further configured to transfer or receive data about the user habits, measurements related with the user's health such as sleeping quality or history, nutrition, heart rate, blood sugar level, blood pressure, blood oxygen level, and the like. Nutritional information may include calories consumed, time of last meal, and the like. The wearable computing device 190 is configured to collect this data as inputs or in real-time.

The wearable computing device 190 may include sensors, such as, but not limited to, accelerometers or similar motion detectors and/or a camera. These motion detectors may be used to count repetitions during exercise in methods similar to the ones known in the art for counting steps and which some of them disclosed above in this disclosure. The camera may be used to count repetitions as well.

The wearable computing device 190 may be used by the training module 100 to interact with the user. For example, the training module 100 may use the wearable computing device's 190 speakers, microphone, touch screen, and the like, to deliver instructions, encouragement, and the like. In an embodiment, some parts or all of the data stored in the database 120 may reside on the wearable computing device 160, in fact the database 120 or parts of it may reside in the WCD.

The training module 110 may also use modems on the wearable computing device 160 for all or some of the training module 110's connections within the training module 110 itself or with the outside world. For example, the training module 110 may use the cellular modem for interacting with a faraway database or a cloud computing infrastructure.

Wearable computing devices may be synonymous with devices attached directly to exercise equipment 190 or "worn" on them. For example, a wearable computing device 190 may be attached to a free weight or weights. Attaching a wearable computing device 190 may allow the training module 110 to identify the weight or weights and the resistance they represent. The attached wearable computing device 190 may include accelerometers and thus the wearable computing device 190 or the training module 110 may count repetitions done with the weights in a similar method to those described above.

The wearable computing device 190 attached to the exercise equipment 190 may be very simple. The example embodiment of FIG. 18 for example can be viewed this way. It can be conceptually said that the weight plates that are attached with an RFID device to identify each plate weight and contain further elements of a computing device in them, are mounted with (Or "wearing") a WCD. Many of the example embodiments are conceptually "wearing" a Wearable Computing Device.

Any reference made to a wearable computing device or a device attached the exercise device or equipment are interchangeable and every reference to one includes the other, both are considered part of the system as depicted in FIG. 1. A wearable computing device 190 or a device attached to the exercise device or equipment 160 can be used for assistance for creating a skeleton model or identifying the exercise performed.

The training module 110 can be configured to use the wearable computing device 190 as a reference when mapping the initial skeleton model or spatial body model of the object to track. The training module 110 may be further configured to track the location of a body part of the user once it obtain the information of which body part the wearable computing device 190 is located on. The exact location of the wearable computing device 190 can be achieved, for example, by using the methods in the next paragraphs.

The "object to track" or "objects to track" in this disclosure, where the word object or objects can sometimes be replaced by "subject" or subjects and the word track can be sometimes replaced by synonyms like "view" or "monitor" or "observe" means: Any plurality elements present in the training environment, or in any physical or virtual environment linked to it, including, but not limited to, a plurality of trainees, coaches or any other humans, a plurality of training apparatuses or training aids, equipment, moving or nonmoving objects and alike.

"2D" means two dimensions and/or two-dimensional. Typically, in this disclosure, 2D refers to an image having image data in a single two-coordinate plane and/or a reconstruction of image data lacking a third dimension, such as depth. "2D" may also refer to an image raster that is an array of pixels configured to an image or comprising an image; therein, each pixel has a grid position in a plane, e.g., XY positions, and RGB color space information.

"3D" means three dimensions and/or three-dimensional. Typically, in this disclosure, 3D refers to a physical non-virtual volume and/or a reconstruction of image data having a third dimension, such as depth. "3D" may also refer to a virtual space having three dimensions, e.g., a focal plane and a distance as measured at a right angle from the focal plane.

Everywhere in this disclosure when referring to camera or optical sensors these sensors may be optical sensors, such as 2D or 3D cameras, or other types of capture devices. Some examples are provided in U.S. Pat. No. 9,011,293 B2. Capture devices may include a depth camera, a video camera, stereo cameras, and/or other suitable capture devices.

For example, in time-of-fight analysis, the capture device may emit infrared light to the target and may then use sensors to detect the backscattered light from the surface of the target. In some cases, pulsed infrared light may be used, wherein the time between an outgoing light pulse and a corresponding incoming light pulse may be measured and used to determine a physical distance from the capture device to a particular location on the target. In some cases, the phase of the outgoing light wave may be compared to the phase of the incoming light wave to determine a phase shift, and the phase shift may be used to determine a physical distance from the capture device to a particular location on the target.

In another example, time-of-fight analysis may be used to indirectly determine a physical distance from the capture device to a particular location on the target by analyzing the intensity of the refracted beam of light over time, via a technique such as shuttered light pulse imaging. In another example, structured light analysis may be utilized by the capture device to capture depth information. In such an analysis, patterned light (i.e., light displayed as a known pattern such as grid pattern or a stripe pattern) may be projected onto the target. Upon striking the surface of the target, the pattern may become deformed in response, and this deformation of the pattern may be studied to determine a physical distance from the capture device to a particular location on the target.

In another example, the capture device may include two or more physically separated cameras that view a target from different angles, to obtain visual stereo data. In such cases, the visual stereo data may be resolved to generate a depth image. In other embodiments, the capture device may utilize other technologies to measure and/or calculate depth values. Additionally, capture device 48 may organize the calculated depth information into "Z layers," i.e., layers perpendicular to a Z axis extending from the depth camera along its line of sight to the viewer.

In some embodiments, two or more different cameras may be incorporated into an integrated capture device. For example, a depth camera and a video camera (e.g., RGB video camera) may be incorporated into a common capture device. In some embodiments, two or more separate capture devices may be cooperatively used. For example, a depth camera and a separate video camera may be used. When a video camera is used, it may be used to provide target tracking data, confirmation data for error correction of target tracking, image capture, face recognition, high-precision tracking of fingers (or other small features), light sensing, and/or other functions.

Other capture devices may include other forms of waves different then light. However the methods achieving an image are similar to what described in the latest paragraphs for light.

For example, ultrasonic sensors may be used in a sonar like scheme where a device transmits ultrasonic waves and the capture device received the backscattered waves in a similar way to what was described above. Also for example, electromagnetic waves can be used in a radar like scheme.

Accelerometers and/or gyros found in the wearable computing device 190 or attached to the exercise equipment 160 can measure the body part or wearable computing device 160 angle, tilt, speed, acceleration, direction of movement, orientation and the like. The accelerometers and/or gyros may count repetitions, measure the speed of performance of an exercise, and measure the length of movement by identifying the extreme points or edge points of an exercise performance. The extreme points are the points where the direction of motion changes above a certain threshold or reverses. The distance between the extreme points can be measured using the accelerometers by integrating their results with respect to time or by other methods known in the art. When the training module 110 identifies an extreme point using the accelerometers it is configured to measure the location by any other method known in the art and then calculate the length of movement by comparing the extreme points' location. Additional types of sensors known in the art may be used.

There can be many applications for the incorporation of the plurality of sensors in the training environment:

1. Tracking the location and or activity of the objects to track. This may help the system or supervisor to monitor, for example, if the trainee is using the correct exercise machine, if the trainee follows correctly his/her training plan, if the trainee spend too much time on recesses between exercise, what is the most popular and unpopular exercise equipment, what is the preferred order of exercise equipment order and more.

2. Motion tracking and monitoring the location of the objects to track body part or devices/apparatuses the user is holding. This can be used, for example, for moving avatar body parts or devices for feedbacking the trainee. Motion tracking can be further used for "Gamification" of the training, or for controlling the training scenario. For example, a training scenario may be given to the trainee in virtual or augmented reality. Tracking the trainee body parts and body movements may be the system's way of recording the trainee's response to the scenario and checking if the response is correct or not. For example, a trainee is training on ball catching in Virtual Reality. The system shows the trainee a ball flying in his direction in VR. The system tracks the trainee hands and fingers movement and decides if he catches the ball or not according to them.

3. Monitor correct performance of an exercise. This may include: correct movements, correct sequence of movement, correct pace, correct range of movement, and alike.

4. Prevent exercise or task performance mistakes, for example by tracking it and notifying about errors in retrospect or perhaps in advance.

5. Estimation of the user ability or attributes. This can be achieved in many ways. For example, the exercise mattress or the gym floor can obtain the trainee's weight and/or body fat percentage. Measurements of BMI and other attributes may be obtained optically in methods given in this disclosure or the references. User strength, for example, can also be obtained in a similar way as described in this disclosure or the references. Tracking the user's performance of an exercise or a routine can indicate the user ability level.

6. Gesture recognition. The sensors may be used to obtain movements or sequences which are used as inputs to the system. These inputs may control certain aspects of the system operation, may control system configurations or may configure the system on the fly, may change sequence of execution, may be used to select options from menus.

Input from a plurality of sensors can be combined to give Machine representation model of the object to track. This model can be for example a 2D or 3D model. Some of these sensors maybe various types of pressure or touch sensors. These sensors may be part of the system and can be installed on various places in the system 100 as explained in the previous example embodiments related to FIGS. 3-25 and will be further explained. For example, touch sensors may be attached on the handle of exercise equipment 160 and/or any places the exercise equipment 160 is expected to touch the body of the user. These sensors are configured to indicate the location and orientation of body parts by identifying that the trainee is, for example, holding a handle, stepping on such a sensor, leaning on it, and the like. For example, by tracking the speed and location of an exercise equipment 190 handle.

The term "Machine Representation model" of the object to track synonymous with the term "Body Model" in this disclosure means: a machine representation of an object to track, which may include one or more data structures that include a set of variables that collectively define the object to track in the language of a computing device a game or other application/operating system. A model of an object to track can be variously configured without departing from the scope of this disclosure. In some examples, a model may include one or more data structures that represent an object to track as a 3D or 2D model comprising rigid and/or deformable shapes, or body parts. Each body part may be characterized as a mathematical primitive, examples of which include, but are not limited to, spheres, anisotropically-scaled spheres, cylinders, anisotropic cylinders, smooth cylinders, boxes, beveled boxes, prisms, and the like.

More examples for Body Models are given in the references, for example US20100303289A1 by Polzin et al. incorporated hereby reference, body model 406 of FIG. 12 of that disclosure. Body model 406 is exemplary in that a body model may contain any number of body parts, each of which may be any machine-understandable representation of the corresponding part of the modeled target.

A model including two or more body parts may also include one or more joints. Each joint may allow one or more body parts to move relative to one or more other body parts. For example, a model representing a human target may include a plurality of rigid and/or deformable body parts, wherein some body parts may represent a corresponding anatomical body part of the human target. Further, each body part of the model may comprise one or more structural members (i.e., "bones"), with joints located at the intersection of adjacent bones. It is to be understood that some bones may correspond to anatomical bones in a human target and/or some bones may not have corresponding anatomical bones in the human target. The bones and joints may collectively make up a skeletal model, which may be a constituent element of the model. The skeletal model may include one or more skeletal members for each body part and a joint between adjacent skeletal members. Exemplary skeletal model 407 in US20100303289A1 by Polzin et al and exemplary skeletal model.

The Machine Representation model or Body model can be a collection of points in 3D or 2D space and/or a collection of 3D and/or 2D shapes. The shapes maybe a collection of polygons, ellipses, cones, cylinders and alike or combination of thereof. The evolution in time from step to step or frame to frame can be viewed as movement in space of the collection of shape and/or points. The shape may be complex and may, for example, represent a part of the target body. For example, if the target is a person, the shape maybe a scaled model of a body part in machine representation—for example a hand. This model may include models of possible movements and constraints. For example, the model may include the joints of the hand in machine representation and the description of possible movements around these joints, machine representation of the possible evolutions in case of movement around the joints and in general in space. Further description of possible forms of machine representation is given in the references.

Additional methods can be used to achieve Machine Representation Model of the object to track. In an embodiment, ultrasonic waves may be used. For example, the speaker of a mobile device may be configured to transmit ultrasonic waves and a microphone of the mobile device may be configured to receive their reflections from the user and background as performed in a sonar device. The speaker and microphone may also be components of a wearable computing device 190 or any other part of the Computing Device Enhanced Training Environment system 100. They can also be dedicated sensors for this purpose specifically positioned or positioned on a moving platform that changes position according to the user's location and exercise performed. Methods known in the art may then be used to achieve a 3D representation of the user. The speaker and microphone may be replaced or be synonymous to an optical sensor or other sensors involved in the 3D mapping.

In this disclosure when the words point or points are used in reference to a body model or a method related with a body model it means: The smallest most possible body model element. In case of 2D model it can mean pixel and in case of 3D it may mean voxel.

Other methods to achieve a Body Model may include use of electromagnetic waves (like RADAR or LIDAR), lasers, and other time-of-flight methods known in the art. In all embodiments the sensors may be on any part of the Computing Device Enhanced Training Environment system 100 including mobile and wearable computing devices 190 or specific platforms. The sensors may be replaced or be synonymous with other sensors involved in the 3D mapping.

Figure 26:
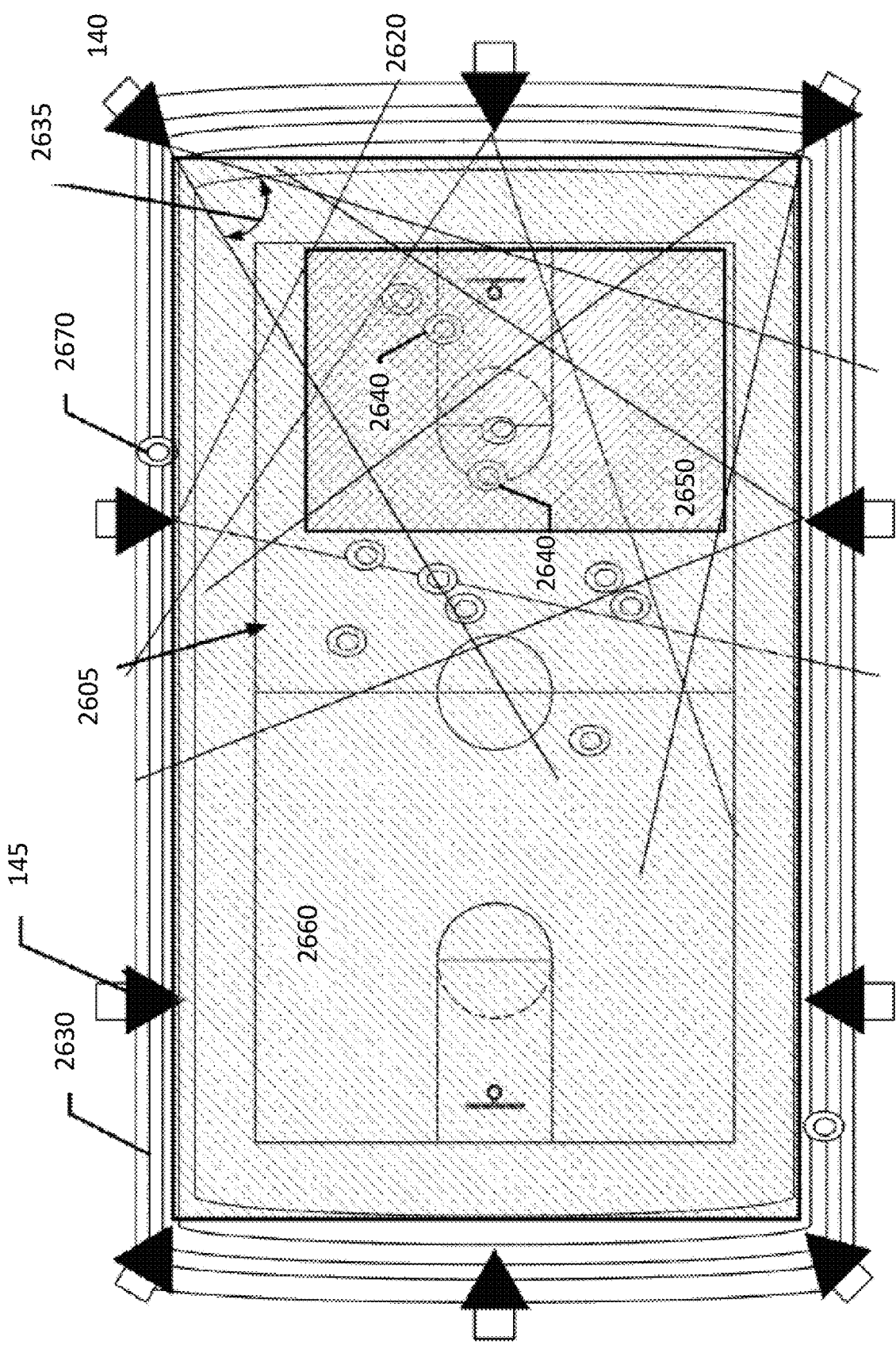
FIG. 26. Is an example embodiment of computing device enhanced training environment, enhanced with a plurality of motion and image sensors.

FIG. 26 depicts an example embodiment in which two or more of the sensors 145, 140 are cameras or capturing devices, such as the ones discussed in the previous paragraph, mounted around the training environment 2630 for example on tripods and/or walls and/or ceiling. The training environment in FIG. 26 is a basketball court, however it can be any training environment described in this disclosure or the references or known in the art. 2635 is the sensor 140 view angles, and 2620 are the edges of the viewing field. 2640 are the objects to track in the active cameras field of view. In the example of a basketball court the objects can be the basketball players and/or the ball (which can be considered a training apparatus 160). In the case of a general training environment the objects can be the training people, the training devices and or machines, the coaches and alike. 2650 denotes a current area of interest in the training environment. 2660 is an area were objects to track are not found temporarily. 2605 is an area were the objects to track are found. The Sensors like 145 and system resources related with that area can be turned off or go to power save mode or be used in a different area, in order to save resources.

US Patent Application publication 20150319424 by Haimovitch-Yogev et al. incorporated herein by reference describes a scenario where images from different cameras around a training environment are used to create 3D mapping of the object in the training environment and then render them from different angles.

These methods can be used in this example implementation. Unwanted objects that can be for example some of the training machines and objects in the background such as furniture, walls, trees, decorations etc. can be removed from the images picked up by the sensors 140, 145. Methods used in U.S. Pat. No. 9,011,293 can be incorporated. For example, reference images of the environment or unwanted objects in it can be taken in a given time and subtracted later from the streaming or live images.

Figure 31:
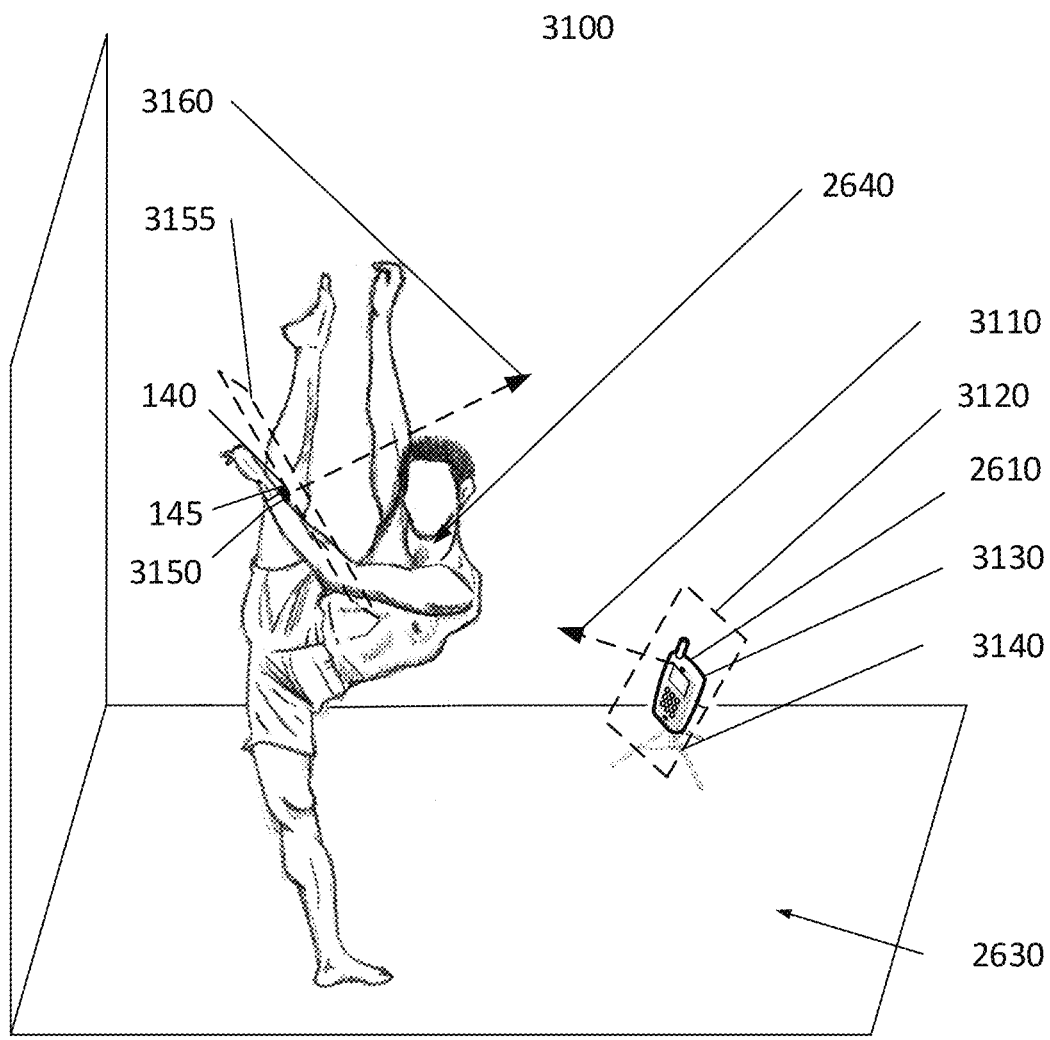
FIG. 31. Describes another example embodiment of a computing device enhanced training environment, enhanced with a plurality of motion and image sensors.

FIG. 31 (3100) depicts an example embodiment. The object to track 2640 in this case is a human trainee performing training without training apparatus 160. Such a training can be for example: Dancing, Martial Arts, Gymnastics, Yoga, Pilates and alike. 2630 is the training environment. The trainee or object to track 2640 in this case is mounted with a WCD 3150. In this example, a smart watch. The smart watch in this example comprises a camera sensor 140 and accelerometers sensors 145. 3160 is the principal axis or line of sight of the smart watch camera 3150 140. 3155 is an infinitely situated plane that is perpendicular to the camera principal axis, also known in the art as image plane. 3130 is a mobile device situated on a tripod 3140 configured so the mobile device camera sensor 140 is directed in the general direction of the object to track 2640. 3110 is the principal axis of the mobile device camera sensor 140. 3120 is the image plane of the mobile device 3130 camera sensor 140.

In all embodiments, the sensors or capturing device (140, 145) may be mounted on tripods or mounting apparatuses located on the training environments' 2630 floor, they may be mounted on training machines, furniture, windows, and/or placed anywhere else in the training environment. They can be mounted on vehicles or moving objects such as UAVs or other types of vehicles. They can be WCD or mobile device cameras or sensors mounted on any of the trainees or coaches and/or objects or placed anywhere in the training environment. Additional sensors can be present in the environment 2630 as part of the exercise equipment, WCDs, the training environment floor for example, etc. as described above. The sensors or capturing devices can be any of the capture device types described in the above paragraphs and can produce ID, 2D or 3D frames like accelerometers or Sonar enabling devices. Data from a plurality of such sensors can be combined for creating a body model. The methods disclosed in this embodiment, the references, and known in the art can be used to create the body model.

In the example embodiment of FIG. 31, to assist in the integration of the different sensor data, the location of the WCD 3150 and/or orientation can be obtained at any time using its onboard accelerometers 145 or other sensors and methods disclosed or known in the art. This allows devising the principal axis 3160 and the image plane 3155 of the WCD's 3150 camera 140. Such methods can be used to find the location and orientation of every moving camera. This knowledge can be used to perform for example bundle adjustment, derive projection, position adjustments and alike. Some or all may be required for the usage of the camera 140 data for creating a body model of the object to track. Vibrations or high frequency unwanted movements can be filtered using low-pass filters, feature matching, or other methods disclosed herein or in the references or known in the art.

The example embodiments of FIGS. 26 and 31 can benefit from the connectivity capabilities in the Computing Device Enhanced Training Environment. WCDs, mobile devices and the rest of the sensors in the environment may be capable of communicating with each other and in general with the system. Thus, for example several WCDs and/or mobiles can create a network of sensors. Such a network can track a plurality of objects at any given time. The objects to track 2640 which is a trainee in FIG. 31 example, can be tracked not only by his own WCD and mobile, but other WCDs like 3150 and or mobiles like 3130 belonging for example to others in the environment and/or found in various locations of the training environment. All can be connected to the system and/or each other at the same time via wired or wireless means and contribute to the creation of the body model of the trainee. They can be complemented by additional sensors of the training environment such as mounted cameras and other examples given in this disclosure or the references or known in the art.

The novice example embodiment methods disclosed herein are not limited to creating body models in a training environment. They can be used in any case for creating body model needed and can be used for any other application of thereof.

In one exemplary embodiment, 2D data may be converted to 3D using methods known in the art, such as WebGL (Web Graphics Library). The WebGL is a JavaScript API for rendering interactive 3D without the use of plug-ins. The WebGL may be integrated completely into the system allowing GPU accelerated usage of physics and image processing and effects as part of an image canvas. The WebGL elements can be mixed with other HTML elements and composited with other parts of image or image background. The WebGL programs typically control code written in JavaScript and shader code that is executed on a computer's Graphics Processing Unit (GPU).

In case two of the sensors or more can produce a 2D image or mapping, Stereoscopic Vision methods known in the art may be used. This may be possible in case the distance between the sensors relative to the expected targets distance is not higher or lower the distance required for Stereoscopic Vision. Stereoscopic Vision can allow obtaining body image and or skeleton mapping and or body mapping and alike.

Before using the sensors image it is possible to: stabilize the image, separate the targets data from the background, correct aberrations or distortions, filter out noise, enhance the frame images, convert raw images to other formats and alike. Methods for these are given in the references reference or known in the art. References like US Patent Application publication 20150319424 by Haimovitch-Yogev et al. or U.S. Pat. No. 9,011,293B2, both incorporated herein by reference. For example, separation of the targets from the background can be achieved by subtracting the on-the-fly (OTF) frames from a reference frame captured when the Targets were not present. Aberration and distortion correction can be achieved by using known filters and transformations on the frames. Configuring the parameters for the filters and transformations can be done by measuring the aberrations and/or distortions on elements in the environments of the targets and/or comparing them to a known reference. Filtering noise and enhancing the frames can also be done by using filters and transformations like, Edge Filtering, Moving Average, Low-Pass filter and alike.

In an example embodiment, two or more of the sensors can produce 3D images of the target/s in methods reviewed above or other methods known in the art. The first steps toward creating body or skeleton mapping can be the steps from the previous paragraphs (Separating from background, reducing noise . . . ) for every 3D sensor. One preferable step is separating the collection of points and/or shapes representing the target/s from the background. One of the next preferable steps would be to unify the collection of points and or shapes in 3D space representing the targets in every sensor, to unified collection from all sensors. This can be achieved, for example, in the following method:

1. In the beginning there are "clouds" of points from all the sensors adjacent in 3D space. Start from a pixel in one collection of points representing a target.
2. For each pixel find its nearest neighboring pixels. The nearest neighboring pixels can be defined as those pixels with a distance in 3D space lower than a certain threshold from the pixel. Mark each pixels for which the nearest neighboring pixels have been found in this step.
3. Add the nearest neighboring pixels to the collection representing the target.
4. Repeat steps 2-3 for every one of the nearest neighboring pixels found in this iteration, except those which were marked, i.e. visited before, i.e. have already gone through steps 2-3.
5. End when all the pixels in the collection are marked, i.e. no more nearest neighbors which were not visited.

The example embodiment of FIGS. 26 and especially 31 present some challenges for the state of the art methods for producing a body model of the objects to track. These challenges may stem from the fact that in an embodiment example like 3100 some of the sensors are moving a great deal of the time. This challenge may increase by the fact that the objects to track are also moving, and in some cases relatively quick. In general, the environment and objects to track may be rapidly evolving in certain training scenarios. This of course adds the obvious challenge of occlusions and limited fields of views. In general, some training scenarios cannot afford a large number of sensors and may not be able to set or control their locations. This adds to the challenge of occlusions and limited fields of view. The result of the above challenges maybe yet another challenge: large angles and/or distances between cameras and sensors which may be very limiting for the usage of stereoscopic vision methods and other methods known in the art.

It is therefore required to present some novel approaches that can allow the creation and monitoring of body models of the objects to track under such challenges. Some of these novel approaches will be further discussed below.

Figure 27:
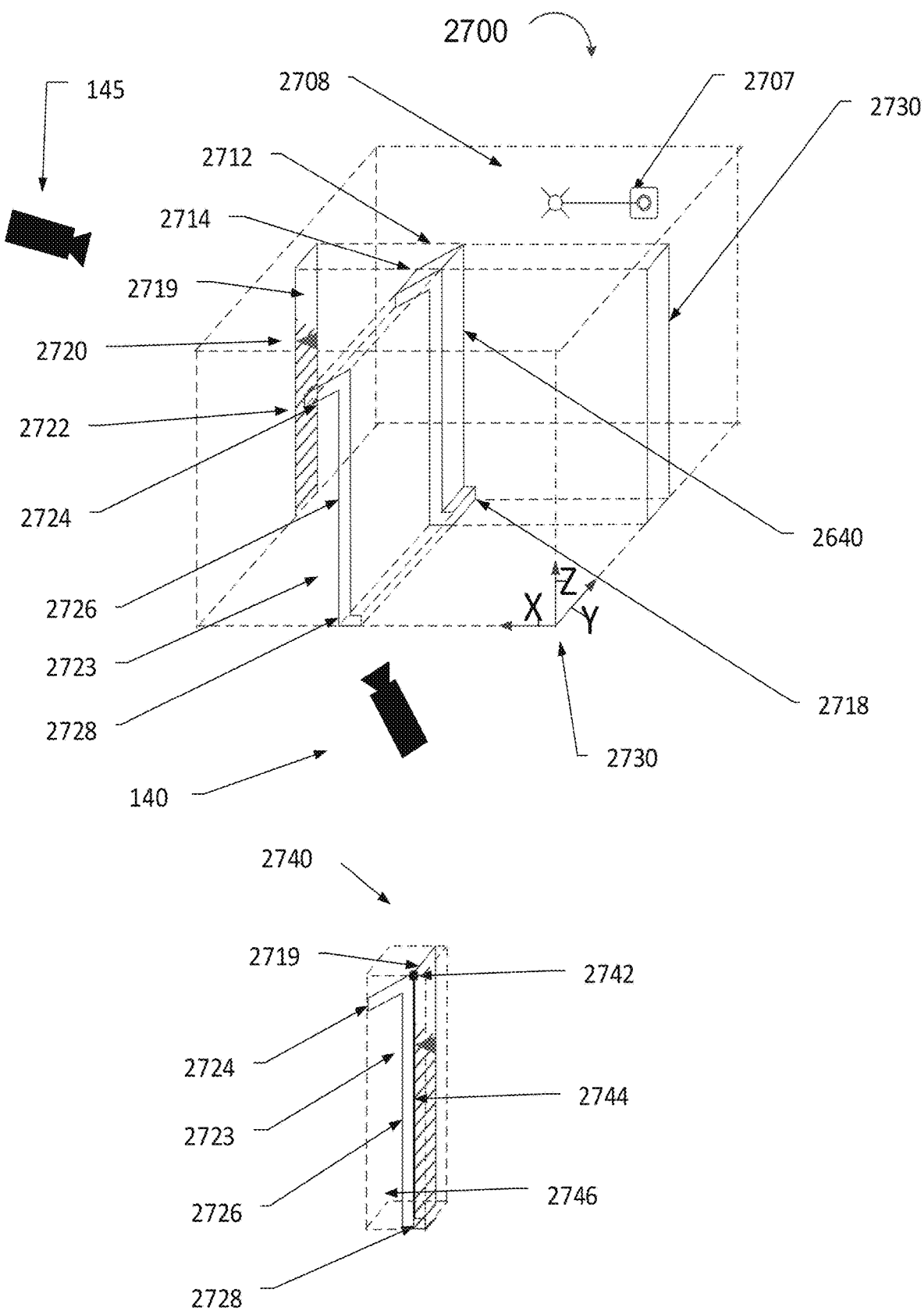
FIG. 27. Is another example embodiment of computing device enhanced training environment, enhanced with a plurality of motion and image sensors.

FIG. 27 (2700) depicts an example embodiment. 2712 is a generic 3D object. 145 and 140 are two sensors or capturing devices cable of capturing frames in 2D. 2707 is an optional wave and/or radiation source for which the sensors 145 and 140 are susceptive. The waves and/or radiation can for example be radio or radar waves, visual light, acoustical waves and alike. For example, 145 and 140 are two 2D optical cameras and 2707 is a light source. 2708 is an imaginary 3D semi-rectangular shape surrounding the 3D target object 2712 (Can be for example a parallelogram). The planes of the semi-rectangular 2708 are chosen to be an infinitely situated planes that are perpendicular to the sensors 145 and 140 principal line of sight. The planes are preferably idealized as having no parallax that would occur with minor sensor shaking or vibration. 2719 and 2723 represent the 2D image seen from its view, by each one of the sensors 145 and 140. They can be seen as projecting of the 3D target object 2712 on the planes of 2708. 2714 is the upper edge of the image plane 2719. Because of the position of the wave source 2707, patterns of shades 2720 and 2722 are created on the reflection 2719. 2730 is the 3D coordinate system used.

In a training facility scenario like FIG. 26, the exact location of points on the 3D target object 2712 can be known. In other cases, the location of the same points (same between the collections of sensors images) or collection of point can be known for all sensors. This has already been explained in this disclosure and the references: for example a WCD worn on the object's body can transmit its exact location to the system. In another example, a feature, a marker or a distinct pattern can be found on the WCD, on the object's body or on the exercise equipment can signal its location in every one of the sensor's images. Many other examples have been given for identifying parts of the exercise equipment location (for example an exercise machine handle) in this disclosure or the references. Also many additional methods for feature recognition and matching between two sensors or more are known in the art and given in the references.

If a location of a certain point or a collection of points have been identified on each one of the different sensor 2D/3D images, they can be adjoined in 3D space in the following way: for example, the images 2719 and 2723 seen from the sensors 145 and 140 can be adjoined: assuming 2742 is the up most (with the largest Z coordinate), left most (lowest Y coordinate) point on the object. And assuming its location is known on both images 2719 and 2723. If the location of 2742 is known in space or relative to the coordinate system 2730, and the location of the sensors 145 and 140 is known, it is then possible using known methods to scale the images 2719 and 2723. The scaling purpose is to give the images 2719 and 2723 their actual size in space at point 2742.

Also, using feature recognition, or identification and matching of known points on the object or in the environment, bundle adjustment, derive projection and position adjustments can be performed as explained in the references (for example US Patent Application publication 20150319424). This can be done prior or during further processing and improve the results quality.

It is to be understood that once a point is identified as common between two sensors or more, its location in space can be found by triangulation (using the two or more sensors location) or other methods known in the art. The vice versa direction is also possible if the exact location in space of a point visible in the two sensors or more is known, it becomes a common point and can match the sensors images.

Possibilities for identifying pixels as common can also emerge from comparison of pixels and their nearest neighbors in one 2D image to pixels and their nearest neighbors in another sensor 2D or 3D image. A grade for comparison can be calculated for each comparison where the grade can be a weighted sum of the differences between the pixels in the matrices of the pixel and its nearest neighbors. Each pixel in the metrics get a grade in the sum for example according to its distance from the center pixel or according to other properties of this pixel. Many methods are known in the art of image processing for making such comparisons.

As 2740 shows the images 2719 and 2723 can then be projected in space, using the data from the common points 2742. Derive projection can be performed of the other sensor/s images to the sensors image plane (The infinitely situated planes that are perpendicular to the sensors like 145 and 140 line of sight). This way additional points from different sensors can be identified as the same and unified. This process can be generalized to any number of sensors, or to a group or collection of common points between the images. Many methods are known in the art to assist determining identity between points from two or more different sensors, Like color matching, nearest neighbors matching, spatial distance under a threshold and more.

Various known transformations and filters can be used to achieve a better unified image. These transformation and filters may include—rotation, scaling, edge filters, low pass, high pass or band pass filters, and alike. Methods that are used in stereoscopy such as image correlation and others can be used to find common points.

If no common points or shapes are identified at all, unification can be done on a common axis 2744 (assuming 2742 in not known to be a common point in this example). The images 2719 and 2723 may have a common axis, or may be rotated to have such. For example the images 2719 and 2723 in 2700 resides on planes—the image 2719 on a plane parallel to the XZ plane, and 2723 on a plane parallel to the YZ plane. These planes cross each other or "share" the Z axis (2744). To unify 2719 and 2723 both images can be first scaled so that the length of the Z axis at the unification point 2744 will be equal, then adjoined on this axis as 2740 shows.

If the location in space of the sensors 145 and 140 is known, and thus the angles between their image planes, the possibilities for the XZ and YZ planes of the outer edges of the object are known. Finding their intersection and common axis 2744 is possible in known geometrical methods.

The full 3D body mapping of the object obtained from a plurality of sensors using any method, may not be known at any stage. This may be caused for example by: occlusions or movements of the objects, points unmatched between sensors, noise, errors in the 3D mapping methods and alike. One of the subjects discussed in the next paragraphs is methods for improving and evolving the 3D mapping given that at some stage the full mapping is not known and/or can be improved.

The attained 3D mapping and 2D/3D sensor images can be used to generate possibilities for the actual 3D mapping. In the example embodiment 2700 and 2740, the unification 2740 defines a 3D polygon in space 2746 which encloses the actual 3D object. The possibilities for the actual 3D object are enclosed or contained in this 3D polygon. For example, possibilities can be generated by assuming the edge lines viewed in the image 2723 are extruded according to the projection of 2719, i.e. every pixel in 2719 is the beginning of a line in the YZ plane. The line length is the length in the image 2719 at the same Z as the pixel which is the starting point. To generate more possibilities, for example, the line lengths in the YZ plane can be random. Another example is to span all possibilities of pixel lengths for all lines. The number of possibilities can be reduced by giving a limited number of possible lengths for each line according to steps—for example give every line 5 possible lengths from 0 to the line length which is the length in the image 2719 at the same Z as the pixel. Using these steps the total number of possibilities is smaller.

The actual 3D mapping does not have to be identical to one of the possibilities. The possibilities may evolve and change in the next frames. The more similar possibilities may be kept and some of them continue to evolve to resemble the actual mapping more and more as time progresses. Other possibilities may be filtered at every step of generating possibilities or as time progresses. This method would be further discussed below.

In an embodiment, it is possible not to generate possibilities for new points, but only use the collection of known 3D points attained for example from identifying common points between the sensors. As the object moves and/or the sensors move additional such 3D points can be added to the collection at each step (step can be a frame) for example when they are out of occlusion, or it becomes possible to find their 3D location. Existing 3D points that become occluded or not possible to obtain their 3D location from the sensors, can be interpolated or extrapolated using motion estimation methods known in the art. Some of these motion estimation methods may give more than one possibility for the new location of such points. They may also give probability estimation for every such point. Based on these possibilities a plurality of possible 3D models of the objects may be possible. All the possible models may be saved in memory or only those with a function of the probabilities higher than a certain threshold. Thus, the 3D mapping is evolving and improving with time. This shall be also further discussed below.

In an embodiment, the method for creating 3D mapping may be based on steps. In each step possibilities for the 3D mapping are generated and some may be filtered out. Such filtering goal is to leave only the best possibilities as a basis for the next step calculations. Many methods are possible for the filtering, disclosed are some non-limiting examples:

Filtering can be done based on captured shadow and non-shadow patterns. For example, in FIG. 27 the light or wave source 2707 location is known. 2720 and 2722 are shadow patterns captured by the sensor 145. Knowing the light source location each one of the possibilities generated for the 3D mapping of the object can be examined. The idea of the examination can be whether the wave source can create the shade pattern given its location, the sensors location and the 3D mapping possibility examined. For every 3D mapping possibility, the expected shade pattern from the wave source can be calculated using methods known in the art. Such methods of shading calculations are commonly used for example in 3D modeling software such as for example Google Sketchup® or Dasult Systems Solidworks®. To save time and processing resources only a small portion of the shading pattern can be calculated for each possibility. This portion can be used for a step of filtering. Thus, after a filtering round, a larger portion can be calculated for the remaining possibilities. This pattern portion can be used in filtering again until the possibilities with the patterns which most resemble the captured shade pattern are left.

In the example of FIG. 27 one of the possibilities generated in the following way: every pixel in 2719 is the beginning of a line in the YZ plane. The line length is the length in the image 2719 at the same Z as the pixel. For this possibility the shade pattern 2720 corresponds to the shade the elongated tilted section 2724 is casting given the light source 2707 location. 2726 is an edge of this casting. Also the shade pattern 2722 corresponds to the shade the body 2640 is casting. Therefore filtering can leave only this possibility. However given the angle of the object 2712 and the wave source 2707, it is not possible to filter between possibilities for the base section 2728 shape. This is because the object 2712 does not obstruct the waves from the wave source 2707 in this direction and therefore this example filtering method cannot be used to filter between the possibilities for the base section 2728 shape. If no other method or sequence of methods can leave only one possibility, the possibilities left will go to the next stages/steps and may be filtered in the future.

Another example embodiment filtering method can be using the collection of 2D frames captured in each stage. The filtering method uses the collection of 3D points representing the objects or the 3D mapping or the possibilities for these. It also uses the known location of the sensors and their viewing angle. Each possibility map can then be used to create it's projections to the sensors viewing planes, like in the example of FIG. 27—2719 and 2722. These projections can then be compared with the real sensor images at this frame. The less similar or less correlated can be filtered.

In an example embodiment, Machine Learning (ML) techniques can be incorporated in the method. Machine Learning methods are disclosed below in this disclosure in the references and known in the art. A Machine Learning method requires the expected result, a measure of success of the result and the attributes/classes for definition and implementation. Measure of success can be binary, i.e. success or failure, a quantity representing the measure of success or error, or a function sometimes known as Cost Function or Error Function. These terms are further explained in this disclosure.

The expected result from the ML method can be the current step 3D representation/s of the subject/s. It may also be a collection of possible 3D representations. The step maybe the first step i.e. Capturing/Creating the first frame of 3D model and/or body image and or skeleton mapping and or body mapping and alike; or one of the following steps.

The measure of success can be for example if the ML method output 3D representation pass this step or future steps filtering. The filtering can be done in any of the methods disclosed or shall be disclosed. Another measure of success, can the measure of resemblance of the ML outputs to the actual subject/s as measured by a human, which can be present at the training stage or even after. This human may rank the algorithm success, and even give a quantity as a measure of success or supply an Error or Cost Function. Further possible measures of success shall be disclosed below.

Other inputs to the ML algorithm can be the 2D sensors output, the previous step 3D representation/s of the subject/s, or if this is the first step there can be a given model of the subject. Further inputs can be from accelerators, location sensors, and any other sensors disclosed herein or in the references. These inputs can all be used as attributes of the ML method.

Attributes of the ML algorithm may also include height of the subject/s in each of the 2D sensors, width of the subject's in each of the 2D sensors, width in certain heights, average of thereof between the sensors or for a given sensor, aspect ratio of the subject's in each of the 2D sensors, location of body parts, acceleration, speed, or other attributes of thereof. Features of the subject (such as facial features or body part features if the subject is a human). Attributes may also include known patterns location on the 2D images, and if these patterns were identified or not, for example facial recognition pattern, the T pattern of hands and torso viewed from the front and alike. Classes may further include the orientation or other identified attributes of identified patterns in the 2D images. Attributes may include color or wave reflection patterns and more.

Classification or identification of the subject's parts can be done (maybe first) on the 2D images. For example, if a subject is a human, his body parts can be identified on each of the 2D images. This identification/classification can be done in various methods known in the art.

Another Machine Learning algorithm can be applied to some or all of the 2D images from the sensors in order to identify/classify the body parts and their location in each. The attributes for this ML algorithm can be all the attributes and classes mentioned in the previous paragraphs and others known in the art. Additionally identified relative locations in certain sensors can be used as an attribute for classification for other sensors. The success criteria may be similar to the ones mentioned before: the success in passing the filters of the 3D possibilities which are formed based on the 2D classification ML algorithm; a human operator feedback, or others known in the art.

In an example embodiment the classified 2D images can be used to define more classes for the 3D ML algorithm. Such classes may include the body parts location—for example the face location and the feet location in each 2D image. The body parts orientation in each image, their size, their acceleration, speed, and alike from additional sensors and alike.

The problem of creating the body model can be separated to two:

1. Capturing/Creating the first frame of body model.
2. Tracking it as it evolves to the next frames.

In an example embodiment, Capturing/Creating the first frame of body image and or skeleton mapping and or body mapping and alike, can be achieved by doing the capture in known posture and/or starting conditions. The subject/s may be prompted or asked to take a certain position and/or posture. The problem of Capturing/Creating the first frame becomes simpler if the posture and/or starting conditions are known. Methods given in this disclosure or in the reference can be used. For example possibilities of skeletal or body models of the known posture can be projected on the 2D or 3D images from the sensors and correlation can be performed to filter out the non-resembling ones and to keep the most resembling model/models or machine representations.

In an embodiment, it is also possible that creating the first frame of body model of the objects to track, will be performed where the object/objects are coerced into a known position and/or posture. One example can be to do the first mapping on a certain known training equipment where the exercise or procedure done is known, or on a known exercise or procedure in the training plan flow. Additional sensors such as WCDs or sensors mounted on exercise equipment or others given in this disclosure and the references can attain the exact location of certain body parts. Using the known exercise, and the known locations the first mapping can be done. From the known exercise a certain known frame or frames from the reference database can be selected as a basis for the mapping, for example the starting point of the exercise, the end point or edge frames, as defined in U.S. Pat. No. 9,011,293 and other references.

There can be many other examples of "concealed coercion" in order to be able to perform the first mapping in a known posture and/or location. For example, when a trainee enters a health club he may need to pass a membership card where the point of passing it is found in a known place. Markings on the floor and walls maybe consciously or subconsciously direct the trine's feet to a certain location or posture and other parts of his body. At this point when the posture in known, or at least partially known, the first frame mapping can be performed.

After creating the first frame of body model, the system can continue to track the subject's. It can continue to track to the next exercises and throughout the training facility or environment. This may eliminate the need to perform the creation of this first body model frame. During this tracking certain sensors maybe partially or fully obstructed and mapping can continue using other sensors or the methods disclosed herein or known in the art.

In an embodiment, a full and/or detailed 3D model of the subject's can be attained at a certain previous time and known conditions. For example, as part of building a training program a full initiated body mapping can take place. In this body mapping dedicated 3D sensors and 3D mapping techniques known in the art can be used. During the initiated mapping the subjects/s can be prompted or asked to take certain postures and or locations to assist the mapping. Other sensors and measurements can be taken and also assist the 3D mapping such as measurements of weight, height, body fat percentage, circumference measurements of body parts (such as hips, bust, waist . . . ), and alike.

This initiated full and or detailed 3D model of the subject's can be used in later times as a reference model or starting point for creating the first frame of body image and or skeleton mapping and or body mapping and alike, and tracking it as it evolves to the next frames.

This model can be used to create possibilities for body mapping of the subject: if an anchor point or points are known—i.e. the location of a certain body part is known using any of the methods given in this disclosure or the references, the initiated model can be located as possibilities according to these points. For example, if the location of the left and right palms of the hands are known (because both are holding an exercise machine handles for example), the initiated 3D model can be projected in 3D space so that the palm of the hands will be in this location. Possibilities for 3D mapping of the subject can then be generated: the known parts are in their known location and the unknown parts of the body are in all possible locations (or only the probable ones) the model can be projected to dictated by: the known parts location, the allowed (possible) movements of body parts around the joints, space limitations: body parts cannot overlap or body parts and other objects (such as the training machine parts, floor, walls, furniture and alike) cannot overlap, etc. Other limitations and constraints given in this disclosure, the references, and known in the art are applied when projecting the model parts.

Before using it, the initiated model can be scaled to fit the current state and location of the trainee. For example, if the user has gained weight or lost weight his model can be modified accordingly. If when the model was attained the user was weighted, he can be weighted again (For example using the gym floor embodiment previously discussed), and the model can be scaled according to the weight proportion. Additional measurements in this case, such as body fat percentage change, can help make the scaling more accurate. Similar scaling can be done as a response to other user attribute changes such as for example height (As a result of child growth for example), body fat percentage, etc.

Methods for creating Skeleton Model or Mapping are identical to the methods for 3D body mapping. To create a skeletal model there is a need to know only the location of the joints. In a human body for example is a maximum of 360 joints, but in most cases the skeleton model will consist of much less joints. So the problem of full 3D body mapping is reduced to mapping only 360 points or usually many less (usually less than a 100).

Figure 28:
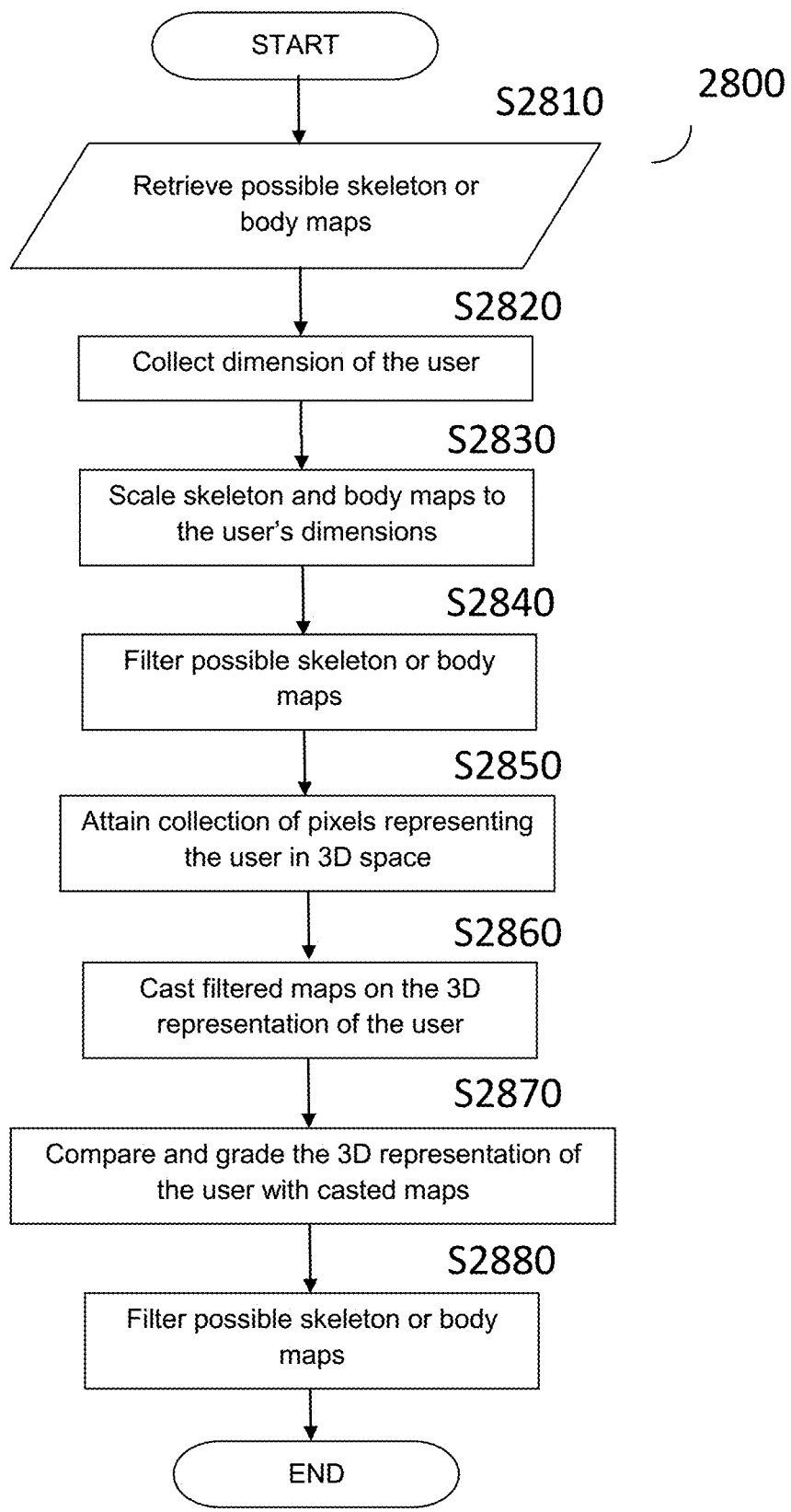
FIG. 28. Is a flow-chart describing a method for generating machine representation model of the objects to track.

FIG. 28 is an exemplary and non-limiting flowchart 2800 depicting a method for creating the skeleton model or 3D body map of the object to track according to an embodiment. It may be advantageous to use it for Capturing/Creating the first frame of body model. At S2810, possible reference skeleton or body mapping representation belonging to different exercises or postures are retrieved from the database 120. The training module 110 can use data from the sensors about locations and orientation of certain body parts to locate the possible skeleton and/or body maps and/or exercises in space.

At S2820, dimensions of the user are collected. The user's dimensions may include height, weight percentage of body fat, existing 3D or 2D mapping of the user, a combination thereof, and the like. The dimensions may be collected in real-time or stored in the database 120 in advance (and pulled from the database when the user is identified). The dimensions may be collected in a method similar to the method described herein above. At S2830, the possible skeleton or body maps saved on the database 120 are scaled to the user's dimensions. For example, if the user is 1.90 meters high and the images saved in the database 120 represent a 1.80 meter high model, the model dimensions can be enlarged by the ratio of 1.90 to 1.80. The dimensions of certain body parts or directions in space can be scaled in a different ratio which can be predefined or calculated. As a non-limiting example, the height can be enlarged by the ratio of 1.90 to 1.80 and the width enlarged by this ratio multiplied by a predefined constant. Such constants can be based on known proportions of the human or object body, known aberrations or distortions of the sensors, and the like.

If the proportions of the user's body are known the possible skeletons or body maps can be scaled accordingly. Alternatively, the required scaling can be attained from an object found in the frame for which the dimensions or relative dimensions are known, for example, a feature of the exercise device which is adjacent to the user's body. The feature's measured dimensions in the frame may be compared to the feature's known dimensions to enable the training module 110 to calculate the required scaling for the candidate skeleton or body maps. Other measurements and methods for scaling described above can be used as well.

At 52840, the collection of possible reference skeleton or body maps is filtered. For example, if the exercise equipment 150 the user is using is known there may be a limited number of exercises that are known to the training module 110 which may be done with this exercise device 150. A movement and/or location and/or orientation and alike of a plurality of body parts can be measured or identified by sensors such as accelerometers 160 or others detailed in this disclosure, the reference or known in the art. This movement and or location and or orientation and alike can be used to filter out postures or exercises in which the location of body part/s, orientation of body part/s, movement of body parts and alike are not compatible with what was captured by the sensors. This filtering can be done based on grading of the similarity with the orientation/movement/location captured: the less similar postures or exercises can be filtered. For example, it may be measured that the hand orientation is between 30 degrees and 40 degrees relative to gravity direction (the "Z axis") at the beginning of the exercise. For example, a threshold of say 15 degrees similarity can be defined. Therefore all postures in which the hand is less than 15 degrees or more than 55 degrees relative to the gravity axis can be filtered. Similarly, all exercises in which the beginning posture does not comply with these rules can be filtered as well. Such capturing and filtering can be based on frames in which the posture of the subject is known or can be estimated. For example, the starting time of an exercise. Method for "coercing" a user to certain known pose and filtering were discussed above.

The training module 110 may identify the expected exercise or possible exercises, and filter to the minimum number of possible of reference postures. Furthermore, inputs from touch or pressures sensors or a wearable computing device 190 can give further information about the location of body parts and thus the possible exercise which may be performed, if the exercise is not already identified. Various other data and methods mentioned in this disclosure, the references, or techniques known in the art, can be used in the filtering. For example, the training module 110 may filter out all exercises the user has already performed before in the same training session, interact with the user and ask him about his intentions, and the like.

Another example filtering method that may be used is according to time. For example, exercises or procedures are saved in database as a series of frames or postures. Every frame or posture may have a time stamp relative to previous frame or a reference point in the sequence. The time of capturing the sensor data in the exercise or procedure flow may be known. For example, as already discussed, if the capture is at the beginning of the exercise, only frames from the beginning of the possible exercises may survive the time filtering. A range in time around the time of capturing the frame by the sensors relative to the beginning of the exercise can be defined. Similarly, if the capture occurs sometime after the beginning of the exercise (start and/or duration of the exercise be identified by movement detection), a range of time in the reference database can be calculated. Frames outside this range in the possible exercises or procedures in the reference database can be filtered out.

At S2850, the collection of pixels or shapes or other form of machine representation ingredients representing the user in 3D/2D space is attained from various sensors and filtered from the background as described herein above. Alternatively, or additionally data from other sensors such as accelerometers or other sensors mentioned in this disclosure or in the references or known in the art, which measure movement and or location and or orientation and alike is obtained. At S2860, the candidate filtered possible reference skeleton or body maps or exercises postures are projected on this stage attained 3D/2D representations of the user in 3D space. Alternatively, or additionally data movement and or location and or orientation and alike is obtained from additional sensors is compared to the locations in the reference skeleton or body maps.

Alternatively, or additionally, derive projection for each one of the surviving reference body models from previous stages can be performed. For example, for each one of the image or image like sensors, derive projection can be performed to the image plane of each one from a collection of the surviving reference body models from previous stages. At S2870 Comparison or correlation or alike can be performed between the casted reference body model and the sensor processed image. A series of such comparisons to different sensors images can leave only the most resembling or correlated reference body models at S2880. This filtering can be performed calculation on the comparison or correlation or alike using one of the methods of "Methods for calculating and finding quantities and configurations used in this disclosure" below to perform it. To complete the filtering the result of this calculation can be compared to a certain threshold.

Surviving reference body models can also be derive projected to 3D sensors image planes or angles of view. Expected locations, speeds, orientations and alike of points, features or shapes and alike in the collection of the surviving reference body models from previous stages can be calculated in known methods. These locations speeds, orientations and alike can then be compared with data about these points, features or shapes and alike from sensors like accelerometers, pressure sensors and other sensor disclosed herein or known in the art. Comparison/Correlation and alike can be performed to data on the same points, features or shapes and alike from 2D or 3D sensors. Comparison/Correlation and alike can leave only the most resembling or correlated reference body models. This filtering can be performed calculation on the comparison or correlation or alike using one of the methods of "Methods for calculating and finding quantities and configurations used in this disclosure" below to perform it. To complete the filtering the result of this calculation can be compared to a certain threshold.

As described the 1D/2D/3D projecting of S2860 may be performed according to anchor point or points found by the various sensors, for example the wearable computing device 190 finding the 3D location and orientation of a certain body part. Other methods may include using data from the touch sensors, identifying body parts such as face or limbs in the known methods and using them as anchor points, or other methods described in this disclosure or known in the art. Some projections can utilize methods of creating several derived projections to the same image plane or viewing angle or alike based on a single body model. This can be done to account for subtle orientation or scale mismatches. An example of such a projection method may be using the anchor point (such as identified feature or location) to cast the reference body map with slightly different angle every time. For example, few projections with angles with 1 degree difference between projections around a certain "central angle". Changing of scale, body parts angles and other methods can be used for this multi-projections method.

As described, at S2870, the 3D/2D representation/s of the body are compared with the candidate filtered possible skeleton or body maps. Alternatively, or additionally, data about direction and/or orientation and/or location and/or speed and alike is compared between the database and the sensor/s output. The comparison may be realized during any correlation techniques or any other method described in this disclosure, the references or known in the art. For example, a tangent is found in 3D/2D space for every joint or for every pixel in the skeleton or body. For each tangent it is determined how much of the tangent is inside the 3D/2D representation of the body and how much from each side of the bone or joint (Or outside the body mapping). The quantity inside the 3D body may be multiplied by a constant and the difference or sum of the quantities from each side may be multiplied by a constant. These results may then be summed up for every joint or pixel on the bones. Certain joints or bones may receive a different weight or formula. The weighted sum of all the joints or points on the bones is the measure of match between the candidate skeleton and the body. It can be thought of measuring how much the skeleton or body map is in the middle of the body.

The shade based filtering method disclosed in reference to FIGS. 26 and 27, and other methods disclosed in reference to FIGS. 26 and 27 or in other parts of this disclosure, given in the references or known in the art can be used in S2870 and S2880 for filtering out body models.

Another example for the execution of S2870 may be realized by measuring the degree of overlap between the body and the possible skeleton or candidate body map/s, for example, giving a grade to every non overlapping pixel which is dependent upon its distance from the nearest body point (grades can be negative for pixels inside the body). The grade can be the sum of these distances. In this case the best match is the lowest grade.

At S2880, the casting/projection of the filtered possible skeleton or body maps with the best weighted sum or grade is chosen. In an embodiment, a certain number of projections with the best grade are chosen, all those over a certain threshold, and the like.

A machine learning algorithm as described in this disclosure may be used to learn the setting of this threshold, the grade calculation method, the casting/projection method, and the filtering method. The machine learning algorithm may grade its success based on successful matching and identification of exercises, human feedback, and the like. The possible attributes or inputs for this ML algorithm can be similar or even identical to the ones given herein above in relation to FIGS. 26-28 in the references or known in the art.

Figure 29:
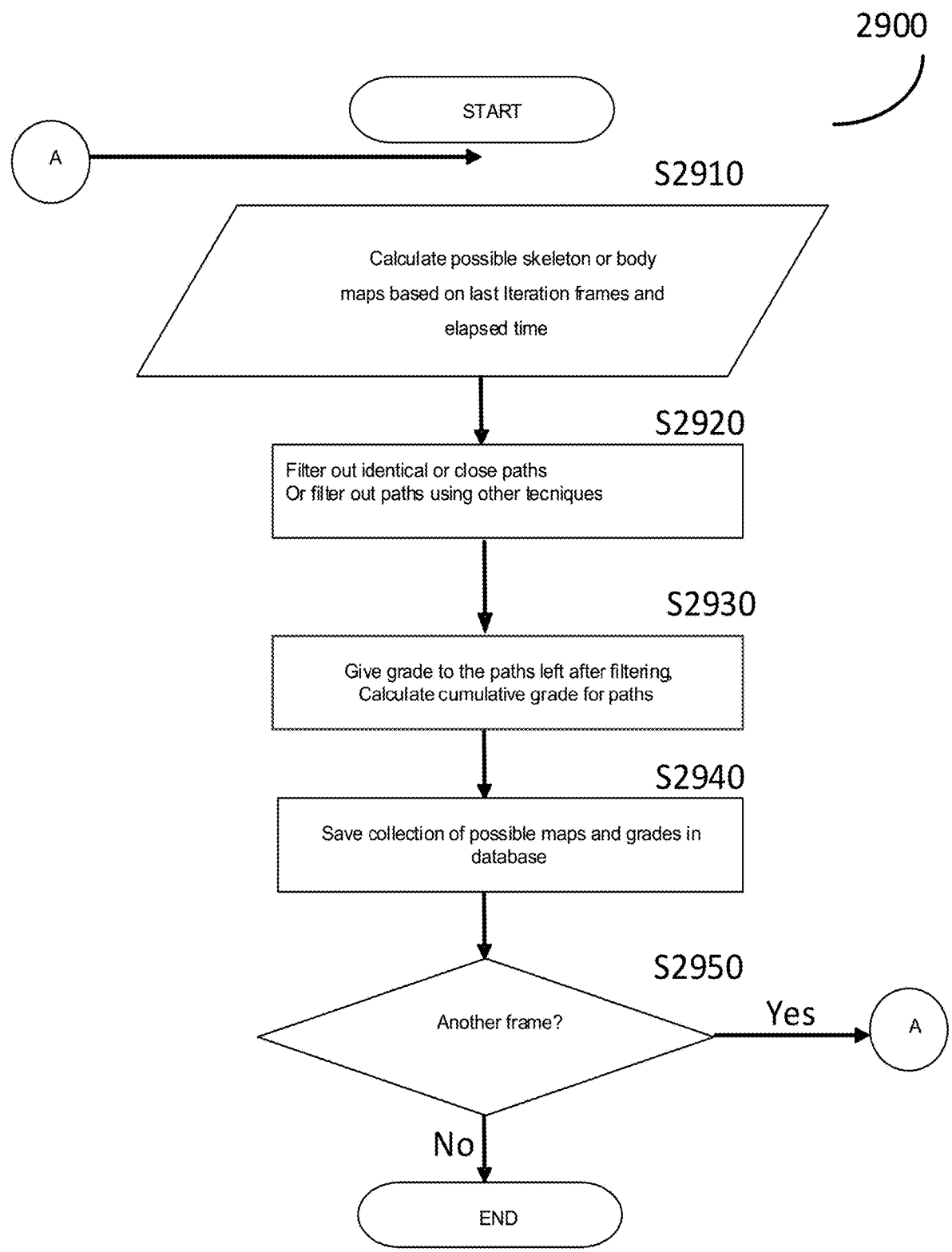
FIG. 29. Is a flow-chart describing a method for generating a machine representation model of the objects to track.

FIG. 29 is an exemplary and non-limiting flowchart 2900 depicting a method for creating or tracking a body model that can be more suitable after the initial or previous stage body model is known.

At S2910, the possible skeleton or body models may be calculated based on the last known matched body model or skeleton model (which can be the initial or first model, or a model from previous step of method 2900 for example) and the elapsed time from the last step/frame. Several possible skeleton or body models may be calculated in this step, based on points, joints or body parts which take a different trajectory from each previous step body model. In an example embodiment, a collection of body models from previous steps serves as a basis for the body models of this step. points, joints or body parts or other ingredients of the collection of body models from previous steps take certain trajectories or certain new locations. Body model ingredients (point and/or joints and/or shapes and alike) from the collection of previous steps body models may be omitted, or new body model ingredients can be added. This way the collection of previous steps body models change and evolve to the collection of body models of the current step.

Some of the example methods used to calculate the possible trajectories may be based on a function of body model ingredient trajectory from previous steps. For example, an average of each body model ingredient trajectory from a collection of several previous steps body models. Another example is random motion of each body model ingredient where the random motion may be put in limits based on the maximum possible acceleration and/or speed the user can exert on each joint and the elapsed time between steps, known anatomical or physical limits, expected motion based on the training module 110 knowing the exercise, the location in the exercise flow, the expected motion, and the like. Another example is adding such random motion to a function of body model ingredient trajectory from previous steps, like the average from previous steps. Alternatively, or additionally, data from sensors such as WCDs, accelerometers, or other sensors (such as mounted on the exercise equipment) may be used to calculate or limit the possible trajectories of the body model ingredients. The calculation may take into account limits of the subject's body, for example, known limits of movement of joints (for example, a knee joint cannot exceed the extension of a straight leg) or the fact that body parts cannot overlap in space. The collection of possible models may be based on several frames or models of the last iteration or iterations. Any one of the methods of "Methods for calculating and finding quantities and configurations used in this disclosure" can be used on a collection of previous steps body model ingredient and sensors data to calculate the trajectory and or location of this step. This may include Machine Learning methods.

More examples: the vectorial speed can be estimated based on previous frames. To calculate the instantaneous speed in each frame the system can calculate the difference in location between the frame and a previous frame and divide by the time elapsed. The instantaneous acceleration can be found by finding the vectorial difference between instantaneous speeds and dividing by the time elapsed. The instantaneous speed or acceleration can be calculated as a function of previous steps instantaneous speeds, accelerations, the time elapsed and sensor data of body model ingredient, its spatial or time neighbors or any other body ingredients. Any other method from "Methods for calculating and finding quantities and configurations used in this disclosure" can be used on this data to find trajectories, location or other kinematical data. When using average higher weight can be given to the latest steps. Filtering can be done for each body model ingredient with its neighbors. For example low pass filter for a body model ingredient can include the weighted sum or other function of a 3D matrix of its neighbors normalized by a certain factor. A value atteined from a function of any observation or size related to the body model ingredients included in such a matrix, or a body model ingredients over time can be compared to a threshold and the comparison used to decide if how to calculate or filter sizes related to such a body model ingredient. For example, to filter out noise spatial average of such a spatial matrix can be calculated. If the body model ingredients instantaneous speed exceeds this average by a certain amount, this exceeding instantaneous speed value will be modified and/or not included in future steps calculations. In a similar manner location of body model ingredients in this step can be estimated. Taking the location of the last step/frame and adding to it integration of the speed of the last step/frame (instantiations or average or calculated and alike) or for example integration of the acceleration found in the last step twice with time, can yield an estimate for this step location. Several methods can be used to achieve several different body maps. Slight changes that can also be random to different sizes like speed and location can be introduced to generate additional possibility body models. These possibility models can account for movement or trend changes in motion. Additional motion estimation and other methods known in the art can be used. These methods can also yield possibilities linked to each body model. Possibility can be calculated using a function of the individual body model ingredients.

Body Model ingredients can be added or reduced from this step set of body models. This can happen for example if the collection of points attained from sensors include points that are not correlated with this step possible body models. The decision to add or remove body model ingredients can be taken according to several methods. An example are the method explained above of threshold spatial distance from near neighbors body model ingredients. Other may include considering the movement estimation in relation to the sensors field of view—i.e. estimation of areas that become occluded or get out of occlusion and other methods disclosed herein, in the references or known in the art.

Figure 30:
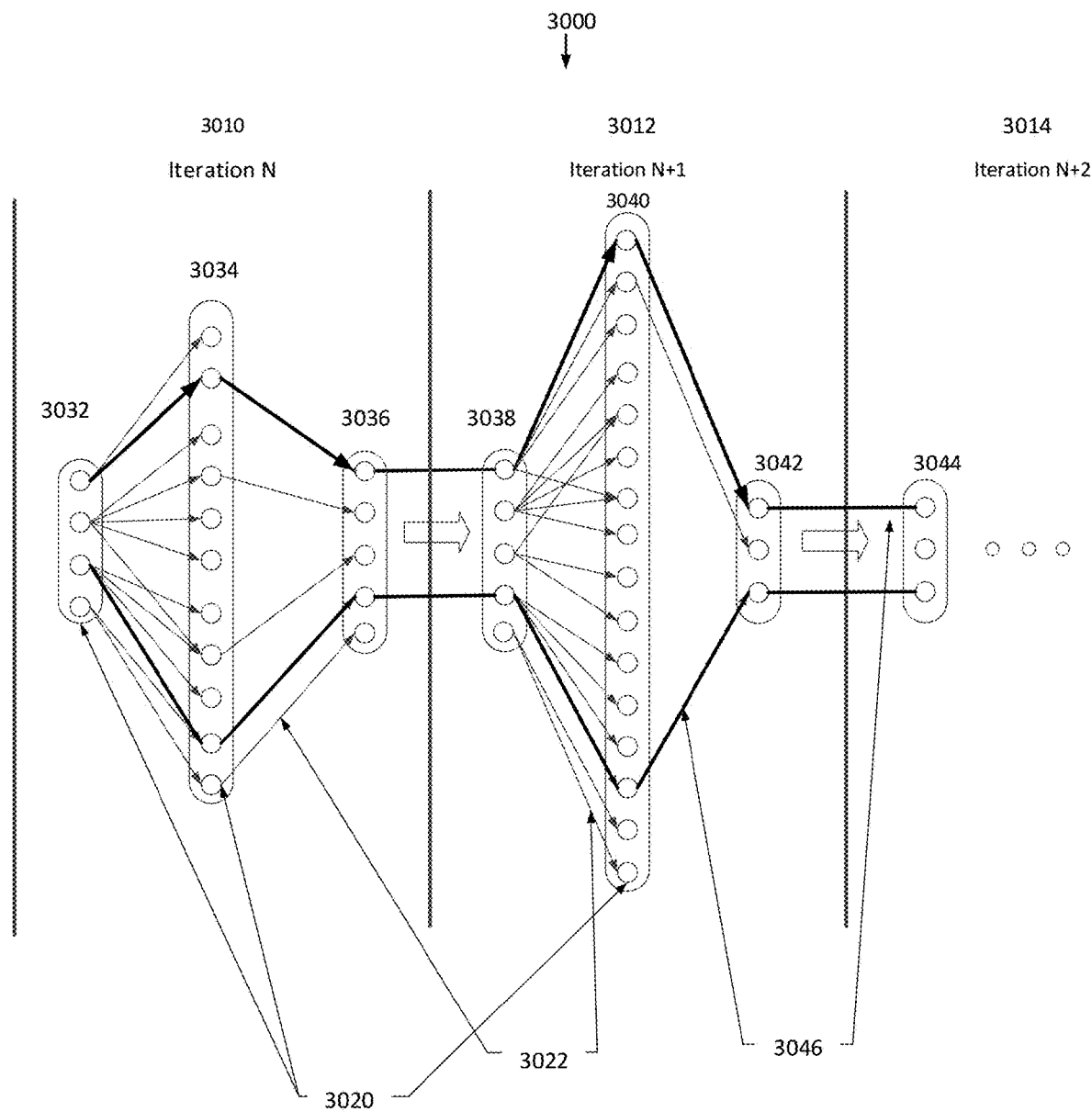
FIG. 30. Is further describing the method for generating a machine representation model of the objects to track.

FIG. 30 example 3000, schematically describe the evolution of the possible example skeleton or body model frame and trajectory according to the example embodiment. Each one of the iterations 3010, 3012, and 3014 describe one iteration of the method 2900. Each one of the dots 3020 is a possibility body or skeleton model. Each one of the arrows 3022 points to a model (3020) which have evolved from the model at the base of the arrow. 3032 is the first stage of a general iteration N. In this example, there are 4 possibility models in 3032 which the iteration starts with. At S2910, as described before, a collection of possible models is calculated respective of each one of the existing possible models from the last iteration. This leads to step 3034 in FIG. 30. 3034 schematically describes the new models generated based on 3032 at step S2910. The iterations (3010, 3012, and 3014) may be repeated for time intervals which may be smaller than the sensors frame rate. At each subsequent repetition a new and possibly larger collection of possible models is calculated based on the existing collection. For example, a certain model (3020) is based on a model (3020) from a previous repetition which in turn is based on a model from a previous repetition. The thick lines 3046 represent possible paths or trajectories in space traveled by the collection body model elements represented by the models 3020 and between the times of the iterations. In an embodiment, the training module 110 may limit the number of models 3020 generated at each step, or saved at the end of the step after filtering of S2920 occurs. This is in order to save memory resources.

Models can be generated in S2910 using any method described above in respect to FIGS. 26-29 and 31, and after. Step S2910 can be considered each time by the method as the first frame and possibilities for the body models. FIG. 30 does not show a creation of models 3020 not based on previous step models (dots without arrows leading to them), but this is possible. Other methods described in the references or known in the art can be used to generate new models in each step.

At S2920, which is optional, filtering takes place. Filtering body or skeleton modeling possibilities can be done in many methods as described before in respect to FIGS. 26, 27, and 28. For example, as described according to shade patterns as described in respect to FIG. 27. An important method of filtering is comparison to the actual sensor or sensors' image/s and/or data. Such methods were described in respect to FIG. 28 at S2870 and in the references. Identical or close models or paths can also be filtered out.

Additional methods for filtering may include, for example, use of data from sensors such as accelerometers or position indicating sensors. The paths which are the closest to the measured direction, location, speed, acceleration, or a combination thereof, can get a better grade or not be filtered. Paths that are closer or above to the physical or given limits of possible motion in a given time can be graded accordingly or filtered. If the exercise is previously known by the system, the grading can be given according to the level of deviance from it or other like factors. A low pass filter may be used and filter out sudden changes in trajectory as a result of sudden grade change (which can be a result of a singular error).

Filtering can be based on grade at each step even if there is no captured frame from the sensors that gives the 2D/3D body representation or other sensor data at this step. This can be based on the probability or other metrics calculated for each of the steps body models. Probability or metrics calculation can bring previous steps body models probability into account. A grade for filtering can also be some other weighted average or a result of a filter or a calculation based on the previous step or previous steps. Alternatively some types of filtering methods are independent of sensor data. For example, filtering according to physical and kinematical limitations imposed on the subject.

As described before, also in respect to FIG. 27 at each step additional points in 3D space may be added to the collection of points representing the subject. Filtering of the possibility models can be done according to the level of overlap of these added points with the possibility models. The level of overlap can be graded (in similar methods to the ones described in respect to FIG. 28) and the lower/higher grades can be filtered.

3036 in FIG. 30 describe the models that have survived the filtering of S2920.

At S2930, which is optional, possibilities, grades or metrics can be given to each one of the models that survived the filtering. Actually, as disclosed, the grading process can take place before the filtering stage and the filtering will be based on it. For example, the filtering will only leave a pre-defined number of the best graded models/paths. Another example is leaving only models/paths which have passed a certain threshold or a combination of these two methods. Grading for this steps surviving paths can be the result of the filtering stage. The grade can be the result of the calculations that led to the decision to filter or not to filter.

In FIG. 30, 3046 are paths which include several models from each step which evolve to other models in the next step. Grading can be given to paths. The path grade maybe based on the accumulation of the individual grades for the models it comprises. It can be a weighted sum of them or some formula or complex calculation based on them. Examples can be: the path grade is a weighted sum of the individual models, where individual models which their grade is based on comparison to image sensor receive a higher weight than ones which are not. Another example can be moving average with higher weights to the latest models, so the path grade gives higher weight to the latest models. Filtering of models in each stage can be according to the path grade and not only the individual model grade or it can be taken into account.

At S2940, the surviving models and grades from this iteration are saved in the database 120. At S2950, it is checked whether another captured frame from the sensors is expected, and if so execution continues with S2910; otherwise execution terminates.

If execution continues, at 2910 we start again with the saved models and grades from S2940. We can see in FIG. 30 that Iteration N+1 starts at stage 3038 with the saved models from stage 3036 and similarly Iteration N+2 starts at stage 3044 with the generated models before filtering at 3040 and the saved models from stage 3042.

The path or model with the best grade may be presented to the user/s at each step, or every number of steps. The presented model may also be based on a frame continuing the last selected path, where the presented path can be allowed change to another (for example better graded) path only at certain points, which will give a good viewing experience to the user. For example, the path can change only at points obscured or occluded by the exercise equipment, point, extremity in movement (where for example a joint reaches the end of its movement in a certain direction, or changes its speed considerably), and the like.

The presented model or path can be synthesized from the collection of the best graded models/paths: The synthesis can be based on averaging the location of the body model elements between the models/paths in the collection or some calculation taking them into account. The max number of models/paths taking part in the calculation can be pre-defined, or a threshold of grade can be defined so that each model/path passing it can participate in the calculation.

Designing, Monitoring, and Feed Backing Training Programs and Sessions.

FIG. 32 of this disclosure describes a non-limiting and exemplary table of a data structure 3200 that resides in the database 120 according to an embodiment. In this embodiment, the training equipment 190 can be for example gym and Pilates exercise devices such as: a Pilates reformer, butterfly machine for chest muscles, treadmill, elliptical, cycling machine, dip machine for triceps, leg extension machine for quadriceps, leg press machine for quadriceps, bench chest press, machine shoulder press, free weights and modifiable bench, standing calf raise machine, leg curl machine, glut-ham raise machine, and the like, or a combination thereof. The exercise devices may include means to automatically configure the difficulty level and/or the machine dimensions to the user. The Computing Device Enhanced Training Environment system 100 may also include a plurality of sensors to track the user performance.

Figure 33:
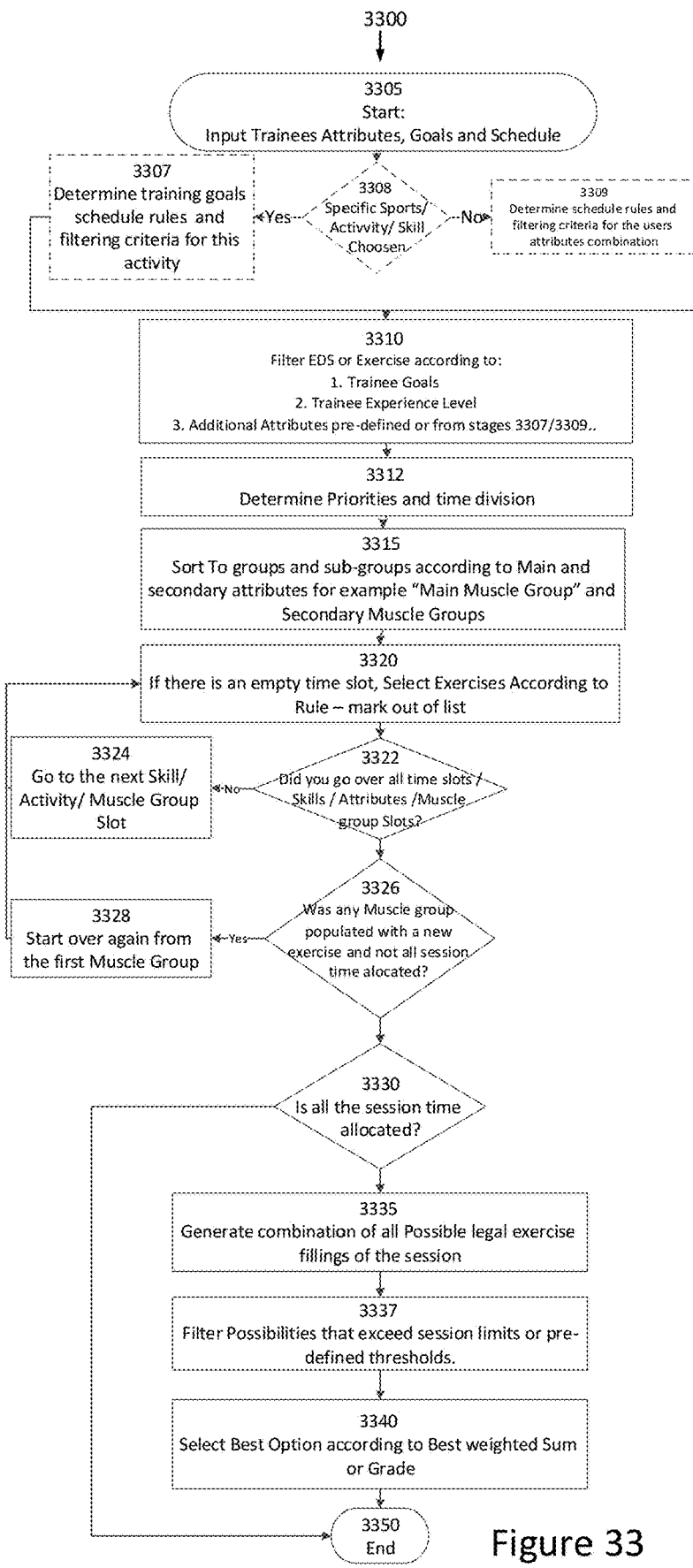
FIG. 33. Is a flow chart describing a method for design of a training program by a Computing Device Enhanced Training Environment.

In FIG. 32. Each part of the data structure like 3240, 3242, 3260, 3262 etc. corresponds to an exercise or a training procedure. These data structures describing an exercise or a training activity and its attributes will be further called Exercise Data Structure or EDS. Not all the exercise attributes are shown in the EDS data structures of FIG. 32. This is done for the sake of clarity and reduced complexity. In the case of the example of physical exercises, further descriptions of exercises with and without exercise machines as well as some of their attributes can be found in well-known websites such as "bodybuilding.com". Other possible entries to the data structures (like 3240, 3242, 3260, 3262 etc.) which are not shown may include: date of creation in the database, date of modification, creator, updater, access permission to parts of the data structure such as for example "read-only" and other permissions, and the like. The table includes a plurality of such members. The table may be held sorted in groups according to one of the entries, for example main muscle group, recommended experience level, and the like. In this example EDS 3210 of FIG. 32A the following fields can be seen: Exercise Name—3211, Serial number—3212, exercise type 3213, exercise machine—3214, Exercise description—3215, Link to frame Data Base—3216, Main Muscle group—3217, Main Muscle group excersion Level—3218, Secondary Muscle Group—3219, Secondary Muscle groups excersion Level—3220, Third Muscle group—3221, Recommended experience level—3222, Time required per rehersal—32232, Recovery Time between sets—3224, Exersion/Fatigue LeveL Formula/Constant—3225, Muscle group Exersion conversion—3226, Exercise grade—3227, Recommended for other sports—3228, Recommended in case of limitation—3229. 3244, 3246, 3248, 3250, 3252, 3254, 3264, 3266, 3268, 3270, 3272, 3274, 3276, 3258, 3261, 3282, 3286, 3278, 3280, 3284, 3288 are all additional examples EDS in FIGS. 32A-N;

FIG. 33 is an exemplary and non-limiting flowchart 3300 of a method for building an exercise plan for a user and supervising the performance or implementation of the plan by a plurality of users. At 3305, inputs for the exercise plan are received. First, data structures are filled with user data. The table below is an example data structure filled for an example user:

| Trainee Attribute | Attribute Value | Units |
|---|---|---|
| Name | James | |
| Gender | Male | |
| Age | 30 | Years |
| Weight | 80 | Kg |
| Height | 177 | cm |
| BMI | 25.535 | |
| Experience Level | Beginner | |
| Known Limitations | None | |
| Total Fat Percentage | 25.00 | % |
| Chest Fat Percentage | 21 | % |
| Back Fat Percentage | 15 | % |
| Legs Fat Percentage | 16 | % |
| Abs Fat Percentage | 30 | % |
| . . . | | | may be filled through the system interface 220. For example, the Computing Device Enhanced Training Environment system 100 may vocally ask the user for his name, gender, age, and the like and process his vocal answers through speech recognition and store the data. In an embodiment, the data is requested and received via the I/O devices 130 and 140. Other data can be attained through measurements such as height, weight, body fat percentage, and the like.

In an embodiment, the Computing Device Enhanced Training Environment system is configured to utilize sensors to perform the measurements. For example, certain training equipment 160 may have pressure sensors on their seat. Such a sensor may measure the user's mass. As another example, an optical sensor may measure the user's height, volume of different body parts, and estimate body fat percentage.

The user's training preferences and schedule are received. In an embodiment, the user selects 3 training goals from a list. Table 2 below is an example list filled by the example user:

| Training Goal | Priority |
|---|---|
| Strength | 2 |
| Fat Lose | 3 |
| Good Body Look | 1 |
| Improve Cardio Vascular ability | |
| Develop Flexibility | |
| Specific Sports | |

To determine the schedule the user is asked the number of times he can train per week and the length in time the user can dedicate for a session. In this example, the input is: number of training sessions per week=2 and time per session=90 minutes. The user inputs are stored in the database 120 and a training plan is built for the user.

The process of building the training program consists of several stages of filtering, sorting, and ordering according to the exercises attributes. A filtering, sorting, or ordering stage may be performed respective of one attribute, a group of attributes, a formula or function taking into account a plurality of attributes, and the like.

At 3308, it is checked whether a specific sport or activity is chosen as a goal or focus of the training. If specific is chosen, at 3307 the specific training goals, filtering rules and schedule rules for this training type are pulled from the database 120. The inputs described in previous paragraphs such as the user data can be taken into consideration and for example refine the selection of goals, filtering rules etc. Further example for this will be given below. The At 3309 such specific activity to use as training goal or focus was not chosen. Determining the rules, filtering rules goals and schedule rules takes place according to the inputs described in previous paragraphs such as the user data, goals from the example feature of goal table like the table above, were chosen. A simple example is a predefined method. If the user selected training goals, sets of rules per each goal can be selected from the Data Base 120. If there are rules defined as contradicting between these sets, the rules belonging to the higher probability prevail. Further refinement can be done for example using the user's gender and age. Different rules can have an attribute which tells the system that they are suited for certain age range or certain gender. In another example the gender and age can be used as the criteria for the first rule sets selection. For example, there can be 6 or more predefined sets called male child, male, male old, female child, female, female old. There can be more ages ranges defining more predefined set. The system will pull the corresponding rule set according to gender and age. It can further refine the selection or filter out rules from the chosen set based on additional input data.

At 3310, unsuitable exercises or EDS are filtered from the exercise/EDS existing in the Data Base 120 to create EDS list. Filtering can take place using rules and methods pulled from the Data-Base 120 at stages 3307-3309 or for example predefined rules. In an embodiment filtering, can be done according to the user's defined goals: If cardio was not selected by the user as a training goal, all exercises of the exercise type "cardio" may be filtered out. In another embodiment, filtering occurs according to the user experience level. For example, if the user is a beginner all exercises that require a higher experience level are removed. EDS Data Base filtering can be done in multiple stages, can repeat and can use any Data-Base filtering method known in the art.

At 3312, the trading priorities, schedule and time division are set according to a set of predefined rules and/or rules achieved from stages 3307 to 3309. In an embodiment, there are limits to the minimum and maximum amount of time per training session. These limits are provided to the user when he inputs his time per session. In a gym embodiment for example, the maximum session length possible is 2.5 hours and the minimum is dependent on the user's selected priorities. For a mixed training session:

(60 [mm] if strength/good body looks selected)+(10 min for warm up and stretches)+(30 [mm]/flexibility priority if flexibility is selected)+(cardio time 20-45 [mm] according to the rules below).

For a cardio session only see the rules below. In this example gym embodiment, the set of rules is (excluding specific sports for which the rules may be different depending on the sport selection):

Rule Set 1:
1. For all sessions—If the session is not a cardio session and does not start with a cardio exercise, start with 5 minutes walking on the treadmill in 6 [Kmh] pace followed by stretches as warm-up.
2. If the session is not a cardio session and starts or ends with a cardio exercise, there shall be one cardio exercise per beginner and intermediate and up to two for an advanced user.
3. If cardio is selected as first priority, or first priority is fat burn and cardio is second, or develop flexibility is one of the priorities and cardio and fat burn are the other priorities, the following rules apply
   a. Up to 4 sessions a week:
      i. For beginner start training with 30 minutes of cardio exercise.
      ii. For intermediate start with 40 minutes and advanced with 45.
   b. 5-6 sessions a week (6 sessions is the maximum allowed per week)—2 sessions for other selected priorities the rest (3-4) for cardio. Select between 5 and 6 total sessions according to user selection, or input schedule preference.
4. If articles 1-3 do not apply, and cardio is second priority, or fat burn is second and cardio is third, or fat burn is first priority:
   a. Up to 4 sessions a week:
      i. For beginner end each training session with 25 minutes of cardio exercise.
      ii. For intermediate end with 35 minutes and advanced with 40.
   b. 5-6 sessions—2 sessions for cardio and the rest for other priorities.
5. If the previous articles do not apply and cardio is third priority or fat burn is second priority:
   a. Up to 4 sessions a week:
      i. For beginner end each training session with 20 minutes of cardio exercise.
      ii. Intermediate end with 30 minutes and advanced with 35 minutes cardio.
   b. 5-6 sessions—2 sessions for cardio/fat burn and the rest for other priorities.
6. If the previous articles do not apply and fat burn is third priority:
   a. Up to 4 sessions a week:
      i. For beginner end each training session with 15 minutes of cardio exercise.
      ii. Intermediate end with 20 minutes' cardio and advanced with 25.
   b. 5-6 sessions—2 sessions for cardio/fat burn and the rest for other priorities.
7. A cardio dedicated exercise is 30 minutes for beginner, 40 for intermediate and 45 for advanced. For beginner it includes one exercise, for intermediate and advanced it can include up to 3 exercises.
8. Strength, good body looks and flexibility take the rest of the non-cardio session.
9. Flexibility if selected takes 30 minutes divided by the flexibility priority. If flexibility is not selected, 5 minutes of stretches according to a pre-defined stretch plan will take place as part of the warm-up and at the end of the session (after the cardio exercise if such was defined as last by previous rules).
10. The order between cardio, flexibility strength and good body looks is the following—strength and good body looks are practiced together, always before flexibility, if cardio is also present in a combined session flexibility will come after it, despite what may be written above that cardio is last.

For example, the User James has selected strength and good body looks as his first priorities and fat burn as his third. He is limited to two training sessions a week of 90 minutes each, and gives this as schedule input to the system. The framework of his sessions is set according to the rules above. Since he has not selected cardio and fat burn is only third priority, according to rules 1 and 6a the session will start with 5 minutes of treadmill exercise and will end with 15 minutes of cardio exercise with low intensity. According to rules 8 and 9 above the 5 minutes of treadmill warm-up will be followed with 5 minutes of stretches. The ending cardio exercise will be followed by another 5 minutes of stretches closing the session. The rest of the session (90−(5+5+15+5)=60 [mm]) according to rules 8,9,10 is dedicated to the strength and good body looks. So each session looks like this:

5 Minutes—Treadmill warm-up
5 Minutes—Stretches warm-up.
60 Minutes—Strength and Good Body looks training.
15 Minutes—Fat Burn (Low intensity Cardio exercise).
5 Minutes—Closing stretches.
90 Minutes—Total time.

This is the session time allocation according to the first attribute of the EDS in FIG. 32—exercise type. This example uses FIG. 32 example Data Base.

Next at 3312, the framework of sessions is populated with exercises and time is allocated for each. Time is allocated respective of exercise attributes. In this example, the main and secondary muscle groups are used by these corresponding rules:

Rule Set 2:
1. For cardio/fat burn:
   a. Specific cardio session:
      i. Beginner—1 exercise of type cardio, the best graded, supplement to exercise change rules (below).
      ii. Intermediate, advanced—2 exercises of type cardio, the best graded, supplement to exercise change rules (below). The first exercise takes around 70% of the time.
   b. Combined session:
      i. 1 Cardio exercise, the best graded, supplement to exercise change rules (below).
2. For flexibility strength and good body looks (where strength and good body share the same type of exercises):
   a. For beginner or less than 4 exercise sessions per week:
      i. In every training session work on the following main muscle groups or body areas: abdominal, lower back, back including traps, lats and middle back, chest, hamstrings and gluteus, quadriceps, calves, shoulders, biceps, triceps.
      ii. Session will include at least 2 exercises for these large muscles/muscle groups: abdominal, back, chest, legs.
      iii. Session will include at least 1 exercise for every other main muscle groups or body areas in article a.
      iv. 48 hours of rest are required between every two sessions.
   b. For intermediate, advanced 4 exercise sessions per week:
      i. At least 2 exercises per muscle group, for large muscles/muscle groups: abdominal, back, chest, legs, and preferably 3 exercises.
      ii. Sessions will be done in the A/B manner in groups of 2.
         1. The first session (A) from the two will include chest, legs and biceps.
         2. The second session (B) will include abdominal, back, shoulders, and triceps.
         3. A is always followed by B. At least 20 hours of rest are required between A exercise and B, At least 40 hours are required between B and the next A.
   c. For advanced—
      i. At least 2 exercises per muscle group, for these large muscles/muscle Groups: abdominal, back, chest, legs, at least 3 exercises.
      ii. Smaller muscle groups are added—specific work on: glutes, forearm and neck—at least one exercise for each, 2 exercises per each muscle group in the back: lower Back, traps, lats and middle back.
      iii. 6 sessions per week: sessions will be done in the A/B/C manner in groups of 3:
         1. The first session (A) from the two will include legs and chest biceps.
         2. The second session (B) will include abdominal and back,
         3. (C) will include shoulders, forearms, neck and triceps.
         4. A is always followed by B followed by C. At least 20 hours of rest are required between A exercise and B, also between B and C. 40 hours are required between C and the next A.
      iv. In case of 5 sessions—the second ABC series is alternated each week AB, BC, AC.
   d. Maximum sessions limit:
      i. For beginner no more than 3 sessions.
      ii. For intermediate no more than 4 sessions.
      iii. For advanced no more than 6 sessions.
   e. Unless the order is defined differently above, large muscles/muscle groups are chosen by algorithm first and exercised by user first.
   f. Unless the order is defined differently above, muscle group is followed by the opposite muscle group if defined as a pair in the following list. The pairs are—abdominal—lower back, biceps-triceps, quads-hamstrings, chest—upper/mid back.
   g. The rest of the ordering is done by priorities:
      i. If fat burn or good body looks are prioritized by the user before strength the priority is set according to the estimated/measured body fat percentage in the body areas, the areas with higher percentage are chosen and exercised first.
      ii. If strength is higher prioritized, core muscles which are abdominals and lower back are first, rest of the muscle groups are ordered according to the level of strength measured in test compared to a pre-defined level per exercise. The exercises which are lower in level of strength compared to the pre-defined level come first.
      iii. In case the rules for fat burn or good body looks together with the previous rules are not enough for decision, the rules for strength are used. The same goes for strength, the rules for fat burn or good body looks are used if strength rules are not enough for decision. In case it is still not enough, comparing exercises grades, and taking the exercise with the highest grade, or random decision can take place.
2. For flexibility the order follows (a) and (b), and then order starts with the less flexible areas first. Where the flexibility level is determined by a test as shall be detailed below.

According to rule 1b, the 15 minutes of fat-burn will include one cardio type exercise. The stretching parts in this example are sets of pre-defined stretching exercises which may not change. In other embodiments, they can be selected in a similar manner to other parts of the session.

According to (2a) the exercise should include the following:

First Priority:
Abdominal—2 Exercises.
Back including Traps, Lats and Middle Back—2 Exercises.
Chest—2 Exercises
Legs—2 Exercises
Lower Back—1 Exercise
Shoulders, Biceps, Triceps—1 Exercise Each.

Since James has selected good body looks as first priority, the order of the exercises is set according to his highest body fat percentage measurements in the table above considering muscle pairing. First the muscle group was selected corresponding to the body area with the highest fat percentage from the ones left unallocated. Next if this muscle group has a pair opposite a muscle group according to rule (2f) the paired muscle group will be selected next. The selected groups are removed from the selection pool. This process is iterated until the muscle groups are ordered or until no more ordering can take place because of insufficient data or inability of the rules above to determine the order.

In our example this process output is:
In the large muscle groups the order is Abdominal, Lower Back, Chest, Back, Legs.
In the small muscle groups say there are no measurements of fat percentage for these body parts, so the Computing Device Enhanced Training Environment system 100 uses the strength rules. Say at this stage the strength have not been tested yet, so an arbitrary ordering takes place: shoulders, biceps, triceps.

At this stage the session map is:
5 minutes—treadmill warm-up
  5 minutes—stretches warm-up.
  60 minutes—strength and good body looks training:
    abdominal—2 exercises (Or more)
    lower Back—1 exercise (Or more)
    chest—2 exercises (Or more)
    back—2 exercises (Or More)
    legs—2 exercises (Or More)
    shoulders—1 exercise (Or more)
    biceps—1 exercise (Or more)
    triceps—1 exercise (Or more)
15 minutes—fat burn:
  1 cardio exercise.
5 minutes—closing stretches.

Another rule set defines the number of sets and rehearsals per set in case of strength, good body looks and flexibility exercises:

Rule Set 3:
1. If strength in higher priority than good body looks—
   a. 3 sets of 10 repetitions each (shall be denoted 3×10).
   b. In case of abdominal muscle exercises 3 sets of 20 repetitions (3×20).
   c. Exercises database may include entries for specific exercises defining the number of sets and repetitions for these exercises depending on the type of exercise, the user experience level, the location of the exercise in the session and more.
2. Good body looks in higher priority—
   a. 3 sets of 12 repetitions each (shall be denoted 3×12).
   b. In case of abdominal muscle exercises 3 sets of 25 repetitions (3×25).
3. Flexibility—
   a. Usually each set is 1 repetition where the time for remaining in the pose is dependent upon the user level:
      i. 30 seconds for beginner.
      ii. 40 second for intermediate.
      iii. 45 seconds for advanced.
   b. Exercises database may include entries for specific exercises defining the number of sets/repetitions etc.

At 3315, the exercises are sorted into groups and subgroups according to—group by type, sub-group by main muscle group, and sub-group of the main muscle group by secondary muscle groups. FIG. 34 (3400) shows the EDS database 3200 of FIG. 32 after the filtering according to this example, of stage 3310 and the sorting of 3315 in FIG. 33 method 3300.

At 3320 the time slot for the session part is populated with the first/next exercise from the database 120 according to the exercise selection rules of the session parts. These rules in this gym example are:
1. In each iteration select at maximum one exercise per muscle group/type.
2. Do not select an exercise if the current muscle group is already populated with the minimum number of exercises and there is any other muscle group not populated with the minimum number of exercises.
3. Each selection is made according to the best exercise not already selected, from the filtered exercises list of 3310 for this muscle group/type. The decision about the best exercise can be made according to any one of the exercise attributes such as, but not limited to, the given exercise grade, the time required per rehearsal (the lower the better, for example) or the number of secondary muscle groups the exercise is working on (the higher the better for example). An exercise may be selected according to a combination of attributes or a formula applied on them. In this specific example, a weighted sum of several attributes is used to decide on the best exercise (one with largest weighted sum):

Weighted Sum=30*Exercise Grade+30*Exertion Level+20*(1 if exercise includes a large muscle group not exercised yet, or 0 otherwise)+10*Secondary Muscle Groups number−12*(Time per Rehearsal+Recovery time between sets).

After selection of each exercise the checking in 3322 and if positive 3326 is performed. Also in 3326 and 3330 a check is performed on whether the performance time of all exercises does not exceed the total time allocated for the session. Another check that can be performed is that the calculation of exertion level does not exceeds the total exertion level allowed. A possible example for the implementation of such a check: it is possible to sum up the exertion levels and verify they do not exceed a certain threshold which is compliant with the user's level or user's request. An example for the time check calculation: in order to calculate the time for a single exercise in our example, the Computing Device Enhanced Training Environment system 100 takes the time required per rehearsal and multiplies it by the number of rehearsals per set. For example, if a set of abs pushups has 25 repetitions and the time per rehearsal is 4 [sec], one set takes 100 [sec]. Upon adding recovery time between sets also multiplied by repetitions we get 100+4*25=200 [sec]. If the exercise requires 3 sets we have a total of 600 [sec] or 10 minutes. Thus, each time an exercise is added to the session its calculated time can be added to the sum and checked against the total time. In this specific example this calculation will not be performed for the sake of clarity and simplicity and it will be assumed that it was performed by the system and the list of selected exercises does not exceed the session time until mentioned otherwise.

In 3322, it is checked whether all muscle groups' slots were covered in this pass and if so, execution continues with 3326; if not, execution continues with 3324. At 3326, it is checked if any of the muscle groups was added an exercise in the last pass and if so, execution continues with 3328; otherwise execution continues with 3330. As mentioned above, 3322 and 3326 may also include checks for session time excess and exertion excess. If such excess was detected execution will continue with 3330. At 3330, it is checked whether all the session time has been allocated.

In our example, the first muscle group slot is for abdominal. Checking the two available abdominal EDS: 3410, 3412, according to the weighted sum equation above the exercise with the higher weighted sum is "abs pushups" 3410, which is selected. Going to the next muscle group, there is one possibility for lower back- hyperextensions 3414, which is selected because of no alternatives. Next is chest possible EDS are: 3416, 3418—using the equation above the exercise selected is chest bench press. Similarly "Wide Grip Lat Pull down" 3420 is selected for back muscle group. Continuing the Iterations results in:

5 minutes—treadmill warm-up
5 minutes—stretches warm-up.
60 minutes—strength and good body looks training:
   abdominal—2 exercises (Or more)
   1. Abs Push Ups (3×25)
   Lower Back—1 Exercise (Or more)
   1. Hyperextensions (3×12)
   Chest—2 Exercises (Or more)
   1. Chest Bench Press (3×12)
   Back—2 Exercises (Or More)
   1. Wide Grip Lat Pull down (3×12)
   Legs—2 Exercises (Or More)
   Shoulders—1 Exercise (Or more)
   Biceps—1 Exercise (Or more)
   Triceps—1 Exercise (Or more)
15 Minutes—Fat Burn:
   1 Cardio exercise
5 Minutes—Closing stretches.

At this stage a leg exercise is required. Note that leg press 3424 receives a higher sum then all other leg exercises 3426, 3228, 3430 not only because it has a higher grade and exertion level, but also because it works on several secondary muscle groups and according to the equation above there is additional grading: (10*Secondary Muscle Groups number). At the end of the first pass the session plan looks like that:

5 minutes—treadmill warm-up
5 minutes—stretches warm-up.
60 minutes—strength and good body looks training:
   abdominal—2 exercises (or more)
   2. abs push-ups (3×25)
   lower back—1 exercise (or more)
   2. hyperextensions (3×12)
   chest—2 exercises (or more)
   2. chest bench press (3×12)
   back—2 exercises (or more)
   2. wide grip lat pull down (3×12)
   legs—2 exercises (or more)
   1. leg press (3×12)
   shoulders—1 exercise (or more)
   1. alternating cable shoulder press (3×12)
   biceps—1 exercise (or more)
   triceps—1 exercise (or more)
   1. triceps push down (3×12)
15 minutes—fat burn:
   1 cardio exercise—
   treadmill
5 minutes—closing stretches.

Note that a biceps exercise was not chosen at the end of the first pass. This is because the weighted sum is equal for both biceps exercises 3436, 3438 in the database 120. One requires less time to perform while the other gives a higher exertion level. Such a situation can be avoided by adding selection rules to the set of rules above. For example, if the weighted sum is equal, choose according to a certain attribute, for example minimum time to perform. Or in case all selection rules do not issue a result, choose randomly or by the order of appearance in the database 120. In our example, such rules were not set and we are left with one empty muscle group slot at the end of the first pass.

Another pass is taken since more than one muscle group was populated with a new exercise in this pass. At the end of the second pass we get:

5 minutes—treadmill warm-up
5 minutes—stretches warm-up.
60 minutes—strength and good body looks training:
   abdominal—2 exercises (or more)
   1. abs push-ups (3×25)
   2. abs air bike (3×25)
   lower back—1 exercise (or more)
   1. hyperextensions
   chest—2 exercises (or more)
   1. chest bench press (3×12)
   2. butterfly (3×12)
   back—2 exercises (or more)
   1. wide grip lat pull-down (3×12)
   2. cable rows (3×12)
   legs—2 exercises (or more)
   1. leg press (3×12)
   2. standing leg curl (3×12)
   shoulders—1 exercise (or more)
   1. alternating cable shoulder press (3×12)
   biceps—1 exercise (or more)
   triceps—1 exercise (or more)
   1. triceps push down (3×12)
15 minutes—fat burn:
   1 cardio exercise—treadmill
5 minutes—closing stretches.

When the leg muscle group was reached in this pass standing leg curl 3426 was selected over leg extension 3430 because each main muscle group not worked on before had a high contribution to the sum in the equation above. In this case, quadriceps is also the main muscle group in the leg press exercise which was already selected in the previous pass. 3422, 3432, 3442, 3444 are example EDS in the example database.

After selecting this leg exercise in 3320 method 3300 there is no more option to select further exercises to any muscle group because the minimum number of biceps exercises cannot be reached while the minimum of all other groups have been reached according to rule 2 in the last rule set above. At 3322 method 3300 the "Yes" branch is therefore chosen leading to 3326. At 3326 since leg exercise was chosen in this pass the "Yes" branch is selected again. 3328 step leads to a new pass.

A third pass is therefore conducted. At this third pass in the loop of steps 3320->3322->3324->3320 no exercise is selected for the same reason (rule 2 of the last rule set).

Therefore, when reaching 3326 again execution continues to 3330. At 3330 not all the session time is allocated, so execution continues to 3335.

At 3335 the possible combinations from the exercises left unselected in the filtered database are generated. The unselected EDS in our example are:
calf press on leg press machine 3428, leg extension 3430, lateral raise with bands 3434, machine preacher curls 3436, alternate curl 3438, cable one arm triceps extension 3440.

An example for a combination is the first combination (all of lift exercises) which is also the longest one. There are many more possible combinations of the remaining exercises—in this example for 6 exercises there are 63 possible combinations including "combinations" that include only one exercise. To be more optimal the system can filter exercises from the base collection (In this case the 6 remaining exercises) before generating the combinations. For example the rule can be filter out EDS according the attribute of main muscle group—filter out main muscle groups already populated by the minimum number of exercises required. Legs muscle group for example is already populated by 2 exercises. Therefore, calf press on leg press machine 3428, leg extension 3430 can be removed from the base collection, and thus only 15 combinations are possible.

At 3337 the list of generated combinations is filtered. An example filtering criteria can be to leave only combinations with exercises belonging to muscle groups which are not yet populated in the training plan with the minimum number of exercises. In this example this is the biceps muscle group. A bit more complicated rule my also require that the left combinations should contain for these not yet minimally populated groups the number of exercises with the attribute of main muscle group, which is required to bring each such group to the minimal required occupancy. To clarify this rule is used in our example: The non filtered combination are those that include at least one of the two left biceps exercises 3436, 3438. Other methods for filtering can be used separately or in combination. For example, filtering, can be done according to session limits such as time, total exertion level etc. Filtering according to time can take place in the following manner: The time which is required to perform the already selected exercises (see example calculation above in description of stage 3322, 3326, 3330) is added to the time it takes to perform the combination. If the total time exceeds the session time limit this combination is filtered out. This process is performed on every one of the left combinations. Other session limits may include a minimum time threshold (Total execution time should exceed a threshold), minimum or maximum exertion level threshold (which may be set according to the trainee experience level) and the like.

At 3340 the best option is selected from the remaining combinations after the filtering of 3337. This can be performed for example according to grading of the remaining combinations. The grading can be a weighted sum or formula on the attributes of the exercises in the combination. For the example let's say the remaining combinations after the filtering are:
calf press on leg press machine 3428, leg extension 3430, lateral raise—with bands 3434, machine preacher curls 3436
calf press on leg press machine 3428, lateral raise—with bands 3434, machine preacher curls 3436, cable one arm triceps extension 3440.
calf press on leg press machine 3428, leg extension 3430, alternate curl 3438.
calf press on leg press machine 3428, lateral raise—with bands 3434, alternate curl 3438.

Note that since according to the EDS alternate curl 3438 requires more than twice the time per rehearsal as opposed to machine preacher curls 3436 the combinations containing it did not pass the time limit filter for more than 3 exercises.

In the example the weighted sum for grading the exercises is the sum the following for all exercises in the combination:

$$100*(\text{main muscle group not selected so far})+ \\ 50*\text{muscle group in priority}+30*\text{exertion} \\ \text{Level}+10*\text{exercise grade}.$$

It is obvious that the greater weighted sum will be one of the 4 exercises combinations. Between them the first combination has a higher sum also because of this part of the equation: 50*muscle group in priority.

Muscle group in priority considers which muscle groups were prioritized at the beginning according to the user priorities and measurements. In our example, the priorities were made according to fat percentage. Muscle group exercises order was set according to priority, so a muscle group coming first in the order have an advantage in the weighted sum.

In this example, the first combination is selected. Here rules can be made for the case where two equal weighted sums are output, such as use additional attribute or combination of attributes or choose randomly. At this point, the session plan is complete:
5 minutes—treadmill warm-up
5 minutes—stretches warm-up.
60 minutes—strength and good body looks training:
   abdominal—2 exercises (or more)
   1. abs push-ups (3×25)
   2. abs air bike (3×25)
   lower back—1 exercise (or more)
   1. hyperextensions (3×12)
   chest—2 exercises (or more)
   1. chest bench press (3×12)
   2. butterfly (3×12)
   back—2 exercises (or more)
   1. wide grip lat pull down (3×12)
   2. cable rows (3×12)
   legs—2 exercises (or more)
   1. leg press (3×12)
   2. calf press on leg press machine (3×12)
   3. standing leg curl (3×12)
   4. leg extension (3×12)
   shoulders—1 exercise (or more)
   1. alternating cable shoulder press (3×12)
   2. lateral raise—with bands (3×12)
   biceps—1 exercise (or more)
   1. machine preacher curls (3×12)
   triceps—1 exercise (or more)
   1. triceps push down (3×12)
15 minutes—fat burn:
   1 cardio exercise—treadmill
5 minutes—closing stretches.

Note that calf press on leg press machine 3428 comes right after leg press machine even though it was not selected after it. This is because the data structure or EDS holding the calf press on leg press machine 3428 has an attribute called order aid. This entry instructs the system to put this exercise right after leg press 3430 if leg press was selected. Additional specific entries can affect the selection, order, number of sets or rehearsals per set and more.

To complete the session plan there is a need to establish the difficulty level for each one of the exercises. In this example, this is achieved in a difficulty level test or "strength test". This test can be done before building the session program or after. For example, the following set of rules:

1. In case the trainee has selected strength at a higher priority than good body looks:
   a. Do the test before building the session plan.
   b. Use a predefined set of exercises for the strength test: One for each one of the main groups (except legs where two exercises are used):
      i. Abs pushups
      ii. Chest bench press
      iii. Wide grip lat pull down
      iv. Leg press
      v. Standing leg curl
      vi. Alternating cable shoulder press
      vii. Machine preacher curls
      viii. Triceps push down
   c. For abdominal muscle test the maximum number of repetitions that the user can do in a row.
   d. For other muscles do RM1 test known in the art.
2. In case the trainee has selected good body looks in higher priority:
   a. Do the test after building the session plan.
   b. Use the first exercise for each main muscle group in the session plan for the test.
   c. In case of legs use the first exercise for hamstrings and the first for quadriceps.
   d. For abdominal muscle test the maximum number the user can do in a row.
   e. For other muscles do RM1 test, except lower back.
   f. Lower back exercises always start at minimum difficulty level. If the user is experienced and has a previous training plan use it to calculate the difficulty level. Example methods for such a calculation shall be given below.

The RM1 test is known in the art of physical exercise as a test which find out the maximum resistance (weight) for which the trainee can perform 1 iteration of the exercise.

Tests known in the art can also be taken for cardio and flexibility in case they are selected in the priorities. The difficulty level of each exercise can then be set. In this example embodiment the following formulas are used in case the exercise is the same as the one done in the test:

1. For abdominals—
   a. Strength plan—for each additional 40 repetitions add 1 [kg] of weight to abs push-ups. Up to 40 reps—no weight, up to 80 1 kg etc.
   b. Good body looks plan—add 1 [kg] of weight for each additional 50 reps.
2. For others—
   a. Strength—Use 60% of the RM1 weight. Reduce additional 2% for each additional exercise starting from the 10$^{th}$ exercise in the session.
   b. Good body looks and other goals—Use 50% and the rest is like (a).
   c. For beginner reduce additional 10% resistance from every exercise. Reduce 5% for Intermediate trainee.

Exercises which were not tested in the test can include a conversion formula for difficulty level based on exercises tested for the same muscle group resistance or for different muscle groups.

Another method for setting resistance level for exercises not tested is of course to test them as well. There may be an advantage with testing some exercises after resistance level was set for previous exercises, and these exercises been performed in the same session as the test. This way the trainee performs the test with the fatigues and exertion level of a normal session. This may prevent the test results from being too good and resulting in setting to high difficulty level for some exercises.

The calculated resistance level can be rounded up or down to the closest possible implementable resistance level. For example in most machines based on weight the minimum difference between levels is 2.5 [kg]. Using additional free weights this interval can be reduced to 0.5 [kg] or less. In our example say the minimum possible difference between resistance levels is 1 [kg]. In many cases it is advantageous to round the resistance down. This is in order to prevent too high efforts at the beginning of the implementation of a new plan.

In the example the tests were conducted according to the last rule set above. For the example the results are:
   i. Abs push-ups—90 reps.
   ii. Chest bench press—80 [kg].
   iii. Wide grip lat pull-down—70 [kg].
   iv. Leg press—80 [kg].
   v. Standing leg curl—25 [kg].
   vi. Alternating cable shoulder press—40 [kg].
   vii. Machine preacher curls—30 [kg].
   viii. Triceps Push Down—30 [kg].

According to the test and the above rule set the below results example the weights set for the exercises:
60 minutes—strength and good body looks training:
   Abdominal—2 exercises (or more)
   3. Abs push- ups (3×25)—1 [kg]
   4. Abs air bike (3×25)—1 [kg]
   Lower back—1 exercise (or more)
   2. Hyperextensions (3×12)—no weight.
   Chest—2 exercises (Or more)
   3. Chest bench press (3×12)—35 [kg]
   4. Butterfly (3×12)—24 [kg]
   Back—2 Exercises (or more)
   3. Wide grip lat pull-down (3×12)—30 [kg]
   4. Cable rows (3×12)—20 [kg]
   Legs—2 exercises (or more)
   5. Leg press (3×12)—35 [kg]
   6. Calf press on leg press machine (3×12)—35 [kg]
   7. Standing leg curl (3×12)—11 [kg]
   8. Leg extension (3×12)—23 [kg]
   Shoulders—1 exercise (or more)
   3. Alternating cable shoulder press (3×12)—17 [kg]
   4. Lateral raise—with bands (3×12)—6 [kg]
   Biceps—1 exercise (or more)
   2. Machine preacher curls (3×12)—12 [kg]
   Triceps—1 exercise (or more)
   Triceps push down (3×12)—11 [kg]

In this session plan the weights were set by the rules above. Weights for not tested exercises were set using a simple conversion formula which took as input the weight in the tested exercise for this muscle group: For example, butterfly takes ⅔ of the calculated weight for bench press and the same goes for cable rows.

Since James is a beginner it is required to teach him the exercises. The first time he is about to perform the exercises (may be in the warm up before the strength test or in the first session) the system can use various methods to teach him the exercise like: showing a video of the exercise explaining about it and giving performance example, explaining by voice, rendering a hologram of the exercise performance which may also be rendered directly on the exercise machine, using a human coach to teach the exercise, using a robot the teach the exercise and alike.

Another exemplary method may be: guiding the user to perform a step in the exercise, receiving feedback on the user's performance—for example from the motion sensors or camera, correcting the user performance while explaining the correction, then guiding the user to the next step. This guidance may repeat every session as long as the system see's it is necessary. The necessity of teaching the exercise can be set by: a predefined number of times after the first performance (this number of times can be set according to the user's experience level), user's request, or as long as the user's exercise performance level is not above a certain threshold.

The system can identify the user in several ways: by his input to the system (the input may be vocal—the system can use voice recognition to identify the user, or ask him to say his name), communicating with the user's smart watch or wearable computing device via any wireless communication method known in the art such as NFC, WiFi, Blue-Tooth, ultrasonic, and the like, communicating with the user's mobile device via a wireless communication method known in the art or wired communication, for example the user may attach his mobile device to one of the exercise devices in the system. The system can use facial recognition using an optical sensor or a camera, body recognition—using a 3D sensor the system can compare the user body profile and/or shape obtained at the measurement stage or any later stage and compare it to an on the fly 3D image of the user and thus identify him), communicating with a device such as a smart-card or any other device that can be used to identify the user, and the identification of the user can be the first function the system performs when the user enters the gym. It may also be done or combined with certain security measures or measures to limit access of non-intended personnel to the gym.

After identifying the user, the system can load its data and start interfacing with him. It can greet him and the interface may be in the form of a coach communicating with the system or a virtual coach rendered by the system.

The system can ask the user how he is and of the status of certain measurements about him, for example how did he sleep, how does he feels how his day was (intensive or not), what did he ate and when, and the like. The system can also communicate with mobile, wearable computing devices found on the user, other smart devices (like for example a "smart drinking bottle") and retrieve important data such as how the user slept, how intensive was his day (For example by reviewing the tasks and appointments in his calendar, receiving the number of steps the user have made, and the like), get data on the user's diet, get data on body measurements such as pulse, temperature, blood pressure, sugar level, and the like. The system may continue this communication throughout the exercise session.

Following the collection of data, the system may perform modifications in the session plan. For example, if the system identifies that the user did not have enough sleep or had a too busy day it may reduce the effort or difficulty level required in exercises. This may include reducing the number of repetitions in certain exercises, the number of sets, the difficulty level, and the like. The system may take these actions or may even remove exercises altogether for reducing the difficulty levels or for responding to injuries, illnesses, exertion in muscle groups as a result of other activities, pains the user is suffering from and alike.

The system may instruct the user to perform certain actions prior to the exercise session according to the collected data. For example, if the user has a low sugar level or his schedule shows that he have not eaten for some time, or when the system asks him he says that his last meal was some time ago or that he is hungry, the system may instruct him to have a meal before training and may even make a recommendation on what to eat.

In some cases, the system may recommend or instruct the user to give up the training session altogether. This may occur for example if the user did not sleep at night or did not sleep or waited the minimum time required since the last training session. In that case, the system may automatically, or in real-time, through interfacing with the user schedule the next training session.

To begin the training the system may review the session plan with the user by voice, video, and the like. It may instruct him to his first exercise and may even show him the way by means of voice, video, turning on lights leading to the exercise machine or training environment, hologram, a robot, a human coach and the like. In the case of a new user (or any user) the system may give further explanations such as explain the safety instructions or some background material about physical exercise. As explained above, the system may teach the exercise(s) to the user.

During the exercise the system may track the user's performance and motivate him, for example in the way reviewed in the above-referenced U.S. patent application Ser. No. 13/359,273. It can track his calorie burn using optical sensors or the like as described in the references.

The system may do a "Gamification" of the training session. For example, a user on a treadmill may be simulated to be a part of a race with other real users on other treadmills or virtual users. The race scene and the other users may be displayed by video on a screen or hologram and voices related to the game and also cheering for the user may be heard. Similarly a trainee doing a strength exercise on a training machine or with an exercise device or without any device or machine, may also be a part of a game with similar real or virtual users (real users' avatars may be displayed to the user if these real users are far away) competing for some goal which can be, for example, completing several repetitions correctly, who lifts the maximum weight, and the like. The game may be based on reaching a goal where each repetition makes the user closer to the goal. For example, a group of users may play the game of "ladders and snakes" where each correct performance is a climb up the ladder and each wrong performance is a few steps down (a snake). The winner can be the user who reached the higher level or reached a certain level first. Other examples will be discussed below and are found in the references.

A simple way to give motivation may be rendering the virtual coach guiding the user and doing the repetitions with him. The virtual coach can also count repetitions out load, say motivational phrases—especially toward the end of a set.

As already mentioned the system may track the user's performance of the exercise. It may issue calls for him to correct his performance on the fly. It may adjust his pace. The system may also use the tracking to later adjust the training session as will be explained. It can grade the user performance and report the quality of performance during or at the end of the session.

During the session the system may further guide the trainee between exercises. At the end of the session the system may issue reports on certain aspects of the training. Reports may include: distance traveled (for example in a cardio exercise), body measurements during the session such as blood pressure, temperature, or pulse (graph during the exercise, highs and lows, at interest points during the session, and the like), flexibility or range of movement in exercises, or a total grade of flexibility or movement range, muscle groups worked in the session and the intensity each muscle group experienced, energy or calories burned (can be sliced per exercise, muscle group, and the like), time per exercise or per achieving a goal (such as certain distance or number of repetitions), total grade of the exercise, the degree of achieving the goals set at the beginning of the exercise, and any additional report that can be generated using the system components and measurements. Each one of the reports may be a comparative report, comparing the results to previous sessions, to other trainees, to baseline levels and the like. Reports can be given to the user by printing them, by presenting them on a screen or hologram, read by voice, shown as graphs or images or videos, and the like.

The system may update the difficulty level from session to session in order to achieve user progress. This can be done using rules or formulas for updating the difficulty levels.

In this example embodiment rules define the levels of the granularity and progress from session to session. In case of the fat burn exercise, it does not change its difficulty level. Strength and good body looks have the following rules:

1. Number of repetitions per set—the number in the first session plan represents the maximal number of repetitions—10 for strength and 12 for good body looks.
2. The number of repetitions starts from the minimum which is 6 for strength and 8 for good body looks. It may rise from session to session by one repetition in the last set, two repetitions in the 2 last sets, or 1 repetition in each set depending upon the rate of effort scale raise.
3. When reaching the maximum number of repetitions the resistance level may rise by the minimum possible difference (1 [Kg] in our example) or more.
4. In case the resistance levels have been raised the number of repetitions goes back to the minimum and continues to rise from there.

A measure of difficulty level can be calculated. For example, in this embodiment the formula is: difficulty level= (weight^A)*B*number of reps*number of sets. In the formula A and B are variables that can have a default value, and an exercise data structure can hold different values more suitable for it or it can hold a different formula altogether. Assuming that in most cases A will be larger than 1, the formula gives much more effect to the rising of the weight over enlargement of the number of repetitions.

Figure 35:
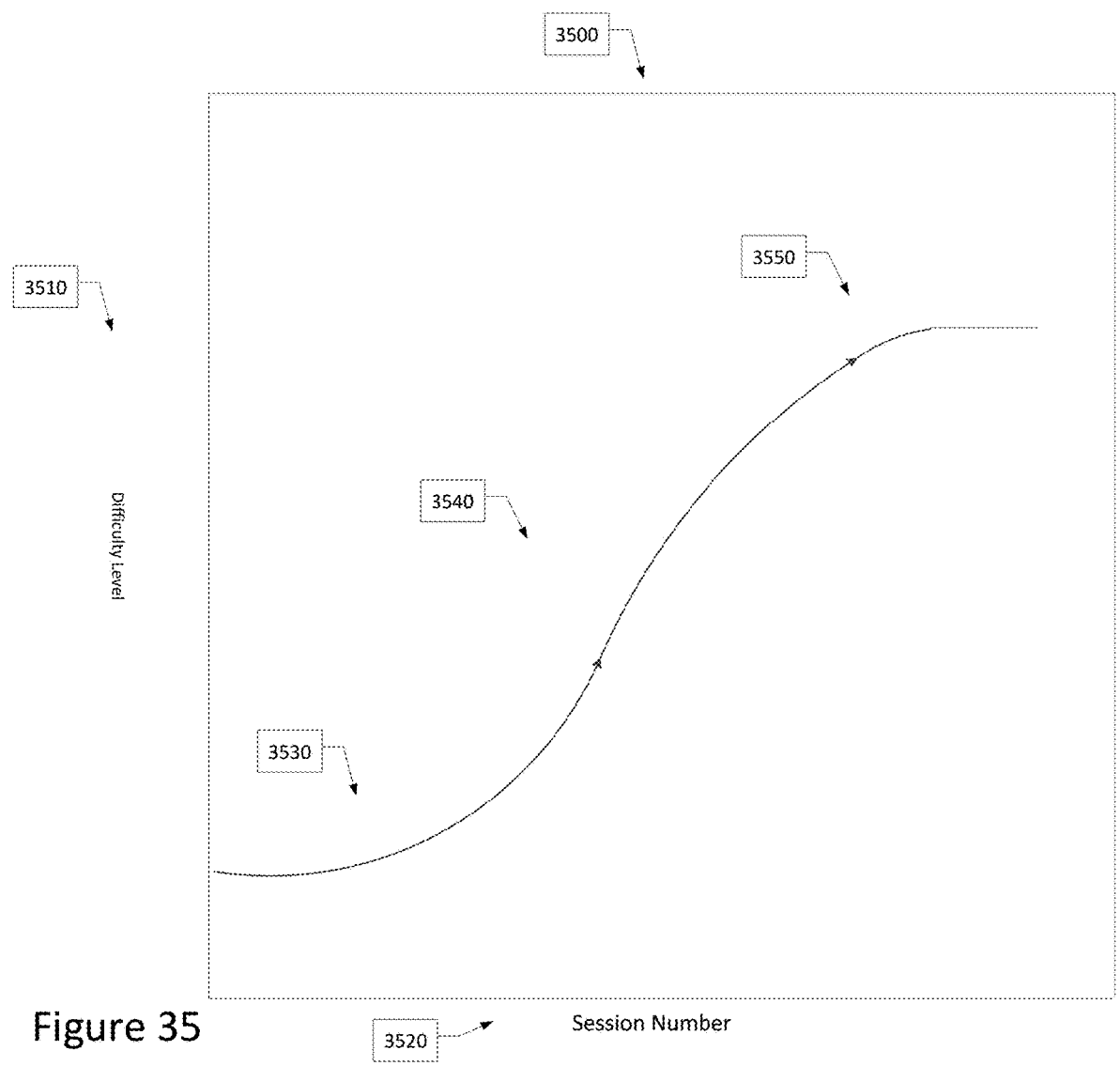
FIG. 35. Is a graph of effort scale.

In our example embodiment a graph of the formula used to raise the difficulty level is depicted in FIG. 35. The Y axis (3510) describes the difficulty level, while the X axis (3520) is the session number. At 3530, the user is learning the exercise. Development takes place in the body and mind. At this stage the difficulty level is required to rise relatively slowly. At 3540, after a certain threshold has been overcome the muscle group or skill learned can show relatively rapid development and so it is good to raise the difficulty level relatively fast. At 3550, a stage is reached were the response of the body and/or mind to the exercise is diminishing until it becomes harder and harder to achieve improvement. The function describing such a graph can be described numerically by a table of session number and corresponding difficulty level. Interpolation or extrapolation can be made where values are missing in the table.

The function can also be described mathematically for example:

$$x \leq C => Y = D \cdot E^x + F$$

$$x > C => Y = G + H \log_j(x-K)$$

x is the session number or time, Y the difficulty level, and C, D, E, F, G, H, J, K are variables set, for example, according to the trainee level, per specific exercise, or group of exercises. Y can be normalized relative to the difficulty level measured at the strength test or starting difficulty level.

Continuing the exemplary embodiment of the difficulty level raising scheme for chest bench press starting at 35[Kg] is provided. The starting difficulty level according to the start difficulty level formula two paragraphs above is $$35^{2.5} * 0.5 * 3 * 12 = 130449.$$

The formula from the paragraph above takes values for the variables C, D, E, F, G, H, J, K.

$$x<95 => Y = 130449 * 1.01^x$$

$$x>95 => Y = 335715 + 3324 * \log_{10}(x-95)$$

D receives the value corresponding to the initial difficulty level—130449, E receives 1.01 to represent a relatively slow raise of 1 percent every session. However this equation has exponential properties and the curve in 3500 will start being sharper like 3540. C takes the value 95: Assuming there are 3 sessions a week there will be 12-13 sessions per month. From experience, it is known that the change in the curve 3550 after about 8 months. G takes a value close to the estimated difficulty level achieved after 8 months, it can be calculated by putting 95 in x in the first formula. It can be re-evaluated when the actual time has elapsed. H and J are set to give the suitable curvature 3550. H can be the change in resistance between the last two sessions before the formula change. In our example it is the change between session 94 and session 95 calculated from the first of the two formulas above. H in this case equals 3324. J is the log value that will give a suitable curvature. It can be determined based on experiments and experience. In our example base 10 was chosen. K is chosen to equal C in order to reflect the fact that after the 95$^{th}$ session the difficulty level the curvature changes.

The difficulty level per session according to the latest formulas can be translated to weight, sets and repetitions according to the rule set. For example the difficulty level rises from 130753 in the first session x=1 to 132060 (x=2). The Weight, Repetitions and number of sets in this example are a solution to the equation from above:

(Weight)^2.5*0.5*Set*Repetitions per set=Difficulty Level

In this example the solution should take into account the previous sessions and the rule set from above rephrased:
1. When difficulty level raises, the weight cannot be decreased.
2. For the set of training goals sleeted the number of sets is 3.
3. The number of repetitions is between 8 and 12.
4. The number of repetitions can increase from 8 to 12. After reaching the maximum of 12 it can be reduced to any number between 8 and 12 if the weight increases. It cannot decrease but increase till 12 and then again decrease to any number between 8 and 12.
5. The result of the equation (Weight)^2.5*0.5*Set*Repetitions=Difficulty Level must not exceed the calculated difficulty level for the session.
6. For better granularity a different number of reps can be done each set and the equation can be written: (Weight)^2.5*0.5*total number of repetitions=Difficulty Level
7. Increase in repetition will follow article 4 for each set individually. Sets with larger number of reps. Will be performed last. Increase will always be performed to the set with the lowest number of repetitions. And if two or more are equal the later performed one will be increased first. In the previous session, the weight was 35 [Kg] and the number of reparations was 12. The minimum weight step in the example is 1 [Kg]. The closest solution to the equation without exceeding the difficulty level 132060 is: $35^{\wedge}2.5*0.5*3*12=130449$ so the weight and number of repetitions for this exercise do not update between session 1 and 2. The first time that the weight or repetitions will update will be in the $7^{th}$ session for which the solution of 36 [Kg] and 12 repetitions will suit. The gap between session for which there will be an update for weight and/or repetitions will decrease exponentially till the $95^{th}$ session.

The rule set above can be used for difficulty level change in different methods. An example for a different method that can be considered simpler is start for a predefined number of sessions without increase in the initial level. Then increase with small steps: one repetition for one set starting from the minimum number of reps (for example 8) increasing to the maximum (for example 12). When reaching the maximum number of repetitions in all sets the next increase is the weight in parallel the repetition number returns to minimum or to a certain number between the minimum and maximum. From there increase in number of reps. Resumes till reaching the maximum again and then increasing the weight. Steps can increase after some time: the number of repetitions added between sessions increases, the weight increase after reaching maximum reps increases and the number of reps does not decrease to the minimum when adding weights but to a higher number. The "steps" size can decrease again when feedback is received that the step size is too high for the user.

A method for increasing the difficulty level that uses feedback that shall be called in this disclosure "The trial and error method for increasing difficulty level" is: when starting a new exercise, the system will start with a pre-defined small difficulty level change per session. This is for safety reasons and to let the user learn the exercise properly and be confident before raising the difficulty level quickly. The number of these sessions can be determined by the user experience level and specific exercise and manners similar to the ones used throughout this document. After this number of sessions, the system may try to find the difficulty level raise slope suitable for the user. It may slowly raise the difficulty level gap between sessions. If, for example, the pre-defined increase in the first stage is one repetition in one of the 3 sets per session, next time the raise can be 1 reputation in two sets which can be considered the smallest step possible and so on. The possible increase levels can be pre-defined the result of a formula, function, calculation etc. The system monitors the user performance especially after every increase. The system can identify, receive feedback from sensors or subsystem like U.S. patent application Ser. No. 13/359,273 or be inputted when the user is not doing the exercise properly or unable to do the number of reps given to him. Based on this the system can deduce that the rate of raise is too high. It may deduce this also if bad performance is seen in later exercises in the session or the user does not finish the session properly. An input from the user about the difficulty level may be also considered. One time that the user is not performing the exercise correctly may not be enough to decide that the difficulty level is too high. Once the user fails to do the exercise correctly above and his performance is below a certain level, the system can log it. It may then decide not to raise the difficulty level for the next session/s. If the wrong performance is repeated several times, or there are number of sessions with insufficient performance in a certain pre-defined amount of time, the system can deduce that the difficulty level is too high.

When the system detects that the rate of difficulty level raise is too high it can reduce the rate to the last rate which was not too quick or below it. How much to reduce rate at this stage can also be a function of the user experience level and experience in the specific exercise. The system continues to monitor the user's performance in the sessions. If there are a few close sessions in which the difficulty level increase was too much for the user the system may further decrease the rate of difficulty level increase. If a certain number of sessions have passed without observed difficulty from the user, the system may re-test the rate of difficulty level change by increasing the rate again and continuing as detailed above.

The system may try to fit the difficulty level change obtained this way to a function in one of the known curve fitting methods. The function can be taken from the database 120 where the curve fitting may only find its coefficients. In this case the difficulty level change in future sessions may be determined using the function found.

The system may continue to monitor the user's performance and test from time to time to verify the correspondence to the function or fit a new function. Full strength tests can be given from time to time in order to assess the difficulty level, the improvement, and the affectivity of the method used to raise the difficulty level.

In a session or a group of sessions, the system may choose not to raise the difficulty level or raise it less than the function or rule requires because of certain measurement or situations, for example if the user have not slept enough before the session if some input measurement have values above or below certain thresholds such as high blood pressure, low sugar level, and the like, if the system identifies fatigue by analyzing the user postures obtained from optical sensors, and the like. Cases where a user did not exercise above a certain amount of time, for example a week, a month, or more, or the user is returning from illness or injury are special cases.

In case of a recess in training the period that requires change in the training plan or difficulty level can be pre-defined. The period may be calculated by a function based on the user's experience, age, sex, the length of the period the user was training continuously and the like.

In many cases the only change in the training plan will be the difficulty level which can be calculated by a function which is affected by similar parameters.

Another method is to do a full or partial strength test when the user resumes training. For example the rules may be:
1. Up to one week of recess—no change in training plan or difficulty level setting.
2. Up to two weeks—difficulty level is not raised in the first session after the recess.
3. From two weeks to 3 months—role the difficulty level back to what it was a difference in time that equals the recess time or a function of it.
4. Above 3 months—perform a full strength test to determine the difficulty level.

The durations of time may change of course depending on the user and activity attributes and parameters. The difficulty level change function or method can be altered after the recess.

For example, the difference in difficulty level just before the recess and the new difficulty level after the recess can be calculated. The difficulty level raise can then be calculated to achieve back the difficulty level before the recess in a fraction of the recess time, for example half of the recess time. The raise may be linear in this time or may take any other predefined or calculated function. Cases of illness or injury may also be treated in a similar manner as recess.

It is many times recommended to change the exercise plan from time to time. As depicted in FIG. 35, at 3550 the difficulty level possible raise becomes asymptotic after some time. At this stage continuing with the same exercise may be inefficient or worse. The system may have several indications to change the training plan, for example a certain amount of time passing such as 6 months (replace exercise plan every 6 months). This time can be a function of the user attributes such as experience level, age, gender, and the like. Another indication can come from the exercises or the Computing Device Enhanced Training Environment. Each exercise may include its recommended time before replacement as an exercise attribute (the attribute may be a formula as well). The indication may be the system monitoring showing a decrease in difficulty level change as described above, when this happens too often, when the difficulty level raise is minimal or below some threshold for some time, or the fitted function show above threshold decrease in slope or derivative.

The system may respond to one or more indications from one or more exercises. It may respond when a certain number of indications and/or indications from exercises performance have been received. The response can range from just replacing the indicating exercises with an exercise selection manner similar to what is described above or different (where the exercise to be replaced is not considered or deleted from the list of course). The response may also be building of a new training plan certainly above a certain threshold. When building this new training plan certain additional aspects can be added to the building process described above.

Indications for the need for a replacement of an exercise can be reaching the 3550 in the 3500 graph which is where improvement rate decreases considerably. This can be determined by when the increase in difficulty level is below a certain threshold. Other indications can be for example user input of being tired of the exercise or wishing a replacement. Low exercise performance below a threshold that reoccurs more than a set number of times in a certain set timeframe may also be an indication. Where the set number of times and time frame can be determined according to the user and activity attributes. Another indication for replacement can be for example the time a certain exercise is found in the exercise plan. An indication for replacing a training plan can be a collection of indications for replacement of exercises in a certain timeframe. It can be for example indications from a collection of exercise not necessarily indicating the replacement of all these exercises. For example, a collection of performance below threshold of a plurality of exercises; a collection of low increase in difficulty level for a plurality of exercise, a certain threshold of time where a plurality of exercises are found in the training plan above it a combination of thereof and alike.

When a replacement training program is built, the user attributes can be updated, for example the user experience level which can be appended with the current program gained experience; the exercises the user did in the current program should be marked and the mark used in future program building. The system can save attributes from the plan before replacement (further referred to as "current plan") like the highest difficulty level the user has reached in a certain exercise, the highest number of repetitions, the quality of performance, the user response to difficulty changes and rates of difficulty changes and the like.

When building the new program and using the methods in this disclosure certain additional rules may apply for exercise selection. For example, a recommended rule is not to use the same exercise in two successive training programs if there are other possible exercises in the filtered EDS list. The difficulty level used in certain exercises in the past may be used to determine the difficulty level in a new assigned exercise: a certain conversion rate or conversion rate formula or function may be used. These can be stored in one of the exercises data structures, be related to the muscle group, to the trainee attribute, and the like.

Another example of the embodiment id now presented. For the sake of the example assume a different user is interested in building a training plan toward a Ski vacation he is going to have in 3 months. He can invest 3 weekly sessions of 100 minutes to achieve this goal.

Referring again to method 3300, at 3305 the system receives these and other user inputs. In this example the user is an intermediate level trainee. At 3308 a specific sport has been chosen—Ski. At 3307, the system retrieves the relevant set of rules from the database. In this example embodiment, the rule set for Ski is based on all the regular rule sets above with added a small portion of specific changes or constraints for Ski. Rules for other sports can be defined in a similar manner. These changes or constraints are summarized here:
1. Training sessions for ski are mixed sessions including cardio and good body looks (stamina). The priorities for Ski training sessions are defined:
   i. Good body looks (stamina)
   ii. Cardio
   iii. Strength.
   b. The muscle group priority is defined as following:
      i. Quadriceps—At least 2 exercises.
      ii. Abdominals—At least two exercises.
      iii. Lower Back—At least one exercise.
      iv. Upper and middle back—At least two exercises.
      v. Triceps—At least two exercises.
      vi. Shoulders—at least one exercise.
   c. Muscle groups are first populated with exercises which Ski is listed in the "recommended for other sports" attribute.
   d. All other muscle groups are populated only after the above muscle groups are populated.
      i. They are populated in order set by the regular (previous) rule sets starting from the larger muscle groups.
      ii. It is only mandatory that there shall be at least 1 exercise for biceps. It is OK if not enough time left in the session for population of other muscle groups.

At 3310 the exercise list is filtered according to the user experience level (intermediate). In this example, the calculation of time and resting time for each exercise will not be performed for the sake of clarity and simplicity. It will be assumed that each strength and good body looks exercise takes 5 minutes including rest time—this can be for example a rule for Ski activity plan building.

At 3312 according to the list of priorities dictated by the rule sets and the time the user has to spare for a session the session looks like this:
5 minutes—treadmill warm-up
5 minutes—stretches warm-up.
50 minutes—strength and good body looks training.
35 minutes—cardio exercise.
5 minutes—closing stretches.
100 minutes—total time.
Going over the database of exercises at FIG. 32 (3200), the cardio exercise which lists ski in "recommended for other sports" is elliptical/ski and thus it is selected as the cardio exercise according to the last rule set.

At the 3320->3322->3324->3320 loop and including 3326 the following exercise list is assigned, in a similar manner to the previous example, reader can follow the method 3300 stage 3320 to 3326 on the example EDS 3200 and receive the result 5 minutes—treadmill warm-up
5 minutes—stretches warm-up.
50 minutes—strength and good body looks training:
  e. Quadriceps:
    i. Legs press
    ii. Legs extension
  f. Abdominals:
    i. Abs crunch machine
    ii. Abs air bike
  g. Lowerback:
    i. Hyperextensions (back extensions).
  h. Upper and middle back:
    i. Chin up
    ii. Cable rows
  i. Triceps
    i. Triceps pushdown
    ii. Cable one arm tricep extension
  j. Shoulders
    i. Dumbbell shoulder press
35 minutes—elliptical/ski exercise.
5 minutes—closing stretches.

After allocating these exercises the 50 minutes of strength and good body looks training are allocated and there is no more room for additional exercises. Therefore, at 3326 the test returns that all the session time is allocated and so is the check in 3330 leading the system to 3350—end of exercise listing.

Next the difficulty level and number of rehearsals are set in a similar manner to the previous example. The flow continues similarly to the previous example.

The next example embodiment concerns a completely different field of training, nonetheless the same method and techniques may be applied. In this case the goal is to create a training program for the mind. Different mind skills replace the attribute of muscle groups in the EDS exercise attributes and in the implementation of the methods. Mind skills may be for example, short term memory, long term memory, attention, reaction speed, mathematical skill, multitasking, verbal skill, perception, coordination, spatial perception, and the like. For the sake of simplicity the skills in this example are: memory, attention, reaction speed, and mathematical skill. In this example, the database 120 contains EDS which in this case are mind games. Each one has attributes in the database 120 that include the main skill it works on and the secondary skill/skills such as the length in time of the game, the user level of experience or skill it is suitable for, a general exercise grade indicating its affectivity, and the like. Many other attributes known in the art are possible, but for the sake of clarity and abbreviation the above attributes were chosen for the example. A list of EDS and their attributes appears in 3600—FIG. 36.

Going to method 3300 again, at 3305 the user enters his attributes. The important ones in this example are that his skill level is a beginner, his goals according to priorities are 1—memory, 2—mathematical skill, 3—attention, and he has 20 minutes 3 times a week for the sessions.

3307, 3308, 3309 are not so relevant for this example embodiment since all activities are part of the mind game training and in this example, cannot be differentiated to different kinds of specific activities. In general, there may be specific types of activities defining additional rules and constraints on the training plan. For example, the user may wish to prepare for a certain exam such as the SAT, GMAT, and the like. In such cases the constraints maybe in the form of setting the appropriate goals, priorities, setting the schedule, adding specific exercises, and the like. (similar to the Ski example for the gym training example embodiment).

At 3310, the EDS 3600 in database 120 is filtered according to the user goals (memory, mathematical skill, and attention) and level (beginner). EDS 3630, 3645, 3650 are thus removed.

At 3312 the time division is set. A rule for time division that is suitable in this example (and naturally can be generalized to other activities as are all the rules in this document) is to divide the time based on a basic time unit where the number of time units is set by the priority for each activity For example time is divided where highest priority skill get X time unit, second priority gets Y and third priority gets Z and so on where X>Y>Z . . . . The basic time unit can be the minimum time for which at least one exercise of the non-filtered activities fits. In our case it is 5 minutes since every one of the exercises in 3600 can fit in 5 minutes considering the chosen activities and the user's level. Another method for time allocation can be demonstrated in this example: The activities are ordered and allocated according to their priority in the session starting with the higher priority. This allocation can repeat until all the session time is allocated or a function that cannot be allocated remains. This can be slightly altered so that higher priorities will be allocated a number of exercises before going to the next priority. The number allocated can be decreased with priority. This will ensure more exercises for the higher priorities. In current example, only one exercise occurs before going to the next priority. In this case using the allocation method according to priority insures that we will have more or equal amount of exercises of the higher priorities. Dividing according to this method we get:

Memory—5 minutes.
Math Skills—5 minutes
Attention—5 Minutes
Memory—5 minutes.

Since all time was allocated in the first round there is no need for further rounds.

At 3315 sorting and ordering according to main and secondary skill of the non-filtered EDS occurs. FIG. 36 is already ordered according to these attributes.

At 3320 the formula chosen in this example for selecting the most suitable exercise is again a weighted sum:

Weighted Sum=30*(exercise grade)+30*(if secondary skill in EDS is in priority)+20*(number additional secondary skills in the EDS).

So the first slot is populated by the Simon game 3635 since both the first memory exercises in FIG. 36 have the same grade; However the Simon game has secondary skill in priority and another secondary skill, this is also the reason why the formula gives higher grade against the third memory exercise 3640 even though it has higher exercise grade attribute.

Continuing the loop 3320->3322->3324->3320 all the time slots are populated using the weighted sum formula in the last paragraph:
Memory—Simon 3635
Math skills—raindrops 3610
Attention—appearing sequence 3660
Memory—rectangle recall 3640

Since at 3326 and 3330 all time slots have been allocated execution goes to 3350 and ends.

Figure 38:
FIG. 38. Is a flow chart describing tracking a training program by a Computing Device Enhanced Training Environment.

In the example there is a need to set the difficulty Level for each exercise. FIG. 38 describes the Trail and Error method for setting difficulty level also described above. Some definitions of difficulty levels can be considered common to many skill based exercises. Difficulty level can be determined by the difficulty of the sequence or routine that need to be performed or repeated, the difficulty of the puzzle or problem needed to be solved, and the like. A specific problem's difficulty level can be determined by its complexity which may sometimes be measured by the number of variables or object participants in the problem/game/sequence. Giving less time for the problem/activity or stages in it or exposing the hints or problem components/participants for a shorter time can raise the difficulty level. Increasing the perceptible sizes in the activity/game/problem can also raise the difficulty level, for example having the figures appear in larger distances from one another in the sniper game. Difficulty level can be further determined by the number of correct sequences, repetitions, or solution in a given amount of time. Difficulty level or user level can further be determined by how long it take the user to accumulate a certain number of wrong answers, bad performances, or failures. In FIG. 36 there are some examples for the descriptions in this paragraph. 3620, 3655 in FIGS. 36A-E are example EDS.

In the latest example the difficulty level test ("strength test") is performed to determine the starting difficulty level. It is performed using the chosen exercise the first time after the exercise or game is learned. The difficulty level the user reaches in the exercise or game is used to update and track him each time he plays. Each training session can be considered as a new difficulty level test.

As in the previous example, the system can track the user performance in similar method to what described above (where it is obvious that the word skill or difficulty level can replace words like "strength" or "weight" or alike). It can be expected that progress in many cases will follow a graph similar to FIG. 35. As in the previous examples, the system may choose to update exercises or change the whole training plan based on similar indications, for example a plurality of exercises reaching their asymptotic area 3550 graph of FIG. 3500. The other indications mentioned in these examples and this document may also be used, for example changing a program or exercise after a certain amount of pre-defined time like 3 months for example.

Other techniques and methods mentioned in the examples above may be applicable in this example as well. The system may guide the user through the exercises, teach him the games/exercises, give him reports on progress and on level of skills, and the like.

Training Measures:

Moving to further generalize the methods of this section in this disclosure; Training measures and training objectives: Training measures and training objectives can be measured/expressed in many forms some examples:

1. Body weight where the training objective can be target body weight.
2. Body Fat percent where the training objective can be Target Body Fat percent.
3. Time for performing a training routine or a group of training routines, where a training routine can be for example a physical exercise, a methodic reassess between exercises, a job procedure, military training exercise, walk, run, run of a certain distance, a game, type of work or any other routine, a combination of thereof and alike. The training objective can be a target time.
4. Performing routines with higher difficulty level thus elevating the user/s level. Where difficulty is as defined, and referenced throughout this disclosure.
5. Heart rate following or while performing training routine or a group of training routines, or heart rate or rates during certain periods of time during the training routine or routines.
6. Target degree of flexibility or improvement in motion limits. This can be measured for example using methods appearing in the references such as U.S. application Ser. No. 13/359,273
7. Movement correctness—can be defined as the path in space (and time) a body and/or a plurality of organs or parts of the body and or a tool/device held or operated by an entity (entity can be for example a human, an animal or a ma-chine like a robot and alike) where this path falls within a certain level of correspondence or correlation to a pre-defined path or calculated path. For example, a hand of a surgeon holding a surgeon's knife where it is desired that the knife tip will travel in a certain pre-defined pattern on a patient body. The movement correctness can be measured by calculating the sum of the distance of all diversions from the pre-defined path which are higher for example then 0.5 [mm], then taking the reciprocal of the sum or subtracting the received sum from a certain constant. Another movement correctness measuring example can be performed by comparing the trainee movement in an exercise performed to a movement recorded in a database. Such techniques are appearing in the references. Such techniques may include comparing the user movement inputted to the system using 2D and/or 3D camera, motion sensors, motion markers or alike, acoustical methods generating 2D or 3D representation and a like. Comparison can be performed suing a Data-Base containing the correct performance. Following the comparison performance can be graded. Example methods for grading performance or movement correctness appear in this disclosure and in the references. like for example comparing angles around joints between the actual performing body and reference body from the Data Base, then multiplying a predefined weight for each joint by the difference angle and summing up the results.
8. Completion of all the required steps and/or performing in the correct order in a routine.
9. Target routines performance level. Performance level can be graded by some manipulation on Movement Correctness in a routine or routines. Completing of all steps in the right order can also be part of the performance level. It can also include measuring the speed of the routines performance or phases in the routines and comparing them to Data-Base of "correct" speeds. Even the speed as is can be used as a performance measure.
10. Target level of weight/weights used in a routine or in groups of routines. For example, the weight lifted in a chest-lift Gym exercise.
11. Target level of strength the user wishes to reach. Where strength can be measured by Force exerted on the training exercise. Methods for such measurements appear in this disclosure and in the references and known in the art.

12. Target amount of energy exerted in a routine or group of routines. The amount of energy can be measured in calories, Kilo-calories or any other suitable unit.
13. Paste of performance during periods of the routine/routines. For example, speed of running during parts of a certain distance run.
14. Target measurement of body organs circumference, for example hips, bust, waist, arm, etc.
15. Level of rehabilitation of a certain body part—can be measured using methods such as given in the references and known in the art.
16. The result of an action or routine. For example, Javelin Throw or Shot Put Discuss. In this case the training measures can be the distance travelled by the training object and/or the location it hits the surface. These training measure are the result of the throwing action done by the trainee. Such training measures can be measured by sensors on the training object itself such as accelerometers, position finders, cameras and alike. Or by external sensors such as optical sensors, radar sensors and alike. Another example can be target practice where the training measure is based on the location an object hits a defined surface and the attributes of this location. For example, how far an arrow hits from the center of a target. This training measure can be measured by sensors on the object, external sensors or sensors on the surface it hits.
17. Measure of human/animal/plant health or physical status such as: blood sugar level, blood pressure, certain hormones level, certain blood chemistry results, a level of pain or certain feeling described by the user, the level of immune system response or allergy, the level of infection etc.
18. Any other measurement defined by a user, operator or technician of the system, and can be measured by the system or by a measuring device interfacing or connected to it.

Possible Inputs to the System:

In a general embodiment, inputs to the system may be plurality of the training measures or other possible inputs described in this disclosure or references. Proposed real-time inputs include, but are not limited to:

1. Any training measures given in this disclosure or in the references or known in the art that can be measured in real-time such as: time, heart rate, blood pressure, quality of exercise performance, paste, cadence and the like. Measurements may be done using sensors integrated into the proposed embodiments or external systems interfacing with it.
2. Visual representation/2D/3D representation input of the training performance. The input can be received via a capture device configured to obtain video or still images/representations which can be 2 dimensional or 3 dimensional, using any of the methods for creating obtaining video with depth information such as stereo cameras, time-of-flight analysis use of structured light, sonar techniques, and the like. The capture device may be configured to obtain images from different parts of the electromagnetic spectrum such as infra-red light, visible light, ultraviolet light, microwaves, radar wave lengths, and the like. The capture device may emit electromagnetic waves from any part of the spectrum and build the image according to reflections or back scatter from surfaces. In some cases pulsed light or electromagnetic waves may be used in methods known to those skilled in the art. Mechanical waves such as ultrasonic waves, sound waves or waves from different parts of the mechanical wave's spectrum may also be used. The capture device may emit mechanical waves from any part of the spectrum and build the image according to reflections or back scatter from surfaces. This input may be analyzed in order to receive on the real-time data on the user and/or exercise routine. For example, techniques such as those shown in "Non-contact, automated cardiac pulse measurements using video imaging and blind source separation methods for synchronization" a non-patent document brought here as reference, may be used. These techniques allow the system to get on real-time information about the user's body measurements such as, but not limited to, pulse and blood pleasure. Similar techniques may be used to get on the fly measurements of the training measures from above. Synchronization techniques such as those used in US 2011/0105278 A1 patent application brought here for reference purposes can be used. These methods enable continuous monitoring of a specific body portion in order to extract measures more easily. Techniques for obtaining skeletal representation of the user or any other form of machine representation such as those described in US 2010/0197388 A1 patent application brought here for reference purposes may be used. These representations may then be used to receive inputs about the exercise or routine performance like those described in US 2012/0190505 patent application brought here for reference purposes.
3. Location of the system parts, for example the location of non-moving parts such as an exercise device non-moving platform, a non-moving target for a target practice, and the like. These can be obtained, for example, by taking reference images when the user is not present before the training session.
4. Locations or possible locations of exercise equipment moving parts. This data can be used for various purposes such as determining the number of repetitions of the exercise/routine, determining the phase of the routine the user is found at, assist obtaining machine representation of the user body, measure training measures, for example speed of routine performance, movement range of different body parts and the like. Location can be obtained using optical markers put on the moving parts, motion/acceleration sensors, pressure sensors, or any other suitable technique known in the art.
5. Exercise results, number of repetitions, what is the current repetition or phase in the exercise/routine performance, performance quality, and the like, may be obtained from external systems or from techniques like those mentioned in 2 and 3 and in US2012/0190505 patent application brought here for reference purposes.
6. User commands for controlling the user interface, the application flow, and controlling the system software execution. This can be achieved through a conventional user interface such as a keyboard, operation buttons, screen touch screen, and the like. It may also be achieved through voice commands, gesture recognition, remote commands from a remote device using wired or wireless communication, and the like.

In an embodiment, the system may produce the following outputs:

1. A group of routines/exercises for a training session. Per each exercise/routine a required level or difficulty level may be outputted. This level may be resistance level, weight, time for performing the routine, level of flexibility or required boundaries of motion, target heart rate, target performance level or any other level of a training measure described in this document or known in the art.
2. A group of training sessions as described in article 1. The level or difficulty level may be adjusted from training session to training session towards achieving the training objectives.
3. A schedule for the training sessions. The schedule may be in a form of specific date and time for each session, in a form of time period between sessions, or in any other suitable form.

More possible outputs are described in this disclosure and the references.

Difficulty Level:

There is significance in defining the training or routine difficulty level and how it can be changed for use in this disclosure. Most of the training objectives and training measures may be used for this definition. Altering or changing the difficulty level is an important stage in some of the methods that are disclosed. Examples for difficulty level setting/definition include, but are not limited to:
1. Time for performing a training routine or a group of training routines as defined above as a training measure. Changing the target time for performing a training routine will in most cases affect the difficulty level. In many cases such as running, cycling, or a skill improvement practice, lowering the target time increases the difficulty level.
2. Heart rate as a training measure. In most cases raising the required heart rate will increase the difficulty level.
3. Target degree of flexibility or improvement in motion limits, as defined above. In most cases increasing the degree of flexibility required or decreasing the motion limits will increase the level of difficulty.
4. Target routines performance level. As defined above, changing the required performance level can change the level of difficulty.
5. Level of weight/weights or resistance used in a routine. Changing the level of resistance will directly affect the difficulty level.
6. Changing the target level of strength the user wishes to reach as defined above, to change the difficulty level.
7. Changing the target amount of energy exerted in a routine or group of routines.
8. Changing the pace of performance during periods of the routine/routines, for example speed of running during parts of a certain distance run.
9. Changing the target measurement goal taken for an external device, for example a certain grade for successful target practice inputted to the proposed embodiments from an external apparatus.

Changing the level of difficulty can take place by changing any of the training measures or a combination thereof.

Methods for Calculating and Finding Quantities and Configurations Used in this Disclosure:

This section elaborates on some of the methods that may be used in this disclosure. These methods are suitable for implementation on the proposed system or possibly on any computing system. These methods are used for determining different sizes and configurations such as the beginning weight in a weight lifting weight test, the beginning distance in a running program, limits for weights distances, and the like. For simplicity of the following explanation the result entity (which may be size, quantity or configuration) shall be denoted "y". The variables used for calculating the result shall be denoted $x_i$ where "i" is the variable index, since in some of the methods several variables shall lead to a result.

The method or function shall be denoted as a function $f(x_i)$ so that $y=f(x_i)$. Throughout this disclosure these methods may be used in parallel to calculate the same quantity or configuration and the final result will be selected between them. Some of the possible methods include:
1. Based on pre-defined thresholds: thresholds are defined so that for a combination of $x_i$'s if one of the $x_i$'s is higher than the limit or lower, or a combination of $x_i$'s or, for example, a weighted sum of them or any formula used on a combination of $x_i$'s is higher or lower then a pre-defined limit, a certain pre-defined result or a pre-defined formula of $x_i$'s is used to give Y. For example, establishing weight limits for strength tests: the limits can be for example the mechanical limits of an exercise device (like maximum weight it can support) which are pre-programmed into the system. Another example can be known limitations of the human body are pre-programmed into the apparatus. The system may be configured to keep the force exerted by a human during the physical exercise below these limits by, for example, refraining from using resistance above such limits.
2. Using a database—the results (Y) can be extracted from a database. An example for storage and extraction method may be storing results in a table like data structures. The most simple can be a one dimensional table. This data structure saves output $f(x_i)$. for each entry (combination of $x_i$). Using the strength test limit example—the entry can be age in years and for every age a maximum difficulty level (limit) is saved in the database, for example limit heart-rate for every age. The table like data structure can have more dimensions. For example, a 3 dimensional table shall contain an output for 3 entries. In a further example, a limit shall be extracted according to age, gender, and weight. These table like data structures can be extended to a plurality of dimensions. For example, $y=f(x_1, x_2 \ldots x_{n2})$ where f takes the form of a table.
3. Formula (or function)—The result Y can be found based on a pre-defined formula, so f in this case takes the form of a formula on the variables. Variables can be any of the system inputs or training attributes, examples:
   a. a formula for finding the limit heart-rate can be: (220−age)*90%
   b. Max running distance can be calculated according to the formula: ((last training running distance)*exp (−(time in weeks from last training)/2))*2.
4. A combination of a formula and a database, where some of the entries to the table may be formulas on a plurality of variables where the result of the formula is the entry to the table. The case where a plurality of table results is then used as a plurality of a function's variables is also possible.
5. Artificial intelligence or machine learning algorithms: Finding Y may be based on the use of learning and classification algorithms, Machine Learning, Deep Learning and alike. Many such algorithms and methods are known in the art. These methods are sometimes referred in this disclosure by the acronym ML. A well-known formal definition for ML (by Tom M. Mitchell) is: "A computer program is said to learn from experience E with respect to some class of tasks T and performance measure P, if its performance at tasks in T, as measured by P, improves with experience E". An example for a ML method is hereby disclosed in FIG. 37. The algorithm result is the result entity or "y". The variables xi can be said to belong to different attributes or classes as will be explained:

a. Algorithm key inputs method 3700, 3720:
   i. The algorithm has a pre-defined and/or configurable set of attributes. This set may be, for example, any group of system-inputs or training measures as defined above, any feature in the user or in the user data or environment. Each attribute used can be measured or sensed by the system, or its measurement/characteristic/size can be inputted to the system. A measurement/characteristic/size of an attribute is also known in the art as "observation". In an example embodiment, these attributes can be the input to the non-hidden layers of a Deep Learning network, or in this example be used as categories or what known in the art as "classes" and denoted Ck where k is an index like i above.
   ii. For the learning or training stage: Datasets of examples to use for training of the algorithm. Each set may contains the desired result or the "ground truth" result y and set of measures $x_1$s of pre-defined attributes linked to each result y.
   iii. At least for the training/learning stage there should be a measure of success in finding the result y. This means the algorithm should be inputted, or should measure or calculate if the result it produced is successful or failure, or at least a grade of the result success. This is the measure P discussed in the formal definition above. If we continue with the limit example the system can check that the limit was not crossed to know if it was successful in choosing it, or it can check how far was the limit from the final results of the strength test and decide if the limit setting was successful or not. i.e. the measure of success can be binary—success or failure. A Cost Function (Also known as "Error Function") can be defined. The algorithm output is sometimes denoted $\hat{Y}$ and the desired or "ground truth" output is sometimes denoted Y. A simple cost function is the difference between the output and the desired output:

$$J(Y)=Y-\hat{Y}$$

The algorithm may have a plurality of outputs. In this case methods known in the art can be used to calculate the total Cost or Error. Many times, the sum squared error or "Quadratic Cost" function is used for one output or more:

$$J(Y)=\tfrac{1}{2}(Y-\hat{Y})^2 \text{ or for a plurality of outputs:}$$

$$J(Y)=\tfrac{1}{2}\Sigma_i(Y_i-\hat{Y}_i)^2$$

Method are known in the art for usage of this measure of success for controlling and optimizing the training process. An example is the Back-Propagation techniques used in Deep Learning.

b. The "training" or "learning" phase (3730): In this example, at first this example method's goal is to find the conditional probability of each "y" possible value or value range separately for each class (or attribute). This conditional probability can be denoted p(y|Ck) and is known in the art as the "likelihood". This likelihood can be given in a form of a formula, probability density function (PDF), histogram, and the like. It may be calculated from a formula or found using different methods. A method to find it is hereby disclosed. At the attributes classification stage 3732 of this example method 3700 the algorithm creates "histograms" 3710 and 3715 for each of the resulting "Y" possible value. As depicted in 3710, for a given possible output Y value or range of values 3711, the probability or number of times 3712 an attribute had a certain measure or value for that result 3714 is recorded in the database thus creating a histogram 3713. This can be generalized to a plurality of algorithm outputs Yi where this process can be performed for each Yi. In this example the word "result" or notation Y refers to a plurality of method outputs. Histograms are created by classifying the training sets, i.e. receiving the training set measurements data and putting them in histograms according to the Y value. Some or all of the histograms or portions of them can also be inputted priory diminishing or lowering the need for training. Other data structures can replace a plurality of the histograms such as probability density functions, formulas or any other structure known in the art. In some cases histograms may be kept for samples of possible results and interpolation or extrapolation may be employed using methods known in the art for completing values between samples. An histogram may depict the probability p(Y|Ck), especially when it is normalized for example by dividing each number of times for each value of Ck by the total number of times. Given a certain Ck value the system can go to a histogram of a certain Y value according to Ck and by the Ck value see what is the probability for Y according to this value.

c. The created histograms can be normalized to give a total probability of 1 (the integration of the histogram will give 1). Curve fitting techniques may be used to fit a function to the histogram attained by measurements.

d. The probability for a result given the inputs or the measures of an attribute can be calculated in the following way: $p(y)=\Sigma_k p(y|C_k)p(C_k)$ where $p(y|C_k)$ are the likelihoods 3710 and 3715 found in the training stage. $p(C_k)$ can be viewed as the a-priory probability for each of the classes. It can be known in advance (pre-defined) or can be also calculated during the training stage. Further elaboration on training to find $p(C_k)$ is given below.

e. The stop training decision stage 3736—possible training ending criteria:
   i. Minimum number of training sets that were classified by the algorithm.
   ii. Minimum range coverage covered in each attribute. For example each attribute possible range may be divided into a bin. A coverage measure to end training may be at least one measurement in each bin, or at least one measurement in certain selected bins or in some number of bins defined as threshold. So the ending criteria may be all or a certain number of the attributes bin coverage.
   iii. Minimum number of measurements in each or in some of the histogram.
   iv. For a histogram or PDF it sometimes may be accessed statistically what is the error in probability the existing sample allows. So a grade can be given to each histogram according to the assessment of its statistical error. A weighted sum of this grade can be calculated. A grade above a certain threshold can be the criteria for ending the training.

v. A level of accuracy in which the algorithm gives the output result y compared to a number of actual tests measurements (the degree of correlation between results classified by the algorithm and measured in reality), or statistically calculated by methods known in the art.

vi. Using a Cost Function like the one exampled above. Conclusions from the behavior of the Cost Function or it's mathematical properties can be made. For example the Cost Function becoming asymptotic, or for example the Cost Function reaching a local or global minimum can be used to decide to end the training.

vii. Any other method known in the art. Further examples will be given below.

f. At the operation stage 3740 the algorithm received the Xi's as measurements/inputs 3742. At the classification stage 3744, each set of measurement of attributes is compared to each of the attributes, histograms, or functions. The result is a vector containing the possible results y and the probability for each of these results, taken from every histogram. This is actually $(y|C_k)$. The system gets a vector of possible y's and a corresponding vector of $p(y|C_k)$ (may also be denoted $p(y|x_i)$) for each y.

g. The probability or weighted sum for each yi can be calculated; $p(Y)=\Sigma_k p(y|C_k)p(C_k)$ or in another notation $P(y_i)=AP_A(y_i)+BP_B(y_i)+\ldots+NP_N(y_i)$ where the link between the two equations is $A=p(C_A)$ and $P_A(y_i)=p(y_i|C_A)\ldots$ h. Any other suitable formula can be used on the probabilities from each attribute, where then each attribute incorporation in the formula can be denoted A for attribute A, B for attribute B, etc. The result Y at 3748 may then be selected from the possible results according to the one which received the highest or the lowest probability or grade. If there are few equal highest or lowest grades an arbitrarily selection can be done. At 3750 the result may be outputted.

i. In stage 3760 the quality of this "estimation" algorithm result is measured or assessed. If the actual result is measured after the estimation, a formula can be applied on the difference between the estimated result and the actual result 3752 as described above. Any other method can be used to access the quality of the result. Stage 3760 and any of the following stages 3770 and 3730 are not mandatory, the algorithm can go back to the operation stage 3740 without any further work on the result, or it can go back to the operation stage before any of the following stages or in the middle of them.

j. The measure of quality of the result may be used to decide whether to go to the training stage and use the output result or return to the operation stage, for example if the actual measured result is not known. In this example a statistical algorithm was used to accesses it's quality. If the quality grade is below a certain threshold this result can be disqualified from being used in the next stages and the algorithm returns to the operation phase to produce the next result. The algorithm can also finish at this stage.

k. If the result was not disqualified the next stage may be an iteration of training using the result and the measurements that led to it as a training set 3730.

l. At 3732 classify the measurements to histograms of attributes preferably according to the actual result.

m. At 3734 improve the probabilities ($p(C_k)$) or weights given to every attribute according to this attribute's contribution to the result finding. In case the success criteria is binary (i.e success or failure) the following method can be used: Each $p(C_k)$ is multiplied by a constant denoted $\Delta$ sometimes referred to as the "Learning Rate". The result is added to $p(C_k)$ by is result is success and subtracted if the result is failure. Normalization stage of all $p(C_k)$ may follow an update of all $p(C_k)$. This way the probabilities most effecting success or failure in each data set are enlarged or decreased proportionally. The enlargement/decrease can be applied only to weights of classes/attributes who gave a probability higher than a threshold to the received result. Any other method known in the art of modifying the weights or $p(C_k)$ following the method success or failure in the result prediction may be used.

n. Another example method for updating $p(C_k)$ may involve an Error Function. If the measure of the error is known for a dataset for example by the function $J(Y)=½(Y-\hat{Y})^2$ The contribution of each $p(C_k)$ to the error can be calculated in a method similar to Back-Propagation or Gradient Decent: The simplest way may be to multiply $p(C_k)$ by the calculated error $j(Y)$ and then multiply this by a constant A sometimes referred to as the "Learning Rate" and deduct this quantity from $p(C_k)$. A normalization stage of all $p(C_k)$ may then be performed. The stage 3734 may be a part of the initial training.

o. Next the algorithm may go back to the operation stage 3740 with the improved database.

Any suitable Machine Learning method known in the art can be used for reaching the plurality of results $Y_i$. As mentioned Neuron Networks and Deep Learning can also be used as well as other Machine Learning methods known in the art like: Genetic Algorithms, Decision Tree Learning, Association Rule Learning, Rule Based Machine Learning etc. Some of the references in the IDS elaborate on these methods.

Outputs:

The outputs of the optional part of the system for designing training program shall be at least one of the following:

1. List of exercises, activities or routines. May be allocated to session.
2. List of initial difficulty levels.
3. Training schedule—list of sessions and/or exercises recommended times and/or recommended periods of times between sessions/exercises.
4. Effort scale or how and/or when to increase the difficulty level
5. When and/or how to change, or modify exercises and or the training plan.
6. Other outputs given in this disclosure or known in the art.

More Examples for Training:

The system may receive any of the inputs described above or in general in this disclosure or known in the art. An important input may be the type of training the user is interested in, in case the system supports several types of training, for example gym exercise, Pilates exercise, running exercise, skill exercise, and the like. The user may further define the type of exercise he is interested in, or the training measure he is interested improving.

In case the type of training is cardio vascular like running, cycling, steps, rowing, and the like, the user may define that he wishes to work on certain attributes, for example to improve speed, distance (or an equivalent measure such as number of steps climbed or rowing strokes), focus on fat burning, focus on calorie burning, reduce average or peak heart rate during activity (improve shape) or any other training measure related with cardiovascular training in this disclosure or in general.

In case of gym, resistance based exercises, Pilates, gymnastics, TRX, rehabilitation, and the like, the user may define that he wishes to work on certain attributes, for example to improve strength, improve muscles volume, improve muscles shape, improve the number of repetition per exercise with a given resistance, improve the peak resistance level per exercise, improve the range of a plurality of body parts movement range or movement limits with or without resistance, improve training objectives related to flexibility as defined above, or any other training measure related with such activities given in this disclosure or known in the art. The user may further define he wishes to focus on muscle groups or body areas/parts. For example, the focus required is leg and back muscles.

In case of motion activities such as dancing, Ballet, ice-skating, floor gymnastics, and the like, the user may define that he wishes to work on certain attributes, for example to improve the movement correctness objective (as defined above), improve the number of (correct) movements per unit of time, improve the speed of movements or a routine, increase the number of routines the user is familiar with, improve the quality of movements or routines performance or any other training measure related with such activities given in this disclosure or known in the art. In this case and the cases below the user may also choose to focus on certain groups of movements, groups of body parts or muscle groups participating in the movements, and the like.

In case of skills improvement training such as medical surgery training, tools operation training, touch typing training, martial arts training, and the like, the user may define that he wishes to work on certain attributes, for example to improve the movement correctness objective (as explained above), improve the number of (correct) movements per unit of time, improve the speed of movements or a routine, increase the number of routines the user is familiar with, improve the quality of movements or routines performance (at any stage of the routine) or any other training measure related with such activities in this disclosure or in general.

In case of other skills training such as target practice, pool table, military ballistics (for example a canon operation), mind skills training, skills involving the movement or action of external device such as, for example, car parking practice, heavy machinery operation practice, and alike, the user may define that he wishes to work on certain attributes, for example to perform a successful routine, where success can be measured in a number of ways related to the action or its results: achieve certain results of a routine—for example hit a certain area of the target in target practice; perform all stages of a procedure and/or in their correct order. For example, control or program a machine to perform a task or a procedure. The attributes can be how well the machine performs the operation, how fast it performs it, if programming or configuring is involved how fast does it occur and alike. When certain skills require performing a series of actions, it is sometimes important to train to perform the series of actions without forgetting or skipping any of the actions and many times in a well-defined order which should not be changed. Examples to such training may include operating potentially dangerous equipment such as heavy machinery and/or weapons. Also in health and therapy procedures this may also be the case.

The following is an example of military training. Operating manually a loaded cannon by a cannon crew. There is a loading and firing procedure in which it is important not to skip important steps and do the steps in a certain order. Nonetheless, the team must be trained to do them, and do them as fast as possible in order to produce the best possible firing rate. This may require training which the proposed embodiment can help with. For example, a part of the loading and firing procedure requires first unloading the empty cartridge from the previous round, then checking whether the barrel is clear by looking into it, loading the correct projectile (high-explosive, smoke, lighting, and the like), loading the correct weight of thrusting charge, closing the rear barrel hatch, aiming the gun, and firing. Forgetting to do one of the steps like checking that the barrel is empty, or inserting the wrong projectile, may have dire consequences. Also, not doing the procedure in the correct order may lead to accidents. The procedure brought as an example is simplified for the sake of clarity. The full procedure may contain more steps and may be more complicated. Some of the steps may have multiple options and may require the users to choose the correct or better option. The success criteria can bring into account also the decisions made during the procedure. The system may measure several training objectives like correct sequence performance, the time the performance took, results of the procedure—how close did the simulated/real projectile hit the target.

Each of the attributes mentioned in this disclosure can be worked on separately, for example training on not omitting steps in the procedure, training on the correct order, training on correct decisions during the procedure, and training on correct performance or quality of performance of each step or of a number of steps. Any combination is also possible. A certain grade can be defined to measure the success in performing a certain procedure. It can be the weighted sum of the measured success in each one of the training measures combining the group that measures success. For example, for each step of the procedure performed 5 points are gained, for each correct performance of a step 10 points are gained, for performing the whole procedure in less than 1 minute another 10 points, and the like. Success is defined when the grade is higher than a certain threshold, grade can also include reference to whether all steps were performed and whether the steps have been done in the correct order.

Another training measure the user wishes to improve may be the number of successful procedures out of trials (where successful is defined by any combination of the measures defined in the previous paragraph, or combination of them with other training measures in this disclosure or any other training measure) or the number of successful procedures per time unit. The user may also wish to improve the time it takes to perform a single correct procedure, or improve its grade for a single performance or a single performance per time unit. These training measures are applicable also to all the other activities mentioned earlier.

As disclosed above possible input to the system is the time the user can train in each training session. Yet another related input is the affordable training schedule for the user, for example how many times a week can he train, what is the time or period between trainings, in what days of the week it is possible to train and in which hours, and the like.

Designing the Training Program—Generalization:

A simple method for producing "List of exercises, activities or routines that May be allocated to session" is selecting a predefined program. The predefined program can be selected by the user. The user may be given a list where several predefined programs are proposed. The system may convey information about each of the programs to the user, for example what is the program focus, the time required for performing it, the exercises or some of them in the program, and the like. By selecting the wanted program the list of exercises or routines and other parameters shall be set.

In some types of trainings the list of exercises or routines may be quite defined to begin with. For example, in cardiovascular training if the selected activity is running or cycling, there may be a small defined set of possible exercises such as, but not limited to, interval running/cycling, distance running/cycling, sprint running/cycling, and hill running/cycling. Other types of training where the list is defined may be, for example, target practice.

In some cases, the system can select and assign a predefined program to a user. For example, in case the user is a beginner and has low skill level the system may assign a predefined program for improving the basic skills in the selected activity. After some time or feedback that the user skills have improved a different program may be devised. In general, the system may use the user skill level, wishes, and other inputs to assign the appropriate predefined plan for him. The process of assigning a predefined program may use any of the methods described above in "Methods for calculating and finding quantities and configurations used in this disclosure". Assigning a predefined program according to select criteria of experience is an example of the table or database method. A formula may be applied to several inputs from the user such as age, gender, level of experience, height, weight, and the like giving a result index that may be used to select a predefined program. Machine learning algorithm may also be used where the result Y is the predefined program which is selected from a set of possible programs. The attributes x, can be the user's inputs described above in "Possible inputs to the system" or throughout this disclosure such as goals, age, gender, experience level, BMI, fat percentage, difficulty level test results etc. Success criteria for the Machine Learning algorithm can be for example one of the following: the user satisfaction of the program where his satisfaction is inputted by him (after a possible question from the system), the time it took the program to bring the trainee to his goals, the program grade as shall be explained below, the amount or the rate of improvement achieved toward the goals in a certain amount of time, the time it takes the user to learn the program and/or reach a performance level above a certain threshold and the like.

In an example embodiment, the system needs to choose from a bank of 50 predefined training programs for Gym, each program is marked by a serial number from 1 to 50. The programs in the bank are divided to sub-banks by the goals they are aimed to improved and ordered by difficulty level inside the sub-banks. In general, initial order of the possible results can improve the ML method performance and time required for training. The input attributes are: Trainee gender, age, height, weight, body fat percentage, experience— measured by the number of years the trainee is training in a Gym, user goals as described in the above Gym example, max session time, and number of session per week. The output of the method is 1 selected training program out of the bank of 50.

In this example embodiment, the system undergoes training stage: in which training sets are fed into the system. Each set contains a value for each attribute like female, age 34, height 170 [cm] . . . and the desired result. The desired result in this example is achieved by using a human expert coach. The expert coach goes over the attributes in each data and chooses the most suitable program from the bank. A combination of a few expert coaches can be utilized. The desired result in each data set will be the majority vote. In case there is no majority either one of the coaches selected programs will be selected at random, or some priority scheme between the coaches will be used. The human coaches can also give the error or cost function by estimating it by comparing their selection to the ML algorithm selection. Another algorithm realized for example on a computing device can assist the human coaches in the selection or can even replace them altogether: The method can calculate a grade for each program and select, or recommend the highest grades based on some of the non-ML methods in this disclosure. For example, such method can calculate the sum as a function of the weighted sum of:

A. Differences from rules sets such as the ones used in the Gym example above for obtaining the training program for John. Each difference can for example reduce the total grade by a certain weight.
B. How many of each priority Muscle Groups are exercised (How many of first priority, how many of second. each priority may receive a different weight or calculation).
C. How much time in absolute value or in part of the total time is allocated for each priority Muscle group. Each priority may receive a different weight or calculation.
D. The difference between the required program time and the ML method result program time. A factor can be added to multiply or increase this difference weight in case the result time exceeds the required time.
E. A sum of all exercises grades in the resulting program.
F. Total difficulty or exertion level achieved in this program (can be calculated by summing of using another function on the individual exercises difficulties, exertion level etc.).
G. Criteria alike.

Of course, this grading method may be itself a non-ML method for selecting a training program. Similar method can be used to yield a cost function by comparing the differences between the desired result and the ML algorithm result and using a function on them.

In the example embodiment, the ML method example 3700 of FIG. 37 can be used: The training data-sets are used to generate histograms for each attribute. Since there are 50 possible results, in this example there are 50 histograms for each attribute. For the gender attribute, each such histogram has two bins according to the possible values of this attribute: male and female. Each bin represents the probability that this result was selected based on the gender. As in explained, this probability can be calculated from counting the number of times the result was selected and the attribute had this value. The age attribute histogram for example is also divided to bins. These bins can be by for example years, or a range of years like 10-13 years, 13-15, 15-17, 18-21, 22-25, 25-35, 35-45 . . .

Based on the histograms the probability of each possible result Y can be calculated for every new data set. As explained above this requires the likelihood—$p(y|C_k)$ which is simply the probability of a result from an attribute given a certain attribute value, and can be taken directly from the histogram. We also require $P(C_k)$ . . . which can be considered as the weight of each attribute for the final result. In this example we can start with random $P(C_k)$ or predefined ones. The example method 3700 explain how to adjust $P(C_k)$ during training.

In the operation stage, the system can find the probability for each one of the 50 possible results based on the equation:

$$p(y) = \Sigma_k p(y|C_k) p(C_k)$$

where k is the number of attributes. The system can then select the training program with the highest probability. If several possible results have similar probability, selection can be random, or in this example based on the highest sum of the program exercises grades (and random if this sum is equal between two or more possible results).

Deep learning method can also be utilized in this example: The attributes are the input non-hidden layer. They feed a few hidden layers which then feed a single output layer of one neuron which gives the selected program number. The same training sets can be used to train the Neural Network. The Error function mentioned above can be used for finding the weights and methods of Back-Propagation.

As in the example explained above for FIG. 33 method 3300, the methods may require a bank of exercises or routines or EDS like 3200 saved in a database 120. Attributes for each exercise may be saved such as the exercise difficulty level relative to other exercises and the training measures, skills that the exercise works on, for example the muscle groups that it works on as shown in the examples above. For each training measure/skill/muscle or muscle group a grade for effectiveness and/or difficulty level may be also saved in the EDS. Other attributes may be the time it takes to perform the exercise measure for the level of fatigue (mental or physical or both) the exercise causes, measure for the level of effort (mental or physical or both) required to perform it, the calories burned during its performance. or any other training measure describe in this disclosure or known.

The method 3300 given in FIG. 33 can be used or used in part for designing the training program. This section complements, further details and further generalizes the explanation given above in relation to FIGS. 32-36. The order of the steps in method 3300 may change and some of the steps may be skipped or not used.

At 3305 the inputs described in the section "Possible Inputs to the system" can be inputted. Additional attributes, preferences and schedule described in this disclosure, references or known in the art can be inputted.

At 3307 or 3309 any of the methods in "Methods for calculating and finding quantities and configurations used in this disclosure" Can be used to pull rule sets from the data base 120 and filter them based on the inputs of 3305. For example, a Machine Learning method can be used. The result Y is the rule set/s which is/are selected from the possible sets. The attributes x, and/or classes $C_k$ can be any of the inputs described above in "Possible inputs to the system" or throughout this disclosure such as user attributes like goals, age, gender, experience level, BMI, fat percentage, etc. Success criteria for the Machine Learning algorithm can be for example one of the following: the user or trainer satisfaction of the rules selection or the overall program generated from them, where his satisfaction is inputted by him (after a possible question from the system); The complexity of generating a training program based on the selected rule sets (Can be measured by computations required, steps required, time required and alike); The time it took the resulting program based on the rule sets to bring the trainee to his goals, the program grade as shall be explained below, the amount or the rate of improvement achieved toward the goals in a certain amount of time, the time it takes the user to learn the program and/or reach a performance level above a certain threshold and the like. In the ML training sets a human can grade the ML method outputs, or he can give the desired results for a set of attributes. Thus, a Cost/Error function can be devised based on either the grade or comparison between the ML method results and the desired results (or both).

At 3310 filtering is performed. As explained above filtering can be done according to the exercises that are not found to be contributing to the goals set by the user, or not bounded by the session or training program boundaries. For example, if the set goal is to train on several training measures, filter all the EDS which in their attributes these training measures do not appear. Specific examples given above. Further screening may be done by removing exercises that take more time then the time of a certain portion of the training session (⅓ of the time for example). Other examples include exercises with a required skill level or difficulty level not suitable to the user level—too difficult or too easy, exercises with a level of effort requiring more than the limit set for one exercise in the session or a certain portion of the effort limit set for the entire training session, and so on.

If the training program is a continuation program, i.e. it follows a previous training program, the screening method may be removing exercises which were part of previous training programs. A threshold for this screening may be set. For example, exercises which were part of a certain number of past training programs or a number of training programs in a row will be screened, exercises that were performed for a certain period of time, and the like. It is known in some activities that changing the exercises in a training program from time to time increases the effectiveness of the training program.

Yet another important screening criterion for exercises may be a low rate of improvement in previous programs or low rate of improvement mentioned or implied in an attribute in the exercise data structure.

Machine Learning algorithms can be used or combined with other methods for the filtering. The ML method plurality of results Y, maybe to select which exercise or exercises to keep or to decide which to filter or both. The attributes x, can be any of the inputs described above in "Possible inputs to the system" or throughout this disclosure, and any of the EDSs fields or features. Success criteria for the Machine Learning algorithm can be for example success criteria of the resulting program as explained above (User satisfaction from the program, user rate of improvement . . . ) or for example grading either the resulting exercises left after the Machine Learning filtering or those filtered. A simple grading method can be how many exercises left after filtering in which a certain attribute is not matching the requirements. In the Gym example—if at 3305-3309 certain muscle groups were selected the grade can be how many EDS left after filtering which their main muscle group attribute does not belong to the groups selected at 3305-3309. A different success criteria can be a certain formula on the attributes of either the EDS left or those filtered or both. An example of a very simple Cost Function formula—If the EDS contain an attribute of exercise grade then sum them up for the exercises which not filtered. In this case a higher sum means better performance of the ML method. After sampling some Cost Function values, curve fitting or other techniques can be used to identify or approximate it. Using this identification/approximation the Training of the ML method may be accelerated or improved. The success criteria can also be binary. For example, the sum of exercise grades should be over a certain threshold indicate success. Several criteria can be combined to indicate success or failure of the ML algorithm, or to be combined in a Cost Function.

At 3315 (and also in other stages) a greedy algorithm may be used to find or filter the list of exercise per session or sessions: there can be a configuration defining priorities between the exercises/EDS attributes for selecting exercises. First, the highest priority attribute may set the order of selection of exercises groups. In the gym example the first priority attribute can be the main muscle group. So this translates to "set the order of groups of exercises according to muscle group's priority (large muscle groups first)". The selection between some groups may not be well defined by this first priority attribute. In the gym example, chest and back muscle groups may have the same priority according to the muscle group attribute. At the next step the next priority attribute is used to settle the tie between groups. The second attribute in priority may also not be enough to settle all the "ties" or even any of them, so the next attribute in priority is used and so on. This happens until all or a set number of the exercises are selected, or the method runs out of attributes in the list. In case the method run out of attributes and there are still ties, a different method can be used to settle, or the user may decide, or a random decision may be taken to settle each tie, or other method. Additional constraints may be added to better order the selection using this method. It may be added that no more than a certain number of exercises may be selected per each skill or group. It can be also added that no more then a certain number per each skill or group before other certain skills/groups were populated by a certain number. This was shown in the gym example above, where for some groups there were no more than 2 exercises selected and 1 exercise for others. Constraints can be added on the total number of exercises, the total time the exercises take or some groups of exercise take, and the like.

A similar "greedy" method is to grade the exercises in the selection pool and select the highest grade exercise each time (as shown in the implementation examples above). Here too constraints may be incorporated to improve the selection flow, for example, no more than 2 exercises for certain skills or group and constraints as described in the previous paragraph. In general a grade in the EDS may be predefined, given by the user or coach, some average or weighted sum or grades given by users (where the weights may be set by users attributes, for example a coach's grading will receive a bigger weight), a formula on the exercise attribute such as a polynomial or a weighted sum, and the like.

Other examples to grading exercises/EDS: the system finds the level of improvement between every two difficulty level tests, or arbitrary points in time, or between the first time the exercise was incorporated in the training program to when it is replaced by another. The system grades the exercise proportionally or as a function of the level of improvement measured. The grade may also be an average or weighted sum or a formula of the results of a plurality of users. The level of improvement may be deduced from comparing the level of improvement between several exercises belonging to the same skill/attribute or group. Other measurements may contribute to the exercise grade, for example measuring the quality of performance of the exercise for different users, or how many mistakes were in performing the exercise in a certain time, for one user or a plurality of users. Any other attribute or quality may be added to the grading. In calculation of the grade the system may use any of the methods in "Methods for calculating and finding quantities and configurations used in this disclosure".

Machine Learning approach may be used to find the list of exercise comprising the training program or a session or part of a session. This approach is preferably used after initial filtering like 3310 that reduces the number of possible exercises, but it may be done also before it or without it.

For example, all combinations of possible exercises are generated from the EDS list like in stage 3335. Stage 3335 can be performed earlier then what is described in method 3300. For example, it can be done before or after stage 3310. It can be limited to working on a plurality of parts of the session or skills/groups. In the Machine Learning approach the result Y is a plurality of combinations selected from all the possible combinations. Some combinations may be filtered out like in 3337 method 3300. This filtering may be done by constraints or rules, as explained above, for example filtering all exercise combinations with total time exceeding a certain time limit. Any other calculation on exercise attributes which is above or below a certain threshold may lead to filtering of exercises combinations. Rules or constraints may be set in advance for possible combinations. For example, a legal combination is such that it contains a certain number of exercises for each skill, for example 1 exercise from each brain game in the example above. Many such rules according to any exercise attribute may exist.

After the building of the combinations (3335) and filtering a group of possible exercise (3337) lists is left. This is the group of possible final results. ML methods can be used to find one or more exercise combination as best fitting to the user. The attributes $x_i$ are the user's inputs, the EDS attributes, a function of them, or any other input or training measure in this disclosure. The desired result in 3340 method 3300 is selecting one or more exercise combination as best fitting to the user. As in the selection from a predefined set of programs, the success criteria for the ML method may be for example similar success criteria for those given for the filtering of exercises in 3310: The user satisfaction of the program where his satisfaction is inputted by him (after a possible question from the system); The time it took the program to bring the user to his goals; The amount or the rate of improvement achieved toward the goals in a certain amount of time; Grading of the selected exercises combination based on at least some of the attributes of some of the exercises in the combination; Grading of the selected combination according to total time or total exertion level or alike; A combination of thereof above a certain threshold that indicates success.

In method 3300 the determination of the schedule is at 3307-3309 or at 3312. This determination may be done before the other stages, like filtering and determining the exercise list, or after them. Scheduling may be done as one of the last stages in designing the exercise plan. Many methods can be used to set the training schedule. The user may define his training schedule himself and input it into the system. In another example embodiment, the user does not input any schedule or schedule constraint into the system. The system may recommend to the user the ideal training schedule for the training program and his goals. In this case, the system can also plan the best training plan to suit the user attributes, priorities, and needs, and the schedule will be a result of this plan instead of constraining it in advance.

As in all stages of method 3300, all the methods in "Methods for calculating and finding quantities and configurations used in this disclosure" can be used to set the schedule. The ideal schedule may be predefined, for example predefined per type of training. The schedule may be a function of user experience or a table divided into ability levels. The preliminary schedule can be given as time allocation in the sessions for each skill/activity/type/muscle group, and the like, for example, 5 minutes for each of the mind games in the selected priorities in each session, or in the gym example 2 sessions of 45 minutes for cardio and 3 sessions for strength where the internal time allocation per each muscle group in these 3 sessions is also predefined. This time allocation can be calculated by any of the methods in the section "Methods for calculating and finding quantities and configurations used in this disclosure" based on the user given schedule frame (how many sessions he can train and how long is each session and the resting time between sessions), or on the ideal schedule frame or any combination of thereof.

Here again (as in all stages of method 3300) a Machine Learning method can be applied. The group of possible results the ML method should choose from is the possible time division of the training session (including or not including order of time slots per activities). The group of possible time divisions can be filtered during or after the build by constraints and rules similar to the ones described in the previous examples of ML use. The attributes x, are the user's inputs; EDS attributes, some may be dealing with time of performance and rest like exercise performance time; or any other input or training measure in this disclosure. The desired result can be determined by selecting one time division out of the possibilities that will lead to the program best fitting to the user. As in the previous example of selection of a set of exercises from a given sets of exercises, the success criteria can be: the user satisfaction of the program generated based on the time division, where his satisfaction is inputted by him (after a possible question from the system), the time it took the program to bring the user to his goals, the amount or the rate of improvement achieved toward the goals in a certain amount of time, and the like. More specific Cost Functions can be used: the Cost Function for example can be a weighted sum or a function of one or more of the following:

- H. The difference between the required program time and the ML method result program time. A factor can be added to multiply or increase this difference weight in case the result time exceeds the required time.
- I. A sum of all exercises grades in the resulting program.
- J. How many of each priority Muscle Groups are exercised (How many of first priority, how many of second. each priority may receive a different weight or calculation).
- K. How much time in absolute value or in part of the total time is allocated for each priority Muscle group. Each priority may receive a different weight or calculation.
- L. Total difficulty or exertion level achieved in this program (can be calculated by summing of using another function on the individual exercises difficulties, exertion level etc.).
- Similar Cost Function can be used in the other examples of this disclosure. The Cost Function can also give a binary or quantified result if the Cost is compared to threshold or thresholds accordingly.

The order of the exercises can be set when the timing division is set (for example the combinations to select from may include the order of performance—i.e. two combinations with the same exercises but in a different order will be considered different) before it or after it. All the methods discussed so far for setting the time division can be applied to setting the exercise order in a similar manner. To set the training time division and/or exercise order, greedy algorithms similar to the ones previously discussed herein can also be used. Here are some example embodiments:

There can be a predefined order in which certain exercises working on certain skills or measures come before others. There is a predefined definition of the order of the skills or training measures. For example, in case of muscle training such as resistance based training (gym, Pilates) there is a known practice of working first on the large muscle groups such as the chest and back and later on smaller muscles such as arms.

The order can also be set according to the user set priorities or priorities determined by the system, for example according to the user measurements or inputs, where higher priorities will be first (see implementation examples).

The order can be set a according to required effort level (mental or physical). For example, high effort exercise shall come before low effort exercises. In general any exercise attribute from the database can be used to set priorities.

Generalization of the method, there can be a configuration defining priorities between the exercises attributes for setting the order of exercises. In the first step, the highest priority attribute can set the order of exercise groups where each group has a similar value of this attribute. For example, the order of groups of exercises may be set such that each one mainly works on a certain muscle group according to that muscle group's priority (large muscle groups first). The order between some groups may not be well defined by this first priority attribute. For example, chest and back muscle groups may have the same priority according to the muscle group attribute. At the next step, the next priority attribute is used to settle the tie between groups. The second attribute in priority may also not be enough to settle all the "ties" or even any of them, so the next attribute in priority is used, and so forth This happens until all groups are ordered or the method run out of attributes. In case the method runs out of attributes and there are still ties, a different method can be used to settle, the user may decide, or a random order can be chosen to settle each tie.

The next step is be to choose the order between the exercises in the group. The same method can be used again (this group can be viewed as similar to the larger group). The highest priority attribute which is not common to the group members can order the group members, and the method repeats until all attributes are exhausted or all group members are ordered or ordered in subgroups. The method is repeated until all members of the initial group are ordered.

Constraints can be introduced to this method, adding a refinement to it. In some cases there is a need to constraint certain exercises to come right after others. For example, in some methods of muscle training the opposing muscle will be always trained right after the original muscle was trained. For example, after a front hand muscle exercise will come a back hand muscle exercise, and so on. Another example can be if a training combines both mental and physical exercises it would, in some cases, be wise to enforce constraint so that after a physical exercise a mental exercise will take place and vice versa. This will allow the mental skills or physical skills to recuperate. The constraints can be integrated in the method presented in the following way. After every round of sorting, match the corresponding (according to the constraint) exercise from the lower priority attribute group to the higher priority attribute group. Matching can be done according to inner group order—first to first, second to second and so on. The order can remain exercise from first priority group, matching exercise from lower priority group, and exercise from first priority group and so on.

Similar to the exercise selection method, another sorting method can be to give each exercise a weighted sum or a grade. The weights can be determined according to the attribute priorities. For example, higher priority may receive higher grade, effort may receive a certain weight, and the like. Summing up the individual grades per attribute or using a formula, each exercise receives a final grade or weighted sum. Sorting can then take place according to this grade.

Another method for setting the time division and/or order is to divide the given time based on a basic time unit where the number of time units is set by the priority for each activity. The basic time unit can be the minimum time for which at least one exercise of the non-filtered activities fits. This method was used in the mind games example embodiment. The activities are ordered according to their priority in the session starting with the higher priority. This can repeat until all the session time is allocated. Using the allocation method according to priority insures that selection will have more or equal amount of exercises of the higher priorities.

At 3320, the methods in the gym or mind games example embodiments above can be generalized for selecting the exercise lists. Additional methods can include the ones described in this chapter such as the greedy algorithms and the use of ML. They can be used in some or all the iterations of 3320 or replace the iteration loop 3320-3328 altogether.

Finally, the selection of the list of exercises and/or time division discussed in this chapter can be viewed as an optimization problem. A set of exercises $E\{e1 \ldots en\}$ should be selected from a wider set of exercises $G\{e1 \ldots em\}$, where the exercises $E\{e1 \ldots en\}$ should give the optimal result to the training requirements $\{R1 \ldots Rk\}$ under the constraints $\{C1 \ldots Cl\}$. Any method known in the art of mathematics, optimization, machine learning, computer science or any other related art can be used.

Difficulty/Skill Level Testing

The system may perform tests on the user in order to have information about the difficulty level the user can work with or the user's skill level in the field of activity. These tests are also referred in this disclosure as "skill tests" or "strength tests" or "(skill) level tests". FIG. 38 describes a method 3800 for performing such tests. These tests can measure any training measure. Examples can be strength tests for gym or weight lifting, time for running a certain distance or distance covered in a certain amount of time, peak heart rate during a training routine, a time required to perform a certain routine, the number of mistakes or the level of performance of a certain routine, the maximum number of times the user can perform a certain routine in a given time or in general, the number of time the user can perform a certain routine, game, or task until he accumulates a certain number of errors, the difficulty level of a game or a skill test that the user can coup with, training measures which are results of user action such as maximum distance or average distance of Javelin throw, and the like.

Difficulty level tests can actually take place before devising the exercise list, preceding 3310 in method 3300. An initial specific exercise list can be predefined and designed specifically for these tests as described in the gym example above. The exercise list can contain specific exercises that are more appropriate for tests. For example, in the case of physical training, which can be generalized to other fields, some requirements from the strength tests exercises can be:

1. Safe to perform with high resistance or in high difficulty level. For example, in many cases machines are safer to use with high weights over free weights.
2. Easy to learn and perform. The exercise may be unique to the strength test and the strength test may be performed by users with different beginner levels, so it may be important that it would be easy to learn.
3. Can easily isolate or measure a specific muscle group, certain skill, activity type, and the like.
4. In some cases, a requirement can be that the exercise can allow the performance of additional test exercises after performing it. This can mean that it does not tire the trainee too much or causes circumstances that do not allow the test session to continue.

Any of the methods used to create an exercise list or a training program can be used to create exercise list for a test. There can be a specific database of exercises for tests, or certain exercises in the general database can be marked as suitable for testing and can have attributes relevant for testing.

Following the difficulty level tests, the list of exercises and their order may change, even after implementing method 3300. For example, the order may change if the system detects that the user skill level or experience level as reflected from the tests is different then what the user has inputted before 3300 was implemented. In this case, the training program generation can start from an initial stage again with the new experience level, and change the training program altogether.

The test results may change other attributes of the user. For example, they can change the priorities of skills, muscles groups, training goals, and the like as exampled in the gym implementation example in the case of strength training where the order of the exercises may only be set after the strength tests.

In some cases of testing certain skills, the difficulty level test may be relatively simple. As explained before, in some cases the difficulty level can be determined by the number of successful performances or achievements required in a certain amount of time. In such cases, the test may be simply measuring the user performance in this amount of time. This test can be repeated several times and the difficulty level can be the average result. If the difficulty level is also determined by additional factors such as, for example, the level of the routine the user has to perform or the level of the problem the user has to solve, the following method 3800 can be used in full or in part. One exercise iteration in the following method 3800 can be defined as performing the routine(s) or solving the problem(s) in a given amount of time.

The method 3800 refers to one routine but skilled in the art can appreciate that it is easily scaled and generalized to multiple routines or exercises. At 3810 the method may receive a plurality of the possible inputs described above. Some of the inputs maybe more relevant for the method 3800 like the users gender, age, the users background, and level of experience in the exercises or routines. Additional inputs shall be described below.

At optional stage 3820, the method establishes limits to the tests in terms of maximum difficulty level. Examples for such limits can be maximum weight to be lifted at a gym strength test, maximum distance to run/walk, maximum number of time to repeat the routine, maximum heart rate, and the like. For every training measure a limit may be established. Any of the methods from the section "Methods for calculating and finding quantities and configurations used in this disclosure" can be used for establishing the limits, with examples as given there and given here:

1. Based on predefined limits: the limits can be for example the mechanical limits of an exercise device which are pre-programmed into the system; known limitations of the human body are pre-programmed into the apparatus; and the like. The system may use the defined limits to keep difficulty level below them. For example keep the force exerted during the physical exercise below them, by for example refraining from using resistance above these limits or a function of them.
2. Using database/table to pull pre-defined limits—For example the entry can be age in years and for every age a limit is saved in the database, for example limit heart rate for every age. The table like data structure can have more dimensions, for example a 3 dimensional table shall contain an output for 3 entries. For example, a limit shall be extracted according to age, gender, and weight.
3. Formula (or function)—For example a formula for finding the limit heart rate can be: (220−age)*90%
   Max running distance can be calculated according to the formula: ((last training running distance)*exp(−(time in weeks from last training)/2))*2.

At 3830 the system sets the starting difficulty level for the test. It can be set very similar to setting the limits and with similar calculation methods, for example extracting the initial difficulty level from a database according to user gender, age, experience level, height and weight. More elaborate methods can be used. The trainee skill level can be estimated by different means prior to the skill test. For example, 3D mapping of the user's body and/or weighing can access the muscle volume of the specific muscle group which is tested. A formula or another method can be used to calculate the expected strength or difficulty level this muscle group can handle according to its volume; the simplest method may be to multiply the volume by a constant. Additional formula can give the beginning resistance of the strength test according to the estimated strength. Additional measurement or user attributes can be used in a formula used to access strength such as height, weight, fat percentage, body parts size, or proportions such as shoulders, width, chest circumference, and the like. ML methods can be used. The attributes or classes such as these, together with other user attributes, can be used to assess the user ability and thus the beginning difficulty level. The required result from the ML algorithm in this case is the beginning difficulty level and the success criteria can be: The user or coach/trainer satisfaction with the beginning difficulty level found; How Long is the following difficulty level test—if the strength test is long or has many iterations it means the beginning difficulty level selected was too low. Otherwise if the user has difficulties with the beginning difficulty level or there is indication that the difficulty level is too high, as will be exampled below, it is also an indication for unsuccessful selection.

In case the ML method or other methods of assessing the beginning difficulty level reach good results, they can replace the difficulty level tests altogether and their result can be considered as the difficulty level test result. In any case, successful estimation of the beginning difficulty level can make the tests much shorter and effective.

In an embodiment step 3840 is optional. The system may configure itself, the training environment, or a connected exercise device for the test. For example, the system may configure the resistance in an exercise device communicating with it like the embodiments presented above in the first sections of this disclosure this or in the references. As another example, the system may set the speed and/or slope and/or time on a treadmill machine. The system may configure itself to measure the routine time or the routine performance level by for example turning on a 3D camera or initializing a system such as the one presented in the above-referenced U.S. application Ser. No. 13/359,273, incorporated herein by reference. In another example, the system may output the required difficulty level to the user for him to set it himself. The system may configure the training environment or exercise machine for the user(s), for example configure a training machine to the user's dimensions like the height of the chair, the height and starting locations of the handles, and the like. After this configuration, the system may notify the user that it is ready to start the test. It may give the user additional time to prepare. It can make notification of the time left to the user using voice, for example reading the time left or saying something like "Ready, Set, Go !". It can also use sounds like a gun shot, increasing pitch and/or cadence and/or volume towards the start, and the like. The system may use other forms to communicate the starting of the measurement with the user such as video, vibration, a trainer avatar making gestures speaking or communicating with the user, and the like. Alternatively or additionally, the system may wait for a user input to start the test. Such input can be pushing a button, voice command, gesture, touching a touch screen, movement of a training apparatus or any other form of input the system can receive as described in this disclosure. Alternatively the sign may be simply starting to perform the exercise or routine. The system may identify this start as described above.

At 3850 of method 3800, the system measures the user performance using any training measures or inputs required. The system can also receive the result performance as an input from a user, trainer, or an external device communicating with the system. Using these it is possible to detect when the exercise has ended. Additionally, the system may identify or get as an input the exercise results. A performance above a certain threshold of performance level can be considered a success. Number of performance errors above a certain threshold, performance level lower than the threshold or even a single error which is considered fundamental can be regarded as a failure. Such a fundamental error can be, for example in the gym case, stopping in the middle of the exercise for too long, not performing the full movement range of the exercise, performing below a certain percentage of the movement range, body parts path to far from a predefined path and alike. In case of mind ability test success or failure in performing a task or solving a problem, right or wrong answer, performing smaller or higher number of routines and alike are indications for failure or success. Thresholds on any of the training measures in this disclosure can define success or failure. Other methods for evaluating performance are given in this disclosure and the references.

At 3860 the system checks whether the exercise has ended or the performance level is unsatisfactory as explained in the previous paragraph and therefore the exercise can be stopped. If yes the system goes to 3862. At 3862 it is checked whether there was unsatisfactory performance as explained in previous paragraph. Even if the exercise ended normally it is still recommended to check also if the accumulated errors in the exercise did not exceed a threshold or the overall performance level was not below the relevant threshold. If not, the method goes to 3864; if yes the method goes to 3866.

At 3864 it is checked if the limits of the difficulty level, number of exercise iterations, user fatigue level, or any other of the set limits have been reached. If such a limit has been reached or exceeded, the method goes to 3890 and terminates. Otherwise the method continues to 3880.

At 3880 the system can increase the difficulty level. The measure in which to increase the difficulty level can be determined in advance or at this stage. The methods for determining the level of increase can be similar to the methods exampled for determining the limits or the methods used to determine the initial difficulty level. In some cases the difficulty level increase can be derived from the initial weight estimated or in practice. It can, for example, be a certain portion of the initial weight. In some cases a formula can be used to determine the increase size. Inputs to the formulas and methods in this paragraph can be the iteration number, the initial difficulty level, the difficulty levels of previous iterations, the level of performance of previous iterations, and any other user attribute or training measure. An example for a formula can be: start increase with 10% of the initial weight. Decrease the increase by 0.5% in every iteration 3880 till 2% is reached. The level of increase can take into account the performance in the last iteration. If the level was not above a certain threshold the increase can be limited or reduced since a lower performance level may indicate that the exercise starts to be difficult or is difficult to the user. Naturally, a ML algorithm can be used here as well. Where the attributes are all the possible inputs to the method mentioned in this paragraph, and previous paragraphs; the desired result is selection of the level of difficulty increase; the criteria for success can be user or trainer/coach/administrator satisfaction from the result, the number of iterations of the difficulty level test (a lower number of iterations may imply good selection of differences), in case of the gym example the long term level of injuries as a result of strength test, and in general other criteria similar to ones used for estimating the initial difficulty level or the entire training plan. Criteria mentioned here can also be used for estimating the success of the ML algorithm used for estimating the initial difficulty level.

After increasing the difficulty level the method can go back to 3840 and configure the system and exercise environment for the new difficulty level. It can also notify the user on a rest period between exercises. The system can configure itself not to allow the user to perform the exercise during the rest period. Additionally or alternatively, the system can mark the beginning and the end of the rest period by various I/O means such as a bell ring sound, a countdown of the rest time, and the like. During the rest period, the system can engage in rest supporting actions like playing soft and calming music or sounds, instructing the user to perform relaxing or stretching exercises (and even guiding him through them), showing the user reports on his achievements and progress, telling him a story, showing movie and the like.

Going back to 3866, the system may check whether the accumulation of the number of errors in the last number of iterations is above some threshold, or the accumulation of bad performance, or the exercise was stopped because of bad performance or fundamental error. In such cases the method will go to 3868 which is a similar check as 3864. A difference from the check in 3864 can be an additional limit for the number of iterations with unsatisfactory performance in a row or in a general number of unsatisfactory iterations. If the limits have been reached or exceeded the system may end the session going to 3890.

Otherwise the system may continue to 3870. In 3870 the method chooses to decrease the difficulty level and by how much. The decrease can be 0 meaning leaving the difficulty level as is for another trial. It is preferred that the decrease in difficulty level will not cause the difficulty level to be lower than the last difficulty level that the user have already passed (succeeded). Methods similar to the ones used in 3880 can be used to determine the level of decrease in difficulty level. Important input to these methods additional to the ones mentioned when discussing 3880 can be the number of failed iterations in a row or in general, the last successful difficulty level, the last level of difficulty level increase, the last unsuccessful difficulty levels, and the like. From 3870 the method goes back to 3840 and the method is similar to what discussed in the passage from 3880 to 3840.

After setting the exercises and the initial loads there is a need to design the evolution of the difficulty level during the training program. All the methods in "Methods for calculating and finding quantities and configurations used in this disclosure" can be used, where the aim is to define how the difficulty level is changed from one training session or lesson to another. Examples were given above in the implementation example (FIGS. 32-36) and further will be given below. Similar methods to the ones used in previous sections especially in the sections discussing difficulty level test and of setting or estimating the initial difficulty can be used for setting or estimating the effort scale.

Difficulty level evolution can be predefined. For example, in many fields of practice it is custom to let very beginners repeat exercises with the same difficulty level for a period of time after they start training. For example, in gym exercise a new beginner may repeat the same exercises with the same resistance for a month or so in order to practice correct performance and have the body get used to the new form of exercise. There is a similar custom in other training disciplines. It then may be custom to raise the resistance in the minimum amount of difficulty level every lesson until reaching a certain threshold. Continuing the gym example, if the training program is comprised of 3 sets per each exercise, then the number of rehearsals of the drill is raised by 1 each lesson in one of the sets or in all 3. The user may start from performing 6 rehearsals×3 sets where in the next lesson performing 6×2 rehearsals and one set of 7 rehearsals, progressing this way to 12×3 rehearsals. When 12×3 the resistance level is reached by raising the minimum level (in many gym exercises the minimum resistance level that can be raised is 0.5 [kg]). The number of rehearsals starts again from 6×3 with the new resistance, and so forth. This is continued until a threshold of resistance is reached, for example the RM1 70%.

Some skill improvement exercises may have a predefined difficulty level evolution. Going back to the cannon crew example, at the first predefined period of time (for example a week or a month) the crew exercises the same routine(s) in order to practice correct performance and sequence. Time is not measured. After the period of time or after performance is measured to be correct for one or more times, time is measured. Starting from a predefined and relatively long time for performing the exercise, time is reduced by a pre-defined amount or factor. The reduction can be done after each drill or session or each time after a correct performance is achieved once or a predefined number of times. This can go on until reaching a certain threshold of time or the training goal. This method of predefined reduction is applicable to other skill training such as dancing, performing tasks, operating equipment, and the like. The correct performance can also be measured (as described above) in certain achievements, such as hitting a target in a certain defined area (distance from the center for example)

one time or a number of times, or in a crane operator training lifting a certain load and putting it in a certain place once or several times.

A table like data structure can be used where the predefined difficulty level increase is selected based on the user attributes, for example age, level, and any other possible user attribute. A function can be used to define the difficulty level evolution scheme. A simple example can be a linear function. In the gym example, the resistance can be modified according to the 3 sections linear function In each section the coefficients A and B for the linear function y=aX+b are different, where X is the session number or some other version of sampled time. Each section, for example, is suitable to the user progress in the exercise or training program. In the first section the slope is moderate or even 0 which is suitable for a user learning to perform the exercise(s) correctly without difficulty level change. The second section may be configured for a relatively fast increase in the effort scale and have a higher slope. The third section may be suitable for a lower increase in the effort scale and have a lower slope then the mid-section The coefficient b in every section may determine the initial effort scale of every section and will be configured to make the sections be continuous.

Another example for use of function in setting the effort scale was given in FIG. 35. FIG. 35 depicts a known graph defining effort scale or learning evolution. The horizontal axis is the lesson number or time or some version of sampled time. The vertical axis is the difficulty level or the trainee skill level. At 3530 the expected improvement rate is slow and so is the difficulty level change is slow. At 3540 the difficulty level increase rate is higher and at 3550 the user is reaching his limits and the improvement rate becomes asymptotic. Reaching this stage, or even before, the system may change exercises, redesign the training program, or inform the user that the training program has reached its end and a new program need to be initiated.

This graph can be mathematically described by, for example, the function (other functions are possible as exampled before):

$$\left\{ \begin{array}{l|l} x < a & K_1 e^{K_2 x} \\ x \geq a & K_3(1 - e^{K_4 x}) \end{array} \right\}$$

A combination of function and table can be used where any of the function variables or even the function itself can be selected from one or multidimensional table like data structure based on any of the user or exercise attributes (gender, age, type of exercise, type of exercise machine used, exercise difficulty level, and the like)

ML methods can be used here as well. The attributes can be all those described above including user attributes, initial difficulty level, difficulty level test results, trainee training schedule, and any other training measure or user attribute. The expected result is an efforts scale or a list of plurality of difficulty level increases. The criteria for success can be similar to those in the previous ML examples, especially examples of the difficulty level test and of setting or estimating the initial weight. In general, it can be measured how suitable is the effort scale for the user as will be further explained in the next section. This measurement can be used as a success criteria or for generating a Cost Function for the ML methods.

The methods of the gym implementation example and other implementation examples above can be generalized for tracking the program performance, adjustments, further capability testing, and continue/replacement programs. In the generalization, muscle group may refer to a certain skill or training measure. Weight or resistance can be replaced with difficulty level. Similar rules to the example defining the relationships between the groups, such as priority, order, number of exercise per group, and the like, can be used in a similar manner to the example embodiment. The exercise equipment may be any and not related to gym.

Teaching the exercise and session can take place in many ways. Some examples may be: showing a video of the exercise explaining about it and giving performance example, explaining by voice, rendering a hologram of the exercise performance which can also be rendered directly on the exercise machine or training environment, and calling from help from a human coach or a robot to teach the exercise.

Another example method can be guiding the trainee to perform a step in the exercise, then receiving feedback on the trainee's performance, for example from the, motion sensors or camera, correcting the trainee performance while explaining the correction, then guiding him to the next step. This guidance can repeat every session as long as the system see's it is necessary. The necessity of teaching the exercise can be set by a predefined number of times after the first performance including it. This number of times can be set according to the user's experience level. The necessity of teaching the exercise can also be set by the user's request, or as long as the user's exercise performance level is not above a certain threshold.

The system can identify the user in several ways, including by his input to the system. The input can be vocal; the system can use voice recognition to identify the user, or ask him to say his name. The system can also identify the user by communicating with the user's smart watch or wearable computing device via any wireless communication method known in the art such as NFC, Wi-Fi, Blue-Tooth, ultrasonic, and the like; communicating with the user's mobile device via wireless communication method known in the art or wired communication, for example the user may attach his mobile to one of the exercise devices in the system; facial recognition using an optical sensor or a camera; body recognition—using a 3D sensor the system can compare the user body profile obtained at the measurement stage or any later stage and compare it to an on the fly 3D image of the user and thus identify him; communicating with a device such as a smart-card or membership-card or any other device that can be used to identify the user. The identification of the user can be the first thing to occur when the user enters the training environment. It may also be done, or combined with, certain security measures or measures to limit access of non-intended personnel to the training environment.

After identifying the user, the system can load its data and start interfacing with him. It can greet him and the interface may be in the form of a coach communicating with the system or a virtual coach rendered by the system.

The system can ask the user how he is and of the status of certain measurements about him, for example how did he sleep, how does he feel, how was his day, and the like. The system can also communicate with mobile and wearable computing devices found on the user and retrieve important data such as how the user slept, how intensive was his day (for example by reviewing the tasks and appointments in his calendar, receiving the number of steps the user have made, and the like), user body measurements such as pulse, temperature, blood pressure, sugar level, and the like. The system may extract or send data about other trainings or activities the user has done in other places or training environments. The system can receive or transmit results of training sessions or goals achieved. The system may continue this communication throughout the exercise session.

Following the collected data the system may perform modifications in the session plan. For example, if the system identifies that the user did not have enough sleep, or had a too busy day, it may reduce the effort required, such as reduce the number of repetitions in certain exercises, the number of sets the difficulty level, and the like. Modifications can also be used in response to data about training or activities in other training environments. For example, if a goal has been achieved in another training environment, or a higher skill level or difficulty level have been achieved, the system may update the user's training plan accordingly. If the system is updated that the trainee has been in recess but collects data about him being training in another environment at this time, it may also update accordingly.

The system may instruct the user to perform certain actions prior to the exercise session according to the collected data. For example, if the user has a low sugar level or his schedule shows that he have not eaten for some time, or when the system asks him he says that his last meal was some time ago or that he is hungry, the system may instruct him to have a meal before training and may even recommend on what to eat.

In some cases, the system may recommend or instruct the user to give up the training session, for example if the user did not sleep at night, or did not sleep, or waited the minimum time required since the last training session. In that case the system may automatically or in real-time interface with the user schedule for the next training session. After these the system may review the session plan with the user (by voice, video, and the like), instruct him to his first exercise, and may even show him the way by means of voice, video, turning on lights leading to the exercise machine or training environment, hologram, a robot and the like. In the case of a new user (or any user) the system may give further explanations such as explain the safety instructions or some background material about physical exercise. As explained above the system may teach the exercise(s) to the trainee.

During the exercise the system may track the user's performance and motivate him, for example in the way reviewed in the above-referenced U.S. patent application Ser. No. 13/359,273. It can track his calorie burn using optical sensors or alike as described in the references.

The system may do a "Gamification" of the training session. For example, a user on a treadmill may be simulated to be a part of a race with other real users on other treadmills or virtual users. The race scene and the other users may be displayed by video on a screen or hologram and voices related to the game and also cheering on the user may be heard.

Similarly a user doing a strength exercise on a training machine or without an exercise device may also be a part of a game of similar real or virtual users (real users' avatars may be displayed to the user if these real users are far away) competing for some goal which can be, for example, completing several repetitions correctly, who lifts the maximum weight, and the like. The game may be based on reaching a goal where each repetition makes the user closer to the goal. For example, a group of users may play the game of "ladders and snakes" where each correct performance is a climb up the ladder and each wrong performance is a few steps down (a snake). The winner can be the user who reached the higher level or reached a certain level first.

A simple way to give motivation can be just rendering the virtual coach guiding the user and doing the repetitions with him. The virtual coach can also count repetitions out loud, say motivational phrases, especially toward the end of a set, and the like.

As already mentioned, the system may track the user's performance of the exercise. The system can issue calls for him to correct his performance in real time. It may adjust his pace. The system may also use the tracking to later adjust the training session as will be explained. It can grade the user performance and report the quality of performance during or at the end of the session.

During the session the system may further guide the user between exercises. At the end of the session the system may issue reports on certain aspects of the training. Reports may include distance traveled (for example in a cardio exercise), body measures during the session such as blood pressure, temperature, or pulse (graph during the exercise, highs and lows, at interest points during the session, and the like), flexibility or range of movement in exercises, or a total grade of flexibility or movement range, muscle groups worked in the session and the intensity each muscle group experienced, energy or calories burned (can be sliced per exercise/muscle group, and the like), time per exercise or per achieving a goal (such as certain distance or number of repetitions), total grade of the exercise, the degree of achieving the goals set at the beginning of the exercise, the mistakes in error performance that may include visualization of them, or any other training measure, or any additional report that can be generated using the system components and measurements. Each one of the reports may be a comparative report, comparing the results to previous sessions, to other trainees, to baseline levels etc. Reports can be given by printing them, by presenting them on screen, by hologram, a video, read by voice, shown as graphs or images or videos, and the like.

Another method to raise the difficulty level or setting the effort scale can be more interactive by "studying the user". The system can start with a certain predefined difficulty level change, for example minimum difficulty level change per session. This can be, for example, for safety reasons and to let the user learn the exercise properly and be confident before raising the difficulty level quickly. The number of these sessions can be determined by the user experience level and specific exercise and manners similar to the ones used throughout this document. After this number of sessions the system can try to access the difficulty level raise slope suitable for the user. It can slowly raise the difficulty level raise rate between sessions. In the gym example, if the minimum raise is one repetition in one of the 3 sets, next time the raise can be 2 reps in two sets and so on.

The system monitors the user performance and identifies when he is not doing the exercise properly, or unable to do the number of reps given to him. Based on this the system can deduce that the rate of raise is too high. It may deduce this also if bad performance is seen in later exercises or the user does not finish the session properly. Of course an input from the user about the difficulty level can be also considered. One time that the user is not performing the exercise correctly may not be enough to decide that the difficulty level is too high. Once the user fails to do the exercise correctly above and his performance is below a certain level, the system can log it. It can then decide not to raise the difficulty level for the next session. If the wrong performance is repeated several times, or there are number of sessions with insufficient performance in a certain predefined amount of time, the system can deduce that the difficulty level is too high. In general the methods used in the difficulty test method (3800) and specifically the steps 3860-3870 in method 3800 can be used here to detect the increase in the difficulty level required.

When the system detects that the rate of difficulty level raise is too quick it can reduce the rate to the last rate which was not too quick or a little bit below it. How much to reduce rate at this stage can also be a function of the user experience level and experience in the specific exercise. The system continues to monitor the user's performance in the sessions. If there are a few close sessions in which the difficulty level increase was too much for the user the system may further decrease the rate of difficulty level increase. On the other hand if a certain number of sessions have passed without observed difficulty from the user, the system may retest the rate of difficulty level change by increasing the rate again and continuing as detailed above.

All these methods can also be used to define success criteria or build a Cost Function for a ML algorithm for determining the difficulty level or effort scale as described above.

The system may try to fit the difficulty level change obtained this way to a function in one of the known curve fitting methods. The function can be taken from the database where the curve fitting may only find its constants, in this case the difficulty level change if future sessions can be done using the function found. The system may continue to monitor the user's performance and test from time to time to verify the correspondence to the function or fit a new function. Full strength tests can be given from time to time in order to access the difficulty level, the improvement, and the affectivity of the method used to raise the difficulty level.

In a session or a group of sessions, the system may choose not to raise the difficulty level or raise it less than the function or rule requires because of certain measurements or situations, for example if the user has not slept enough before the session, if some input measurement have values above or below certain thresholds like high blood pressure, low sugar level, and the like, if the system identifies fatigue by analyzing the user postures obtained from optical or other sensors, cases where a user did not exercise above a certain amount of time, for example a week a month or more, or the user is returning from illness or injury are special cases.

In case of recess in training or any of the situations in the above paragraph. A change in the training program may be required. The period that requires change in the training plan or difficulty level can be predefined. It may be calculated by a function based on the user's experience, age, sex, the length of the period the trainee was training continuously, and the like. In many cases the change in training plan will be only difficulty level, which can be calculated by a function which is affected by similar parameters.

Another method is to do a full or partial difficulty level test when the user is back to training, or back to healthy/good condition. For example, the rules may be:

1. Up to one week of recess—no change in training plan or difficulty level setting.
2. Up to two weeks—difficulty level is not raised in the first session after the recess.
3. From two weeks to 3 months—roll the difficulty level back to what it was a difference in time that equals the recess time.
4. Above 3 months—perform a full difficulty level test to determine the difficulty level.

The difficulty level change function or method can be altered after the recess.

For example, the difference in difficulty level just before the recess and the new difficulty level after the recess can be calculated. The difficulty level raise can then be calculated to be such to achieve back the difficulty level before the recess in a fraction of the recess time, for example half of the recess time. The raise may be linear in this time or can take any other predefined or calculated function. Cases of illness or injury can also be treated in a similar manner as recess.

It is recommended to change the exercise plan from time to time. As depicted in FIG. 35, at 3550 the difficulty level possible raise becomes asymptotic after some time. At this stage continuing with the same exercise may be inefficient or worse. The system may have several indications to change the training plan such as a certain amount of time passing, for example 4 months (replace exercise plan every 4 months). This time can be a function of the user attributes such as experience level, age, and gender, and the like. Another indication can come from the exercises or the monitoring. Each exercise may include its recommended time before replacement as an exercise attribute (the attribute can of course be a formula as well). The indication can be the system monitoring showing a decrease in difficulty level change as described above. When this happens too often, or when the difficulty level raise is minimum or below some threshold for some time, or the fitted function show above threshold decrease in slope or derivative.

The system may respond to one or more indications from one or more exercise. It may respond when a certain number of indications and/or indications from exercises have been received. The response can range from just replacing the indicating exercises in an exercise selection manner similar to what is described above or different. The response may also be building of a new training plan. When building this new training plan certain additional aspects can be added to the building process described above.

The user attributes should be updated, for example the user experience level which is added with the current program gained experience. The exercises the user did in the current program should be marked and the mark used in future program building. The system can save attributes like the highest difficulty level the user has reached in a certain exercise, and the like.

When building the new program, certain rules may apply for exercise selection. For example, a recommended rule is not to use the same exercise in two successive programs if there are other possible exercises in the filtered database. The difficulty level used in certain exercises in the past may be used to determine the difficulty level in a new exercise plan. A certain conversion rate or conversion rate formula may also be used (any of the methods of "Methods for calculating and finding quantities and configurations used in this disclosure" can be used to calculate the new difficulty level based on the old one). These can be stored in one of the exercise data structures, be related to the muscle group, to the user attribute, and the like.

The system may perform some of the interactions with the user in the form of a virtual coach. The embodiment of the virtual coach can be a voice interacting with the user, a video projection of a human coach or an animation figure, a hologram of a human figure or animation, a figure or animation in virtual reality (for example trough virtual reality glasses), a robot and the like. The interactions may include motivational talk, input and output of user information, explanation about the training program, session exercise, warnings about exercise performance issues, training status and reports, guidance on the exercise facility, machines, and the like. The virtual coach may actually show or demonstrate how to perform exercises, correction of mistakes in performance, or perform the exercise with the user for example for motivation and pace.

The virtual coach can also be a robot humanoid. This robot can perform some or all of the functions described above. The system can send the robot the information about the user, the training session, the next exercise, and the like. The sending can be done by any interface known in the art, for example Wi-Fi or Bluetooth. The robot may use its own computing system for analyzing the information and performing its tasks. It may be fully or partially guided by the system. For example the system may instruct the robot to show the user a correct performance of an exercise. The robot can then pull from its own database the exercise performance instructions and start performing them using the processing of its computing system. It may, for example, receive the set of instructions one by one from the system through the interface. In this case, the robot computing system may only be used for translating the instructions to actual motors and activators instructions and for control of their movement. The system may use its sensors for control of the robots movements, actions, voice, and the like. The sensors can be used to feedback the robots actions and may be part of its control feedback loop.

The system may perform some of the interactions with the user through a plurality of virtual peers, contestants, players, the like, and a combination thereof. They can perform some or all of the interactions mentioned above. Preferably they can be used in a game scenario. They can also be avatars for distant real users, and so a competition or game can be held between distant training partners.

The system may perform some of the interactions with the user through a human coach. In this case the system may serve as an aid to the human coach. It can give him instructions for all of the above detailed interactions. It can remind him about the training plan, how to perform an exercise, remind him to motivate the user, point him to when and what the user is doing wrong, and the like. The human coach may request for information on the fly or in retrospect. He may also modify data or aspects of the training (for example change exercise, difficulty level, or update the user details) in real-time or in retrospect. The system may interface with the human coach through any of its possible input/output devices or methods. For example the human coach can interactively interact with the system through a tablet like device.

The database for the system can be global and can be saved in the cloud. Each exercise saved to the system's database in a certain location can be transferred or saved in advance on the global or cloud based database. Thus each exercise added can be used by all other users of the system.

This is true for every aspect of the methods using a database. For example, every process of machine learning can be made global. When the system learns to improve the generation of exercise programs the machine learning method can be fed with the data from all the locations where systems are deployed and thus speed up and improve the quality of the learning and results.

The system can learn, using machine or man guided learning, which exercises give the best results, for example the exercises that give the maximum improvement in a muscle group between two sequence strength tests. It can then rate or grade the exercises globally improving the quality of the training programs devised using also the attribute of exercise grade.

Exercise grade can also be affected by users/coaches preferences, and/or selection patterns. Exercises that were better graded by users/coaches or selected more often in manual mode can be graded accordingly. The grade can also be a formula based on selection patterns, i.e. on exercises selected before in the selection process. The grade of an exercise in the database can include a formula which is conditional, for example it adds different amounts and/or multiply with different constants depending on the exercises selected before in the exercise selection processes. These amounts and/or constants and/or weights can be determined by users/coaches selection patterns, how many times they select a certain exercise before another or a certain sequence of exercise. Using data gathered by the system from many users, and possibly in many training facilities, statistical sample can be achieved. Based on it the amounts and/or constants and/or weights for the formula can be set in methods known in the art. Machine Learning can also be utilized: The classes will be sequences of exercises from the database and the success criteria's and measures of success be those disclosed herein for building a training plan.

In all these example processes the selections or preferences of certain groups or types of users may have a larger effect on the calculations for users belonging to these same groups or other groups which are pre-defined to be affected from them. This way similar profile trainees may benefit the preferences and learned experience from trainees similar to them.

Data on users such as their habits, tendency for illness or injury, level of fitness, and others can be gathered and be used by, for example, insurance companies to fit the best possible policy and insurance rate for each user.

The system may learn exercises from users without needing to actively input them to the system. For example, the system can identify that an exercise is not in the database by comparing it to the exercises already in the database. If the comparison or correlation results are lower than a certain threshold the system can decide that the exercise is new. Methods for comparison and correlation are given in this disclosure and the references or maybe known in the art. New exercises may also include new training machines or environments not known to the system before.

In case the system decides that the exercise is new it can record its performance using its sensors. The recording can start for every exercise in order to prevent missing the exercise start in the database. If the exercise is not new the recording may be abandoned. The recording may be saved in the database in the form of image frames, skeleton diagram frames, or any other form given in this disclosure, the references, or known in the art. The system may receive the fact that the exercise is new and additional information about it from the user. For example, if it reaches the conclusion the exercise may be new, it may confirm the observation by asking the user. It can then ask or prompt the user to give additional information, for example after the exercise has concluded.

The system may create a data structure for the exercise and identify or calculate the exercise attributes. For example, in physical training, the system can identify the muscle groups the exercise is working on by identifying around which joints there is movement and its direction. Small movements can be filtered. By identifying the direction in which the performance is done against resistance the system may further refine the muscle groups list. For example in a free weights exercise, the system can identify the movements in which their direction has a noticeable component of movement against gravity. Further identifying which joints and bones are involved will give the active muscle groups. The system can identify the start position and the end position of the exercise in methods similar to those described in the references. The start position can be simply identified by identifying the start of movement. Difficulty level coefficients can be deduced by comparing the resistance the user had set to other exercises or to his strength tests for the same muscle group.

The system may refer the exercise to an appointed human instructor or instructors. They can fill in attributes the system was not able to identify or calculate. They can also rank the exercise and correct the initial user's performance if necessary. The system can use the help of other users to fill in attributes or improve its recordings of the exercise. The system can give the exercise to random users or users selected by their experience level or other attributes. It can then record them doing the exercise and use the recording to average frames with the initial recording. If the given user is known to be of high level, his performance can receive a higher coefficient in the averaging, or replace the previous recording altogether. The system may ask the users to rank the exercise. It can measure their responses to difficulty levels to understand the difficulty level scale. It can ask them about missing attributes where. The system may limit the number of questions per user in order not to affect the good user experience. For example, it may ask each user one question about one attribute. It can collect all the answers and decide about each missing attribute by majority vote for example. More experience users vote may receive a higher weight in the decision.

The system can check the new exercise affectivity. It can incorporate it in some of the new training programs it builds. It can then measure the affectivity and ranking of the exercise by checking the increase in effort scale or the improvement between strength tests, or any other success measure for training program. A machine learning algorithm can be used.

The system may receive from users, or detect in a similar manner, additional possible results for sizes or quantities not known to the system before. For example, the system assumes that the minimum difficulty level increase in a gym in 1 [kg] but then receives from the user or detects increases by only 0.5 [kg]. The system may now add the possibility to modify the difficulty level by only 0.5 [kg] to its calculations. Specifically it can add it as an additional possible result for a ML algorithm and start machine learning the classification of this possible result with all the existing attributes. New attributes not known before can be added or detected. A user or a trainer/coach can tell the system what attributes help him make a decision on any of the aspects described in this disclosure. If this aspect in not known, or not used as an attribute in the specific ML algorithm for this decision, the system can add it and start its ML training. The system can perform from time to time correlations between estimated or deduced quantities and training measures or attributes which are not already in use for deducing these quantities. The selection of attributes to do correlations with can be random. If in a certain number of measurements correlation higher than a certain threshold is found, this attribute can be added to a ML algorithm for deducing this quantity or another deduction or calculation scheme. A human supervisor may be notified upon detection or at a later stage and may be thus incorporated in the process of adding new result possibilities, attributes or exercises. The supervisor can take measures to improve accordingly, such as changing configurations, coefficients, methods, and the like.

Random "errors" can be introduced by the system to certain processes in this disclosure. For example, in the method for selecting exercises for the training program, when the method selects an exercise according to the best weighted sum or grade, an exercise not having the best grade may be selected at a random or predefined time as a deliberate error introduction. This may solve cases where, for example, some exercises are rarely or never selected and so the system and users do not have a chance to experience them and grade them. As a result of their introduction to the training program these exercise may "experience" changes in their attributes and grade which may improve their chances of being selected in the future and may improve the training program. The situation resembles an understudy actor or player who gets his chance in random and being discovered. Other types of such deliberate "errors" can be in difficulty level Other such intended "errors" can be introduced at random, predefined or calculated times in all the processes and methods described in this disclosure.

In an example embodiment of a health club or training facility, monitoring users or trainees can have added values: For example, the proposed embodiments in this disclosure and the references can: track the users' location and path during the training sessions, they can monitor their exercise performance and recess times, they can track other activities like talking to other trainees or caches and more. This way, for example, what is known in fields of marketing and ergonomics as spaghetti charts can be generated. Such charts can map the most popular areas, facilities or machines, the order in which they are used, the amount of time spent on each etc. This may aid arrange the health club or training facility in a better way, detect problems or difficulties, receive marketing voluble information and more.

Such tracking of users by the system in the example embodiment may also assist in user's retention and satisfaction and improve the overall training experience and affectivity. Patterns of users behavior can be saved to the database analyzed and give insight about the users' behavior and satisfaction level. Recognized patterns or indicators can be compared on the fly to the patterns of the users being recorded. For example the system can identify users thinking about leaving. Known patterns, identified states or series of states, indicating dissatisfaction or pointing to users thinking of not continuing the training can be put in the database. The system may be pre-programmed to warn when it detects certain such states or series of states. For example identifying a user that spends too much time (relative to a threshold) on each exercise, a user who takes long recesses, a user which performs above a threshold number of exercises incorrectly, a low level of improvement or rise in effort scale over a period of time, a user which performs many exercises faster than required, a user which skips exercises repeatedly, In a gym a user who "throws weights", or does not make an effort to prevent weight plates machines from banging, and other patterns.

Machine-Learning algorithms can be used on recorded and on the fly patterns of users to learn when a user is probably satisfied and when a user is probably unsatisfied and thinking about leaving. The expected result from such a ML algorithm can be indication that a user is dissatisfied or want's to leave the training. A measure of success can be achieved by checking with the users that the system has indicated as dissatisfied or thinking about leaving. The attributes x, can be for example all of those mentioned in the previous paragraph: recess times, time spent on exercises, relative number of bad performance of exercises, speed of performance in several exercises etc., the user improvement or low rise in effort scale for a period of time, where low improvement may indicate dissatisfaction etc. Other user attributes can be used as attributes—for example user gender, age, weight, how much time the user is a member, etc. Rate of change of achieving the users goal, for example if a goal is reduce body weight or body fat percentage a change in the rate the weight or fat percentage is reduced can be an indication or an attribute. In general, any of the user or training attributes or training measures mentioned in this disclosure, in the reference or known in the art can be used for the classes.

As a result of detecting a user dissatisfied or thinking about leaving the training, the system or the training facility management may then take steps to improve the satisfaction level of the identified users or take steps to improve their retention. For example the system or the system operators can initiate a change in the training plan or a substitution of it altogether. The system or operators may initiate lowering of the number of training session in a week or period of time, they may shorten the sessions or change the order of the exercises and alike. The user may be consulted as for the reason of his dissatisfaction and the steps to take in order to improve the situation. The user may be prompted to change his goals or schedule or other attributes and as a result the training plan can be built again. The system or operator may initiate a controlled recess of days weeks or months in training. They may suggest to the user changes in training habits, sleeping habits, nutrition habits and alike. What steps to take to retain trainee's or what are the best steps can also be found using ML Algorithms. The required result is step or steps with highest probability to retain the trainee. The measure of success is whether the trainee was retained (can be for a threshold amount of time) or not. Attributes can be all those from the last paragraph with addition of the reasons for the trainee wanting to leave and alike.

The system may include a social network implemented using cloud computing, the users PCs, mobile devices, wearable computing devices or other computing systems, various methods of communication between computing systems, or computer programs or methods running on the computing systems involved in the social network. The social network may allow users to open personal accounts. These personal accounts may contain a plurality of their user's attributes. The system may use the user account to obtain these attributes. A user account may be interfacing or synchronized with various computing devices such as mobile devices and wearable computing devices and may obtain from them data, training measures, user attributes, and the like. The system may use the account to synchronize with this data. The system may further use the user's account for interfacing with him in many of the possible ways mentioned in this disclosure. It can use the account to schedule his training sessions, obtain all the data required for building a training plan and build a training plan, remind him about upcoming session, track his habits, sleeping, nutrition, and the like. The user can use his account for producing and receiving all types of reports mentioned in this disclosure.

The system may further use the social network to enhance its big data and machine learning capabilities. Users may give feedback on exercises, training sessions, difficulty levels, user interface, and all other aspects of the system operation. The system may use these feedbacks to improve its operation. Feedback on exercises, for example, can be in general about the exercise or specific to a plurality of its attributes, such as too long, too difficult to learn, too easy, and the like. Using these feedbacks the system may update the exercise grading or a plurality of its attributes in the EDS. Similar methods for handling the user's feedback and applying it to exercises which were discussed above can be used here, specifically the number of similar feedbacks and the type or attributes of the users that gave them can be considered when the system calculates the feedback effect. And such methods can be applied to all feedbacks discussed in this disclosure. Feedbacks on full exercise sessions or on any other aspect can also be considered. They can be used as success criteria, or for building Cost Functions for ML algorithms as discussed throughout this disclosure. If the system is using several methods in parallel to decide upon a certain size or quantities, the feedbacks can rate the best method. The feedbacks or feedbacks summary can be reviewed by a human or a computer which can take measures to improve accordingly, such as changing configurations, coefficients, methods, and the like.

Users may use the social network and give ideas for new exercises, session planning, interfaces, difficulty level setting, and the like. The system may learn from these ideas in a similar manner to what described above. New exercises may be added to the database this way. New results possibilities or attributes for classification can be added to any of the ML algorithms or other algorithms used.

Users may use the social network and give ideas for improvement. These can be reviewed by a human or a computer which can take measures to improve accordingly, such as changing configurations, coefficients, methods, and the like.

The system can use any method known in the art to scan blogs, chats, e-mail messages, wall messages, and the like, and to extract from them feedback about exercises, session planning, interfaces, difficulty level setting, and the like. It can also extract ideas for new exercises, session planning, interfaces, difficulty level setting, and the like or ideas for improvement. It can then handle them in the methods described above.

The users may further use the social network for their needs and motivation. They can use it to find peers for training sessions or games. They can use it to find trainers or coaches. They can use the social network to design an avatar for them to use in games and training sessions. They can schedule their training sessions with their peers or trainers and they can initiate the training session from the social network and interface the system from it. A plurality of users can decide about mutual training goal(s). The goal can be, for example, the same for each of the individual participants. It can be a, for example, certain level of a training measure for each participant, or it can be the sum of the individual achievements passing a certain threshold. A mutual goal can be defined and attained using a "relay race" scheme where each individual or group continues another individual group against another "relay race" group or where the combined achievement of the "relay race group" is above a certain threshold.

The social network may also have a prize or reward scheme to motivate users. It can motivate the users or groups with the best scores, the most diligent or persistent user or groups, and the like. Users may be able to compare their scores and any other of their results, attributes, training measures, and the like to other users for motivation. This may be subject to users consent. Specifically users may watch other users training in real-time and the related data such as their real-time training measures, corrections to performance, level of performance, and the like. This way, for example, users can watch and take example from more experienced users or coaches, or even compete with them.

Users may also be able to track other users and see their training plans, exercises, difficulty levels and improvement levels. This may be for example also a way for novice trainees to learn from more experienced trainees. Users may be able to request similar exercises in their training plan, similar training sessions, a difficulty level increase, and the like. The system may take their request into account in any of the methods described.

Additional inputs to the system described in this document can be the users DNA or gene profile. The system can compare the certain genes or DNA combinations or sequences to ones stored in its database and thus conclude on user attributes and ability to improve skills. For example, the system's database may include DNA sequences that imply a certain hereditary heart condition. In that case, the system can decide or be preconditioned to limit the maximum strain level or heart rate which is allowed for this user. The characterization of the user's DNA can give the system indications on many things, such as the trainee limitations, potential strength, effort scale, difficulty level rate of change, potential of each muscle group, and the like. These indications can be incorporated in the methods described in this document. A simple example can be identification of gender and race according to the DNA. The system can then pull out of the database the characteristics of the gender and race. For example, females may have lower limits and lower difficulty level rate of change for their upper body muscle groups. There are differences between races in these characteristics as well.

The system can use facial and other body parts recognition to determine a level of matching between the individual and certain DNA or gene sequences it has in its database. If certain sequences imply certain shapes or proportions of facial features or body parts the system may determine the level of matching between the DNA or Gene sequence and the individual by the number of these features found on the individual. It can then decide to match a certain set of attributes related to this DNA sequence with the specific individual. The matching can further be verified or excluded during the tracking of this individual. A machine learning algorithm can be utilized to improve the matching between body and facial features and individual attributes, where the measure of success is how many and how well these attributes were matching the individual as found during his strength tests, and other tracking done by the system. Machine learning can also be utilized for improving the matching between users' attributes and DNA or gene sequences.

In an embodiment the exercise and/or routine and/or session and/or training plan data and reports can be presented on Virtual Reality (VR) or Augmented Reality (AR) devices 197. For example the following data can appear on AR or VR device: current exercise, the number of repetitions required and the number of repetitions done, the number of sets expected and the number of sets done, the next exercise in the session plan or parts of the session plan or all of it, indication for speed of performance, guidance on the exercise done, or remarks from a virtual coach of what to improve—on the fly or in retrospect. Additionally or alternatively reports about the exercise, session or training plan can also be presented to the user. Reports can include for example exercises or routines performance grade, what was good and what requires improvement in the exercises, what skills or muscle groups were exercised and what is the level of exercise and performance in each, improvement over a plurality of sessions, effort scale and alike.

In an embodiment, the Virtual Coach can take the form of a human or an avatar in VR and/or AR and take the tasks of a human coach or others as described herein.

In an embodiment, parts of the training can be presented on the VR or AR device 197 as disclosed herein as part of the training. For example opponents, competitors or peers can be presented on the VR or AR device. Alternatively or additionally targets for the training, or objects which are parts of the training tasks can be presented. For example, if the training involves tools operation the tools can be presented in VR or AR and can be operated or move according to the trainee/s actions. The entire training environment can be presented and change according to the trainee actions or movements. For example, a trainee running can have a scenery displayed to him which changes according to the virtual way he passes. Training opponents and/or coaches and/or partners and alike can also be presented to the user as already disclosed. They can also be changed according to the user responses or movements.

The sensors in the system, described in this disclosure and in the references, or known in the art, can monitor the user's motion, body parts location, forces and accelerations excreted and alike, as disclosed. This way it is possible to close the control loop with the AR and/or VR devices 197. As disclosed the system can modify the display of the training environment, tools, opponent, etc. according to what is monitored by the sensors.

An exemplary embodiment can be the minor warfare tactics embodiment disclosed herein. In this embodiment scenery such as urban scenery or natural scenery can be displayed on the VR/AR and also opponents can be displayed making use of the scenery for their tactics. Even the weapons and other tools used by the trainees can be VR/AR displayed, or they can be actual equipment which incorporates additional sensors. Such additional sensors may include grip/pressure sensors, trigger pressing sensors, accelerometers, sensors for indicating where the weapon is punting to (optical or based on triangulation or laser or others known in the art). Target tracking sensors can monitor the users location and movement and based on it together with the weapons and tools monitoring can change and evolve the scenery, obstacles and opponents. Similarly the canon crew implementation disclosed or similar implementations can have the tools and scenery displayed to the trainees and change in accordance to their actions and movements.

In a similar way other embodiments can use VR/AR. For example a surgeon training on operating a medical operation machine. For example training in precision operation of a tool such as a surgeon's knife. The tool/s can be either real, and/or training tools and/or VR/AR rendered. The system can monitor the trainee's movements and manipulation of the tool/s using its sensors. For example motion tracking sensors. It can then move AR/VR rendered tools accordingly, and change other attributes of the training environment accordingly. Alternatively or additionally, the training tools can include sensors that can help the monitoring task like theses disclosed in this disclosure and the references. For example pressure sensors, grip sensors, accelerometers, markers or location sensors etc. The knife in the example can have for example a marker for the motion tracking sensors, grip sensors at its handles, accelerometers for further tracking of its movement and pressure sensor on the blade.

As disclosed Gamification of the training sessions can make use of VR/AR devices and/or other I/O devices of the system. Gamification may present the training activity in a form of a race or a strive toward a goal. For example it may present the actual training activity and render a competitor doing the same activity and/or a coach. The trainee/s need to either win against the competitor by doing the training activity goal better (for example doing a routine more correct and/or faster and or with higher resistance, etc.), or follow the coach actions, and alike.

Gamification can display or render a different activity and/or scenario then the actual training activity. For example, it may present situations or a race, such as a car race, Athletes running or skiing race, Rowing competition and alike. Every performance of the training activity and/or exercise and/or routine according to the training goals may advance the avatar representing the actual trainee in the race scenario. The advance can be proportional or affected from the level of achievement of the training goal or goals. For example doing the exercise and/or routine more correctly, or faster for example will advance the avatar faster.

Other Gamification scenarios may express striving toward achieving a goal. For example, climbing (e.g., a mountain or a tree, and can also be a race against another climber) where the goal can be reaching the top. Another example can be building something like a tower or a building or some tool or even a puzzle. Yet another example can be demolishing something, like for example breaking an iceberg with a hammer, or a brick wall or alike. In all these scenarios the progress be proportional or affected from the level of achievement of the training goal or goals as described above.

The various embodiments disclosed herein can be implemented as hardware, firmware, software, or any combination thereof. Moreover, the software is preferably implemented as an application program tangibly embodied on a program storage unit or non-transitory computer readable medium. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such computer or processor is explicitly shown. In addition, various other peripheral units may be connected to the computer platform such as an additional data storage unit and a printing unit.

All examples and conditional language recited herein are intended for pedagogical purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:

1. A system for enhancing training of a person, for use with a training environment that comprises a first physical exercise equipment that is controllable or configurable to be in one of multiple training difficulty levels, and for use with a database that comprises multiples training activities, wherein at least one training activity in the database comprises an identifier of the first physical exercise equipment, a training difficulty level of the first physical exercise equipment, and a respective attribute, the system comprising first and second computing devices that communicates over a network, the first computing device comprising:
an input component for obtaining a first attribute from the person;
  a plurality of sensors for capturing physiological data of the person; and
  a display component for visualizing a training program to the person,
  wherein the first computing device is configured to send to the second computing device over the network, the first attribute and the physiological data, and to receive and display by the display component, from the second computing device over the network, the training program,
the second computing device comprising a memory for storing the database and a processor for executing an algorithm,
wherein the second computing device is configured to:
receive from the first computing device over the network the first attribute and the physiological data; and
execute, by the processor, the algorithm for generating the training program on the database based on the first attribute and the physiological data, and
wherein the training program comprises multiple training activities from the database, and
wherein the algorithm is based on, or uses, a Machine Learning (ML) algorithm that is trained to optimize a training program according to a criterion, wherein the said algorithm uses:
i. algorithm output comprising one or more pre-defined possible outcomes, wherein each outcome can be one of: selecting a rule set from a collection of rule sets, selecting a training routine from a collection of training routines, selecting a combination of training routines from a collection of possible combinations, selecting a session total time from a collection, selecting a session time division from a collection, selecting a session training goals priorities from a collection, and selecting the number of training routines in the session from a collection;
ii. a set of pre-defined attributes or input nodes that can be one of: system inputs, one or more training measures, user data and training environment data;
iii. inputs or measurements that can be one or more of said system inputs, wherein at least one of said one or more of the system inputs can activate at least one of said input nodes or be classified by at least one attribute;
iv. a measure of success and/or an error function and/or a cost function that can grade and/or determine success of the Machine Learning algorithm in selecting said one or more pre-defined possible outcomes;
v. a training phase for said algorithm,
wherein said algorithm combines more than one of:
said input nodes,
possible hidden nodes connecting input nodes to output nodes or to additional hidden nodes, and
dependent probabilities of possible outcomes on said attributes;
wherein based on this combination, said algorithm selects the outcome; and
wherein at least one of the following is optimized during the training phase: weights for said input nodes, weights for said attributes, weight for said hidden nodes, weights for said output nodes, and selection of said pre-defined possible outcomes.

2. The system according to claim 1, wherein the first computing device is part of, is integrated with, or is mechanically attached to, the first physical exercise equipment.

3. The system according to claim 1, wherein the first computing device is configured to control the first physical exercise equipment to be in difficulty level selected from the multiple training difficulty levels in response to the received training program.

4. The system according to claim 1, wherein the first physical exercise equipment is configured for controlled movements of a person for at least one of: improving flexibility, building strength, developing control, gaining mass, improving stamina, improving body look, developing endurance; or any combination thereof, of a part of a human body or of an entire human body.

5. The system according to claim 4, wherein the part of the human body comprises, or consists of, an abdominal muscle, a chest muscle, a shoulder muscle, biceps, triceps, quadriceps, calves, leg muscle, forearm muscle, glutes, hamstrings, or any combination thereof.

6. The system according to claim 1, wherein the first physical exercise equipment comprises, or consists of, Pilates equipment, gym training equipment, or exercise equipment.

7. The system according to claim 1, wherein the first physical exercise equipment comprises, or consists of, a Pilates reformer or a butterfly machine, a treadmill machine, an elliptical machine, a cycling machine, a leg press machine, a bench chest press machine, a shoulder press machine, a free weights and modifiable bench machine, a standing calf raise machine, a leg curl machine, a glute-ham raise machine, or any combination thereof.

8. The system according to claim 1, wherein the first physical exercise equipment is configured for affecting or simulating a military training, a game, a work type, walking, or running.

9. The system according to claim 1, wherein the first physical exercise equipment is configured for affecting health or physical status.

10. The system according to claim 9, wherein the health or physical status comprises blood sugar level, blood pressure, a hormone level, blood chemistry, pain level, immune system response, allergy state, infection level, or any combination thereof.

11. The system according to claim 1, wherein the first physical exercise equipment is configured for affecting cardiovascular training.

12. The system according to claim 11, wherein the first physical exercise equipment is configured for a person running, cycling, or climbing.

13. The system of claim 1, wherein the ML algorithm is based on, or uses, Genetic Algorithms, Decision Tree Learning, Association Rule Learning, or Rule Based Machine Learning.

14. The system according to claim 1, wherein the first computing device comprises, or consists of, a portable or wearable device.

15. The system according to claim 14, wherein the network comprises a wireless network.

16. The system according to claim 15, wherein the wireless network uses, or is based on, Near-Field Communication (NFC), Wireless Local Area Network (WLAN), or Wireless Personal Area network (WPAN).

17. The system according to claim 16, wherein the WLAN uses, or is based on, WiFi, and wherein the WPAN uses, or is based on, Bluetooth®.

18. The system according to claim 1, wherein at least one of the plurality of sensors comprises a microphone for capturing the person voice or a camera for capturing the person image.

19. The system according to claim 1, wherein at least one of the plurality of sensors comprises a position sensor or motion sensor.

20. The system according to claim 1, configured to use a method for designing a training session, the method comprising the following steps:
a. attaining at least one of: trainee attributes, trainee goals, trainee schedule, training measures, system inputs; at least one of them being used in the following steps:
b. selecting at least one rule set, from a collection of rule sets;
each one of the following steps based on a rule-based and/or machine learning algorithm that is configured by the selected rule set;
c. at least one of: determining the session total time, determining session time division, determining session training goals priorities, and determining number of training routines in the training session;
d. sorting and filtering of Exercise Data Structure (EDS) residing in a system database to retrieve at least one training routine;
e. checking if EDS is allocated to a session training goal;
f. checking if at least one of the following conditions is met: all session time is allocated and a required number of exercises are met;
g. if all session time is allocated or the required number of exercises are met, then the training session design;
h. if not and a training routine is not allocated a session training goal, then repeating steps d to h;
i. else if all session time is not allocated- or the required number of training routines is not met but a training routine is allocated to each of the session training goals, then generating a group of all possible legal combinations of training routines not selected from an EDS collection stored at a database, and then selecting a best combination from that group; and
j. completing the training session design.

* * * * *